US012173349B2

(12) United States Patent
Bhatia et al.

(10) Patent No.: US 12,173,349 B2
(45) Date of Patent: Dec. 24, 2024

(54) LUNG PROTEASE NANOSENSORS AND USES THEREOF

(71) Applicant: Massachusetts Institute of Technology, Cambridge, MA (US)

(72) Inventors: Sangeeta N. Bhatia, Lexington, MA (US); Jesse Kirkpatrick, Cambridge, MA (US); Jaideep S. Dudani, Boston, MA (US); Colin Buss, Cambridge, MA (US); Andrew David Warren, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 408 days.

(21) Appl. No.: 16/582,053

(22) Filed: Sep. 25, 2019

(65) Prior Publication Data

US 2020/0096514 A1   Mar. 26, 2020

Related U.S. Application Data

(60) Provisional application No. 62/736,388, filed on Sep. 25, 2018.

(51) Int. Cl.
*G01N 33/574* (2006.01)
*C12Q 1/04* (2006.01)
*C12Q 1/37* (2006.01)

(52) U.S. Cl.
CPC ............. *C12Q 1/37* (2013.01); *C12Q 1/04* (2013.01); *G01N 33/57423* (2013.01); *G01N 2333/21* (2013.01); *G01N 2800/12* (2013.01)

(58) Field of Classification Search
CPC .............................. C12Q 1/37; G01N 2800/12
See application file for complete search history.

(56) References Cited

U.S. PATENT DOCUMENTS

| | | | |
|---|---|---|---|
| 5,500,161 A | 3/1996 | Andrianov et al. |
| 5,811,252 A | 9/1998 | Verheijen |
| 5,885,775 A | 3/1999 | Haff et al. |
| 6,312,390 B1 | 11/2001 | Phillips |
| 6,335,429 B1 | 1/2002 | Cai et al. |
| 6,339,069 B1 | 1/2002 | Meers et al. |
| 6,592,847 B1 | 7/2003 | Weissleder et al. |
| 6,597,996 B1 | 7/2003 | Venkataraman et al. |
| 6,629,040 B1 | 9/2003 | Goodlett et al. |
| 6,824,981 B2 | 11/2004 | Chait et al. |
| 7,041,453 B2 | 5/2006 | Yang |
| 7,045,296 B2 | 5/2006 | Parker et al. |
| 7,169,892 B1 | 1/2007 | Atsushi et al. |
| 7,179,655 B2 | 2/2007 | Patricelli |
| 7,329,506 B2 | 2/2008 | William |
| 7,412,332 B1 | 8/2008 | Venkataraman et al. |
| 7,456,269 B2 | 11/2008 | Gurney et al. |
| 7,468,258 B2 | 12/2008 | Owen |
| 7,544,518 B2 | 6/2009 | Aebersold et al. |
| 7,595,155 B2 | 9/2009 | Murakami |
| 7,820,108 B2 | 10/2010 | Lampotang et al. |
| 7,879,574 B2 | 2/2011 | Packard et al. |
| 7,985,401 B2 | 7/2011 | Jiang et al. |
| 8,673,267 B2 | 3/2014 | Bhatia et al. |
| 8,841,085 B2 | 9/2014 | Kwon et al. |
| 8,969,027 B2 | 3/2015 | Bossmann et al. |
| 9,006,415 B2 | 4/2015 | Ren et al. |
| 9,072,792 B2 | 7/2015 | Jiang et al. |
| 9,155,471 B2 | 10/2015 | Lee et al. |
| 9,416,195 B2 | 8/2016 | Sagi et al. |
| 9,657,326 B2 | 5/2017 | Ruether et al. |
| 9,808,532 B2 | 11/2017 | Tsien et al. |
| 9,913,917 B2 | 3/2018 | Groves et al. |
| 9,970,941 B2 | 5/2018 | Bhatia et al. |
| 10,006,916 B2 | 6/2018 | Kwong et al. |
| 10,253,365 B1 | 4/2019 | Doudna et al. |
| 10,527,619 B2 | 1/2020 | Bhatia et al. |
| 10,702,474 B2 | 7/2020 | Sailor et al. |
| 10,883,998 B2 | 1/2021 | Bhatia et al. |
| 11,054,428 B2 | 7/2021 | Bhatia et al. |
| 11,428,689 B2 | 8/2022 | Bhatia et al. |

(Continued)

FOREIGN PATENT DOCUMENTS

| AU | 2005227364 A1 | 11/2005 |
|---|---|---|
| CN | 102558362 A | 7/2012 |

(Continued)

OTHER PUBLICATIONS

Salaün et al., "MMP-13 In-Vivo Molecular Imaging Reveals Early Expression in Lung Adenocarcinoma", PLOS One, vol. 10(7), pp. 1-19. (Year: 2015).*

(Continued)

*Primary Examiner* — Michelle F. Paguio Frising
*Assistant Examiner* — Grant C Currens
(74) *Attorney, Agent, or Firm* — Wolf, Greenfield & Sacks, P.C.

(57) ABSTRACT

Aspects of the present disclosure relate to methods and compositions useful for in vivo and/or in vitro profiling of proteases present in the lung. In some embodiments, the disclosure provides methods of in vivo enzymatic processing of exogenous molecules followed by detection of detectable markers as representative of the presence of active proteases associated with a lung disease, for example, lung cancer and lung infections. In some embodiments, the disclosure provides compositions and methods for production of a lung disease signature and diagnosis of lung disease.

20 Claims, 45 Drawing Sheets

Specification includes a Sequence Listing.

(56) References Cited

U.S. PATENT DOCUMENTS

| | | |
|---|---|---|
| 11,448,643 B2 | 9/2022 | Bhatia et al. |
| 11,519,905 B2 | 12/2022 | Bhatia et al. |
| 11,703,510 B2 | 7/2023 | Bhatia et al. |
| 2002/0119490 A1 | 8/2002 | Aebersold et al. |
| 2003/0059952 A1 | 3/2003 | Chait et al. |
| 2004/0014652 A1 | 1/2004 | Dubois et al. |
| 2004/0091943 A1 | 5/2004 | Schneider |
| 2005/0107583 A1 | 5/2005 | Jiang et al. |
| 2005/0260695 A1 | 11/2005 | Fleming et al. |
| 2006/0008856 A1 | 1/2006 | Singh et al. |
| 2006/0257883 A1 | 11/2006 | Bjoraker et al. |
| 2006/0292631 A1 | 12/2006 | Broberg et al. |
| 2007/0010433 A1 | 1/2007 | Albrechtsen et al. |
| 2007/0048752 A1 | 3/2007 | Yan et al. |
| 2007/0207555 A1 | 9/2007 | Guerra et al. |
| 2007/0258894 A1 | 11/2007 | Melker et al. |
| 2008/0026480 A1 | 1/2008 | Guerra |
| 2008/0064607 A1 | 3/2008 | Yang |
| 2008/0095758 A1 | 4/2008 | Lee et al. |
| 2008/0113875 A1 | 5/2008 | Chaurand et al. |
| 2008/0213377 A1 | 9/2008 | Bhatia et al. |
| 2008/0226562 A1 | 9/2008 | Groves et al. |
| 2008/0241955 A1 | 10/2008 | Purkayastha et al. |
| 2008/0253960 A1 | 10/2008 | Zheng et al. |
| 2009/0016988 A1 | 1/2009 | Buckley |
| 2009/0088332 A1 | 4/2009 | Ju et al. |
| 2009/0156424 A1 | 6/2009 | Thompson |
| 2009/0230300 A1 | 9/2009 | Trevejo et al. |
| 2009/0246142 A1 | 10/2009 | Bhatia et al. |
| 2009/0252677 A1 | 10/2009 | Bogyo et al. |
| 2010/0022408 A1 | 1/2010 | Singh et al. |
| 2010/0124757 A1 | 5/2010 | Kwon et al. |
| 2010/0190193 A1 | 7/2010 | Calatzis et al. |
| 2010/0240050 A1 | 9/2010 | Bhatia et al. |
| 2010/0317542 A1 | 12/2010 | Lim et al. |
| 2011/0014125 A1 | 1/2011 | Bossmann et al. |
| 2011/0021908 A1 | 1/2011 | Lee et al. |
| 2011/0104052 A1 | 5/2011 | Barnett et al. |
| 2011/0104071 A1 | 5/2011 | Lee et al. |
| 2011/0277538 A1 | 11/2011 | Haick |
| 2012/0039990 A1 | 2/2012 | Reshetnyak et al. |
| 2012/0150164 A1 | 6/2012 | Lee et al. |
| 2012/0183949 A1 | 7/2012 | Hyde et al. |
| 2013/0078188 A1 | 3/2013 | Tsein et al. |
| 2013/0295129 A1 | 11/2013 | Irvine et al. |
| 2013/0315906 A1 | 11/2013 | Lowman et al. |
| 2014/0207129 A1 | 7/2014 | Lee |
| 2014/0234431 A1 | 8/2014 | Bhatia et al. |
| 2014/0255313 A1 | 9/2014 | Vasiljeva et al. |
| 2014/0276102 A1 | 9/2014 | Lee et al. |
| 2014/0276103 A1 | 9/2014 | Lee et al. |
| 2014/0301950 A1 | 10/2014 | Lee et al. |
| 2014/0303014 A1 | 10/2014 | Kwong et al. |
| 2014/0363833 A1 | 12/2014 | Bhatia et al. |
| 2014/0364368 A1 | 12/2014 | Lin et al. |
| 2015/0051153 A1 | 2/2015 | Reshetnyak et al. |
| 2015/0080721 A1 | 3/2015 | Novak et al. |
| 2015/0104381 A1 | 4/2015 | Maina-Nock et al. |
| 2015/0165062 A1 | 6/2015 | Liao et al. |
| 2015/0344523 A1 | 12/2015 | Deyle et al. |
| 2016/0025632 A1 | 1/2016 | Lee et al. |
| 2016/0096869 A1 | 4/2016 | Hansen et al. |
| 2016/0184459 A1 | 6/2016 | Ueki et al. |
| 2016/0289324 A1 | 10/2016 | Moore et al. |
| 2016/0317037 A1 | 11/2016 | Lee et al. |
| 2017/0267727 A1 | 9/2017 | Thevenin et al. |
| 2017/0305968 A1 | 10/2017 | Tsein et al. |
| 2018/0021090 A1 | 1/2018 | Lee et al. |
| 2018/0196058 A1 | 7/2018 | Kwong et al. |
| 2018/0328941 A1 | 11/2018 | Bhatia et al. |
| 2018/0335429 A1 | 11/2018 | Bhatia et al. |
| 2019/0076081 A1 | 3/2019 | Hyde et al. |
| 2019/0128873 A1 | 5/2019 | Bhatia et al. |
| 2019/0144917 A1 | 5/2019 | Bhatia et al. |
| 2019/0212291 A1 | 7/2019 | Dudani et al. |
| 2019/0271704 A1 | 9/2019 | Bhatia et al. |
| 2019/0345534 A1 | 11/2019 | Kwong et al. |
| 2019/0376113 A1 | 12/2019 | Kwong et al. |
| 2020/0116725 A1 | 4/2020 | Bhatia et al. |
| 2020/0225231 A1 | 7/2020 | Bhatia et al. |
| 2020/0232986 A1 | 7/2020 | Bhatia et al. |
| 2020/0249194 A9 | 8/2020 | Dudani et al. |
| 2021/0148926 A1 | 5/2021 | Bhatia et al. |
| 2021/0262025 A1 | 8/2021 | Bhatia et al. |
| 2022/0128571 A1 | 4/2022 | Bhatia et al. |
| 2022/0404349 A1 | 12/2022 | Bhatia et al. |
| 2023/0040528 A1 | 2/2023 | Bhatia et al. |
| 2023/0076516 A1 | 3/2023 | Bhatia et al. |
| 2023/0111954 A1 | 4/2023 | Bhatia et al. |
| 2023/0194544 A1 | 6/2023 | Bhatia et al. |

FOREIGN PATENT DOCUMENTS

| | | |
|---|---|---|
| CN | 103012595 A | 4/2013 |
| CN | 108484847 A | 9/2018 |
| EP | 1808188 A1 | 7/2007 |
| JP | 2004-506900 | 3/2004 |
| JP | 2004-129651 | 4/2004 |
| JP | 2004-533610 A | 11/2004 |
| JP | 2005-315688 A | 11/2005 |
| JP | 2007-24631 A2 | 2/2007 |
| JP | 2007-206054 A | 8/2007 |
| JP | 2009-108037 | 5/2009 |
| JP | 2009-159985 A | 7/2009 |
| JP | 2009-524688 | 7/2009 |
| JP | 2009-538430 A | 11/2009 |
| JP | 2013-060452 | 4/2013 |
| JP | 2016-520327 | 7/2016 |
| WO | WO 99/05319 A2 | 2/1999 |
| WO | WO 2002/014867 A2 | 2/2002 |
| WO | WO 2006/034370 A2 | 3/2006 |
| WO | WO 2006/067221 A2 | 6/2006 |
| WO | WO 2007/060921 A1 | 5/2007 |
| WO | WO 2007/063300 A2 | 6/2007 |
| WO | WO 2007/072070 A1 | 6/2007 |
| WO | WO 2008/072676 A1 | 6/2008 |
| WO | WO 2008/093513 A1 | 8/2008 |
| WO | WO 2008/127019 A1 | 10/2008 |
| WO | WO 2009/124265 A1 | 10/2009 |
| WO | WO 2010/101628 A2 | 9/2010 |
| WO | WO 2011/008996 A2 | 1/2011 |
| WO | WO 2012/031250 A2 | 3/2012 |
| WO | WO 2012/085080 A1 | 6/2012 |
| WO | WO 2012/125808 A1 | 9/2012 |
| WO | WO 2013/019681 A2 | 2/2013 |
| WO | WO 2014/107599 A2 | 7/2014 |
| WO | WO 2014/120619 A2 | 8/2014 |
| WO | WO 2014/120974 A1 | 8/2014 |
| WO | WO 2014/176284 A1 | 10/2014 |
| WO | WO 2014/197816 A1 | 12/2014 |
| WO | WO 2014/197840 A1 | 12/2014 |
| WO | WO 2015/042202 A1 | 3/2015 |
| WO | WO 2017/044894 A2 | 3/2017 |
| WO | WO 2017/120410 A1 | 7/2017 |
| WO | WO 2017/177115 A1 | 10/2017 |
| WO | WO 2017/180789 A2 | 10/2017 |
| WO | WO 2017/181149 A1 | 10/2017 |
| WO | WO 2017/193070 A1 | 11/2017 |
| WO | WO 2018/049285 A1 | 3/2018 |
| WO | WO 2018/064383 A1 | 4/2018 |
| WO | WO 2018/187688 A1 | 10/2018 |
| WO | WO 2018/227132 A1 | 12/2018 |
| WO | WO 2019/071051 A1 | 4/2019 |
| WO | WO 2019/075292 A1 | 4/2019 |
| WO | WO 2019/089804 A1 | 5/2019 |
| WO | WO 2019/089820 A1 | 5/2019 |
| WO | WO 2019/126577 A2 | 6/2019 |
| WO | WO 2019/126716 A1 | 6/2019 |
| WO | WO 2019/126762 A2 | 6/2019 |
| WO | WO 2019/148206 A1 | 8/2019 |
| WO | WO 2019/173332 A1 | 9/2019 |
| WO | WO 2020/068920 A1 | 4/2020 |

(56) References Cited

FOREIGN PATENT DOCUMENTS

| WO | WO 2020/081635 A1 | 4/2020 |
|---|---|---|
| WO | WO 2020/150560 A1 | 7/2020 |

OTHER PUBLICATIONS

Pilcer et al., "Formulation strategy and use of excipients in pulmonary drug delivery", International Journal of Pharmaceutics, vol. 392, pp. 1-19. (Year: 2010).*
Park et al., "Pathophysiological Changes Induced by Pseudomonas aeruginosa Infection Are Involved in MMP-12 and MMP-13 Upregulation in Human Carcinoma Epithelial Cells and a Pneumonia Mouse Model", Infection and Immunity, vol. 83, No. 12, pp. 4791-4799 (Year: 2015).*
Holt et al., "Nanosensors to Detect Protease Activity In Vivo for Noninvasive Diagnostics", Journal of Visualized Experiments, vol. 137, pp. 1-6. (Year: 2018).*
MD Anderson <<https://www.mdanderson.org/cancer-types/lung-cancer/lung-cancer-treatment.html>>, webpage, accessed Feb. 2023. (Year: 2023).*
Bassetti et al., "How to manage Pseudomonas aeruginosa infections", Drugs in Context, vol. 7, pp. 1-18). (Year: 2018).*
National Center for Biotechnology Information <<https://pubchem.ncbi.nlm.nih.gov/compound/Bodipy>>, webpage, accessed Feb. 2023 (Year: 2023).*
Shin et al., "Synthesis of Microgel Sensors for Spatial and Temporal Monitoring of Protease Activity", ACS Biomaterials Science and Engineering, vol. 4, pp. 378-387. (Year: 2018).*
Invitation to Pay Additional Fees mailed Feb. 25, 2020, for Application No. PCT/US2019/052868.
International Search Report and Written Opinion mailed Jun. 25, 2020, for Application No. PCT/US2019/052868.
Invitation to Pay Additional Fees mailed Apr. 8, 2021, for Application No. PCT/US2019/052868.
[No Author Listed] Summary for peptidase S01.010: granzyme B. Merops. Retrieved from <https://www.ebi.ac.uk/merops/cgi-bin/pepsum?id=S01.010;type=P>. Apr. 26, 2019. 2 pages.
[No Author Listed] Summary for peptidase S01.135: granzyme A. Merops. Retrieved from <https://www.ebi.ac.uk/merops/cgi-bin/pepsum?id=S01.135;type=P>. Apr. 26, 2019. 2 pages.
[No Author Listed] Summary for peptidase S01.146: granzyme K. Merops. Retrieved from <https://www.ebi.ac.uk/merops/cgi-bin/pepsum?id=S01.146;type=P>. Apr. 26, 2019. 2 pages.
[No Author Listed], Amidase Protein Classification Interpro. 2021. 2 pages.
[No Author Listed], DQ™ Gelatin From Pig Skin, Fluorescein Conjugate—Special Packaging. ThermoFisher Scientific. ENZCHEK® Gelatinase/Collagenase Assay Kit Product Information Sheet. Accessed on Jul. 14, 2020. Retrieved from: <https://www.thermofisher.com/order/catalog/product/D12054#/D12054>. 4 pages.
[No Author Listed], EMBOSS Needle Sequence Alignment. 2021. 2 pages.
Aalipour et al., Engineered immune cells as highly sensitive cancer diagnostics. Nat Biotechnol. 2019;37:531-9.
Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.
Abudayyeh, Nanoparticle-Chaperoned Urinary "Synthetic Biomarkers" for Profiling Proteases in Cancer. Thesis. Department of Mechanical Engineering. Jun. 2012.
Acharige et al., Breath-based diagnosis of fungal infections. J Breath Res. Feb. 6, 2018;12(2):027108. doi: 10.1088/1752-7163/aa98a1.
Adli, The CRISPR tool kit for genome editing and beyond. Nat Commun. May 15, 2018;9(1):1911.
Amstad et al., Photo- and thermoresponsive polymersomes for triggered release. Angew Chem Int Ed. 2012;51:1-6.

Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.
Asai et al., A colorimetric assay for plasma antithrombin III using a new synthetic peptide substrate (PS-915). Clin Chim Acta. Dec. 29, 1984;144(2-3):163-71.
Badeau et al., Engineered modular biomaterial logic gates for environmentally triggered therapeutic delivery. Nat Chem. Mar. 2018;10(3):251-258. doi: 10.1038/nchem.2917. Epub Jan. 15, 2018.
Barchetta et al., Circulating dipeptidyl peptidase-4 is independently associated with the presence and severity of NAFLD/NASH in individuals with and without obesity and metabolic disease. J Endocrinol Invest. May 2021;44(5):979-988. doi: 10.1007/s40618-020-01392-5. Epub Aug. 27, 2020. PMID: 32852705; PMCID: PMC8049937.
Bartlett, Diagnostic tests for agents of community-acquired pneumonia. Clin Infect Dis. May 2011;52 Suppl 4:S296-304. doi: 10.1093/cid/cir045.
Baruch et al., Enzyme activity—it's all about image. Trends Cell Biol. Jan. 2004;14(1):29-35.
Bascomb et al., Use of Enzyme Tests in Characterization and Identification of Aerobic and Facultatively Anaerobic Gram-Positive Cocci. Clin Microbiol Rev. Apr. 1998; 11(2): 318-340.
Beauchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.
Becker et al., Thrombin: Structure, Biochemistry, Measurement, and Status in Clinical Medicine. J Thromb Thrombolysis. Jul. 1998;5(3):215-229.
Berger, Helicobacter pylori breath tests. BMJ. 2002;324:1263.
Blum et al., Noninvasive optical imaging of cysteine protease activity using fluorescently quenched activity-based probes. Nat Chem Biol. Oct. 2007;3(10):668-77. Epub Sep. 9, 2007.
Bohm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.
Bonomi et al., Detection of enzyme activity through catalytic signal amplification with functionalized gold nanoparticles. Angew Chem Int Ed. 2011;50:2307-12.
Bounameaux et al., Plasma measurement of D-dimer as diagnostic aid in suspected venous thromboembolism: an overview. Thromb Haemost. Jan. 1994;71(1):1-6.
Buss et al., Protease activity sensors noninvasively classify bacterial infections and antibiotic responses. EBioMedicine. Dec. 2018;38:248-56. doi:10.1016/j.ebiom.2018.11.031.
Caliendo et al., Better Tests, Better Care: Improved Diagnostics for Infectious Diseases. Clin Infect Dis. Dec. 2013;57(3):S139-S170.
Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.
Chakravarty et al., Nanobody: the "magic bullet" for molecular imaging? Theranostics. Jan. 29, 2014;4(4):386-98. doi: 10.7150/thno.8006.
Chan et al., Engineering synthetic breath biomarkers for respiratory disease. Nature Nanotechnol. Jul. 20, 2020;15:792-800.
Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.
Chen et al., A unique substrate recognition profile for matrix metalloproteinase-2. J Biol Chem. Feb. 8, 2002;277(6):4485-91.
Chen et al., CRISPR-Cas12a target binding unleashes indiscriminate single-stranded DNase activity. Science. Apr. 27, 2018;360(6387):436-439. doi: 10.1126/science.aar6245. Epub Feb. 15, 2018. Erratum in: Science. Feb. 19, 2021;371(6531).
Cheng et al., Multifunctional nanoparticles: Cost versus benefit of adding targeting and imaging capabilities. Sci. Nov. 16, 2012;338(6109):903-10.

(56) References Cited

OTHER PUBLICATIONS

Cheng et al., Ultrasensitive scanometric strategy for detection of matrix metalloproteinases using a histidine tagged peptide—Au nanoparticle probe. Chem Commun. 2011;47:2877-9.

Choi et al., Targeting kidney mesangium by nanoparticles of defined size. Proc Natl Acad Sci U S A. Apr. 19, 2011;108(16):6656-61. doi: 10.1073/pnas.1103573108. Epub Apr. 4, 2011.

Coelho et al., Usefulness of C-reactive protein in monitoring the severe community-acquired pneumonia clinical course. Crit Care. Aug. 2007; 11(4):R92.

Cohen et al., Detection and localization of surgically resectable cancers with a multi-analyte blood test. Science. 2018;3247(80):1-10.

Dahlman et al., Barcoded nanoparticles for high throughput in vivo discovery of targeted therapeutics. Proc Natl Acad Sci U S A. Feb. 21, 2017;114(8):2060-2065. doi: 10.1073/pnas.1620874114. Epub Feb. 6, 2017.

Daniel et al., Implantable diagnostic device for cancer monitoring. Biosens Bioelectron. Jul. 15, 2009;24(11):3252-7. Epub Apr. 16, 2009.

Danino et al., Programmable probiotics for detection of cancer in urine. Sci Transl Med. May 27, 2015;7(289):289ra84. doi: 10.1126/scitranslmed.aaa3519. PMID: 26019220; PMCID: PMC4511399.

De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.

Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.

Dennis et al., Albumin binding as a general strategy for improving the pharmacokinetics ofproteins. J Biol Chem. Sep. 20, 2002;277(38):35035-43. Epub Jul. 15, 2002.

Deshpande et al., Current trends in the use of liposomes for tumor targeting. Nanomedicine (Lond). Sep. 2013;8(9):1509-28. doi:10.2217/nnm.13.118.

Dranoff, Cytokines in cancer pathogenesis and cancer therapy. Nat Rev Cancer. Jan. 2004;4(1):11-22.

D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.

Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.

Dudani et al., Harnessing Protease Activity to Improve Cancer Care. Ann Rev Cancer Biol. Mar. 2018;2:353-376.

Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.

Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.

El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.

Elegbede et al., Mechanistic studies of the triggered release of liposomal contents by matrix metalloproteinase-9. J Am Chem Soc. Aug. 13, 2008;130(32):10633-42. doi: 10.1021/ja801548g. Epub Jul. 22, 2008.

Elston et al., New continuous and specific fluorometric assays for Pseudomonas aeruginosa elastase and LasA protease. Anal Biochem. Sep. 2007;368(1):87-94.

English et al., Programmable CRISPR-responsive smart materials. Science. Aug. 23, 2019;365(6455):780-785.

Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.

Farwell et al., PET/CT imaging in cancer: current applications and future directions. Cancer. Nov. 15, 2014;120(22):3433-45. doi: 10.1002/cncr.28860. Epub Jun. 19, 2014. PMID: 24947987.

Fernandez et al., Volatile Biomarkers in Breath Associated With Liver Cirrhosis—Comparisons of Pre- and Post-liver Transplant Breath Samples. EBIOM. 2015;2:1243-50.

Figueiredo et al., Near infrared thoracoscopy of tumoral protease activity for improved detection of peripheral lung cancer. Int J Cancer. Jun. 2006;118(11):2672-7. doi: 10.1002/ijc.21713.

Fowlkes et al., Proteolysis of insulin-like growth factor binding protein-3 during rat pregnancy: a role for matrix metalloproteinases. Endocrinology. Dec. 1994;135(6):2810-3.

Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.

Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.

Galati et al., Increased resistance of peptides to serum proteases by modification of their amino groups. Resist peptides against serum proteases. Jan. 8, 2003;58:558-61.

Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.

Gatter et al., Transferrin receptors in human tissues: their distribution and possible clinical relevance. J Clin Pathol. May 1983;36(5):539-45. doi: 10.1136/jcp.36.5.539. PMID: 6302135; PMCID: PMC498283.

Genbank Submission; NIH/NCBI, Accession No. 2WV1_A; Kovalevskiy et al.; Mar. 24, 2010.

Genbank Submission; NIH/NCBI, Accession No. CAG01641; Mar. 17, 2004.

Genbank Submission; NIH/NCBI, Accession No. NP_731669; Hoskins et al.; Dec. 18, 2009.

Genbank Submission; NIH/NCBI, Accession No. NP_938673; Cerdeno-Tarraga et al.; Jun. 3, 2010.

GenPept NIH/NCBI, Accession No. XP_001385378; Jeffries et al.; Apr. 11, 2008.

GenPept NIH/NCBI, Accession No. XP_002097000; Clark et al.; Aug. 12, 2009.

GenPept NIH/NCBI, Accession No. XP_00234527.; Jul. 7, 2006.

GenPept Submission; NIH/NCBI, Accession No. ZP_03507634; Gonzalez et al.; Dec. 19, 2008.

GenPept Submission; NIH/NCBI, Accession No. ZP_06431346; Small et al.; Jun. 9, 2010.

Ghadiali et al., Enzyme-Responsive Nanoparticle Systems. Advanced Materials, 2008 vol. 20(22):4359-4363.

Ghoshal et al., How to Interpret Hydrogen Breath Tests. J Neurogastroenterol Motil. 2011;17:312-7.

Giljohann, et al., Drivers of biodiagnostic development. Nature. Nov. 26, 2009;462(7272):461-4. doi: 10.1038/nature08605.

Ginsberg et al., Sensitivity and specificity of a rapid whole-blood assay for D-dimer in the diagnosis of pulmonary embolism. Ann Intern Med. Dec. 15, 1998;129(12):1006-11.

Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.

Gootenberg et al., Nucleic acid detection with CRISPR-Cas13a/ C2c2. Science. Apr. 28, 2017;356(6336):438-442. doi: 10.1126/science.aam9321. Epub Apr. 13, 2017.

Grayson et al., Multi-pulse drug delivery from a resorbable polymeric microchip device. Nat Mater. Nov. 2003;2(11):767-72.

Gross, Mass Spectrometry: A Textbook. Springer. 2nd ed. Mar. 1, 2011. Chapter 9. 415-452.

Guimaraes et al., Site-specific C-terminal internal loop labeling of proteins using sortase-mediated reactions. Nat Protoc. 2013;8:1787-99.

(56) References Cited

OTHER PUBLICATIONS

Haiko et al., The omptins of Yersinia pestis and *Salmonella enterica* cleave the reactive center loop of plasminogen activator inhibitor 1. J Bacteriol. Sep. 2010;192(18):4553-61. doi: 10.1128/JB.00458-10. Epub Jul. 16, 2010.

Hao et al., CRISPR-Cas-amplified urine biomarkers for multiplexed and portable cancer diagnostics. bioRxiv Jun. 17, 2020.

Haro et al., Matrix metalloproteinase-7-dependent release of tumor necrosis factor-alpha in a model of herniated disc resorption. J Clin Invest. Jan. 2000;105(2):143-50.

Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.

Harris et al., Protease-triggered unveiling of bioactive nanoparticles. Small. 2008;4(9):1307-12. doi: 10.1002/smll.200701319. Epub Aug. 8, 2008.

Haskins, The application of stable isotopes in biomedical research. Biomed Mass Spectrom. Jul. 1982;9(7):269-77.

Haun et al., Micro-NMR for rapid molecular analysis of human tumor samples. Sci Transl Med. Feb. 23, 2011;3(71):71ra16. doi: 10.1126/scitranslmed.3002048.

Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.

Herbig et al., Towards standardization in the analysis of breath gas volatiles. J Breath Res. 2014;8:1-11.

Holliday et al., Rapid Identification of *Staphylococcus aureus* by Using Fluorescent Staphylocoagulase Assays. J Clin Microbiol. Apr. 1999;37(4):1190-2.

Imai et al., Degradation of decorin by matrix metalloproteinases: identification of the cleavage sites, kinetic analyses and transforming growth factor-beta1 release. Biochem J. Mar. 15, 1997;322 (Pt 3):809-14.

Ito et al., Degradation of interleukin 1beta by matrix metalloproteinases. J Biol Chem. Jun. 21, 1996;271(25):14657-60.

Iwasaki et al., Control of adaptive immunity by the innate immune system. Nat Immunol. Mar. 19, 2015;16(4):343-53.

Jaffer et al., In vivo imaging of thrombin activity in experimental thrombi with thrombin-sensitive near-infrared molecular probe. Arterioscler Thromb Vasc Biol. Nov. 1, 2002;22(11):1929-35.

Jambunathan et al., Prolyl endopeptidase activity in bronchoalveolar lavage fluid: a novel diagnostic biomarker in a guinea pig model of invasive pulmonary aspergillosis. Med Mycol. Aug. 2013;51(6):592-602. doi: 10.3109/13693786.2012.761360. Epub Jan. 28, 2013.

Janzen et al., Colorimetric sensor arrays for volatile organic compounds. Anal Chem. Jun. 1, 2006;78(11):3591-600.

Jiang et al., Tumor imaging by means of proteolytic activation of cell-penetrating peptides. Proc. Natl. Acad. Sci. U. S. A. 2004;101:17867-17872.

Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.

Johnson et al., Computer program (SEQPEP) to aid in the interpretation of high-energy collision tandem mass spectra of peptides. Biomed Environ Mass Spectrom. Nov. 1989;18(11):945-57.

Kalinska et al., Substrate specificity of Staphylococcus aureus cysteine proteases—Staphopains A, B and C. Biochimie. Feb. 2012;94(2):318-27. doi: 10.1016/j.biochi.2011.07.020. Epub Jul. 23, 2011.

Kalubowilage et al., Early detection of pancreatic cancers in liquid biopsies by ultrasensitive fluorescence nanobiosensors. Nanomedicine. Aug. 2018;14(6):1823-1832. doi: 10.1016/j.nano.2018.04.020. Epub May 18, 2018. PMID: 29782949.

Kaman et al., Evaluation of a FRET-Peptide Substrate to Predict Virulence in Pseudomonas aeruginosa. PLoS One; Nov. 2013;8(11):e81428.

Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.

Kaminski et al., A CRISPR-based assay for the detection of opportunistic infections post-transplantation and for the monitoring of transplant rejection. Nat Biomed Eng. Jun. 2020;4(6):601-609. doi: 10.1038/s41551-020-0546-5. Epub Apr. 13, 2020.

Kasperkiewicz et al., Design of ultrasensitive probes for human neutrophil elastase through hybrid combinatorial substrate library profiling. PNAS. 2014;111:2518-23.

Kastelic et al., Stefin B, the major low molecular weight inhibitor in ovarian carcinoma. Cancer Lett. Jul. 15, 1994;82(1):81-8.

Kim et al., Applications of stable, nonradioactive isotope tracers in in vivo human metabolic research. Exp Mol Med. Jan. 2016; 48(1):e203. Epub Jan. 15, 2016. doi: 10.1038/emm.2015.97.

Kircher et al., A dual fluorochrome probe for imaging proteases. Bioconjug Chem. Mar.-Apr. 2004;15(2):242-8.

Kirkpatrick et al., Noninvasive lung cancer detection via pulmonary protease profiling. bioRxiv. 36 pages. doi: https://doi.org/10.1101/495259.

Kirkpatrick et al., Urinary detection of lung cancer in mice via noninvasive pulmonary protease profiling. Sci Transl Med. Apr. 1, 2020;12(537):eaaw0262.

Klan et al., Photoremovable protecting groups in chemistry and biology: reaction mechanisms and efficacy. Chem Rev. Jan. 9, 2013;113(1):119-91. doi: 10.1021/cr300177k. Epub Dec. 21, 2012. PMID: 23256727; PMCID: PMC3557858.

Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.

Kojima et al., Preparation and characterization of complexes of liposomes with gold nanoparticles. Colloids Surf B Biointerfaces. Oct. 15, 2008;66(2):246-52. doi: 10.1016/j.colsurfb.2008.06.022. Epub Jul. 9, 2008.

Koo et al., Merging new-age biomarkers and nanodiagnostics for precision prostate cancer management. Nat Rev Urol. May 2019;16(5):302-317.

Krebs et al., Molecular analysis of circulating tumour cells-biology and biomarkers. Nat Rev Clin Oncol. 2014;11:129-44.

Krilaviciute et al., Detection of cancer through exhaled breath : a systematic review Literature search. Oncotarget. 2015;6:38643-57.

Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.

Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.

Kulkarni et al., MMP-9 Responsive PEG Cleavable Nanovesicles for Efficient Delivery of Chemotherapeutics to Pancreatic Cancer. Mol Pharm. Jul. 7, 2014; 11(7): 2390-2399. doi: 10.1021/mp500108p.

Kwak et al., Volatile disease biomarkers in breath: a critique. Curr Pharm Biotechnol; 2011;12:1067-74.

Kwon et al., Porous Silicon Nanoparticle Delivery of Tandem Peptide Anti-Infectives for the Treatment of Pseudomonas aeruginosa Lung Infections. Adv Mat. Sep. 20, 2017;29(35). 21pages.

Kwon et al., Ultrasensitive tumour-penetrating nanosensors of protease activity. Nat Biomed Eng. 2017;1. pii: 0054. doi:10.1038/s41551-017-0054. Epub Apr. 10, 2017.

Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.

Kwong et al., Mathematical framework for activity-based cancer biomarkers. Proc Natl Acad Sci U S A. Oct. 13, 2015;112(41):12627-32. doi: 10.1073/pnas.1506925112. Epub Sep. 28, 2015.

Lange et al., Selected reaction monitoring for quantitative proteomics: a tutorial. Mol Syst Biol. 2008;4:222. doi: 10.1038/msb.2008.61. Epub Oct. 14, 2008.

(56) References Cited

OTHER PUBLICATIONS

Larsen et al., Assay of plasma heparin using thrombin and the chromogenic substrate H-D-Phe-Pip-Arg-pNA (S-2238). Thromb Res. Aug. 1978; 13(2):285-8.

Laupland et al., The changing culture of the microbiology laboratory. Can J Infect Dis Med Microbiol. 2013 Autumn; 24(3):125-128. doi: 10.1155/2013/101630.

Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.

Levi et al., Matrix metalloproteinase 2 releases active soluble ectodomain of fibroblast growth factor receptor 1. Proc Natl Acad Sci U S A. Jul. 9, 1996;93(14):7069-74.

Lin et al., Drug-induced amplification of nanoparticle targeting to tumors. Nano Today. Oct. 2014;9(5):550-559. doi:10.1016/j.nantod.2014.09.001. Epub Sep. 23, 2014.

Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.

Liou et al., Nonisotropic Enzyme-Inhibitor Interactions: A Novel Nonoxidative Mechanism for Quantum Proteolysis by Human Neutrophils. Biochem. 1995;34(49):16171-7.

Liu et al., Structure-based programming of lymph-node targeting in molecular vaccines. Nature. Mar. 27, 2014;507(7493):519-22. doi: 10.1038/nature12978. Epub Feb. 16, 2014.

Longo et al., In Vivo Imaging of Tumor Metabolism and Acidosis by Combining PET and MRI-CEST pH Imaging. Cancer Res. Nov. 15, 2016;76(22):6463-6470. doi: 10.1158/0008-5472.CAN-16-0825. Epub Sep. 20, 2016. PMID: 27651313.

Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.

Loynachan et al., Renal clearable catalytic gold nanoclusters for in vivo disease monitoring. Nat Nanotechnol. Sep. 2019;14(9):883-890. doi: 10.1038/s41565-019-0527-6. Epub Sep. 2, 2019. PMID: 31477801; PMCID: PMC7045344.

Mallick et al., Computational prediction of proteotypic peptides for quantitative proteomics. Nat Biotechnol. Jan. 2007;25(1):125-31. Epub Dec. 31, 2006.

Mañes et al., The matrix metalloproteinase-9 regulates the insulin-like growth factor-triggered autocrine response in DU-145 carcinoma cells. J Biol Chem. Mar. 12, 1999;274(11):6935-45.

Martinez et al., Diagnostics for the developing world: microfluidic paper-based analytical devices. Anal Chem. Jan. 1, 2010;82(1):3-10. doi: 10.1021/ac9013989.

Matheeussen et al., Method comparison of dipeptidyl peptidase IV activity assays and their application in biological samples containing reversible inhibitors. Clin Chim Acta. Feb. 18, 2012;413(3-4):456-62. doi: 10.1016/j.cca.2011.10.031. Epub Nov. 7, 2011. PMID: 22093941.

Matsumoto et al., Role of bacterial proteases in pseudomonal and serratial keratitis. Biol Chem. Jan. 2004;385(11):1007-16.

McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.

McLennan et al., Subcutaneous drug delivery and the role of the lymphatics. Drug Discov Today Technol. 2005 Spring;2(1):89-96. doi:10.1016/j.ddtec.2005.05.006.

Meyer et al., Respiratory protease / antiprotease balance determines susceptibility to viral infection and can be modified by nutritional antioxidants. Am J Physiol Lung Cell Mol Physiol. 2015;308:L1189-L1201.

Mira et al., Insulin-like growth factor I-triggered cell migration and invasion are mediated by matrix metalloproteinase-9. Endocrinology. Apr. 1999;140(4):1657-64.

Mirtti et al., Expression of cystatins, high molecular weight cytokeratin, and proliferation markers in prostatic adenocarcinoma and hyperplasia. Prostate. Mar. 1, 2003;54(4):290-8.

Mitchell et al., Assay for plasma heparin using a synthetic peptide substrate for thrombin: introduction of the fluorophore aminoisophthalic acid, dimethyl ester. Thromb Res. Jul. 1978;13(1):47-52.

Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.

Morihara, Pseudolysin and other pathogen endopeptidases of thermolysin family. Methods in Enzymol. 1995;248:242-53.

Morris et al., Urine and plasma levels of fibrinopeptide B in patients with deep vein thrombosis and pulmonary embolism. Thromb Res. May 1, 2003;110(2-3):159-65.

Murray, What Is New in Clinical Microbiology—Microbial Identification by MALDI-TOF Mass Spectrometry. JMDI. 2012;14:419-23.

Myhrvold et al., Field-deployable viral diagnostics using CRISPR-Cas13. Science. Apr. 27, 2018;360(6387):444-448.

Naba et al., The matrisome: in silico definition and in vivo characterization by proteomics of normal and tumor extracellular matrices. Mol Cell Proteomics. Apr. 2012;11(4):M111.014647. doi: 10.1074/mcp.M111.014647. Epub Dec. 9, 2011.

Nagase et al., Matrix metalloproteinases. J Biol Chem. Jul. 30, 1999;274(31):21491-4.

Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA.109.193086. Epub Jul. 16, 2009. Supplemental Material.

Nizio et al., In vitro volatile organic compound profiling using GCxGC-TOFMS to differentiate bacteria associated with lung infections: a proof-of-concept study. J Breath Res. Apr. 27, 2016;10:026008, 12 pages.

Nomura et al., Activity-based protein profiling for biochemical pathway discovery in cancer. Nat Rev Cancer. Sep. 2010;10(9):630-8. doi: 10.1038/nrc2901. Epub Aug. 12, 2010.

Nouh et al., Cathepsin B: a potential prognostic marker for inflammatory breast cancer. J Transl Med. 2011;9(1):8 pages.

Olson et al., In vivo characterization of activatable cell penetrating peptides for targeting protease activity in cancer. Integr Biol (Camb). Jun. 2009; 1(5-6):382-93.

Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.

Ong et al., Inhalable nanosensors for rapid breath-based pathogen identification in respiratory infection. Adv Res Technol Symp. Mar. 5, 2018. 2 pages.

Ong et al., Use of Mass Spectrometric Vapor Analysis To Improve Canine Explosive Detection Efficiency. Anal Chem. 2017;89:6482-90.

Pan et al., Size-dependent cytotoxicity of gold nanoparticles. Small. Nov. 2007;3(11):1941-9.

Park et al., Magnetic Iron Oxide Nanoworms for Tumor Targeting and Imaging. Adv Mater. May 5, 2008;20(9):1630-1635.

Park et al., Systematic surface engineering of magnetic nanoworms for in vivo tumor targeting. Small. Mar. 2009;5(6):694-700. doi: 10.1002/smll.200801789.

Parker et al., Folate receptor expression in carcinomas and normal tissues determined by a quantitative radioligand binding assay. Anal Biochem. Mar. 15, 2005;338(2):284-93. doi: 10.1016/j.ab.2004.12.026. PMID: 15745749.

Parks et al., Matrix metalloproteinases as modulators of inflammation and innate immunity. Nat Rev Immunol. Aug. 2004;4(8):617-29.

Patton et al., Inhaling medicines: delivering drugs to the body through the lungs. Nat Rev Drug Discov. Jan. 2007;6(1):67-74.

Patton et al., The lungs as a portal of entry for systemic drug delivery. Proc Am Thorac Soc. 2004;1(4):338-44.

Peer et al., Nanocarriers as an emerging platform for cancer therapy. Nat Nanotechnol. Dec. 2007;2(12):751-60.

Phillips et al., Variation in volatile organic compounds in the breath of normal humans. J Chromatogr B. 1999;729:75-88.

(56) References Cited

OTHER PUBLICATIONS

Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.
Pornpattananangkul et al., Bacterial toxin-triggered drug release from gold nanoparticle-stabilized liposomes for the treatment of bacterial infection. J Am Chem Soc. Mar. 23, 2011;133(11):4132-9. doi: 10.1021/ja111110e. Epub Feb. 23, 2011.
Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.
Potempa et al., Corruption of innate immunity by bacterial proteases. J Innate Immun. 2009;1(2):70-87.
Powell et al., The metalloproteinase matrilysin proteolytically generates active soluble Fas ligand and potentiates epithelial cell apoptosis. Curr Biol. Dec. 16-30, 1999;9(24):1441-7.
Prensner et al., Beyond PSA: the next generation of prostate cancer biomarkers. Sci Transl Med. Mar. 28, 2012;4(127):127rv3. doi:10.1126/scitranslmed.3003180.
Rajah et al., Elevated levels of the IGF-binding protein protease MMP-1 in asthmatic airway smooth muscle. Am J Respir Cell Mol Biol. Feb. 1999;20(2):199-208.
Rashidian et al., Noninvasive imaging of immune responses. Proc Natl Acad Sci U S A. May 12, 2015;112(19):6146-51. doi: 10.1073/pnas.1502609112. Epub Apr. 20, 2015. Erratum in: Proc Natl Acad Sci U S A. Jul. 3, 2018;115(27):E6387. PMID: 25902531; PMCID: PMC4434737.
Rashidian et al., Predicting the response to CTLA-4 blockade by longitudinal noninvasive monitoring of CD8 T cells. J Exp Med. Aug. 7, 2017;214(8):2243-2255. doi: 10.1084/jem.20161950. Epub Jun. 30, 2017. PMID: 28666979; PMCID: PMC5551571.
Rawlings et al., The MEROPS database of proteolytic enzymes, their substrates and inhibitors in 2017 and a comparison with peptidases in the PANTHER database. Nucleic Acid Res. Jan. 4, 2018;46(D1):D624-D632.
Ren et al., Enrichment of cysteine-containing peptides from tryptic digests using a quaternary amine tag. Anal Chem. Aug. 1, 2004;76(15):4522-30.
Rennke, How does glomerular epithelial cell injury contribute to progressive glomerular damage? Kidney Int Suppl. Feb. 1994;45:S58-63.
Rijkers et al., Design and synthesis of thrombin substrates with modified kinetic parameters. Thromb Res. Sep. 15, 1995;79(5-6):491-9.
Roepstorff et al., Proposal for a common nomenclature for sequence ions in mass spectra of peptides. Biomed Mass Spectrom. Nov. 1984;11(11):601.
Ronald et al., Detecting cancers through tumor-activatable minicircles that lead to a detectable blood biomarker. Proc Natl Acad Sci U S A. Mar. 10, 2015;112(10):3068-73. doi: 10.1073/pnas.1414156112. Epub Feb. 23, 2015.
Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.
Ross et al., Volatile compounds in blood headspace and nasal breath. J Breath Res. Sep. 13, 2017;11(4):046001. doi: 10.1088/1752-7163/aa7d10.
Rousalova et al., Granzyme B-induced apoptosis in cancer cells and its regulation (review). Int J Oncol. Dec. 2010;37(6):1361-78. doi: 10.3892/ijo_00000788. PMID: 21042704.
Roy et al., Matrix metalloproteinases as novel biomarkers and potential therapeutic targets in human cancer. J Clin Oncol. 2009;27:5287-97.
Ruoslahti et al., Targeting of drugs and nanoparticles to tumors. J Cell Biol. Mar. 22, 2010;188(6):759-68. doi: 10.1083/jcb.200910104. Epub Mar. 15, 2010.
Santini et al., A controlled-release microchip. Nature. Jan. 28, 1999;397(6717):335-8.
Sawyers, The cancer biomarker problem. Nature. Apr. 3, 2008;452(7187):548-52. doi: 10.1038/nature06913.
Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.
Schonbeck et al., Generation of biologically active IL-1 beta by matrix metalloproteinases: a novel caspase-1-independent pathway of IL-1 beta processing. J Immunol. Oct. 1, 1998;161(7):3340-6.
Schuerle et al., Magnetically Actuated Protease Sensors for in Vivo Tumor Profiling. Nano Lett. Oct. 12, 2016;16(10):6303-6310. Epub Sep. 13, 2016.
Sethi et al., Clinical application of volatile organic compound analysis for detecting infectious diseases. Clin Microbiol Rev. Jul. 2013;26(3):462-75. doi: 10.1128/CMR.00020-13.
Shariat et al., Urine detection of survivin is a sensitive marker for the noninvasive diagnosis of bladder cancer. J Urol. Feb. 2004;171(2 Pt 1):626-30.
Shaw et al., The role and regulation of the extracellular proteases of *Staphylococcus aureus*. Microbiol. Jan. 2004;150:217-28. doi: 10.1099/mic.0.26634-0.
Shearer et al., Targeting Liver Fibrosis with a Cell-penetrating Protease-activated Receptor-2 (PAR2) Pepducin. J Biol Chem. Oct. 28, 2016;291(44):23188-23198. doi: 10.1074/jbc.M116.732743. Epub Sep. 9, 2016.
Shibuya et al., Pseudomonas aeruginosa alkaline proteinase might share a biological function with plasmin. Biochim Biophys Acta. Apr. 29, 1991; 1077(3):316-24.
Smith et al., Rapid identification of highly active and selective substrates for stromelysin and matrilysin using bacteriophage peptide display libraries. J Biol Chem. Mar. 24, 1995;270(12):6440-9.
Soleimany et al., Activity-Based Diagnostics: An Emerging Paradigm for Disease Detection and Monitoring. Trends Mol Med. May 2020;26(5):450-468. doi: 10.1016/j.molmed.2020.01.013. Epub Apr. 5, 2020. PMID: 32359477; PMCID: PMC8290463.
Stach et al., Unique Substrate Specificity of Sp1E Serine Protease from *Staphylococcus aureus*. Structure. Apr. 3, 2018;26(4):572-579.e4. doi: 10.1016/j.str.2018.02.008. Epub Mar. 8, 2018.
Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.
Sugahara et al., Coadministration of a tumor-penetrating peptide enhances the efficacy of cancer drugs. Science. May 21, 2010;328(5981):1031-5. doi: 10.1126/science.1183057. Epub Apr. 8, 2010.
Sun et al., A PET imaging approach for determining EGFR mutation status for improved lung cancer patient management. Sci Transl Med. Mar. 7, 2018;10(431):eaan8840. doi: 10.1126/scitranslmed.aan8840. PMID: 29515002.
Sutherland et al., RGD-Binding Integrins in Prostate Cancer: Expression Patterns and Therapeutic Prospects against Bone Metastasis. Cancers (Basel). Oct. 26, 2012;4(4):1106-45. doi: 10.3390/cancers4041106.
Suzuki et al., Matrix metalloproteinase-3 releases active heparin-binding EGF-like growth factor by cleavage at a specific juxtamembrane site. J Biol Chem. Dec. 12, 1997;272(50):31730-7.
Sweeney et al., Robust classification of bacterial and viral infections via integrated host gene expression diagnostics. Sci Transl Med. Jul. 2016;8(346):346ra91.
Tascilar et al., Role of tumor markers and mutations in cells and pancreatic juice in the diagnosis of pancreatic cancer. Ann Oncol. 1999;10 Suppl 4:107-10.
Taylor et al., Integrative genomic profiling of human prostate cancer. Cancer Cell. Jul. 13, 2010;18(1):11-22. doi: 10.1016/j.ccr.2010.05.026. Epub Jun. 24, 2010.
Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.
Thompson et al., Tandem mass tags: a novel quantification strategy for comparative analysis of complex protein mixtures by MS/MS. Anal Chem. Apr. 15, 2003;75(8):1895-904. Erratum in: Anal Chem.

(56) References Cited

OTHER PUBLICATIONS

Sep. 15, 2003;75(18):4942. Johnstone, R [added]. Anal Chem. Jun. 15, 2006;78(12):4235. Mohammed, A Karim A [added].

Thorek et al., Internalization of secreted antigen-targeted antibodies by the neonatal Fc receptor for precision imaging of the androgen receptor axis. Sci Transl Med. Nov. 30, 2016;8(367):367ra167.

Tockman et al., Considerations in bringing a cancer biomarker to clinical application. Cancer Res. May 1, 1992;52(9 Suppl):2711s-2718s.

Trapani et al., Killing by cytotoxic T cells and natural killer cells: multiple granule serine proteases as initiators of DNA fragmentation. Immunol Cell Biol. 1993;71(3):201-8.

Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.

Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011.04.115. Epub May 3, 2011.

Tung et al., A novel near-infrared fluorescence sensor for detection of thrombin activation in blood. Chembiochem. Mar. 1, 2002;3(2-3):207-11.

Udukala et al., Early detection of non-small cell lung cancer in liquid biopsies by ultrasensitive protease activity analysis. J Cancer Metastasis Treat 2020;6:25.

UNIPROTKB Submission; Accession No. A0A182DWE3.

Van Der Schee et al., Breathomics in lung disease. Chest. 2015;147:224-31.

Vandooren et al., Zymography Methods for Visualizing Hydrolytic Enzymes. Nat Methods. Mar. 2013;10(3):211-20. doi: 10.1038/nmeth.2371.

Vasiljeva et al., Monitoring protease activity in biological tissues using antibody prodrugs as sensing probes. Sci Rep. Apr. 3, 2020;10(1):5894.

Vessillier et al., Hydrolysis of glycine-containing elastin pentapeptides by LasA, a metalloelastase from Pseudomonas aeruginosa. Eur J Biochem. Feb. 2001;268(4):1049-57.

Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.

Warren et al., Disease detection by ultrasensitive quantification of microdosed synthetic urinary biomarkers. J Am Chem Soc. 2014;136:13709-14.

Warren et al., Harnessing protease activity to improve cancer care. Annual Rev Cancer Biol. 2018;2:353-76.

Warren et al., Point-of-care diagnostics for noncommunicable diseases using synthetic urinary biomarkers and paper microfluidics. Proc Natl Acad Sci U S A. Mar. 11, 2014;111(10):3671-6. doi:10.1073/pnas.1314651111. Epub Feb. 24, 2014.

Weerakkody et al., Family of pH (low) insertion peptides for tumor targeting. Proc Natl Acad Sci U S A. Apr. 9, 2013;110(15):5834-9. doi: 10.1073/pnas.1303708110. Epub Mar. 25, 2013. PMID: 23530249; PMCID: PMC3625278.

Weissleder et al., In vivo imaging of tumors with protease-activated near-infrared fluorescent probes. Nat Biotechnol. Apr. 1999;17(4):375-8.

Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.

Welser et al., Protease sensing with nanoparticle based platforms. Analyst. Jan. 7, 2011;136(1):29-41. doi: 10.1039/c0an00429d. Epub Sep. 28, 2010.

Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.

Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.

Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie.201205721. Epub Oct. 18, 2012.

Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.

Wilson et al., Applications and Advances in Electronic-Nose Technologies. Sensors (Basel). 2009;9(7):5099-148. doi: 10.3390/s90705099. Epub Jun. 29, 2009.

Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.

Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.

Wu et al., Expression and clinical significance of matrix metalloproteinase-9 in lymphatic invasiveness and metastasis of breast cancer. PLOS One. 2014;9(5):e97804.

Xia et al., Multiplex detection of protease activity with quantum dot nanosenors prepared by Intein-Mediated specific bioconjugation. Analytical Chemistry. Nov. 15, 2008; 22(80) 8649-8655.

Yager et al., Point-of-care diagnostics for global health. Annu Rev Biomed Eng. 2008;10:107-44. doi: 10.1146/annurev.bioeng.10.061807.160524.

Yan et al., In Situ Zymography: A Molecular Pathology Technique to Localize Endogenous Protease Activity in Tissue Sections. Vet Pathol May 2003;40(3):227-36.

Yoo et al., 2'-O-methyl-modified phosphorothioate antisense oligonucleotides have reduced non-specific effects in vitro. Nucleic Acids Res. Apr. 2, 2004;32(6):2008-16. doi: 10.1093/nar/gkh516. PMID: 15064360; PMCID: PMC390367.

Yu et al., Cell surface-localized matrix metalloproteinase-9 proteolytically activates TGF-beta and promotes tumor invasion and angiogenesis. Genes Dev. Jan. 15, 2000;14(2):163-76.

Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.

Zheng et al., Dual-reaction triggered sensitivity amplification for ultrasensitive peptide- cleavage based electrochemical detection of matrix metalloproteinase-7. Biosens Bioelectronics. 2018;103:46-52. Epub Feb. 21, 2018.

Zhou et al., Thermo-sensitive microgels supported gold nanoparticles as temperature-mediated catalyst. Chinese J Polym Sci. 2019;37:235-42. Epub Aug. 30, 2018.

Zhu et al., Detecting bacterial lung infections: in vivo evaluation of in vitro volatile fingerprints. J Breath Res. Jan. 10, 2013;7(1):016003, 7 pages.

Zieske, A perspective on the use of iTRAQ reagent technology for protein complex and profiling studies. J Exp Bot. 2006;57(7):1501-8. Epub Mar. 30, 2006.

Zinnhardt et al., Combined PET Imaging of the Inflammatory Tumor Microenvironment Identifies Margins of Unique Radiotracer Uptake. Cancer Res. Apr. 15, 2017;77(8):1831-1841. doi: 10.1158/0008-5472.CAN-16-2628. Epub Jan. 30, 2017. PMID: 28137769.

Zumla et al., Rapid point of care diagnostic tests for viral and bacterial respiratory tract infections-needs, advances, and future prospects. Lancet Infect Dis. 2014;14(11):1123-35.

Adiguzel et al., Breath sensors for lung cancer diagnosis. Biosens Bioelectron. Mar. 15, 2015;65:121-38. doi: 10.1016/j.bios.2014.10.023. Epub Oct. 19, 2014.

Figueiredo et al., Folic acid and prevention of colorectal adenomas: a combined analysis of randomized clinical trials. Int J Cancer. Jul. 1, 2011;129(1):192-203. doi: 10.1002/ijc.25872. Epub Apr. 1, 2011.

(56) References Cited

OTHER PUBLICATIONS

Grimm et al., Use of Gene Expression Profiling to Direct in Vivo Molecular Imaging of Lung Cancer. PNAS. Oct. 4, 2005;102(40):14404-9.

Peng et al., Diagnosing lung cancer in exhaled breath using gold nanoparticles. Nat Nanotechnol. Oct. 2009;4(10):669-73. doi: 10.1038/nnano.2009.235. Epub Aug. 30, 2009.

Salaun et al., MMP-13 In-Vivo Molecular Imaging Reveals Early Expression in Lung Adenocarcinoma. Plos One. 2015;10(7):e0132960, 19 pages. Epub Jul. 20, 2015. doi: 10.1371/journal.pone.0132960.

Schulenburg et al., A FRET-based biosensor for the detection of neutrophil elastase. Analyst. Mar. 7, 2016;141(5):1645-8. doi: 10.1039/c5an01747e.

Aung et al., Low protease activity in B cell follicles promotes retention of intact antigens after immunization. Science. Jan. 27, 2023;379(6630):eabn8934. doi: 10.1126/science.abn8934. Epub Jan. 27, 2023.

Aung et al., Low protease activity in B cell follicles promotes retention of intact antigens after immunization. Supplementary Materials. Science. Jan. 27, 2023;379(6630):eabn8934. doi: 10.1126/science.abn8934. Epub Jan. 27, 2023.

Bahroun et al., Use of exogenous volatile organic compounds to detect *Salmonella* in milk. Anal Chim Acta. 2018; 1028: 121-30.

Chatre et al., Induced-volatolomics for the design of tumour activated therapy. Chem Sci. Apr. 11, 2023;14(18):4697-4703.

Corey, Chemical modification: the key to clinical application of RNA interference? J Clin Invest. Dec. 2007;117(12):3615-22.

Cui et al., Biomimetic peptide nanosensors. Acc Chem Res. May 15, 2012;45(5):696-704. doi: 10.1021/ar2002057. Epub Jan. 31, 2012.

Czyzewska J et al. "The Expression Of Matrix Metalloproteinase 9 And Cathepsin B In Gastric Carcinoma Is Associated With Lymph Node Metastasis, But Not With Postoperative Survival", Folia Histochemica et Cytobiologica, 46(1):57-64; Feb. 26, 2008. (Feb. 26, 2008).

Djago et al., Induced volatolomics of pathologies. Nat Rev Chem. Mar. 2021;5(3):183-196. doi: 10.1038/s41570-020-00248-z. Epub Feb. 2, 2021.

Fischer et al., Structure-activity relationship of truncated and substituted analogues of the intracellular delivery vector Penetratin. J Pept Res. Feb. 2000;55(2):163-72.

Garcia-Echeverria et al., A new Antennapedia-derived vector for intracellular delivery of exogenous compounds. Bioorg Med Chem Lett. Jun. 4, 2001;11(11):1363-6.

Khvorova et al., The chemical evolution of oligonucleotide therapies of clinical utility. Nat Biotechnol. Mar. 2017;35(3):238-248. doi: 10.1038/nbt.3765. Epub Feb. 27, 2017.

Kim et al., Immunogene therapy with fusogenic nanoparticles modulates macrophage response to *Staphylococcus aureus*. Nat Commun. May 17, 2018;9(1):1969. doi: 10.1038/s41467-018-04390-7.

Kim et al., Securing the Payload, Finding the Cell, and Avoiding the Endosome: Peptide-Targeted, Fusogenic Porous Silicon Nanoparticles for Delivery of siRNA. Adv Mater. Aug. 2019;31(35):e1902952. doi: 10.1002/adma.201902952. Epub Jul. 3, 2019.

Kratschmer et al., Effect of Chemical Modifications on Aptamer Stability in Serum. Nucleic Acid Ther. Dec. 2017;27(6):335-344. doi: 10.1089/nat.2017.0680. Epub Sep. 25, 2017.

Lange et al., Volatile Organic Compound Based Probe for Induced Volatolomics of Cancers. Angew Chem Int Ed Engl. Dec. 2, 2019;58(49):17563-17566. doi: 10.1002/anie.201906261. Epub Oct. 22, 2019.

Lokugamage et al., Testing thousands of nanoparticles in vivo using DNA barcodes. Curr Opin Biomed Eng. Sep. 2018;7:1-8. doi: 10.1016/j.cobme.2018.08.001. Epub Aug. 21, 2018.

Pasut et al., PEG conjugates in clinical development or use as anticancer agents: an overview. Adv Drug Deliv Rev. Nov. 12, 2009;61(13):1177-88. doi: 10.1016/j.addr.2009.02.010. Epub Aug. 9, 2009.

Tait et al., Analysis of pathogenic bacteria using exogenous volatile organic compound metabolites and optical sensor detection. RSC Advances. Jan. 2015; 5(20): 15494-9.

Tam et al., Peptide asparaginyl ligases—renegade peptide bond makers. Sci China Chem. Mar. 2020; 63(3): 296-307.

Taylor et al., Analysis of Listeria using exogenous volatile organic compound metabolites and their detection by static headspace-multicapillary column-gas chromatography-ion mobility spectrometry (SHS-MCC-GC-IMS). Anal Bioanal Chem. Jul. 2017;409(17):4247-4256. doi: 10.1007/s00216-017-0375-x. Epub May 8, 2017.

Thompson et al., Detection of β-alanyl aminopeptidase as a biomarker for Pseudomonas aeruginosa in the sputum of patients with cystic fibrosis using exogenous volatile organic compound evolution. RSC Adv. Mar. 12, 2020;10(18):10634-10645.

Wilkinson et al., Ventilator-Associated Pneumonia Is Characterized by Excessive Release of Neutrophil Proteases in the Lung. Chest. Dec. 2012;142(6):1425-32.

Yaari et al., Theranostic barcoded nanoparticles for personalized cancer medicine. Nat Commun. Nov. 10, 2016;7:13325.

\* cited by examiner

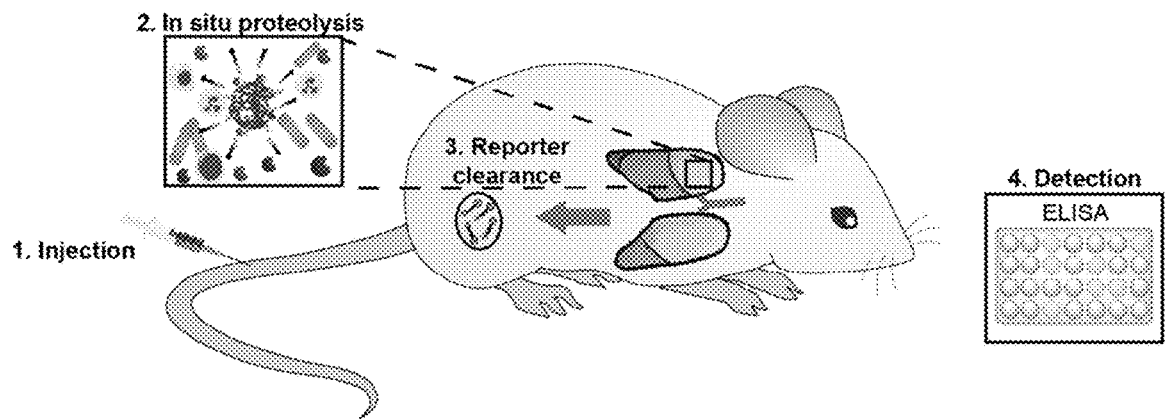
FIG. 10A
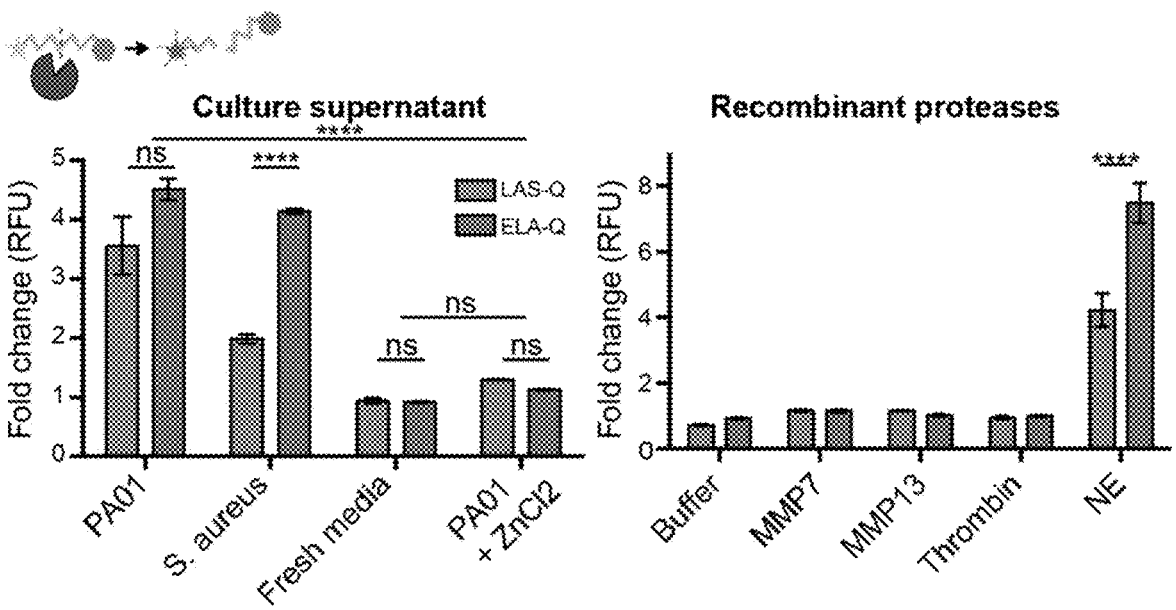
FIG. 10B
FIG. 10C
FIG. 10D

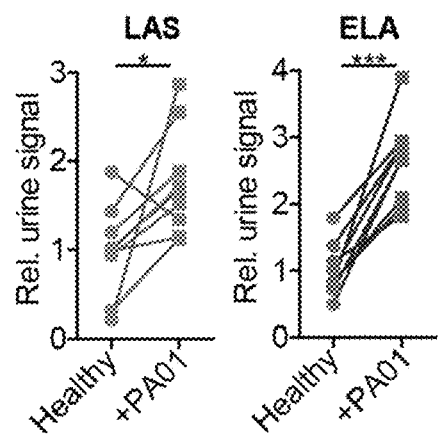
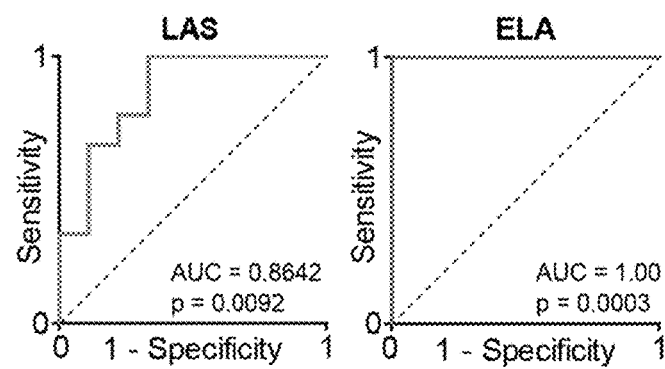
FIG. 11C
FIG. 11D
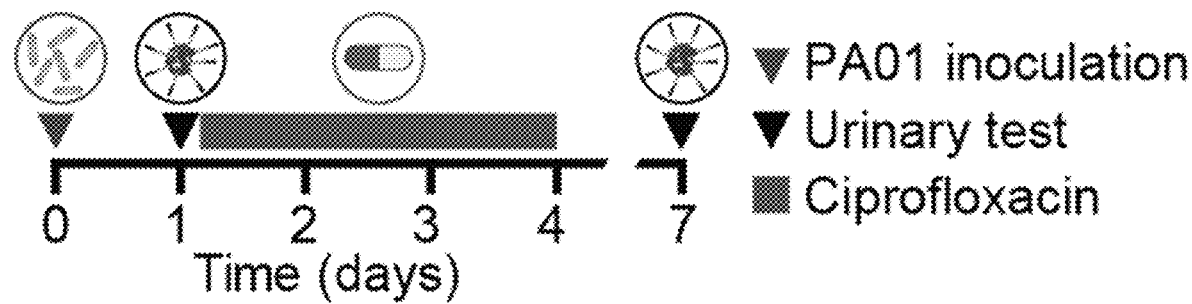
FIG. 12A

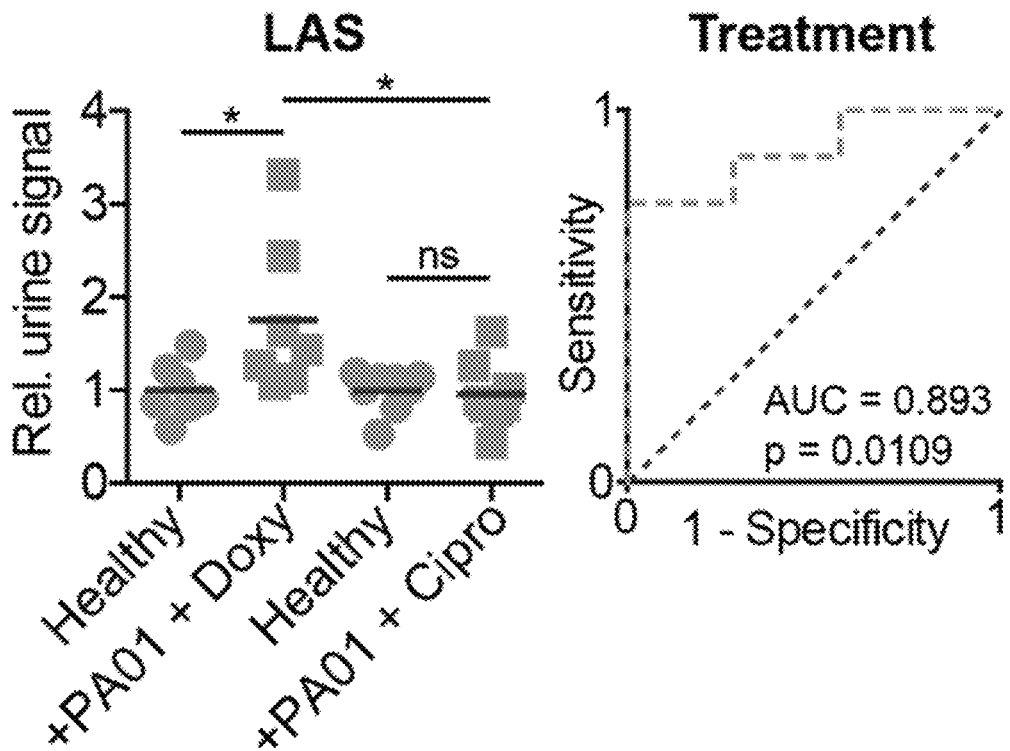
FIG. 13B
FIG. 13C
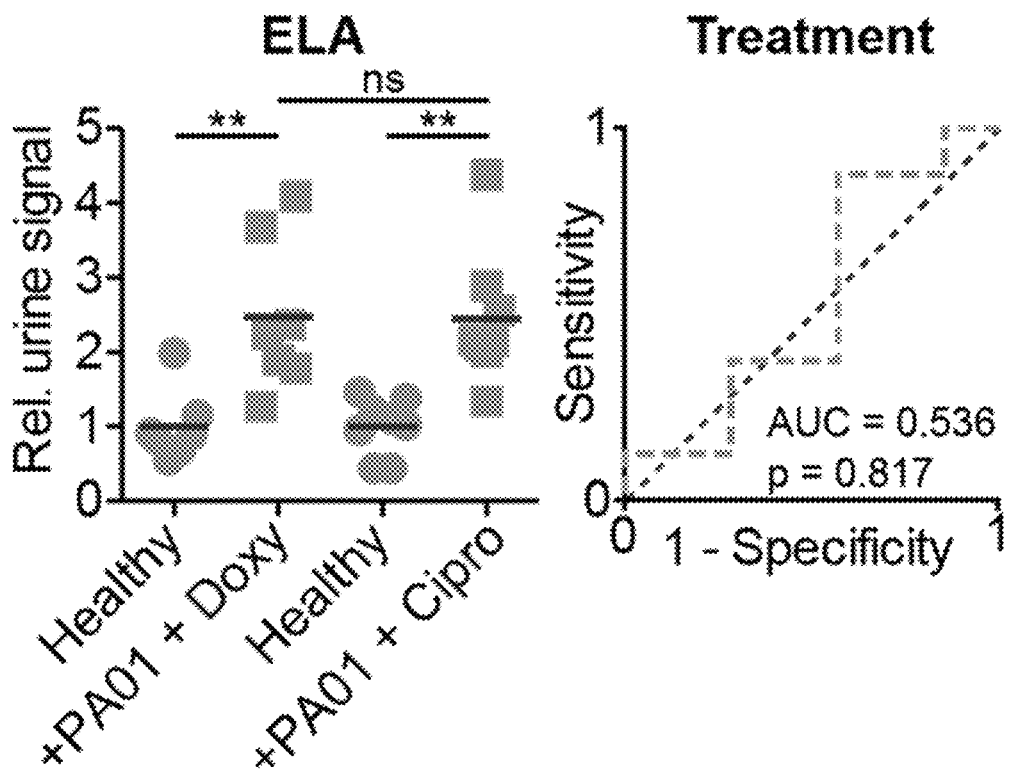
FIG. 13D
FIG. 13E

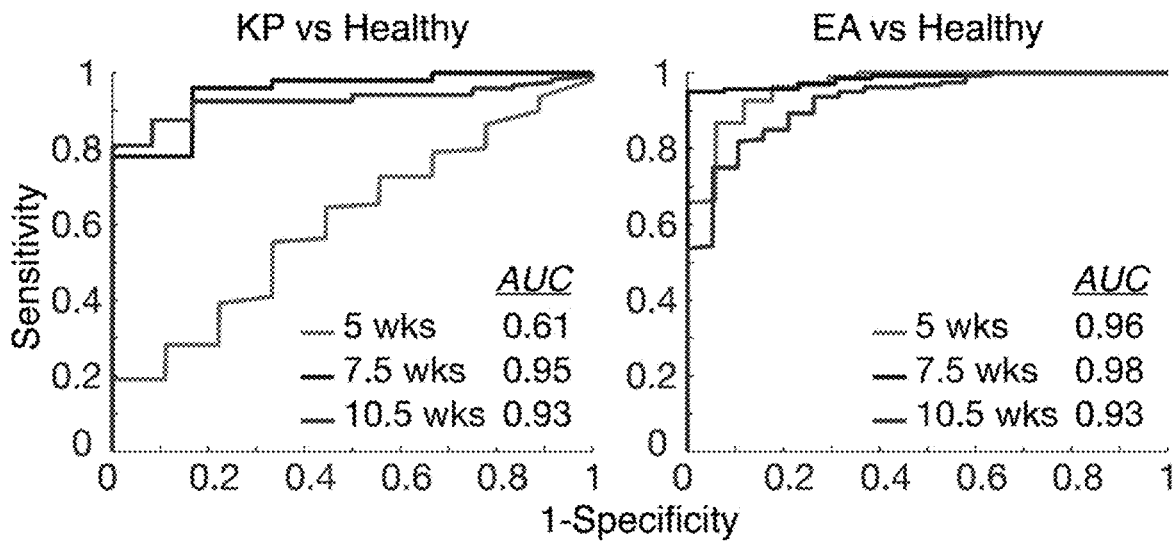
FIG. 17A FIG. 17B
FIG. 17C FIG. 17D
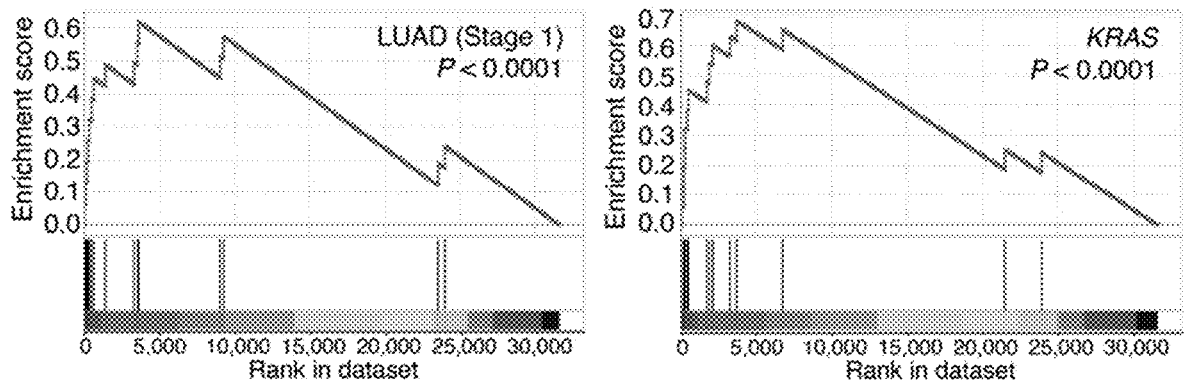
FIG. 18A FIG. 18B

LUNG PROTEASE NANOSENSORS AND USES THEREOF

CROSS-REFERENCE TO RELATED APPLICATIONS

This application claims the benefit of priority under 35 U.S.C. § 119(e) of U.S. provisional application Ser. No. 62/736,388, filed Sep. 25, 2018, the disclosure of which is incorporated by reference here in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 15, 2022, is named M065670438US01-SUBSEQ-FL and is 23,211 bytes in size.

BACKGROUND

Lung diseases, including lung cancer and lung infections, impact a large portion of the world's population and pose significant public health risks. For example, lung cancer is the most common cause of cancer-related death in the U.S. (46.0 deaths per 100,000 individuals (Group, United States Cancer Statistics: 1999-2001 Incidence and Mortality Web-based Report (2014)) and the world, with dismal 16.8% five-year survival rates (Howlader N, SEER Cancer Statistics Review, 1975-2011 (2014)). Key to this mortality is the fact that 57% of lung cancer patients have distant spread of disease at time of diagnosis (Howlader N, SEER Cancer Statistics Review, 1975-2011 (2014)). Patients with regional or localized disease have six- to 13-fold higher five-year survival rates than patients with distantly spread disease (Howlader N, SEER Cancer Statistics Review, 1975-2011 (2014)). Therefore, there is an urgent need for improved diagnostic sensitivity in lung cancer.

Similarly, lung infections are also common. For example, the prevalence of pathogenic bacterial pneumonias, particularly in the context of decreasing efficacy of commonplace antibacterial agents, has emerged as a substantial threat to human health (Mizgerd, N. Engl. J. Med., vol. 358, no. 7, pp. 716-727, February 2008; Mizgerd, PLoS Med., vol. 3, no. 2, pp. 0155-0158, 2006. The ability to robustly classify and monitor such infections has also lagged Caliendo et al., Clin. Infect. Dis., vol. 57, no. suppl 3, pp. S139-S170, December 2013; Bartlett et al., Clin. Infect. Dis., vol. 52, no. SUPPL. 4, pp. S296-S304, May 2011). Early effective treatment is critical for decreasing the morbidity and mortality associated with pneumonia (Irequi et al., Chest, vol. 122, no. 1, pp. 262-268, July 2002; Bartlett et al., Clin. Infect. Dis., vol. 26, no. 4, pp. 811-838, April 1998), though use of antibiotics that are inappropriate, unnecessary, or ineffective increases morbidity and promotes the development of antimicrobial resistance (Caliendo et al., Clin. Infect. Dis., vol. 57, no. suppl 3, pp. S139-S170, December 2013; Dupont et al., Intensive Care Med., vol. 27, no. 2, pp. 355-362, February 2001; Leroy et al., Intensive Care Med., vol. 29, no. 12, pp. 2170-2173, December 2003; Kollef et al., Chest, vol. 115, no. 2, pp. 462-474, February 1999; Erental et al., PLoS Biol., vol. 10, no. 3, p. e1001281, January 2012). Following the initiation of antibiotic therapy, monitoring patients for drug efficacy is often needed to decide whether to continue, modify, or halt an antibiotic regimen (Caliendo et al., Clin. Infect. Dis., vol. 57, no. suppl 3, pp. S139-S170, December 2013; Irequi et al., Chest, vol. 122, no. 1, pp. 262-268, July 2002; Dupont et al., Intensive Care Med., vol. 27, no. 2, pp. 355-362, February 2001). Therefore, timely and accurate diagnostic platforms are also needed for lung infections.

SUMMARY

Aspects of the disclosure relate to the surprising discovery that lung protease nanosensors are useful for noninvasive detection of lung enzymatic (e.g., protease) activity.

Accordingly, one aspect of the present disclosure provides a lung protease nanosensor comprising a scaffold linked to a substrate, wherein the substrate is conjugated to a detectable marker, whereby the detectable marker is capable of being released from the nanosensor when exposed to a protease present in a lung, and wherein the lung protease nanosensor is inhalable.

In some embodiments, the scaffold comprises a high molecular weight protein, a high molecular weight polymer, or a nanoparticle, optionally wherein the protein, polymer or nanoparticle is at least about 40 kDa.

In some embodiments, the scaffold comprises a multi-arm polyethylene glycol molecule (multi-arm PEG), optionally wherein the multi-arm PEG comprises 2-20 arms. In some embodiments, the scaffold is greater than 5 nm in size. In some embodiments, the detectable marker is less than 3 nm in size.

In some embodiments, the protease is selected from the group consisting of a serine protease, a metalloproteinase, an aspartic protease, or a cysteine protease. In some embodiments, the serine protease is selected from the group consisting of F12, F7, KLK13, KLK14, KLK6, PRSS22, PRSS3, PRSS8, and TMPRSS11E. In some embodiments, the metalloproteinase is selected from the group consisting of TLL2, ACE2, ADAM12, MMP1, MMP10, MMP11, MMP12, MMP13, and MMP3. In some embodiments, the aspartic protease is selected from the group consisting of NAPSA and CTSD.

In some embodiments, the protease is associated lung cancer, optionally wherein the lung cancer is lung adenocarcinoma. In some embodiments, the protease associated with lung cancer is TMPRSS11E, MMP13, MMP11, MMP1, MMP3, MMP10, ADAM12, F7, TLL2, and F12.

In some embodiments, the protease is a lung cancer stage-specific protease. In some embodiments, the scaffold is linked to a single substrate.

In some embodiments, the scaffold is linked to 2 to 20 different substrates. In some embodiments, the scaffold is linked to 2 to 4 different substrates.

In some embodiments, the substrate is conjugated to the detectable marker via a cleavable linker, optionally wherein the cleavable linker is a photocleavable linker.

In some embodiments, the substrate comprises a sequence selected from the group consisting of SEQ ID NOs: 1-14.

Another aspect of the present disclosure provides a composition comprising at least two lung protease nanosensors.

In some embodiments, the composition comprises at least fourteen nanosensors.

In some embodiments, the substrate of each nanosensor is independently selected from the group consisting of a substrate that is capable of being cleaved by ACE2, CTSD, F7, KLK13, KLK14, KLK6, MMP1, MMP11, MMP12, MMP13, MMP3, NAPSA, PRSS22, PRSS3, PRSS8, or a combination thereof.

In some embodiments, the substrate comprises a sequence selected from the group consisting of SEQ ID NOs: 1-14.

Another aspect of the present disclosure provides a method comprising: detecting a detectable marker in a biological sample obtained from a subject that has been administered to the lung of the subject by inhalation a lung protease nanosensor comprising a scaffold linked to a substrate, wherein the substrate includes the detectable marker, whereby the detectable marker is released from the lung protease nanosensor when exposed to an enzyme present in the lung.

In some embodiments, the lung protease nanosensor is delivered to the lung using an aerosol delivery device which is not reliant on propellant or compressed air.

In some embodiments, the substrate comprises a sequence selected from the group consisting of SEQ ID NOs: 1-14.

Another aspect of the present disclosure provides a method comprising: detecting a detectable marker in a biological sample obtained from a subject that has been administered to the lung of the subject by inhalation a lung protease nanosensor comprising a scaffold linked to a substrate, wherein the substrate includes the detectable marker, whereby the detectable marker is released from the lung protease nanosensor when exposed to an enzyme present in the lung, the scaffold comprises a multi-arm polyethylene glycol molecule (multi-arm PEG), optionally wherein the multi-arm PEG comprises 2-20 arms.

In some embodiments, the biological sample is a urine sample or blood sample.

In some embodiments, the detecting comprises a method selected from mass spectrometry (such as liquid chromatography-mass spectrometry), PDR analysis, ENA microarray, fluorescence analysis, a capture assay (e.g., ELISA), optical imaging, magnetic resonance (MR) imaging, positron emission tomography (PET) imaging, intraoperative imaging or any combination thereof.

In some embodiments, the subject has or is suspected of having lung cancer.

In some embodiments, the method further comprises the step of diagnosing the subject as having lung cancer based upon the presence of the detectable markers in the biological sample.

In some embodiments, the subject is diagnosed as having lung cancer based upon the presence of detectable markers released from a lung protease nanosensor having a substrate that is cleaved by ACE2, CTSD, F7, KLK13, KLK14, KLK6, MMP1, MMP11, MMP12, MMP13, MMP3, NAPSA, PRSS22, PRSS3, PRSS8, or a combination thereof.

In some embodiments, the subject has or is suspected of having a lung infection, optionally wherein the lung infection is a *Pseudomonas aeruginosa* infection.

In some embodiments, the protease is a pathogen protease.

In some embodiments, the pathogen protease is a pathogen-specific protease.

In some embodiments, the method further comprises diagnosing the subject as having a lung infection.

In some embodiments, the method further comprises administering to the subject any of the lung protease nanosensors described herein and/or a composition comprising any of the lung protease nanosensors described herein.

In some embodiments, the substrate comprises a sequence selected from the group consisting of SEQ ID NOs: 1-14.

Another aspect of the present disclosure provides a method for classifying lung disease in a subject, comprising:
(i) detecting in a biological sample obtained from a subject that has been administered any of the lung protease nanosensors described herein or the composition comprising any of the lung protease nanosensors described herein, wherein the biological sample is not derived from the lung of the subject, one or more detectable markers that have been released from one or more lung protease nanosensors when exposed to an enzyme present in the lung of the subject; and
(ii) classifying the subject as having a type of lung disease based on the identity of the detectable markers present in the biological sample, wherein the presence of the detectable markers in the biological sample is indicative of one or more cancer-associated enzymes being present in an active form within the lung of the subject.

In some embodiments, the type of lung disease is selected from the group consisting of lung cancer, interstitial lung disease (ILE) or chronic obstructive pulmonary disease (COPD).

In some embodiments, the type of lung disease is classified based upon the presence of detectable markers released from a lung protease nanosensor having a substrate that is cleaved by one or more proteases selected from TMPRSS11E, MMP13, MMP11, MMP1, MMP3, MMP10, ADAM12, F7, TLL2, and F12.

In some embodiments, the substrate comprises a sequence selected from the group consisting of SEQ ID NOs: 1-14.

Another aspect of the present disclosure provides a method of treating lung cancer in a subject, the method comprising administering a therapeutic agent for treatment of lung cancer to or performing a therapeutic intervention on a subject who has been classified as having lung cancer according to any of the methods described herein.

Another aspect of the present disclosure provides a method comprising:
(i) detecting in a biological sample obtained from a first subject that has been administered a composition of any of the lung protease nanosensors described herein, detectable markers that have been released from one or more lung protease nanosensors when exposed to an enzyme present in the lung of the subject, wherein the biological sample is not derived from the lung of the subject, and wherein the subject has lung cancer; and
(ii) generating a first detectable marker signature, wherein the first detectable marker signature is indicative of lung cancer.

In some embodiments, the method further comprises:
(iii) detecting in a biological sample obtained from a second subject that has been administered the composition of any of the lung nanosensors described herein, one or more detectable markers that have been released from one or more lung protease nanosensors when exposed to an enzyme present in the lung of the second subject, wherein the biological sample is not derived from the lung of the second subject; and
(iv) generating a second detectable marker signature and comparing the second detectable marker signature with the detectable marker signature of lung cancer.

In some embodiments, the method further comprises: (v) diagnosing the second subject with lung cancer.

Another aspect of the present disclosure provides a lung protease nanosensor comprising a scaffold linked to a pathogen-specific substrate, wherein the pathogen-specific substrate is conjugated to a detectable marker, whereby the detectable marker is capable of being released from the nanosensor when exposed to a protease present in a lung.

In some embodiments, the scaffold comprises a high molecular weight protein, a high molecular weight polymer, or a nanoparticle, optionally wherein the protein, polymer or nanoparticle is at least about 40 kDa.

In some embodiments, the scaffold comprises a multi-arm polyethylene glycol molecule (multi-arm PEG), optionally wherein the multi-arm PEG comprises 2-20 arms.

In some embodiments, the scaffold is greater than 5 nm in size.

In some embodiments, the detectable marker is less than 3 nm in size.

In some embodiments, the nanosensor is inhalable.

In some embodiments, the pathogen is selected from the group consisting of a bacteria, virus, fungi, or protozoa. In some embodiments, the bacteria is *Pseudomonas aeruginosa*.

In some embodiments, the protease is selected from the group consisting of LasA, LepA, protease IV, and AprA. In some embodiments, the substrate comprises the amino acid sequence LGGGA (SEQ ID NO: 43).

In some embodiments, the scaffold is linked to a single substrate. In some embodiments, the scaffold is linked to 2 to 20 different substrates. In some embodiments, the scaffold is linked to 2 to 4 different substrates.

In some embodiments, the substrate is conjugated to the detectable marker via a cleavable linker, optionally wherein the cleavable linker is a photocleavable linker.

Another aspect of the present disclosure provides a method comprising:
  (a) administering to the lung of a subject, by inhalation, a lung protease nanosensor comprising a scaffold linked to a lung infection substrate, wherein the substrate includes a detectable marker, whereby the detectable marker is released from the lung protease nanosensor when exposed to an enzyme present in the lung, and wherein the subject has or is suspected of having a lung infection; and
  (b) detecting and quantifying the detectable marker from a biological sample from the subject, optionally wherein the biological sample is urine.

In some embodiments, the method further comprises (c), wherein (c) comprises repeating (a) and (b).

In some embodiments, the subject has been administered an antibiotic, optionally wherein the antibiotic has been administered prior to (a) or (b).

In some embodiments, the method further comprises characterizing the subject as responsive or resistant to a therapeutic agent.

In some embodiments, the method further comprises continuing, stopping or altering treatment based on the amount of the detectable marker that was detected.

In some embodiments, the substrate comprises a sequence selected from the group consisting of SEQ ID NOs: 1-14.

Further aspects of the disclosure provide methods comprising detecting a plurality of detectable markers in a biological sample obtained from a subject that has been administered, to the lung of the subject by inhalation, a lung protease nanosensor comprising a scaffold linked to a plurality of substrates, wherein each substrate includes a detectable marker that is associated with the substrate, whereby each detectable marker is released from the lung protease nanosensor when exposed to at least one enzyme present in the lung.

In some embodiments, the lung protease nanosensors comprise at least fourteen substrates.

In some embodiments, the plurality of substrates independently comprise a sequence selected from the group consisting of SEQ ID NOs: 1-14. In some embodiments, the lung protease nanosensor comprises SEQ ID NOs: 1-14.

Further aspects of the present disclosure provide methods comprising detecting a plurality of detectable markers in a biological sample obtained from a subject that has been administered, to the lung of the subject by inhalation, a plurality of lung protease nanosensors, wherein each lung protease nanosensor comprises a scaffold linked to a substrate, wherein each substrate includes a detectable marker that is associated with the substrate, whereby each detectable marker is released from each lung protease nanosensor when exposed to at least one enzyme present in the lung.

Further aspects of the present disclosure provide lung protease nanosensors comprising a scaffold linked to a plurality of substrates, wherein each substrate is conjugated to a detectable marker, whereby the detectable marker is capable of being released from the nanosensor when exposed to a protease present in a lung, and wherein the lung protease nanosensor is inhalable.

In some embodiments, the plurality of substrates independently comprise a sequence selected from the group consisting of SEQ ID NOs: 1-14. In some embodiments, the lung protease nanosensor comprises SEQ ID NOs: 1-14.

In some embodiments, a lung protease nanosensor is administered to a subject having a tumor that is less than 3 mm$^3$.

In some embodiments, the probability of a method described herein correctly diagnosing, classifying, or characterizing a subject is at least 80%.

BRIEF DESCRIPTION OF DRAWINGS

FIG. 1A is a schematic showing activity-based nanosensors (ABNs or lung protease nanosensors) administered intratracheally and reach the lung epithelium. FIG. 1B is a schematic showing that at the tumor periphery, disease-associated proteases cleave protease substrates, liberating mass-encoded (MS) reporters from the PEG scaffold. FIG. 1C is a schematic showing that the lung protease nanosensors release reporters that are small enough to diffuse into the bloodstream and passively filter into the urine for detection. FIG. 1D is a schematic showing that synthetic disease reporters are detected in the urine by liquid chromatography followed by tandem mass spectrometry (LC-MS/MS). FIG. 1E is a schematic showing that random forest classification is performed on a training cohort of mice and subsequently tested on an independent validation cohort in order to provide a positive or negative diagnosis of malignancy.

FIG. 2A is a schematic depicting RNA-Seq data from The Cancer Genome Atlas (TCGA) included 527 patient tumors and 59 matched normal adjacent tissue (NAT) samples. Gene expression analysis was performed by DESeq to identify extracellular endoproteases overexpressed in human LUAD compared to matched NAT. The top 20 proteases are shown. See FIG. 2D for proteases that were included in the final "LUAD protease panel. " FIG. 2B shows RNA-Seq data for the KP model was generated by Chuang and colleagues and included two normal mouse lungs and 25 tumors from across disease stages. Gene expression fold changes were determined by averaging FPKM across all K and KP tumors and dividing by the average FPKM for the two normal lungs. FIG. 2C shows microarray data for the K model, which was generated by Sweet-Cordero and colleagues and included 19 normal mouse lungs and 31 K tumors. Differential gene expression was assessed by significance analysis of microarrays (SAM). FIG. 2D shows a set of 15 proteases that were selected as the "LUAD protease panel" based on overexpression across the three datasets (TCGA, KP and K). Dark Grey: Fold$_{Disease}$>1. Light Grey: Fold$_{Disease}$<1. Black: Not included in dataset. FIG. 2E shows a generalized linear model classification performed on the TCGA dataset using the 15 proteases in the "LUAD protease panel" as indicators. Area under the receiver operating characteristic curve (AUC) is shown as a function of the number of proteases included in the classifier. Horizontal line represents median, hinges represent the first and third quartiles, and whiskers span from the hinge to either the highest or lowest point within 1.5× the interquartile region (IQR) above or below the hinge. Outliers are shown as individual points. FIG. 2F shows gene set enrichment analysis (GSEA) was performed in the TCGA (human) dataset using the top 20 overexpressed proteases in KP tumors. Enrichment score (ES, line) was calculated by walking down the ranked list of all genes in the TCGA dataset, increasing a running sum statistic when a gene in the KP protease set (represented as a bar) was encountered and decreasing it otherwise. Bars 2, 3, 7, 8, 9, 11, 15, and the second to last bar along the bottom were genes included in the "LUAD protease panel." The other bars are genes that were not included. The maximum ES was 0.455 (P=0.0002). A total of 8 of the bars were included in the LUAD protease panel (Bar 2=KLK6; Bar 3=MMP13; Bar 7=PRSS22; Bar 8=KLK14; Bar 9=KLK13; Bar 11=ACE2; Bar 15=PRSS8; Bar 19=NAPSA). FIG. 3A is a schematic showing that all 15 proteases in the "LUAD protease panel" were screened against a panel of 14 FRET-paired protease substrates and fluorescence was monitored over 45 minutes. FIG. 3B includes graphs which show kinetic fluorescence curves are shown for 14 FRET-paired substrates with (upper panel) and without (lower panel) addition of MMP3. FIG. 3C is a heatmap showing fluorescence fold changes at 45 minutes (average of 2 replicates) were tabulated and hierarchical clustering was performed to cluster proteases by their substrate specificities and substrates by their protease specificities. MMP3, MMP1, MMP12, MMP13, ACE2, and MMP11 are metalloproteases. PRSS8, PRSS22, F7, PRSS3, KLK13, KLK14, and KLK6 are serine proteases. NAPSA and CTSD are aspartic proteases.

FIG. 4A is a schematic in which wild-type mice were treated intratracheally or intravenously with VT750-labeled PEG-8$_{40\ kDa}$ and biodistribution was assessed. FIG. 4B shows fluorescent imaging of organs was performed 60 min post-IT delivery. Clockwise from top-left: lung, spleen, heart, liver, kidneys. FIG. 4C is a graph showing organ-specific biodistribution was quantified (n=4 each condition). Error bars represent SD. FIG. 4D depicts immunohistochemical staining for biotin in lungs excised from healthy mice that were either untreated (above, n=1) or treated with IT administration of biotin-labeled PEG scaffold (below, n=2), followed by excision of lungs. FIG. 4E shows immunohistochemical staining as in FIG. 4D. in which advanced-stage (16.5 week) KP mice were either untreated (above, n=3) or treated with IT administration of biotin-labeled PEG scaffold (below, n=3), followed by excision of lungs.

FIG. 5A shows disease was induced in the KP model by intratracheal instillation of adenovirus containing Cre recombinase under the control of the SPC (surfactant protein C) promoter, which results in activation of mutant K-rasG12D and excision of both copies of p53 in type II alveolar cells. FIG. 5B shows that histologically, disease progresses from low grade dysplasia to invasive adenocarcinoma over 18-20 weeks. FIG. 5C shows tumor development was monitored by microCT in healthy (left, n=11) and KP mice at 5 weeks (n=11), 7.5 weeks (n=11) and 10.5 weeks (n=11) after tumor induction. Right three panels represent time series of a single mouse, with arrow indicating development of a single nodule over time. Size of the largest tumor nodule was assessed by a blinded radiation oncologist (quantification at right of each image). FIG. 5D shows ABNs were administered to KP and control animals at 5 weeks (KP: n=11; Control: n=9), 7.5 weeks (KP: n=11; Control: n=12) and 10.5 weeks (KP: n=12; Control: n=12) after tumor initiation, bladder was voided at 1 hr and urine was collected and pooled over the following 1 hour interval. LC-MS/MS was performed, peak area ratio (PAR, peak area of reporter divided by peak area of spiked-in internal standard) was calculated and all reporters were mean normalized within each sample. Fold difference (MeanNormPARKP/MeanNormPARControl) is shown at 5 weeks, 7.5 weeks and 10.5 weeks after tumor initiation. PP06 is presented on a larger scale y axis. Asterisks indicate significant differences from 5 weeks. *P<0.05, P<0.01, *P<0.001, ****P<0.0001; by two-tailed t-test. Error bars represent SEM. FIG. 5E is a schematic showing unsupervised clustering by principal component analysis (PCA) on mean normalized MS data for KP mice and controls at 5 weeks (left), 7.5 weeks (middle) and 10.5 weeks (right).

FIG. 6A is a schematic of an approach. Random forest classifier was trained on mean normalized urinary reporters from KP mice at 7.5 weeks, as well as control mice at 5 weeks, 7.5 weeks and 10.5 weeks. Classifier was validated on KP mice and control mice at all 3 time points.

FIG. 6B is a graph showing random forest classifier returned the probability that each mouse was either "Control" or "KP". P<0.01, **P<0.0001; by two tailed t-test. Error bars represent SEM. FIG. 6C is a graph showing that ROC analysis was performed on probability data to generate AUC values for the validation cohorts at 5 weeks (AUC=0.58), 7.5 weeks (AUC=0.96) and 10.5 weeks (AUC=0.95).

FIG. 7A shows RNA-Seq data curated by the Lung Genomics Research Consortium (LGRC) was analyzed to assess the classification efficiency of human lung cancer-associated proteases in interstitial lung disease (ILD, n=31) and chronic obstructive pulmonary disease (COPD, n=41) vs normal lung (n=17). Of the top 20 overexpressed proteases in human LUAD, 10 were included in the LGRC dataset with FPKM values greater than zero for at least half of the samples. ROC analysis was performed for LUAD (from TCGA) and ILD and COPD (from LGRC) against their respective controls, using FPKM values for each protease. FIGS. 7B-7D show ROC curves for individual proteases in the panel are shown.

FIG. 8A show goodness of fit was assessed by linear regression and is given as Pearson's $R^2$. Glu-fib reporters were spiked into urine at concentrations ranging from 1 to 1000 ng/mL and LC-MS/MS was performed. FIG. 8B is a graph of data in which healthy mice (n=4 each group) were administered MS-encoded free reporters (IT and IV) at doses ranging from 2.5 ng to 25 ng and urinary concentrations at 1 hour were assessed by LC-MS/MS($R^2$=1.00). Error bars represent SD. FIG. 8C is a graph of data in which Cy7-labeled free reporters were administered IT and IV and concentration in the blood was assessed over the following 6 hours. Error bars represent SD.

FIGS. 10A-10F show that diagnostic protease substrates respond to bacterial and host proteases in vitro. FIG. 10A shows an overview of activity-based nanosensor (ABN) platform for the detection of infection-associated proteases. Multiplexed ABNs are injected intravenously into mice and encounter proteases in situ, which liberate stable peptide reporter molecules. These small reporters are cleared by the kidneys and concentrated in the urine, where they are quantified by ELISA. FIG. 10B shows design of substrates against pathogen and host proteases. LAS-Q includes SEQ ID NO: 45, LAS-E includes SEQ ID NO: 46, ELA-Q includes SEQ ID NO: 47, and ELA-E includes SEQ ID NO: 48. FIG. 10C shows supernatants from PA01 or *Staphylococcus aureus* cultures were collected and incubated with FRET-paired substrates (LAS-Q and ELA-Q), alongside fresh media or PA01 supernatant supplemented with ZnCl2, and cleavage was monitored by fluorescence signal. Data are presented as relative fold change before and after incubation. FIG. 10D show that the same substrates assayed in FIG. 10C (LAS-Q and ELA-Q) were incubated with various disease-associated recombinant proteases, and examined for the reversal of FRET-quenched fluorescent signal. FIG. 10E shows that supernatants from *P. aeruginosa* clinical isolate strains and PA01 were collected and incubated with LAS-Q and ELA-Q substrates and cleavage was monitored by fluorescence signal, as in (FIG. 10C). FIG. 10F shows that colony forming units (CFU) present in lasA-sensitive *S. aureus* cultures grown in the presence of supernatants from clinical isolates and PA01 after 6 hours in culture. Striped bars indicate which clinical isolates produced supernatants that do not cleave ELA-Q and LAS-Q sensors. (****P<0.0001; 2-way ANOVA with Sidak's multiple comparisons test; n=3 for each condition).

FIGS. 11A-11D show that LAS and ELA ABNs are able to diagnose *P. aeruginosa* infection. FIG. 11A shows that cysteine-terminated peptides barcoded with ligand-encoded urinary reporters were coupled to 8-arm PEG-MAL. Each substrate is uniquely barcoded with one of two ligands (dark/light stars) and a biotin (closed circles). FIG. 11B shows characterization of ELISA measurements of AF488 liberated from cleaved LAS-E and FAM liberated from cleaved ELA-E after incubation with their respective specific proteases. FIG. 11C shows LAS and ELA reporter urine signal from healthy and subsequently PA01-infected mice administered ABNs intravenously 24 hours post infection. Signal is normalized in each case to the mean healthy urine signal. Connectors indicate paired measurements in the same mice (LAS p=0.0281, ELA p=0.0001; two-tailed paired t-test, n=9 mice). FIG. 11D shows ROC curves determining the diagnostic accuracy of the assay for each substrate's ability to distinguish infected from healthy urine signal. An AUC of 1 represents a perfect classifier, and an AUC of 0.5 (dashed line of identity) represents a random classifier. P values relative to a random classifier.

FIGS. 12A-12F show that ABNs monitor bacterial infections and resolution after antibiotic therapy. FIG. 12A shows an experimental overview: PA01-infected mice are injected with nanosensors to assess the baseline levels of reporter signal, then started on a 4 day course of ciprofloxacin treatment. Seven days following infection, diagnostic injections and urine collections are repeated to monitor for nanosensor readout. FIGS. 12B-12C show LAS-E (FIG. 12B) and ELA-E (FIG. 12C) urine signal from infected mice (+PA01) or infected and treated with ciprofloxacin (+PA01+Cipro) relative to healthy control measurements and ROC curves for each substrate to distinguish infected from healthy (Infection, solid curves; ELA AUC=1.00, p<0.001 from random classifier, LAS AUC=0.92, p=0.002 from random classifier) or ciprofloxacin treated from pre-treatment signal (Treatment, dashed curves; ELA AUC=0.72, p=0.096 from random classifier, LAS AUC=0.88, p=0.004 from random classifier). FIG. 12D shows gross histology (left) and immunofluorescence staining for *Pseudomonas* (middle) and neutrophils (right) in lung sections from healthy, acutely infected (24 hours), and ciprofloxacin-treated mice. FIGS. 12E-12F show quantification of *Pseudomonas* (FIG. 12E) and neutrophil (FIG. 12F) immunofluorescence staining in lung sections from uninfected, infected, and ciprofloxacin-treated infected mice. (**P<0.0001, *P<0.001, **P<0.01, *P<0.05; 1way ANOVA with Tukey's multiple comparisons test; n=10 mice (b-c), n=3-4 mice, 3 representative fields per mouse FIGS. 12E-12F)

FIGS. 13A-13G show ABNs identify acute drug sensitivity versus resistance in developing infections. FIG. 13A shows experimental overview: mice are infected with PA01, then treatment with either ciprofloxacin or doxycycline is initiated 5 hours post-infection. Nanosensors are injected and urine is collected 24 hours post-infection. FIG. 13B shows relative LAS urine signal before infection and after initiation of ciprofloxacin or doxycycline treatment. FIG. 13C shows a ROC curve for LAS signal differentiating between effective and ineffective treatment (doxycycline-treated vs ciprofloxacin-treated). FIG. 13D shows relative ELA urine signal before infection and after initiation of ciprofloxacin or doxycycline treatment. FIG. 13E shows a ROC curve for ELA signal differentiating between effective and ineffective treatment. FIG. 13F shows lung histology (left) and immunofluorescence staining for *Pseudomonas* (right) of doxycycline and ciprofloxacin-treated mice 24 hours post-infection, after 19 hours of antibiotic therapy. FIG. 13G shows quantification of *Pseudomonas* immunofluorescence signal in doxycycline- and ciprofloxacin-treated mice lung sections. (**P<0.01, *P<0.05; 1way ANOVA with Tukey's multiple comparisons test, n=7-8 mice (FIG. 13B, FIG. 13D); P-values relative to a random classifier (FIG. 13C, FIG. 13E); two-tailed Student's t-test, n=6-9 fields from 2-4 mice per group (FIG. 13G)).

FIGS. 17A-17D show that machine learning allowed for robust classification of two genetic subtypes of non-small cell lung cancer. FIGS. 17A-17C include ROC curves showing performance of a single random forest classifier trained on urinary ABN output from a subset of $KP_{7.5\ wk}$, $EA_{7.5\ wk}$, and healthy controls in discriminating KP (FIG. 17A), EA (FIG. 17B), or a combination of KP and EA (FIG. 17C) mice from healthy controls at all three time points. FIG. 17D is a graph with a ROC curve showing performance of a random forest classifier trained on urinary ABN output from $KP_{7.5\ wk}$ and $EA_{7.5\ wk}$ mice (as "disease") and LPS and healthy control mice (as "control") in discriminating $KP_{7.5\ wk}$, $EA_{7.5\ wk}$, and a combination of the two (termed "LUAD") from healthy and LPS-treated mice. All ROC curves are averages over 10 independent train/test trials. Cohort compositions are shown in Table 5.

FIGS. 18A-18F include data showing that LUAD protease panel genes were enriched across genetic and histological lung cancer subtypes. FIGS. 18A-18F are GSEA plots showing enrichment of LUAD protease panel genes. FIG. 18A shows enrichment of LUAD protease panel genes in stage I LUAD ($n_{LUAD}$=302, $n_{NAT}$=29; P<0.0001). FIG. 18B shows enrichment of LUAD protease panel genes in KRAS-mutant LUAD ($n_{LUAD}$=75, $n_{NAT}$=58; P<0.0001). FIG. 18C shows enrichment of LUAD protease panel genes in TP53-mutant LUAD ($n_{LUAD}$=64, $n_{NAT}$=58; P=0.0002). FIG. 18D shows enrichment of LUAD protease panel genes in EGFR-mutant LUAD ($n_{LUAD}$=28, $n_{NAT}$=58; P=0.0004). FIG. 18E shows enrichment of LUAD protease panel genes in BRAF-mutant LUAD ($n_{LUAD}$=17, $n_{NAT}$=58; P=0.0002). FIG. 18F shows enrichment of LUAD protease panel genes in LUSC ($n_{LUSC}$=233, $n_{NAT}$=17; P=0.0002).

FIG. 21A shows fold changes in mouse weights after treatment with either peptide-functionalized ABNs (red; n=9, days 0 to 1; n=6, days 4 to 11) or mannitol buffer ('Vehicle'; n=8). FIG. 21B include representative H&E images of mouse organs at 2 hours, 1 day, and 11 days after intrapulmonary ABN treatment. Scale is 200 m.

FIGS. 22A-22F include data showing that the ABNs were stable to aerosolization. FIG. 22A show a device used for intratracheal administration of aerosolized nanosensors. FIG. 22B show aerosol produced from 50 μL of buffer. Scale for FIG. 22A and FIG. 22B is 1 cm. FIGS. 22C and 22D show TEM images of nanoparticle $PEG-8_{40\ kDa}$ scaffold pre- (FIG. 22C) and post- (FIG. 22D) aerosolization. Scale is 200 nm. FIG. 22E show representative DLS quantification of particle sizes pre- and post-aerosolization of $PEG-8_{40\ kDa}$ scaffold (n=3). FIG. 22F show fluorescent dequenching by MMP13 of fluorogenic nanosensor PEG-PPQ5, pre (n=4) and post (n=4) aerosolization. PEG-PPQ5 fluorescence change without addition of MMP13 is shown in black (n=4).

FIGS. 23A-23F include data showing that aerosolized nanoparticles penetrated deep within the lung and avoid distribution to off-target organs. FIG. 23A show a representative image of lungs from a mouse treated with aerosolized fluorophore-labeled $PEG-8_{40\ kDa}$. Scale is 5 mm. FIG. 23B shows organ-specific biodistribution of fluorophore-labeled $PEG-8_{40\ kDa}$ 60 minutes after aerosol (n=2) or intravenous (n=2) delivery. FIGS. 23C-23F show stained sections of untreated lungs (FIGS. 23C-23D) or lungs fixed 10 min post-aerosol delivery of biotin labeled $PEG-8_{40\ kDa}$ (FIGS. 23E-23F). Scale bar for (FIGS. 23E-23F) is 200 m.

FIG. 24A shows mean normalized urinary ABN output for healthy control mice (n=5) or mice bearing flank LS174T tumors (n=5). FIG. 24B is a volcano plot shows no differential enrichment of any of the 14 reporters detected in the urine of diseased mice relative to healthy controls.

FIG. 25A are volcano plots of urinary ABN output in EA mice relative to healthy controls at 5 weeks (n=19 each group) (left), 7.5 weeks (EA, n=20; Control, n=19) (middle) and 10.5 weeks (EA, n=16; Control, n=19) (right) after tumor induction. (The sensitivity of each substrate for metalloprotease, serine protease, and aspartic protease are indicated in FIG. 19). FIG. 25B show PCA of urinary ABN output of EA mice and healthy controls at 5 weeks (n=19 each group) (left), 7.5 weeks (EA, n=20; Control, n=19) (middle) and 10.5 weeks (EA, n=16; Control, n=19) (right) after tumor induction.

FIGS. 26A-26B are volcano plots of urinary ABN outputs from $KP_{7.5\ wk}$ (n=11) (FIG. 26A) and $EA_{7.5\ wk}$ (n=20) (FIG. 26B) mice relative to LPS-treated mice (n=11). FIG. 26C show PCA of urinary ABN outputs from $KP_{7.5\ wk}$ (n=11), $EA_{7.5\ wk}$ (n=20), and LPS (n=11) mice, as well as healthy control mice from all three experiments (n=47).

FIG. 27A shows tumor development as monitored by microCT in healthy and KP animals at indicated weeks. In FIG. 27A, healthy (left, n=11) and $KP_{5\ wk}$ (n=12), $KP_{7.5\ wk}$ (n=12), and $KP_{10.5\ wk}$ (n=14). Right three panels represent time series of a single mouse, with arrow indicating development of a single nodule over time. Size of the largest tumor was assessed by a blinded radiation oncologist (quantification at right of each image). FIG. 27B show urine output of ABNs administered to KP and control animals at 5 weeks (KP: n=11; Control: n=9), 7.5 weeks (KP: n=11;

Control: n=12), and 10.5 weeks (KP: n=12; Control: n=12) after tumor induction. For clarity, PP06 is presented on a larger scale y axis. Asterisks indicate significant differences from 5 weeks. *$P_{adj}$<0.05, **$P_{adj}$<0.01; by two-tailed t-test with adjustment for multiple hypotheses using the Holm-Sidak method. Error bars represent SEM.

Figure 19:
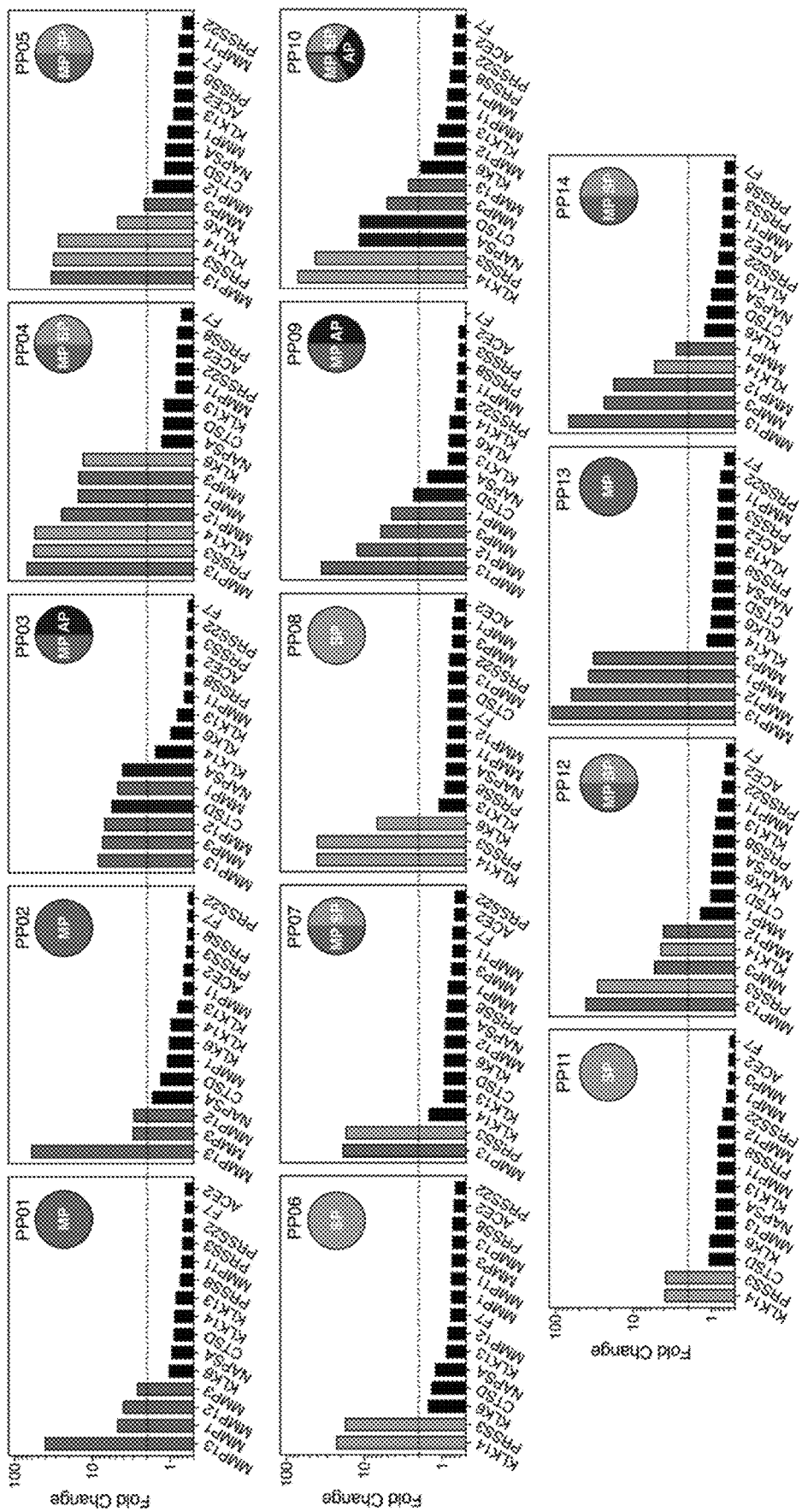
FIG. 19 includes data showing that peptide substrates were cleaved by one or a combination of metallo-, serine, and aspartic proteases. Quantification of in vitro proteolytic cleavage of fluorogenic peptide substrates is shown. Y axis represents fluorescence fold change after 45 minutes of incubation with recombinant protease and dotted line is at fold change=2. Bars also indicate catalytic class of the protease (metalloprotease-specific; serine protease-specific; aspartic protease-specific).
Figure 28:
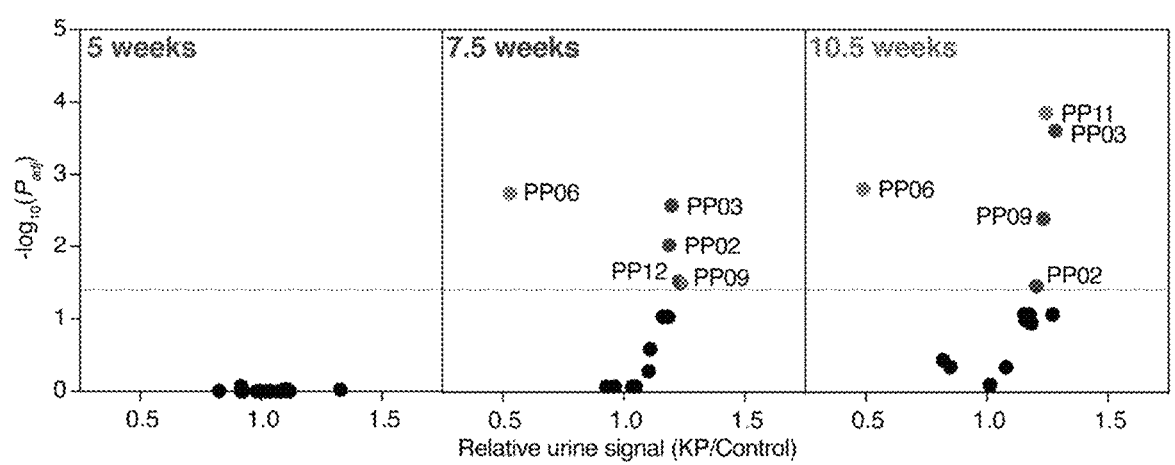

FIG. 28 shows multiple reporters were differentially enriched in the urine of healthy mice and KP mice at 7.5 and 10.5 weeks. Mean normalized urinary reporter concentrations in KP mice and healthy mice were compared at 5 weeks (KP: n=11; Control: n=9), 7.5 weeks (KP: n=11; Control: n=12), and 10.5 weeks (KP: n=12; Control: n=12) after tumor induction and $-\log_{10}(P_{adj})$ was plotted against fold change between KP and control. Significance was calculated by two-tailed t-test followed by adjustment for multiple hypotheses using the Holm-Sidak method. Dotted line is at $P_{adj}$=0.05. The classes of protease that cleave the corresponding peptide substrates are provided in FIG. 19.

DETAILED DESCRIPTION

Aspects of the disclosure relate to methods and compositions for detecting and monitoring protease activity within the lung as an indicator of certain lung disease states (e.g., presence of lung disease, type of lung disease, severity of lung disease etc.). The disclosure relates, in some aspects, to the discovery that delivery of lung protease nanosensors to a subject, for example, to the lung of a subject, enables minimally invasive classification of the type of lung disease (e.g., infectious versus non-infectious or cancerous versus non-cancerous) and the stage of disease (e.g., non-metastatic cancer, metastatic cancer etc.) in the lung of the subject. Without wishing to be bound by any particular theory, protease nanosensors described herein can detect enzymatic activity in vivo and noninvasively quantify physiological processes by harnessing the capacity of the nanosensors to circulate and sense the environment of the lung while providing a read-out (e.g., detection of a detectable marker) at a site that is remote (e.g., a urine sample) from the lung.

For instance, as described in the Examples section herein, lung protease activity can be assessed in order to classify the type of lung disease in a subject (including but not limited to lung infections, including *Pseudomonas aeruginosa* infection, Interstitial Lung Disease (ILD), chronic obstructive pulmonary disease (COPD) and lung cancer).

Aspects of the present disclosure are also based on the surprising discovery that delivery of the nanosensors of the invention into the pulmonary space resulted in a significant reduction in background signals and increase in signal to noise in contrast to other detection systems. It was discovered that nanosensors that are directly delivered to the pulmonary space accumulate in the pulmonary tissue and are not released into the blood until cleavage occurs, thus enhancing the signal. This finding was unexpected. Without wishing to be bound by any particular theory, the combination of nanosensors that are capable of accumulating in lung tissue, and protease substrates that interact with lung proteases in situ result in molecules configured to produce populations of detectable markers (e.g., a detectable marker signature) that are indicative of whether the subject has a lung disease (e.g., lung cancer or lung infection), and in some cases, which stage of lung disease. Furthermore, it was found that the lung protease nanosensors could be used to accurately detect localized disease in two different lung cancer models with 100% specificity and 81% or 95% sensitivity in the KP and EA models, respectively. The methods described herein also allow for specific detection of lung cancer as classification of samples was not confounded by LPS-driven lung inflammation (e.g., LPS-driven lung inflammation did not result in false positives, see FIGS. 17 and 26).

In some embodiments, the disclosure relates to the delivery of a set of protease nanosensors comprising protease-sensitive substrates to the lung of a subject. Upon encountering their cognate proteases, substrates are cleaved by enzymes (e.g., proteases) and reporter fragments may be excreted into urine, providing a non-invasive diagnostic readout (FIGS. 1A-1E and FIGS. 10A-10B).

In some embodiments, the delivered nanosensors are responsive to proteases enriched in different stages of lung tumor invasiveness (e.g., metastasis) and provide a high resolution, functionality driven snapshot of the lung tumor microenvironment.

Great strides in the field of molecular diagnostics have yielded promising approaches that may improve upon low-dose CT for lung cancer screening. Transcriptional profiling of bronchial brushings enhances the diagnostic sensitivity of bronchoscopy alone, even for peripheral and early-stage pulmonary lesions, an approach that leverages the "field of injury" that results from smoking and other environmental exposures (Silvestri et al., N Engl J Med 373, 243-251 (2015); Whitney et al., BMC Med Genomics 8, 18 (2015)). However, this approach is non-specific (47% specificity) and requires an invasive bronchoscopy, limiting its utility as a screening tool. However, as with any invasive procedure, bronchoscopy carries the risk of attendant complications such as pneumothorax (Durand et al., Thorax 68 Suppl 1, i1-i44 (2013)). Circulating tumor DNA (ctDNA) has emerged as a promising tool for noninvasive molecular profiling of lung cancer (Newman et al., Nat Med 20, 548-554 548-554 (2014).; Simmons et al., Nat. Commun. 7, 1-14 (2016); A. C. Society, Non-Small Cell Lung Cancer 2018 (2018); Massie et al., Nat. Rev. Cancer 17, 223-238 (2017).; Cohen et al., Science 3247, 1-10 (2018)). However, the presence of ctDNA has been shown to scale with tumor burden and there are fundamental sensitivity limits for early stage disease (Newman et al., Nat Med 20, 548-554 (2014); Massie et al., Nat. Rev. Cancer 17, 223-238 (2017); Bettegowda et al., Sci. Transl. Med. 6, 224ra24 (2014)). To achieve high-sensitivity detection of ctDNA in stage I-II cancer patients, it is estimated that large (>80 ml) blood volumes would be needed with current methodologies, potentially limiting the widespread adoption of this approach (Haque et al., bioRxiv (2017)). Furthermore, these screening tests are expensive ($81,000 per quality-adjusted life year gained (Black et al., N Engl J Med 371, 1793-1802 (2014)) with high false positive rates (Aberle et al., N Engl J Med 365, 395-409 (2011)) and potentially expose patients to radiation, and biopsy-related complications, raising concern for overdiagnosis and increased healthcare-associated cost burden (Brenner et al., Radiology 231, 440-445 (2004); O'Connor et al., JAMA J. Am. Med. Assoc. 307, 2434-2435 (2015); Bach et al., JAMA—J. Am. Med. Assoc. 307, 2418-2429 (2012); Wiener et al., Clin Pulm Med 20, 29-35 (2013); Silvestri et al., N Engl J Med 373, 243-251 (2015)).

Alternatively, circulating tumor DNA (ctDNA) has been explored for both detection and molecular profiling of lung cancer (Newman et al., Nat Med 20, 548-554 (2014); Chabon et al., Nat Commun 7, 11815 (2016)). However, the presence of ctDNA in circulation scales with tumor burden and while sensitivity is generally good in advanced disease, it presently lacks accuracy in early detection (~82% sensitivity in stage IV vs. ~47% sensitivity in stage I across multiple cancer types) (Wan et al., Nat Rev Cancer 17, 223-238 (2017)). Similarly, circulating tumor cells (CTCs) may be detected in patients with advanced-stage NSCLC, enabling remote, longitudinal assessment of mutational burden without the need for biopsy (Krebs et al., Nat Rev Clin Oncol 11, 129-144 (2014); Park et al., Proc Natl Acad Sci USA 113, E8379-E8386 (2016)). However, the sensitivity of CTCs for detection of non-metastatic lung cancer remains low (65% in a study of patients undergoing definitive radiation therapy) (Dorsey et al., Cancer 121, 139-149 (2015)).

Whereas conventional techniques often rely on imaging techniques or detection of endogenous biomarkers in circulation, the lung protease nanosensors developed herein monitor for a disease state by detecting aberrant protease activity at the site of disease (e.g., the lung). To drive accurate diagnosis in a heterogeneous disease, a diagnostic should be highly specific. Without being bound by a particular theory, the lung protease nanosensors described herein allow for specific and sensitive detection of heterogenous lung diseases including lung cancer.

Typically, aberrantly expressed proteases (e.g., proteases aberrantly expressed by a subject) are candidate enzymes for lung disease (e.g., lung cancer) detection and analysis. Non-limiting examples of lung cancer-associated enzymes are provided in FIGS. 2A, 2B, 2C, 7A, and Table 1. Protease activity is dysregulated in cancer and proteases across catalytic classes play a direct role in all of the hallmarks of cancer, including tumor growth, angiogenesis, invasion and metastasis (Hanahan et al., Cell 144, 646-674 (2011)); Dudani et al., Annual Review of Cancer Biology 2, 353-376 (2018); Lopez-Otin et al., Nat Rev Cancer 7, 800-808 (2007); Gocheva et al., Cell Cycle 6, 60-64 (2007); Kessenbrock et al., Cell 141, 52-67 (2010); Borgono et al., Nat Rev Cancer 4, 876-890 (2004)). In some embodiments, the lung protease nanosensors of the present disclosure leverage dysregulated protease activity to overcome the insensitivity of previous biomarker assays, amplifying lung disease-associated signals generated in the lung disease (e.g., tumor or lung infection) microenvironment and providing a highly concentrated urine-based readout.

Upon administration, in some embodiments, these peptide-functionalized lung protease nanosensor agents passively home to diseased tissues. There, disease-associated proteases liberate multiplexed reporters that are small enough to concentrate efficiently into the urine where they may be detected by mass spectrometry or immunoassays.

National guidelines recommend screening for patients with a high risk for cancer with low-dose computed tomography (LDCT), but this approach suffers from high false positive rates, leading to overdiagnosis and associated morbidity to patients with unnecessary, invasive follow-up. As demonstrated herein, in some embodiments, a multiplex panel of activity-based nanosensors (ABNs) that simultaneously query dysregulated pulmonary proteases in the setting of lung adenocarcinoma. Upon intratracheal administration, ABNs are cleaved by disease-associated enzymes in the lung, releasing mass-encoded reporters that traverse into the systemic circulation and are subsequently concentrated into the urine for collection. Urine is then analyzed by mass spectrometry and disease classification is performed in silico by machine learning. The design of the panel of sensors was informed by comparative transcriptomic analysis of human and mouse lung adenocarcinoma data sets and in vitro FRET-based cleavage assays with recombinant candidate proteases. In some embodiments, when employed in a model of Kras and p53 mutant lung adenocarcinoma, this approach enabled accurate detection of localized lung cancer in mice, with 100% specificity and 81% sensitivity. This approach was generalizable to an alternative autochthonous model of lung adenocarcinoma (with 100% specificity and 95% sensitivity) and was not confounded by lipopolysaccharide (LPS)-driven lung inflammation. The techniques of the invention allow for enhanced non-invasive procedures with significantly improved accuracy. Without being bound by a particular theory, the methods described herein may be useful for detection of lung cancer in the clinic.

The lung protease nanosensors may be used clinically, e.g., to detect localized lung adenocarcinoma. As non-limiting examples, the efficacy of the lung protease nanosensors in detecting disease in two autochthonous, immunocompetent models of localized lung adenocarcinoma are described herein. Stage-specific differences, as well as proteolytic contributions from immune cells, have been determined herein. As a non-limiting example, the lung protease nanosensors detected disease as early as 7.5 weeks after initiating the KP model, when only grade 1 atypical adenomatous hyperplasia (AAH) and grade 2 adenomas are present (DuPage et al., Nat. Protoc. 4, 1064-1072 (2009). In some embodiments, the lung protease nanosensors described herein may be used to determine the role of a protease in disease. For example, although metalloprotease-sensitive ABNs were, preferentially cleaved in KP mice at both 7.5 and 10.5 weeks, the activation of PP11 (a serine protease-sensitive substrate, FIG. 19) in $KP_{10.5\ wk}$ could point to an unexpected role of serine protease activity in tumor progression at this disease stage (FIG. 28). Without being bound by a particular theory, tumor-infiltrating immune cells, which secrete a multitude of serine proteases (Pham et al., Nat. Rev. Immunol. 6, 541-550 (2006); Henry et al., Cell Rep. 14, 708-722 (2016)), may contribute to lung protease nanosensor cleavage in $KP_{10.5\ wk}$ mice. Indeed, neutrophils have been shown to infiltrate KP tumors around 10 weeks after tumor induction (Busch et al., J. Immunol. 197, 4493-4503 (2016)), and these immune cells have been implicated as playing critical role in the tumor microenvironment (Faget et al., Cell Rep. 21, 3190-3204 (2017)). Without being bound by a particular theory, the lung protease nanosensors may be useful to measure immune-mediated protease activity raises the prospect of rapid, noninvasive, and longitudinal immunotherapy response monitoring.

In some embodiments, the lung protease nanosensors described herein have improved sensitivity relative to existing and emerging diagnostics of cancer, including blood-based diagnostics. As shown herein, the lung protease nanosensors could be used to detect tumors in $KP_{7.5\ wk}$ mice, whose total tumor volume was, on average, just 2.78 mm$^3$ (see, e.g., Table 4) more than an order of magnitude smaller than one of the most sensitive methods to date (e.g., as compared to 36 mm$^3$ in an orthotopic ovarian cancer model) (Kwon et al., Nat. Biomed. Eng. 1 (2017), doi:10.1038/s41551-017-0054). By comparison, in the LS174T colorectal cancer xenograft model, ctDNA is detectable when tumor volumes reach 1,000 mm$^3$ (Aalipour et al., Nat. Biotechnol. 37, 531-539 (2019)), carcinoembyonic antigen (CEA) is detectable around 135-330 mm$^3$ (Aalipour et al., Nat. Biotechnol. 37, 531-539 (2019), and intravenously administered ABNs have previously been shown to detect disease in this model around 130 mm$^3$ (Kwong et al., Nat. Biotechnol. 31, 63-70 (2013)). Finally, in the autochthonous $Kras^{G12D}$-mutant "K" lung cancer model, ctDNA bearing the $Kras^{G12D}$ mutation was only detectable when average tumor volumes were 7.1 mm$^3$ (Rachit et al., Dis. Model. Mech. 12, dmm036863 (2019)), even with collection of 2.5% of the total mouse blood volume scaling to 125 ml in humans.

Figure 25A:
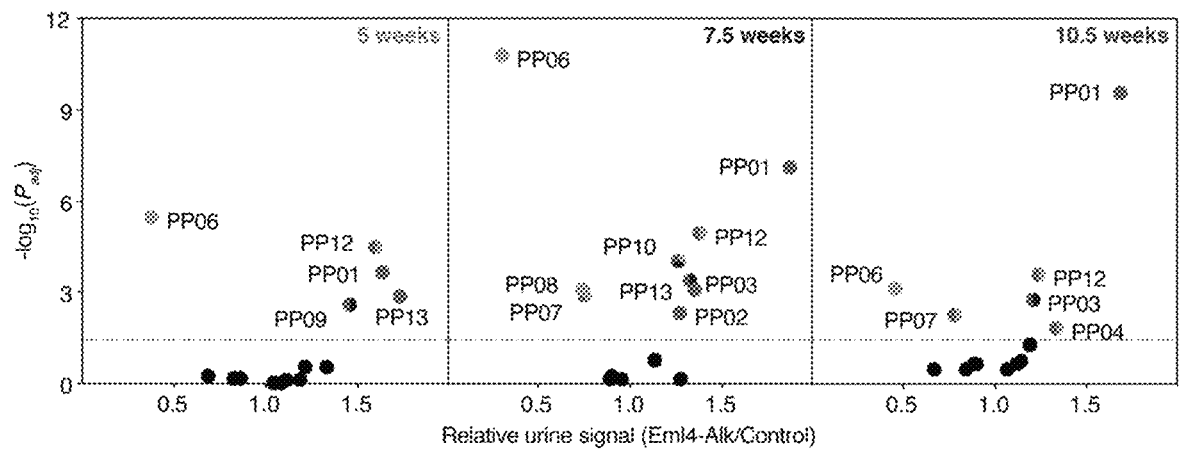
FIGS. 25A-25B include data showing that intrapulmonary ABNs allowed for classification of Alk-driven lung cancer.
Figure 26A:
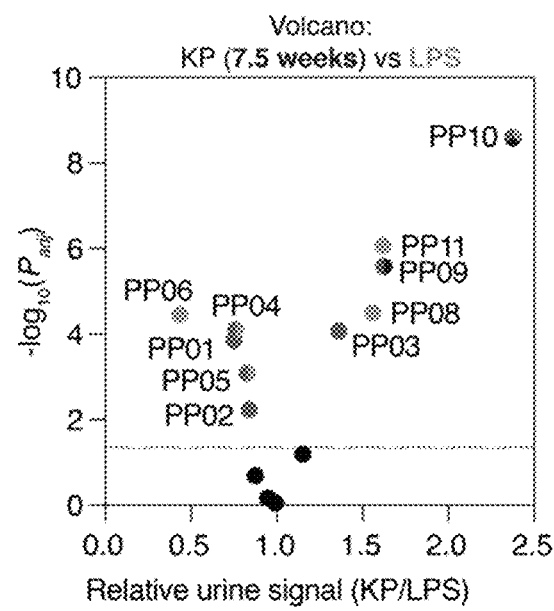
FIGS. 26A-26C include data showing that the pulmonary ABN cleavage profile was distinct in lung cancer and benign lung inflammation.
Figure 26B:
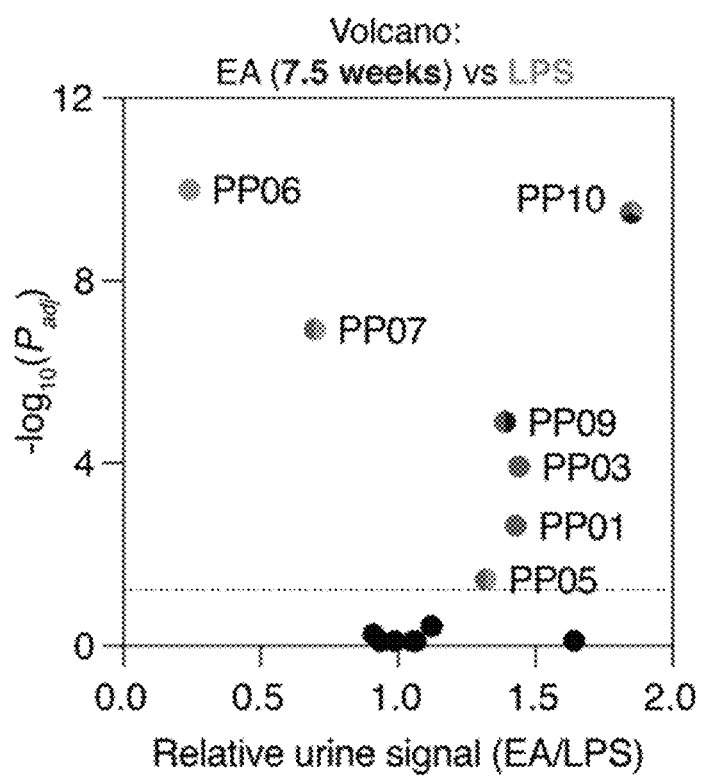

In the NLST, 96.4% of positive LDCT findings were false positives (National Lung Screening Trial Research Team, N. Engl. J. Med. 365, 395-409 (2011); Bach et al., JAMA—J. Am. Med. Assoc. 307, 2418-2429 (2012)), and the frequency of major complications in a patient undergoing diagnostic workup for a LDCT finding is 33 per 10,000 (Black et al., N. Engl. J. Med. 371, 1793-1802 (2014); O'Connor et al., JAMA J. Am. Med. Assoc. 307, 2434-2435 (2015); Bach et al., JAMA—J. Am. Med. Assoc. 307, 2418-2429 (2012)). Aspects of the present disclosure provide noninvasive methods that can be used to distinguish between lung cancer and benign lung disease. In some embodiments, the lung protease nanosensors allow for multiplexing and may be used in combination with machine learning for specific detection of lung cancer, rather than benign lung inflammation. As a non-limiting example, though fewer than half of the 14 lung protease nanosensors were differentially enriched in the urine of KP mice and healthy controls (FIG. 9), several more had diagnostic power in EA mice (FIG. 25A), and others were informative in the classification of malignant vs. inflammatory disease (FIGS. 26A-26B). In some embodiments, the results disclosed herein show that a pre-trained random forest classifier could almost perfectly distinguish between lung cancer-bearing mice (regardless of subtype) and benign disease controls (see, e.g., FIG. 17D).

Aspects of the present disclosure also demonstrate that the lung protease nanosensors are stable after aerosolization and penetrate deep within the lung. In some embodiments, intrapulmonary delivery may be achieved via dry powder inhalation and nebulization. Without being bound by a particular theory, intrapulmonary delivery and aerosolization may allow for noninvasive lung protease nanosensor administration without the need for a skilled operator.

In some embodiments, the intrapulmonary lung protease nanosensors can be used for highly sensitive and specific detection of localized lung cancer in via a noninvasive urine test. As a non-limiting example, results have been shown in autochthonous mouse models. The lung protease nanosensors may be designed to detect proteases that are active at the earliest stages of lung cancer development (e.g., in humans). As a non-limiting example, high throughput screening methods may be used to design lung protease nanosensors that are highly specific for the proteases that are active at the earliest stages of lung cancer development and the responsiveness of the lung protease nanosensors may be evaluated in human biospecimens. Clinically, in some embodiments, lung protease nanosensors may be used in conjunction with LDCT to enhance specificity and reduce the number of patients referred for invasive follow up procedures. In some embodiments, the lung protease nanosensor methods described herein provide an accurate, noninvasive, and radiation-free strategy for lung cancer testing.

Figures 1A, 1B:
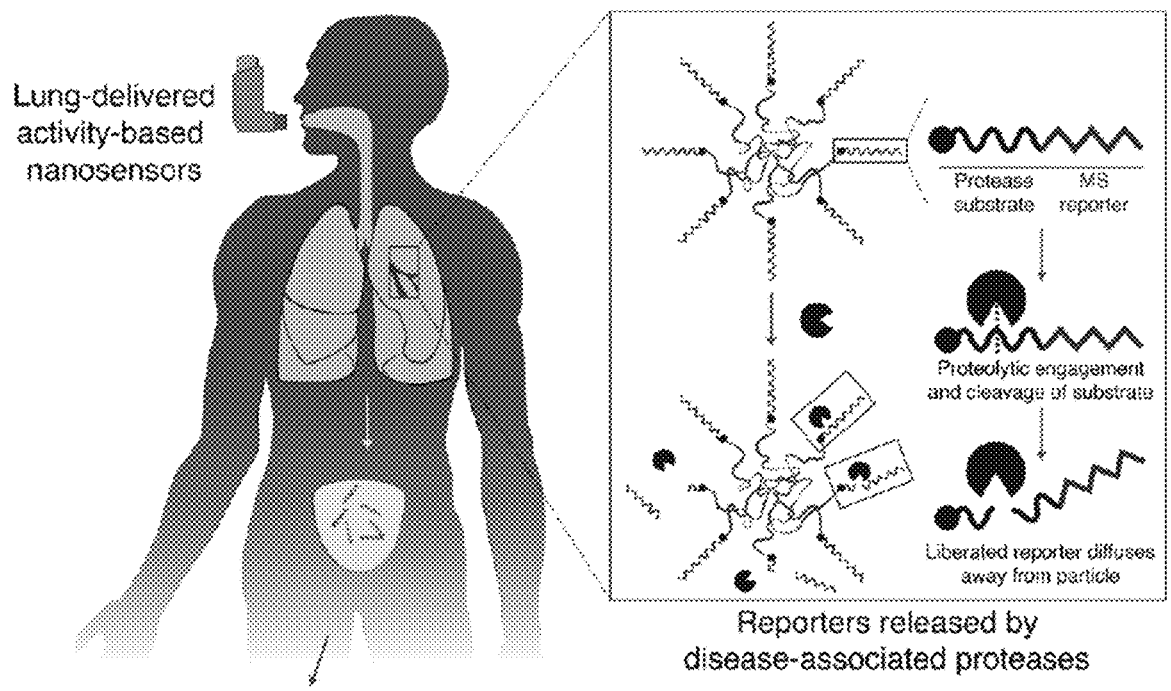
FIGS. 1A-1E include non-limiting schematic overviews depicting a method of using a lung protease nanosensor to diagnose lung cancer in a subject.
Figures 1C, 1D, 1E:
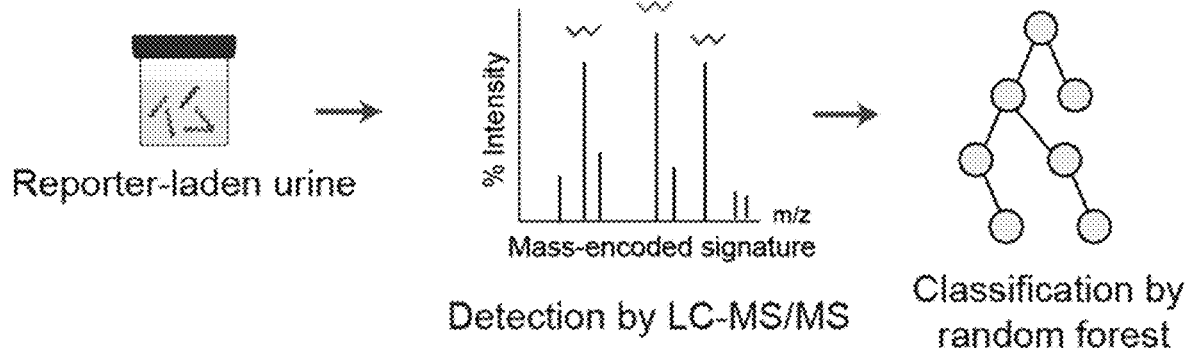

A non-limiting depiction of such a lung protease nanosensor is shown in FIG. 1A. In some embodiments, exploiting organ-specific delivery enables the lung protease nanosensors to specifically address proteases dysregulated in the lung, without interacting with background proteases (e.g., in blood or other tissues; FIG. 1B). Further, efficient size-dependent communication between the lung and the bloodstream ensures that reporters released by disease-associated proteases rapidly enter the urine via the blood, where they may be detected by mass spectrometry (FIGS. 1C-1D). Finally, in some embodiments, a machine learning classification algorithm, termed random forest, was leveraged to achieve diagnostic specificity of 100% and sensitivity of up to 81% in detecting localized disease in a model of Kras and p53 mutant lung adenocarcinoma (FIG. 1E).

The present disclosure is also based, in part, on the unexpected discovery that activity-based lung nanosensors can be used to detect a lung infection noninvasively in vivo. Without being bound by a particular theory, a protease secreted by a pathogen can interact with a cognate substrates on a lung protease nanosensor in a lung of a subject and release the detectable marker that is attached to the substrate. The released detectable marker is indicative of whether the subject has a lung infection (e.g., *Pseudomonas aeruginosa* infection).

A non-limiting depiction of such a lung nanosensor is shown in FIGS. 10A-10B. For example, a lung nanosensor may identify a lung infection (e.g., *P. aeruginosa* infection) by sensing host and pathogen (e.g., bacteria) protease activity in vivo. The presence of an active host or pathogen protease may be detected using urinary detection. In the non-limiting examples shown in FIGS. 10A-10B, one lung protease sensor is comprised of a peptide substrate for the *P. aeruginosa* protease LasA, and can be activated by proteases secreted by a laboratory strain, PA01, as well as by several clinical isolate strains. As described herein, a second lung sensor that is capable of detecting elastases was shown to be responsive to recombinant neutrophil elastase, as well as to secreted proteases from bacterial strains. In mice infected with *P. aeruginosa*, use of these lung protease sensors—also referred to as activity-based nanosensors (ABNs)—noninvasively detect the presence of infection and also monitor bacterial clearance from the lung microenvironment over time. Additionally, lung protease nanosensors were able to differentiate between appropriate and insufficient antibiotic treatments in an acute setting, within hours after the initiation of therapy. These findings demonstrated, in some embodiments, how activity measurements of disease-associated proteases can provide a noninvasive window into the dynamic process of bacterial infection and resolution, offering an opportunity for the detection, monitoring, and treatment characterization of lung infections.

The ability to robustly classify and monitor lung infections has also been lacking (Caliendo et al., Clin. Infect. Dis., vol. 57, no. suppl 3, pp. S139-S170, December 2013; Bartlett et al., Clin. Infect. Dis., vol. 52, no. SUPPL. 4, pp. S296-S304, May 2011). Early effective treatment helps decrease the morbidity and mortality associated with pneumonia (Irequi et al., Chest, vol. 122, no. 1, pp. 262-268, July 2002; Bartlett et al., Clin. Infect. Dis., vol. 26, no. 4, pp. 811-838, April 1998), though use of antibiotics that are inappropriate, unnecessary, or ineffective often increases morbidity and promotes the development of antimicrobial resistance (Caliendo et al., Clin. Infect. Dis., vol. 57, no. suppl 3, pp. S139-S170, December 2013; Dupont et al., Intensive Care Med., vol. 27, no. 2, pp. 355-362, February 2001; Leroy et al., Intensive Care Med., vol. 29, no. 12, pp. 2170-2173, December 2003; Kollef et al., Chest, vol. 115, no. 2, pp. 462-474, February 1999; Erental et al., PLoS Biol., vol. 10, no. 3, p. e1001281, January 2012). Following the initiation of antibiotic therapy, monitoring patients for drug efficacy can be helpful in deciding whether to continue, modify, or halt an antibiotic regimen (Caliendo et al., Clin. Infect. Dis., vol. 57, no. suppl 3, pp. S139-S170, December 2013; Irequi et al., Chest, vol. 122, no. 1, pp. 262-268, July 2002; Dupont et al., Intensive Care Med., vol. 27, no. 2, pp. 355-362, February 2001). Conventional monitoring techniques often rely on nonspecific or slow measures, such as imaging the site of disease, measuring general markers of inflammation, or laboratory cultures of patient specimens, most of which are unable to identify patients for whom alternate therapeutics would be beneficial, and also fail to distinguish effective treatments from those that are unnecessary in a timely manner (Bruns et al., J. Gen. Intern. Med., vol. 25, no. 3, pp. 203-206, March 2010; Coelho et al., Crit. Care, vol. 11, no. 4, p. R92, August 2007). Existing molecular diagnostics for bacterial infections often rely on the measurement of a large and complex set of genes in blood samples, and thus may not capture the underlying pathogenesis in real-time and in broadly applicable ways (Sweeney et al., Sci. Transl. Med., vol. 8, no. 346, p. 346ra91, July 2016; Zumla et al., Lancet Infect. Dis., vol. 14, no. 11, pp. 1123-1135, 2014). As such, simple diagnostic tools are urgently needed for the identification and characterization of bacterial pneumonias and their responses to treatment.

Proteases are intricately involved in the development of and response to bacterial infections, and therefore offer an attractive route for diagnosis (Matsumoto et al., Biol. Chem., vol. 385, no. 11, pp. 1007-1016, January 2004; Parks et al., Nat. Rev. Immunol., vol. 4, no. 8, pp. 617-629, August 2004; Iwasaki et al., Nat. Immunol., vol. 16, no. 4, pp. 343-353, March 2015). The human host response to pathogenic bacteria is highly proteolytically dependent, involving a number of proteases secreted by a range of innate immune cell types (Wilkinson et al., Chest, vol. 142, no. 6, pp. 1425-1432, December 2012). In addition, pathogen-derived proteases often act as virulence factors (Matsumoto et al., Biol. Chem., vol. 385, no. 11, pp. 1007-1016, January 2004; Potempa et al., "Corruption of innate immunity by bacterial proteases," Journal of Innate Immunity, vol. 1, no. 2. NIH Public Access, pp. 70-87, 2009). Previous work from our group has shown that protease-sensing nanoparticles, called activity-based nanosensors (ABNs) (Kwong et al., Nat. Biotechnol., vol. 31, no. 1, pp. 63-70, January 2013; Kwon et al., Nat. Biomed. Eng., vol. 1, no. 4, p. 54, April 2017), can detect the inflammation associated with infection based on their cleavage by the metalloprotease, MMP9 (Dudani et al., Adv. Funct. Mater., vol. 26, no. 17, pp. 2919-2928, 2016). However, while the measurement of activity of a target protease-rather than transcript levels or analyte concentrations-provides an amplified signal as well as a readout of the function of the biomarker, relying solely on MMP9-mediated detection hampers specificity of the sensor for infection, as MMP9 is associated with a variety of pathologies.

Current diagnostic and monitoring techniques also often rely on non-specific or slow readouts, such as radiographic imaging and sputum cultures, which fail to specifically identify infections (e.g., bacterial infection) and take several days to identify optimal antibiotic treatments.

Here, a modified formulation of lung protease nanosensors that harnesses the proteolytic processes inherent to the progression of lung disease (e.g., lung cancer or lung infections) is described.

Accordingly, in some aspects, the disclosure provides a lung protease nanosensor comprising a scaffold linked to a lung disease substrate, wherein the lung disease substrate includes a detectable marker, whereby the detectable marker is capable of being released from the lung protease nanosensor when exposed to a protease present in a lung (e.g., a lung cancer-associated protease or an lung infection-associated protease).

Scaffolds

The lung protease nanosensors described herein comprise a modular structure having a scaffold linked to a substrate (e.g., a protease substrate). A modular structure, as used herein, refers to a molecule having multiple domains.

The scaffold may include a single type of substrate, such as, a single type of substrates (e.g., one or more substrates cleaved by the same protease), or it may include multiple types of different substrates (e.g., substrates cleaved by different proteases). For instance each scaffold may include a single (e.g., 1) type of substrate or it may include 2-1,000 different substrates, or any integer there between. Alternatively, each scaffold may include greater than 1,000 different substrates. Multiple copies of the lung protease nanosensor are administered to the subject. In some embodiments, a composition comprising a plurality of different lung protease nanosensors may be administered to a subject to determine whether multiple enzymes and/or substrates are present. In that instance, the plurality of different protease nanosensors includes a plurality of detectable markers, such that each substrate is associated with a particular detectable marker or molecules.

The scaffold may serve as the core of the nanosensor. A purpose of the scaffold is to serve as a platform for the substrate and enhance delivery of the nanosensor to the lung of the subject. As such, the scaffold can be any material or size as long as it can enhance delivery and/or accumulation of the nanosensors to the lung of a subject. Preferably, the scaffold material is non-immunogenic, i.e. does not provoke an immune response in the body of the subject to which it will be administered. Non-limiting examples of scaffolds, include, for instance, compounds that cause active targeting to tissue, cells or molecules (e.g., targeting of nanosensors to the lung), microparticles, nanoparticles, aptamers, peptides (RGD, iRGD, LyP-1, CREKA, etc.), proteins, nucleic acids, polysaccharides, polymers, antibodies or antibody fragments (e.g., herceptin, cetuximab, panitumumab, etc.) and small molecules (e.g., erlotinib, gefitinib, sorafenib, etc.).

In some aspects, the disclosure relates to the discovery that delivery to the lung of a subject is enhanced by protease nanosensors having certain polymer scaffolds (e.g., poly (ethylene glycol) (PEG) scaffolds). Polyethylene glycol (PEG), also known as poly(oxyethylene) glycol, is a condensation polymer of ethylene oxide and water having the general chemical formula $HO(CH_2CH_2O)[n]H$. Generally, a PEG polymer can range in size from about 2 subunits (e.g., ethylene oxide molecules) to about 50,000 subunits (e.g., ethylene oxide molecules. In some embodiments, a PEG polymer comprises between 2 and 10,000 subunits (e.g., ethylene oxide molecules).

A PEG polymer can be linear or multi-armed (e.g., dendrimeric, branched geometry, star geometry, etc.). In some embodiments, a scaffold comprises a linear PEG polymer. In some embodiments, a scaffold comprises a multi-arm PEG polymer. In some embodiments, a multi-arm PEG polymer comprises between 2 and 20 arms. Multi-arm and dendrimeric scaffolds are generally described, for example by Madaan et al. *J Pharm Bioallied Sci.* 2014 6(3): 139-150.

Additional polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly(lactic-co-glycolic acid) (PLGA).

In some embodiments, a scaffold (e.g., a polymer scaffold, such as a PEG scaffold) has a molecular weight equal to or greater than 40 kDa. In some embodiments, a scaffold is a nanoparticle (e.g., an iron oxide nanoparticle, IONP) that is between 10 nm and 50 nm in diameter (e.g. having an average particle size between 10 nm and 50 nm, inclusive). In some embodiments, a scaffold is a high molecular weight protein, for example an Fc domain of an antibody.

As used herein the term "particle" includes nanoparticles as well as microparticles. Nanoparticles are defined as particles of less than 1.0 μm in diameter. A preparation of nanoparticles includes particles having an average particle size of less than 1.0 μm in diameter. Microparticles are particles of greater than 1.0 μm in diameter but less than 1 mm. A preparation of microparticles includes particles having an average particle size of greater than 1.0 μm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid, etc.), synthetic polymer materials (including poly-lactide-coglycolide, poly-glycerol sebacate, etc.), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide.

A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

The scaffold may be composed of inorganic materials. Inorganic materials include, for instance, magnetic materials, conductive materials, and semiconductor materials. In some embodiments, the scaffold is composed of an organic material (e.g., a biological material that enhances delivery of the nanosensor to the lung of a subject).

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle.

The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the scaffolds (e.g., based on the volume of the aqueous solution or other channel-forming reagent) or by microscopic inspection of the scaffolds post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The disclosure contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

The scaffold can serve several functions. As discussed above, it may be useful for targeting the product to a specific region, such as a lung (e.g., lung tissue). In that instance, it could include a targeting agent such as a glycoprotein, an antibody, or a binding protein.

Further, the size of the scaffold may be adjusted based on the particular use of the protease nanosensor. For instance, the scaffold may be designed to have a size greater than 5 nm. Particles, for instance, of greater than 5 nm are not capable of entering the urine, but rather, are cleared through the reticuloendothelial system (RES; liver, spleen, and lymph nodes). By being excluded from the removal through the kidneys any uncleaved protease nanosensor will not be detected in the urine during the analysis step. Additionally, larger particles can be useful for maintaining the particle in the blood or in a tumor site where large particles are more easily shuttled through the vasculature. In some embodiments the scaffold is 500 microns-5 nm, 250 microns-5 nm, 100 microns-5 nm, 10 microns-5 nm, 1 micron-5 nm, 100 nm-5 nm, 100 nm-10 nm, 50 nm-10 nm or any integer size range therebetween. In other instances the scaffold is smaller than 5 nm in size. In such instance, the protease nanosensor will be cleared into the urine. However, the presence of free detectable marker (as opposed to uncleaved protease-specific substrate) can still be detected for instance using mass spectrometry. In some embodiments the scaffold is 1-5 nm, 2-5 nm, 3-5 nm, or 4-5 nm.

Optionally the scaffold may include a biological agent. In one embodiment, a biological agent could be incorporated in the scaffold or it may make up the scaffold. Thus, the compositions of the invention can achieve two purposes at the same time, the diagnostic methods and delivery of a therapeutic agent. In some embodiments the biological agent may be an enzyme inhibitor. In that instance the biological agent can inhibit proteolytic activity at a local site and the detectable marker can be used to test the activity of that particular therapeutic at the site of action.

Substrates

The substrate is a portion of the modular structure that is connected to the scaffold. A substrate, as used herein, is the portion of the modular structure that promotes the enzymatic reaction in the subject, causing the release of a detectable marker. The substrate typically comprises an enzyme-sensitive portion (e.g., protease substrate) linked to a detectable marker.

The substrate is dependent on enzymes that are active in a specific disease state (e.g., lung disease state including lung cancer and lung infection). For instance, a particular lung disease may be associated with a specific set of enzymes and the specific set of enzymes may distinguish one lung disease from another. See, for example, the Examples described below.

Lung diseases include but are not limited to lung cancer, interstitial lung disease (ILD), and chronic obstructive pulmonary disease (COPD), and lung infections. The lung diseases may be primary or secondary diseases.

There are at least two types of lung cancer (e.g., non-small cell lung cancer (NSCLC) and small cell lung cancer (SCLC)). NSCLC accounts for about 85% of lung cancer cases and include adenocarcinoma, squamous cell carcinoma and large cell carcinoma. NSCLC may be characterized into stages I-IV by assessing the size and extent of the primary tumor, whether or not the cancer has spread to nearby lymph nodes and metastasis to distant sites (e.g., brain bones, kidneys, liver, or adrenal glands, or other lung). See, e.g., American Joint Committee on Cancer. Lung. In: AJCC Cancer Staging Manual. 8th ed. New York, NY: Springer; 2017: 431-456. SCLC includes small cell carcinoma (oat cell cancer) and combined small cell carcinoma.

Lung cancer may also be characterized by genetic alterations. See, e.g., Imielinski et al., Cell. 2012 Sep. 14; 150 (6):1107-20. For example, a lung cancer may comprise an oncogenic mutation in KRAS and/or P53. In some embodiments, a lung cancer comprises a Eml4-Alk (EA) fusion.

Interstitial lung disease (ILD) refers to disorders that cause fibrosis of the lungs. Non-limiting examples of ILDs include sarcoidosis, asbestosis, hypersensitivity pneumonitis, and idiopathic pulmonary fibrosis. In some cases, ILD is caused by exposure to hazardous chemicals, medical treatments, or medications.

Chronic obstructive pulmonary disease (COPD) may also be referred to as chronic bronchitis or emphysema. COPD is often characterized by obstructed airflow and difficulty breathing. Causes of COPD include tobacco smoke, air pollution and genetic alterations (e.g., alterations resulting in alpha 1 antitrypsin deficiency).

Lung infections are lung diseases associated with a pathogen (e.g., bacteria, viruses, fungi, and protozoa). Non-limiting examples of pathogenic bacteria include *Streptococcus pneumoniae, Staphylococcus aureus, Streptococcus pygenes, Haemophilus influenza, Klebsiella pneumoniae, Escherichia coli, Pseudomonas aeruginosa, Mycoplasma pneumoniae, Legionella* spp, Anaerobic bacteria, *Mycobacterium tuberculosis, Mycoplasma* spp, *Coxiella burnelil, Chlamydia psittaci, Chlamydia trachomatis,* and *Chylamydia pneumoniae*. Non-limiting examples of viral pathogens include adenoviruses, influenza viruses, and respiratory syncytial viruses. Lung infections caused by pathogens include pneumonia and bronchitis. In some embodiments, a lung infection (e.g., a lung infection-specific) protease is a pathogen-derived protease (e.g., a pathogen-specific protease). In some embodiments, a lung infection-specific protease is a protease that is not in healthy subjects or samples from healthy subjects. In some embodiments, a lung infection-specific protease is a protease that is present in one type of lung infection but not in another type of lung infection.

As used herein, a substrate (e.g., protease substrate) may be enzymatically cleaved by one or more proteases (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, or at least 100) proteases.

A lung protease nanosensor of the present disclosure may detect the activity of an endogenous and/or an exogenous protease. An endogenous protease is a protease that is naturally produced by a subject (e.g., subject with a particular lung disease or a host with a lung infection). An exogenous protease is a protease that is not naturally produced by a subject and may be produced by a pathogen (e.g., a bacteria, a fungi, protozoa, or a virus). In some embodiments, a protease is only expressed by a subject (e.g., a human) and not by pathogen. In some embodiments, a protease is pathogen-specific and is only produced by a pathogen not by the pathogen's host. Without being bound by a particular theory, a lung protease nanosensor that comprises a substrate for a pathogen-specific protease would not be cleaved by a host-specific protease. In some embodiments, a pathogen-specific protease is produced by one pathogen but not another. Such pathogen-specific proteases may be useful in distinguishing between different pathogen-induced diseases. In some embodiments, a protease that is produced by a host, a pathogen or both, but is not active does not promote the release of a detectable marker from a lung protease nanosensor.

In some embodiments, lung cancer (e.g., NSCLC including lung adenocarcinoma or SCLC) is associated with one or more proteases listed in Table 1, FIG. 2A, 2B, 2C, or FIG. 7. In some embodiments, lung cancer is associated with ACE2, CTSD, F7, KLK13, KLK14, KLK6, MMP1, MMP11, MMP12, MMP13, MMP3, NAPSA, PRSS22, PRSS3, and/or PRSS8 activity. In some embodiments, F12, F7, KLK13, KLK14, KLK6, PRSS22, PRSS3, PRSS8, and/or TMPRSS11E activity is associated with lung cancer and distinguishes lung cancer from non-cancerous lung diseases including interstitial lung disease (ILE) and chronic obstructive pulmonary disease (COPD).

TABLE 1

Non-limiting Examples of Lung Cancer Proteases

| Protease | Alternative Names | Type | Protein GenBank Accession No. |
| --- | --- | --- | --- |
| CTSD | CPSD; CLN10; HEL-S-130P; cathepsin D | aspartic protease | NP_001900.1 |
| NAPSA | KAP; Kdap; NAP1; NAPA; SNAPA; napsin A aspartic peptidase | aspartic protease | NP_004842.1 |
| ADAM12 | metallopeptidase domain 12; MCMP; MLTN; CAR10; MLTNA; MCMPMltna; ADAM12-OT1 | metalloproteinase | NP_001275902.1 |
| TLL2 | tolloid-like protein 2 | metalloproteinase | NP_036597.1 |
| ACE2 | ACEH; angiotensin I converting enzyme 2 | metalloproteinase | NP_068576.1 |
| MMP1 | CLG; CLGN; matrix metallopeptidase 1 | metalloproteinase | NP_001139410.1; NP_002412.1 |
| MMP10 | matrix metallopeptidase 10; SL-2; STMY2 | metalloproteinase | NP_002416.1 |
| MMP11 | ST3; SL-3; STMY3; matrix metallopeptidase 11 | metalloproteinase | NP_005931.2 |
| MMP12 | ME; HME; MME; MMP-12; matrix metallopeptidase 12 | metalloproteinase | NP_002417.2 |
| MMP13 | CLG3; MDST; MANDP1; MMP-13; matrix metallopeptidase 13 | metalloproteinase | NP_002418.1 |
| MMP3 | SL-1; STMY; STR1; CHDS6; MMP-3; STMY1; matrix metallopeptidase 3 | metalloproteinase | NP_002413.1 |

TABLE 1-continued

Non-limiting Examples of Lung Cancer Proteases

| Protease | Alternative Names | Type | Protein GenBank Accession No. |
| --- | --- | --- | --- |
| F12 | coagulation factor XII; HAF; HAE3; HAEX | serine protease | NP_000496.2 |
| F7 | coagulation factor VII; SPCA | serine protease | NP_000122.1 |
| KLK13 | KLKL4; KLK-L4; kallikrein related peptidase 13 | serine protease | NP_001335106.1; NP_001335107.1; NP_056411.1 |
| KLK14 | KLK-L6; kallikrein related peptidase 14 | serine protease | NP_001298111.1; NP_071329.2 |
| KLK6 | hK6; Bssp; Klk7; SP59; PRSS9; PRSS18; kallikrein related peptidase 6 | serine protease | NP-001012982.1; NP_001012983.1; NP-001306877.1; 001306878.1; NP_002765.1 |
| PRSS22 | BSSP-4; SP001LA; hBSSP-4; serine protease 22 | serine protease | NP_071402.1 |
| PRSS3 | T9; MTG; TRY3; TRY4; PRSS4; serine protease 3 | serine protease | NP_001184026.2; NP_001184027.1; NP_002762.2; NP_031369.2 |
| PRSS8 | serine protease 8; CAP1; PROSTASIN | serine protease | NP_002764.1 |
| TMPRSS11E | DESC1; TMPRSS11E2; transmembrane serine protease 11E | serine protease | NP_054777.2 |

In some embodiments, lung infection is associated with a virulence factor (e.g., a protease secreted by a pathogen). In some embodiments, a pathogen-specific (e.g., *Pseudomonas aeruginosa*-specific) infection is LasA (e.g., UniProtKB—Q02L18), Large ExoProtease A (LepA, e.g., UniProtKB—Q02L18), protease IV (e.g., UniProtKB—P08395), Protease IV, or alkaline protease (AprA, e.g., UniProtKB—Q4Z8K9). A non-limiting example of a LasA substrate is a sequence comprising the amino acid sequence LGGGA (SEQ ID NO: 43).

In some embodiments, lung infection is associated with a host factor (e.g., a protease secreted by an immune cells). For example, neutrophil elastase (ELA, e.g., NP_001963.1) is often secreted by neutrophils in response to an infection. A non-limiting example of a neutrophil elastase substrate is AAFA (SEQ ID NO: 44).

A nanosensor is designed with one or more substrates that match those of the enzymes expressed by diseased tissue (e.g., lung disease tissue). Alternatively, the substrate may be associated with enzymes that are ordinarily present but are absent in a particular disease state. In this example, a disease state would be associated with a lack of signal associated with the enzyme, or reduced levels of signal compared to a normal reference.

An enzyme, as used herein refers to any of numerous proteins produced in living cells that accelerate or catalyze the metabolic processes of an organism. Enzymes act on substrates and may be derived from a host or a pathogen (e.g., pathogen associated with an infection). The substrate binds to the enzyme at a location called the active site just before the reaction catalyzed by the enzyme takes place. Enzymes include but are not limited to proteases, glycosidases, lipases, heparinases, phosphatases.

In some embodiments, a substrate comprises an amino acid sequence that is cleaved by an enzyme (e.g., a protease substrate). In some embodiments, the enzyme-specific substrate comprises an amino acid sequence cleaved by a serine protease, an alkaline protease, a lysine-specific protease, cysteine protease, threonine protease, aspartic protease (e.g., AspA), glutamic protease, and/or a metalloproteinase (i.e.: metalloprotease). As their names suggest, serine, cysteine, threonine, and aspartic proteases use a catalytic serine, cysteine, threonine, or aspartate residue, respectively, for catalysis. Mechanistically, metalloprotenaises use a metal in catalysis.

In some embodiments, a substrate comprises a sequence that is at least 90% identical to a sequence selected from SEQ ID NOs: 1-14. In some embodiments a substrate comprises SEQ ID NOs: 1-14. In some embodiments, a substrate further comprises two glycines (e.g., the glycines. In some embodiments, the two glycines (G) are located at the N-terminus of the substrate. In some embodiments, one of the two glycines is conjugated to the carrier domain of a lung protease nanosensor. In some embodiments, a substrate may further comprise a cysteine (C). In some embodiments, the cysteine in a substrate is conjugated to the detectable marker.

In some embodiments, the serine protease is selected from the group consisting of F12, F7, KLK13, KLK14, KLK6, PRSS22, PRSS3, PRSS8, and TMPRSS11E.

In some embodiments, the metalloprotease is selected from the group consisting of TLL2, ACE2, ADAM12, MMP1, MMP10, MMP11, MMP12, MMP13, and MMP3.

In some embodiments, the aspartic protease is selected from the group consisting of NAPSA and CTSD.

A substrate may be attached directly to the scaffold. For instance it may be coated directly on the surface of microparticles using known techniques, or chemically bonded to a polymeric scaffold, such as a PEG scaffold (e.g., via a peptide bond). Additionally, the substrate may be connected to the scaffold through the use of a linker. As used herein "linked" or "linkage" means two entities are bound to one another by any physicochemical means. Any linkage known to those of ordinary skill in the art, covalent or non-covalent, is embraced. Thus, in some embodiments the scaffold has a linker attached to an external surface, which can be used to link the substrate. Another molecule can also be attached to the linker. In some embodiments, two molecules are linked using a transpeptidase, for example Sortase A.

The substrate is preferably a polymer made up of a plurality of chemical units. A "chemical unit" as used herein is a building block or monomer which may be linked directly or indirectly to other building blocks or monomers to form a polymer (e.g., a multi-arm PEG scaffold).

Linker Molecules

A substrate (e.g., protease substrate) may be attached directly to the carrier. For instance it may be coated directly on the surface of particles (e.g., microparticles or nanoparticles) using known techniques. Alternatively if the carrier is a protein material it may be directly connected through a peptide bond. Additionally, the enzyme susceptible detectable marker may be connected to the scaffold through the use of a linker. As used herein "linked" or "linkage" means two entities are bound to one another by any physicochemical means. Any linkage known to those of ordinary skill in the art, covalent or non-covalent, is embraced. Thus, in some embodiments the carrier has a linker attached to an external surface, which can be used to link the enzyme susceptible detectable marker. Another molecule can also be attached to the linker. In some embodiments, two molecules are linked using a transpeptidase, for example Sortase A.

The sensitivity and specificity of a lung protease nanosensor may be significantly improved by modulating presentation of the substrate to its cognate enzyme, for example by varying the distance between the scaffold and the substrate of the lung protease nanosensor. For example, in some embodiments, a polymer comprising one or more linking molecules is used to adjust the distance between a scaffold and a substrate, thereby improving presentation of the substrate to an enzyme.

In some embodiments, the distance between a scaffold and a substrate (e.g., protease substrate) ranges from about 1.5 angstroms to about 1000 angstroms. In some embodiments, the distance between a scaffold and substrate ranges from about 10 angstroms to about 500 angstroms (e.g., any integer between 10 and 500). In some embodiments, the distance between a scaffold and a substrate ranges from about 50 angstroms to about 800 angstroms (e.g., any integer between 50 and 800). In some embodiments, the distance between a scaffold and an substrate ranges from about 600 angstroms to about 1000 angstroms (e.g., any integer between 600 and 1000). In some embodiments, the distance between a scaffold and an substrate is greater than 1000 angstroms.

Examples of linking molecules include but are not limited to poly(ethylene glycol), peptide linkers, N-(2-Hydroxypropyl) methacrylamide linkers, elastin-like polymer linkers, and other polymeric linkages. Generally, a linking molecule is a polymer and may comprise between about 2 and 200 (e.g., any integer between 2 and 200, inclusive) molecules. In some embodiments, a linking molecule comprises one or more poly(ethylene glycol) (PEG) molecules. In some embodiments, a linking molecule comprises between 2 and 200 (e.g., any integer between 2 and 200, inclusive) PEG molecules. In some embodiments, a linking molecule comprises between 2 and 20 PEG molecules. In some embodiments, a linking molecule comprises between 5 and 15 PEG molecules. In some embodiments, a linking molecule comprises between 5 and 25 PEG molecules. In some embodiments, a linking molecule comprises between 10 and 40 PEG molecules. In some embodiments, a linking molecule comprises between 25 and 50 PEG molecules. In some embodiments, a linking molecule comprises between 100 and 200 PEG molecules.

Detectable Markers

A detectable marker is capable of being released from a lung protease nanosensor when exposed to an enzyme in vivo or in vitro. In some embodiments, the detectable once released is free to travel to a remote site for detection. A remote site is used herein to refer to a site in the body that is distinct from the bodily tissue (e.g., lung) housing the enzyme where the enzymatic reaction occurs. In some embodiments, the bodily tissue housing the enzyme where the enzymatic reaction occurs is a tumor (e.g., lung tumor). In some embodiments, a remote site is a biological sample that is non-invasively obtained from a subject, for example a urine sample, or a blood sample.

Modification of the enzyme susceptible domain by an enzyme in vivo or in vitro, results in the production of a detectable marker (e.g., a detectable marker). In some embodiments, the detectable marker is composed of two ligands joined by a linker, as described above. The detectable marker may be comprised of, for instance one or more of a peptide, nucleic acid, small molecule, fluorophore/quencher, carbohydrate, particle, radiolabel, MRI-active compound, inorganic material, organic material, with encoded characteristics to facilitate optimal detection.

Aspects of the disclosure relate to the surprising discovery that lung protease nanosensors are useful for noninvasive detection of lung enzymatic activity. For example, the detectable markers may be detected in a biological sample that is not taken from the lung (e.g., urine, mucous secretion, lymph nodes or blood). Accordingly, in some embodiments, a detectable marker is cleaved by one or more proteases in the lung and the detectable marker travels to a site that is remote from the lung. In some embodiments, a detectable marker remains bound to a carrier domain (e.g. directly or indirectly) after cleavage of an enzyme susceptible domain. For example, in some embodiments, a detectable marker comprises a FRET pair (e.g., a fluorophore and a quencher) linked by an enzyme susceptible domain, configured such that cleavage of the enzyme susceptible domain results in release of the quencher molecule from the carrier domain and detection of the carrier domain-linked fluorophore.

A detection ligand is a molecule that is capable of being detected by any of a variety of methods. A lung protease nanosensor may be heterobifunctional and comprise a capture ligand and a different detection ligand. While a capture ligand and a detection ligand will be distinct from one another in a particular detectable marker, the class of molecules that make up capture and detection ligands overlap significantly. For instance, many molecules are capable of being captured and detected. In some instances these molecules may be detected by being captured or capturing a probe. The capture and detection ligand each independently may be one or more of the following: a protein, a peptide, a polysaccharide, a nucleic acid, a fluorescent molecule, or a small molecule, for example. In some embodiments the detection ligand or the capture ligand may be, but is not limited to, one of the following: Alexa488, TAMRA, DNP, fluorescein, Oregon Green, Texas Red, Dansyl, BODIPY, Alexa405, Cascade Blue, Lucifer Yellow, Nitrotyrosine, HA-tag, FLAG-tag, His-tag, Myc-tag, V5-tag, S-tag, biotin or streptavidin. In some embodiments, the capture ligand and a detection ligand are connected by a linker. See, e.g., WO2014/197840, which was filed on Jun. 6, 2014, the entire contents of which are incorporated herein by reference. The purpose of the linker is prevent steric hindrance between the two ligands. Thus, the linker may be any type of molecule that achieves this. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib. Optionally, the linker may be 8 nm-100 nm, 6 nm-100 nm, 8 nm-80 nm, 10 nm-100 nm, 13 nm-100 nm, 15 nm-50 nm, or 10 nm-50 nm in length.

In some embodiments, a detectable marker is a mass encoded reporter, for example an iCORE as described in WO2012/125808, filed Mar. 15, 2012, the entire contents of which are incorporated herein by reference. In some embodiments, a detectable marker comprises a sequence selected from the group consisting of SEQ ID NOs: 15-28. In some embodiments, a detectable marker comprises a reporter sequence selected from Table 3. Upon arrival in the diseased microenvironment, the iCORE agents interface with aberrantly active proteases to direct the cleavage and release of surface-conjugated, mass-encoded peptide substrates into host urine for detection by mass spectrometry (MS) as synthetic biomarkers of disease.

The detectable marker may be detected by any known detection methods to achieve the capture/detection step. A variety of methods may be used, depending on the nature of the detectable marker. Detectable markers may be directly detected, following capture, through optical density, radioactive emissions, nonradiative energy transfers, or detectable markers may be indirectly detected with antibody conjugates, affinity columns, streptavidin-biotin conjugates, PCR analysis, DNA microarray, and fluorescence analysis.

The capture assay in some embodiments involves a detection step selected from the group consisting of an ELISA, including fluorescent, colorimetric, bioluminescent and chemiluminescent ELISAs, a paper test strip or LFA, bead-based fluorescent assay, and label-free detection, such as surface plasmon resonance (SPR). The capture assay may involve, for instance, binding of the capture ligand to an affinity agent.

The analysis step may be performed directly on the biological sample or the detectable marker component may be purified to some degree first. For instance, a purification step may involve isolating the detectable marker from other components in the biological sample. Purification steps include methods such as affinity chromatography. As used herein an "isolated molecule" or "purified molecule" is a detectable marker that is isolated to some extent from its natural environment. The isolated or purified molecule need not be 100% pure or even substantially pure prior to analysis.

The methods for analysing detectable markers by identifying the presence of a detectable marker may be used to provide a qualitative assessment of the molecule (e.g., whether the detectable marker is present or absent) or a quantitative assessment (e.g., the amount of detectable marker present to indicate a comparative activity level of the enzymes. The quantitative value may be calculated by any means, such as, by determining the percent relative amount of each fraction present in the sample. Methods for making these types of calculations are known in the art.

The detectable marker may be labeled. For example, a label may be added directly to a nucleic acid when the isolated detectable marker is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidites such as fluoreprime (Pharmacia, Piscataway, NJ), fluoredite (Millipore, Bedford, MA), FAM (ABI, Foster City, CA), rhodamine, polymethadine dye derivative, phosphors, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed"). Radionuclides such as $^3$H, $^{125}$I, $^{35}$S, $^{14}$C, or $^{32}$P are also useful labels according to the methods of the invention. A plurality of radioactively distinguishable radionuclides can be used. Such radionuclides can be distinguished, for example, based on the type of radiation (e.g. α, β, or δ radiation) emitted by the radionuclides. The $^{32}$P signal can be detected using a phosphoimager, which currently has a resolution of approximately 50 microns. Other known techniques, such as chemiluminescence or colormetric (enzymatic color reaction), can also be used.

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET), such as fluorescence resonance energy transfer (FRET). Cleavage of the peptide results in separation of the chromophore and fluorophore, removal of the quench, and generation of a subsequent signal measured from the donor fluorophore. Examples of FRET pairs include 5-Carboxyfluorescein (5-FAM) and CPQ2, FAM and DABCYL, Cy5 and QSY21, Cy3 and QSY7, etc.

The disease or condition assessed according to the methods of the invention is any lung disease or condition that is associated with an enzymes. For example, lung diseases include lung cancer, Chronic Obstructive Pulmonary Disease (COPD), and interstitial lung disease (ILD). Exemplary lung cancers include non-small cell lung cancer (NSCLC) (e.g., squamous cell carcinoma, adenocarcinoma, and large cell carcinoma), small cell lung cancer (SCLC), and lung carcinoid tumor (i.e., lung neuroendocrine tumors). In some embodiments, the lung disease is lung adenocarcinoma and proteases associated with lung adenocarcinoma include NAPSA, CTSD, MMP13, MMP11, MMP1, MMP12, MMP3, ACE2, KLK6, PRSS3, F7, PRSS22, KLK14, KLK13, and PRSS8. Proteases associated with infectious disease (e.g., *Pseudomonas aeruginosa* infection) include LasA (e.g., UniProtKB—Q02L18), Large ExoProtease A (LepA, e.g., UniProtKB—Q02L18), protease IV (e.g., UniProtKB—P08395), Uni, Protease IV, or alkaline protease (AprA, e.g., UniProtKB—Q4Z8K9).

Further Modifications of the Lung Protease Nanosensor

Lung protease nanosensors may further comprise tumor-penetrating ligands to increase the sensitivity and selectivity of the lung protease nanosensor with regard to detection of the detectable marker at a site that is not the lung. A lung protease nanosensor, in some embodiments, comprises a modification that localizes the reagent to a target tissue (e.g., tissue of a tumor microenvironment). In some embodiments, the lung protease nanosensor comprises a tumor-penetrating peptide, for example a peptide that binds to a receptor involved in the active transport pathway of a cancer cell (e.g., p32 or NRP-1). Without wishing to be bound by any particular theory, a lung protease nanosensor comprising a tumor-penetrating peptide increases on-target (e.g., cell-type specific) and decreases off-target protease cleavage that occurs in vivo relative to a lung protease nanosensor that does not comprise a tumor-penetrating peptide.

Methods to Spatially Profile Protease Activity in Lung

Aspects of the disclosure relate to the surprising discovery that lung protease nanosensors comprising a detectable marker, are useful for detecting enzymatic activity (e.g., protease activity) in lung. As an example, a lung protease nanosensor of the present disclosure may be used to detect in vivo protease activity in a lung of a subject.

As used herein, a biological sample is a tissue sample (such as a blood sample, a hard tissue sample, a soft tissue sample, etc.), a urine sample, saliva sample, fecal sample, seminal fluid sample, cerebrospinal fluid sample, etc. In preferred embodiments, the biological sample is a tissue sample. The tissue sample may be obtained from any tissue of the subject, including brain, lymph node, breast, liver, pancreas, colon, liver, lung, blood, skin, ovary, prostate, kidney, or bladder. The tissue from which the biological sample is obtained may be healthy or diseased. In some embodiments, a tissue sample comprises tumor cells or a tumor.

A tissue sample for use in methods described by the disclosure may be unmodified (e.g., not treated with any fixative, preservative, cross-linking agent, etc.) or physically or chemically modified. Examples of fixatives include aldehydes (e.g., formaldehyde, formalin, gluteraldehyde, etc.), alcohols (e.g., ethanol, methanol, acetone, etc.), and oxidizing agents (e.g., osmium tetroxide, potassium dichromate, chromic acid, potassium permanganate, etc.). In some embodiments, a tissue sample is cryopreserved (e.g., frozen). In some embodiments, a tissue sample is embedded in paraffin.

A lung protease nanosensor of the present disclosure may also be used to detect protease activity in vitro. As an example, a lung protease nanosensor may be added to a biological sample (e.g., lung tissue) to assess protease activity.

Methods for Detecting Lung Disease in a Subject

In some aspects, the disclosure provides methods for detecting a lung disease (e.g., lung cancer or lung infection) in a subject. As used herein, a subject is a human, non-human primate, cow, horse, pig, sheep, goat, dog, cat, or rodent. In all embodiments human subjects are preferred. In aspects of the invention pertaining to cancer diagnosis in general the subject preferably is a human suspected of having cancer, or a human having been previously diagnosed as having cancer (e.g., lung cancer). In aspects of the invention pertaining to lung infection diagnosis in general the subject preferably is a human suspected of having a lung infection, or a human having been previously diagnosed as having a lung infection (e.g., *Pseudomonas aeruginosa* infection). Methods for identifying subjects suspected of having a lung disease (e.g., cancer or lung infection) may include physical examination, subject's family medical history, subject's medical history, biopsy, or a number of imaging technologies such as ultrasonography, computed tomography, magnetic resonance imaging, magnetic resonance spectroscopy, or positron emission tomography.

The disclosure is based, in part, on the discovery that lung protease nanosensors described herein are capable of detecting tumors smaller than 5 mm in diameter in a subject, which is surprising because generally the ability to identify cancer lesions with endogenous biomarkers was previously thought to be limited to detection of tumors greater than 1 cm in diameter. In some embodiments, methods described by the disclosure result in identification (e.g., detection) of a tumor smaller than 1 cm in a subject. In some embodiments, a tumor that is less than 1 cm, less than 0.5 cm, or less than 0.005 cm is detected using methods described by the disclosure. In some embodiments, the tumor that is detected is between 1 mm and 5 mm in diameter (e.g., about 1 mm, 2 mm, 3 mm, 4 mm, or about 5 mm) in diameter.

In some embodiments, the presence of a tumor or a pathogen in a subject is identified by obtaining a biological sample from a subject that has been administered a lung protease nanosensor as described by the disclosure and detecting the presence of a detectable marker in the biological sample. Generally, the biological sample may be a tissue sample (such as a blood sample, a hard tissue sample, a soft tissue sample, etc.), a urine sample, saliva sample, fecal sample, seminal fluid sample, cerebrospinal fluid sample, etc.

Detection of one or more detectable markers in the biological sample may be indicative of a subject having a lung disease (e.g., lung infection, lung cancer, COPD, or ILD). In some instances, detection of one or more detectable markers in the biological sample is indicative of a specific stage of lung cancer (e.g., stages I-IV, metastatic or non-metastatic). In some embodiments, detection of one or more detectable markers in the biological sample is indicative of a type of lung infection (e.g., pneumonia or bronchitis).

The lung nanosensors described herein may be used to monitor the effect of a particular treatment. A lung nanosensor may be administered more than once (e.g., at least twice, at least three times, at least four times, at least five times, or at least 10 times) to a subject. In some embodiments, the subject has been treated with a therapeutic agent (e.g., a chemotherapy, an antibiotic, a targeted agent including a various kinase inhibitors). A subject may be treated with a the therapeutic agent prior to the first administration of a lung protease nanosensor or be treated with a therapeutic agent after administration of a lung protease nanosensor (e.g., between two administrations of a lung nanosensor, or after one administration of a lung nanosensor).

The method may further comprise characterizing a subject as responsive or resistant to a treatment. For example, a subject may be administered a lung protease nanosensor comprising a lung disease-specific substrate (e.g., a lung infection-specific substrate or a lung cancer-specific substrate) before and after treatment with a biological agent. A decrease in the amount of detectable marker (e.g., at least 10% decrease, at least 20% decrease, at least 30% decrease, at least 40% decrease, at least 50% decrease, at least 60% decrease, at least 70% decrease, at least 80% decrease, or at least 90% decrease) detected in a biological sample from the subject in the post-treatment sample compared to the pre-treatment sample may indicate that the subject is responsive to treatment. A subject whose levels of detectable marker in a biological sample stays the same or increases (e.g., by at least 10%, at least 20%, at least 30%, at least 40%, at least 50%, at least 60%, at least 70%, at least 80%, at least 90%) may be characterized as being resistant to the biological agent.

A detectable marker may be detected using any of the methods described herein. In some embodiments, a subject's treatment is continued, stopped, or altered (e.g., a different therapeutic agent is used) following quantification of one or more detectable markers.

Methods of Producing a Lung Disease Signature

As described above, widely accepted endogenous biomarkers for lung diseases (e.g., lung cancer or lung infections) are lacking. Furthermore, detection of expression of one or more endogenous proteases in the lung provides no information regarding protease activity. The lung protease nanosensors of the present disclosure, in some embodiments, seek to address these limitations.

To produce a lung disease signature, a population of lung protease nanosensors (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, or at least 100) may be administered to a subject (including a population of subjects) diagnosed with a particular lung disease (e.g., lung infection, lung cancer, ILD, or COPD). Any detectable markers that have been released from the lung protease nanosensors may then be detected to produce a detectable marker signature indicative of the lung disease (i.e.: signature of active proteases in the lung disease).

Similarly, a detectable marker signature may be produced for various stages (e.g., stages I-IV, metastatic or non-metastatic, infectious or non-infectious) and/or types (e.g., NSCLC or SCLC, type of infection) of lung disease. A population of lung nanosensors may be administered to a subject with a known stage of a lung disease or type of lung disease and any detectable markers that have been released from the lung protease nanosensors may then be detected to produce a signature of a particular stage or type of lung disease.

A lung disease detectable marker signature may be used to diagnose a subject with a type and/or stage of lung disease. For example, the same population of lung protease nanosensors that were administered to determine the lung disease type or stage detectable marker signature may be administered to another subject whose lung disease status is unknown (e.g., a subject suspected of having lung cancer or a lung infection). A detectable marker signature may then be generated from this subject and compared with the known detectable marker signature to diagnosis the subject.

In some embodiments, the methods described herein may be used to distinguish between healthy subjects and subjects with a particular type and/or stage of lung disease, distinguish between types and/or stages of lung disease, or between subjects who are sensitive to a treatment as compared to subjects who are resistant to a treatment with a specificity of at least 10%, at least 20%, at least 30%, at least 40%, at least 50%, at least 60%, at least 70%, at least 75%, at least 80%, at least 85%, at least 90%, at least 95%, or 100%. In some embodiments, a method described herein is capable of correctly diagnosing, characterizing or classifying a subject with a probability of at least 10%, at least 20%, at least 30%, at least 40%, at least 50%, at least 60%, at least 70%, at least 75%, at least 80%, at least 85%, at least 90%, at least 95%, or 100%. For example, specificity may be determined by the ability of a test to correctly identify a subject as having a particular type and/or stage of lung disease. In some embodiments, the false positive rate is less than 50%, less than 40%, less than 30%, less than 20%, less 10%, or less than 5%.

In some embodiments, the methods described herein may allow for sensitive detection of a lung disease. In some embodiments, a method described herein is capable of detecting a tumor that is less than 500 $mm^3$, less than 400 $mm^3$, less than 300 $mm^3$, less than 200 $mm^3$, less than 100 $mm^3$, less than 50 $mm^3$, less than 25 $mm^3$, less than 20 $mm^3$, less than 15 $mm^3$, less than 10 $mm^3$, less than 5 $mm^3$, less than 4 $mm^3$, less than 3 $mm^3$, less than 2 $mm^3$, less than 1 $mm^3$, less than 0.5 $mm^3$, less than 0.4 $mm^3$, less than 0.3 $mm^3$, less than 0.2 $mm^3$, less than 0.1 $mm^3$, less than 0.5 $mm^3$, or less than 0.01 $mm^3$. In some embodiments, a subject has a tumor that is less than 500 $mm^3$, less than 400 $mm^3$, less than 300 $mm^3$, less than 200 $mm^3$, less than 100 $mm^3$, less than 50 $mm^3$, less than 25 $mm^3$, less than 20 $mm^3$, less than 15 $mm^3$, less than 10 $mm^3$, less than 5 $mm^3$, less than 4 $mm^3$, less than 3 $mm^3$, less than 2 $mm^3$, less than 1 $mm^3$, less than 0.5 $mm^3$, less than 0.4 $mm^3$, less than 0.3 $mm^3$, less than 0.2 $mm^3$, less than 0.1 $mm^3$, less than 0.5 $mm^3$, or less than 0.01 $mm^3$. In some embodiments, a subject has had a disease for at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 1 month, at least 2 months, at least 3 months, at least 4 months, at least 5 months, at least 6 months, at least 7 months, at least 8 months, at least 9 months, at least 10 months, at least 11 months, at least a year, at least 2 years at least 3 years at least 4 years, at least 5 years, at least 6 years, at least 7 years, at least 8 years, at least 9 years, at least 10 years, at least 11 years, at least 12 years, at least 13 years, at least 14 years, at least 15 years, at least 20 years, at least 30 years, at least 40 years, or at least 50 years.

Administration

Compositions described herein can be administered to any suitable subject. In some embodiments, lung protease nanosensors of the disclosure are administered to the subject in an effective amount for detecting enzyme activity. An "effective amount", for instance, is an amount necessary or sufficient to cause release of a detectable level of detectable marker in the presence of an enzyme. The effective amount of a compound of the invention described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Aspects of the disclosure relate to systemic administration of a lung protease nanosensor to a subject. In some embodiments, the systemic administration is injection, optionally subcutaneous injection. Preferably the material is administered to the lung of a subject. Non-limiting examples of methods of administration to the lung include intratracheal injection and inhalation (e.g., aerosol inhalation). Intrapulmonary administration may include dry powder inhalation and nebulization. The lung protease nanosensors may also be administered through any other suitable routes. For instance, the compounds of the present invention can be administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

In some embodiments, a detectable marker is detected at least 1 hour, at least 2 hours, at least 3, hours, at least 4 hours, at least 5 hours, at least 12 hours, at least 24 hours, at least two days, at least 3 days, at least 4 days, at least 5 days at least 6 days, at least 1 week, at least 2 weeks, at least 4 weeks at least 5 weeks, or at least 6 weeks following administration of the biomarker nanoparticle.

EXAMPLES

Example 1. Noninvasive Lung Cancer Detection Via Pulmonary Protease Profiling

Protease Targets Identified by RNA-Seq can Classify Human Lung Adenocarcinoma Vs Normal Tissue.

Figure 2A:
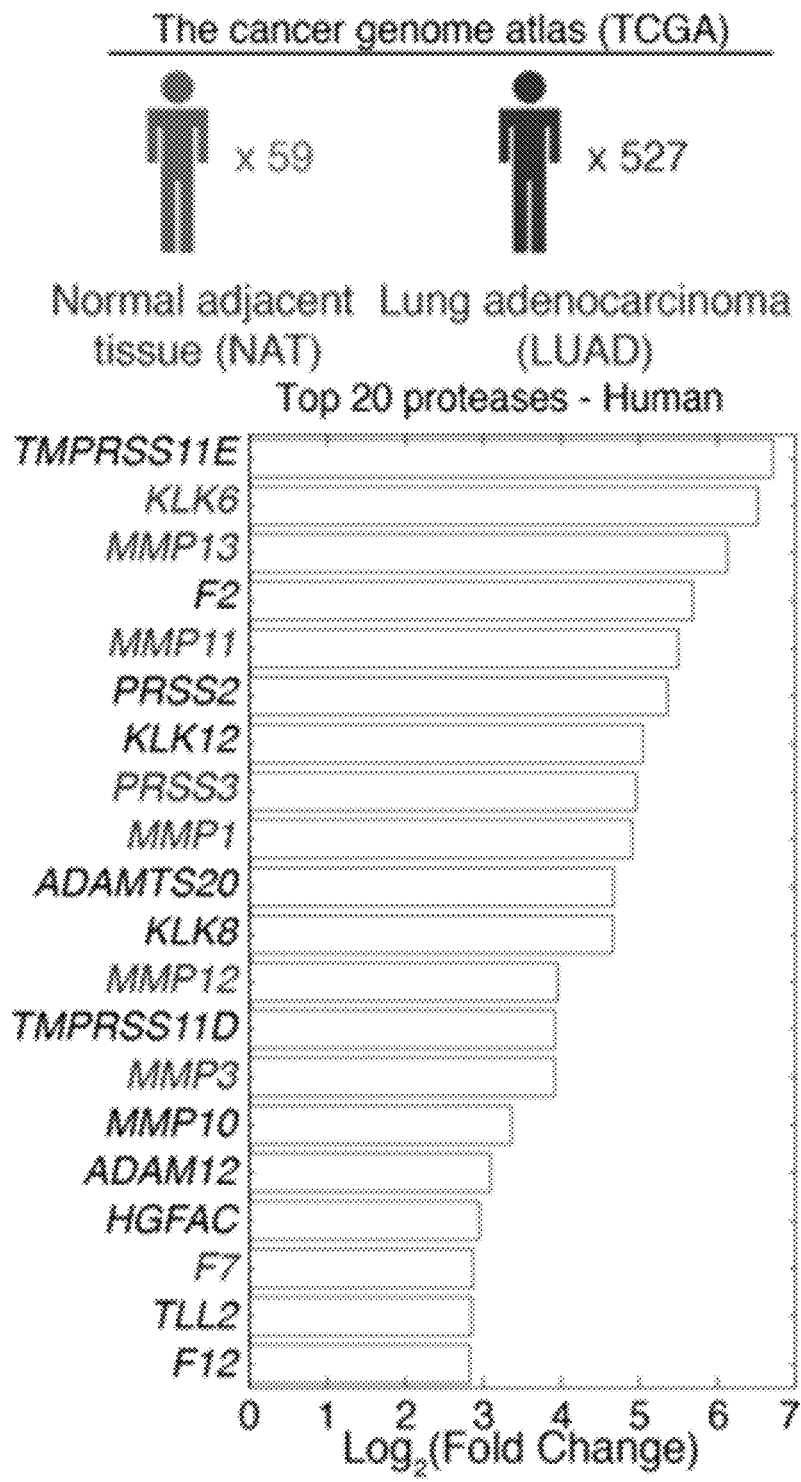
FIGS. 2A-2F include schematics showing that proteases are overexpressed in lung cancer and enable classification of human disease.

To nominate a panel of ABNs (e.g., lung protease nanosensors) tuned to detect human malignancies, proteases upregulated in human LUAD were identified (Olson et al., Nat Rev Cancer 15, 712-729 (2015); Ueno et al., Br J Cancer 88, 1229-1233 (2003); Roy et al., J Clin Oncol 27, 5287-5297 (2009)). Toward this end, The Cancer Genome Atlas (TCGA) was mined with mRNA sequencing (RNA-Seq) and clinical data was collected from 527 LUAD patients (Network, Nature 511, 543-550, 2014). Expression levels of 168 candidate human extracellular endoprotease genes were analyzed in these patients using the DESeq2 differential expression analysis package (FIG. 2A) (Love et al., Genome Biol 15, 550, 2014). Of the 527 TCGA patients with RNA-Seq data for primary LUAD (294 stage I, 123 stage II, 84 stage III, and 26 stage IV), 59 had matched normal adjacent tissue suitable for use as a comparison (FIG. 2A, upper panel). Of the 20 most highly upregulated proteases, nine were metalloproteases and 11 were serine proteases (FIG. 2A, lower panel).

Figures 7A, 7B, 7C, 7D:
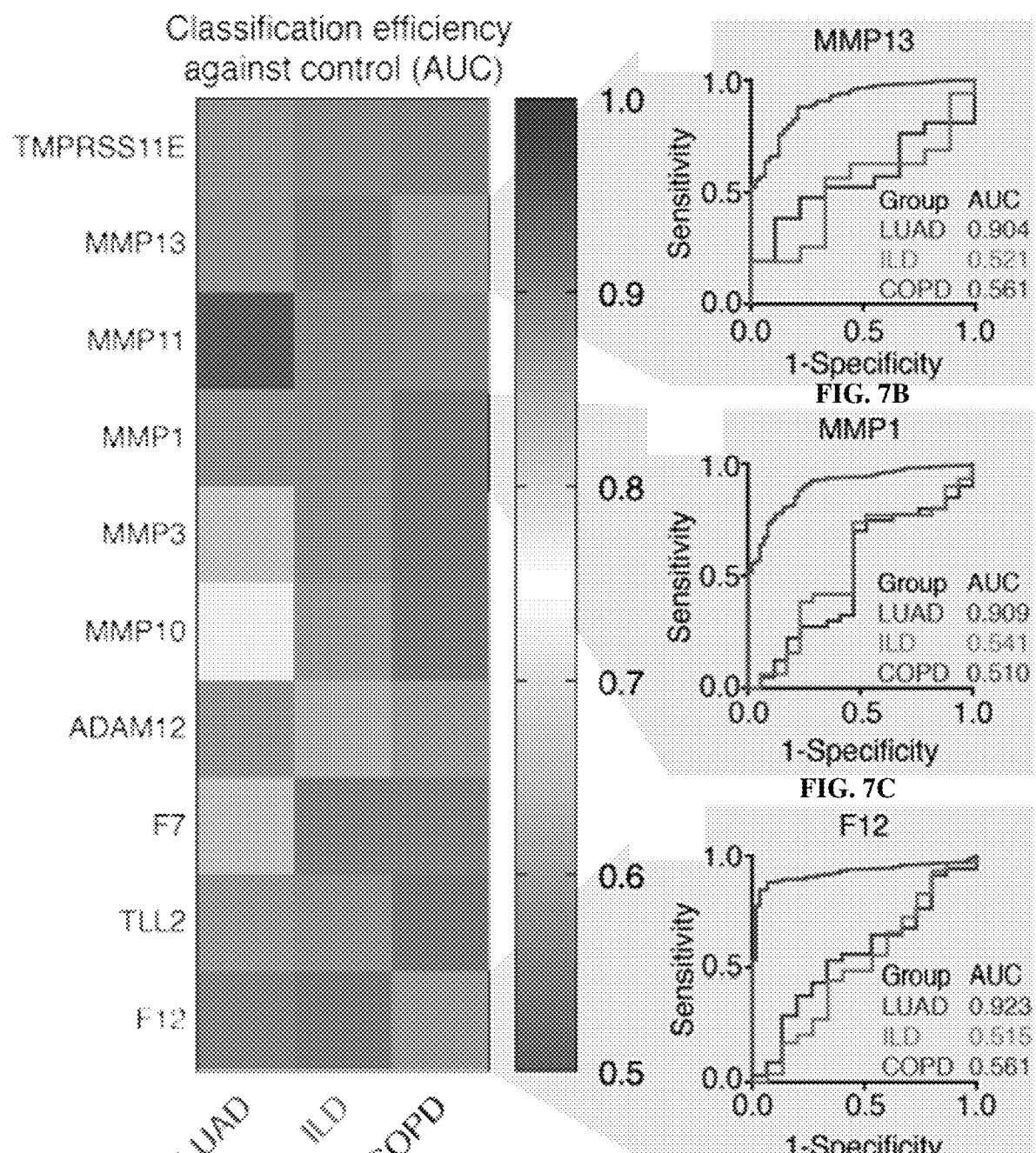
FIGS. 7A-7D show human LUAD-associated proteases are not overexpressed in benign lung diseases.

Analysis of RNA-Seq data from related pathologies [interstitial lung disease (ILD) and chronic obstructive pulmonary disease (COPD), curated by the Lung Genomics Research Consortium (LGRC)] revealed that proteases overexpressed in LUAD were not increased in COPD or ILD (FIG. 7A) (Kusko et al., Am J Respir Crit Care Med 194, 948-960, 2016). Indeed, none of the 10 proteases included in the analysis classified benign lung diseases from healthy lungs with an AUC greater than 0.6. In contrast, classification efficiency in LUAD reached above 0.9 in eight out of ten cases (FIGS. 7B-7D). The finding that genes upregulated in LUAD are not overexpressed in COPD or ILD may reflect our use of NAT as "normal" tissue when nominating proteases for the panel, as NAT is known to harbor inflammatory gene expression changes that distinguish it from "true normal" tissue (Aran et al., Nat Commun 8, 1077 (2017)). Therefore, the genes of the LUAD protease panel are more likely to be specific to cancer, rather than inflammation or other nonspecific disease-associated processes.

Figure 5A:
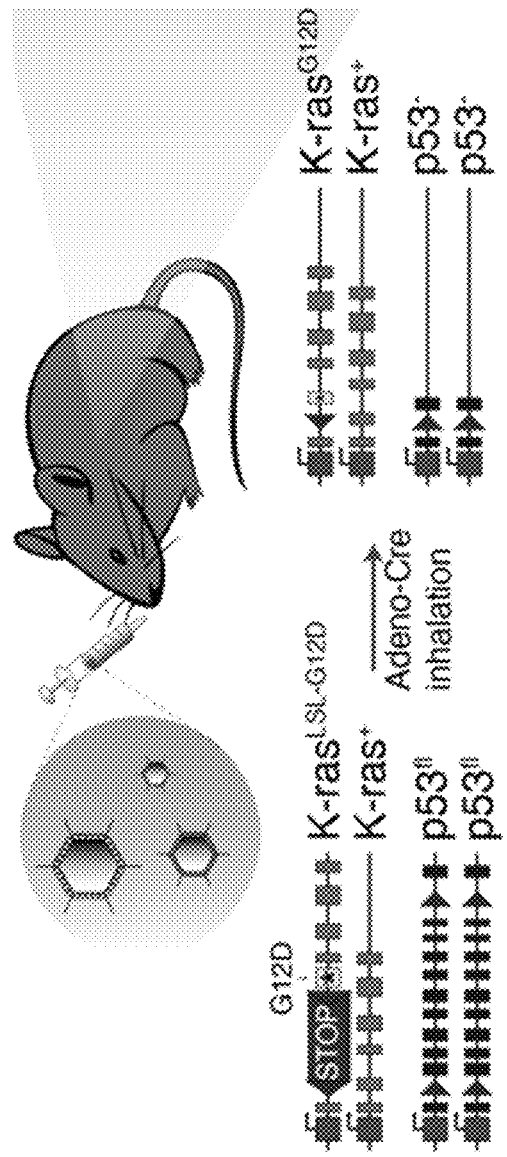
FIGS. 5A-5E show that the KP model genetically and histologically recapitulates human lung adenocarcinoma and ABNs distinguish between diseased and healthy mice.
Figure 5B:
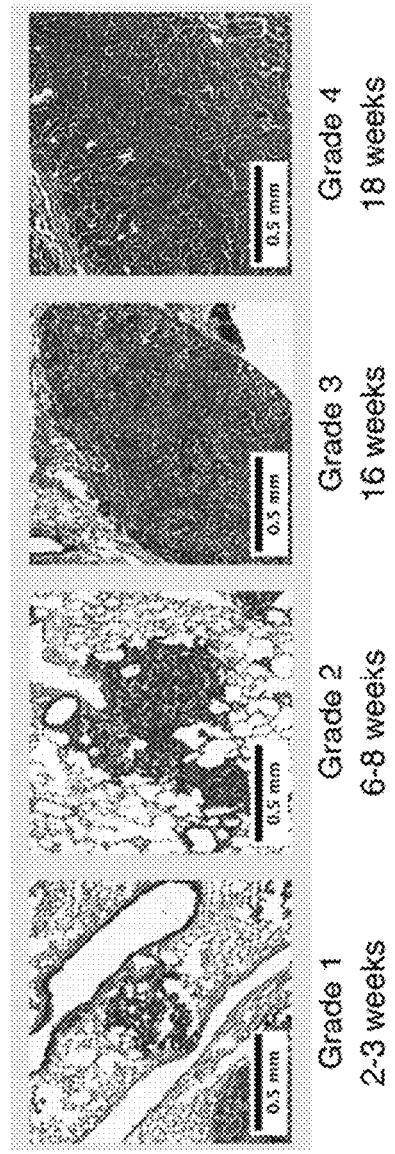

A Panel of Proteases Selected from Human and Mouse Gene Expression Datasets Enables Robust Classification of Human Lung Adenocarcinoma Nearly all lung cancers (>95%) are classified as non-small cell lung cancer (84%; NSCLC) or small cell lung cancer (13%; SCLC)(Howlader et al., SEER Cancer Statistics Review, 1975-2011, 2014). Common driver mutations of NSCLC are those that activate KRAS (10-30%) or inactivate function of TP53 (50-70%) (Herbst et al., N Engl J Med 359, 1367-1380, 2008). To examine the ability of the ABNs to detect lung cancer in a relevant mouse model, a genetically driven model of adenocarcinoma (a type of NSCLC that accounts for 38% of all cases of lung cancer (Howlader et al., SEER Cancer Statistics Review, 1975-2011, 2014)) was selected that incorporates mutation in these genes. This extensively characterized model uses intratracheal administration of virus expressing Cre recombinase to activate mutant $Kras^{G12D}$ and delete both copies of Trp53 in the lungs of $Kras^{LSL-G12D/+}$; $Trp53^{fl/fl}$ (KP) mice (FIG. 5A), initiating tumors that closely recapitulate human disease progression from alveolar adenomatous hyperplasia to grade IV adenocarcinoma over the course of about 18-20 weeks (FIG. 5B) (DuPage et al., Nat Protoc 4, 1064-1072, 2009).

Figure 2B:
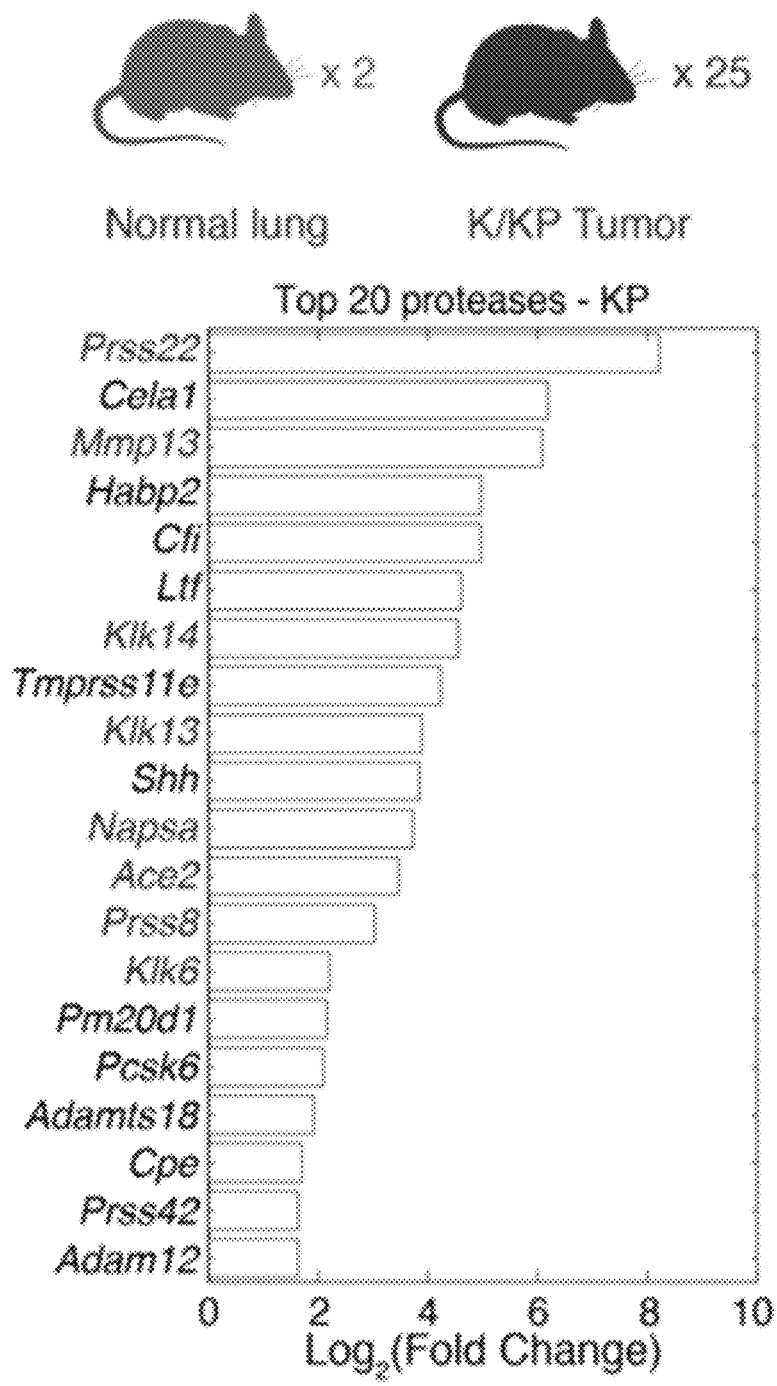

To use the KP model to validate ABNs in vivo, protease expression in tumor-bearing KP mice was sought to be characterized to nominate additional protease targets and assess homology to human disease. To that end, a recently published RNA-Seq dataset that profiled KP tumors across disease stages was selected and used to identify overexpressed secreted protease genes (Chuang et al., Nat Med 23, 291-300, 2017). In this study, tumor cells expressing a fluorescent reporter had been isolated by FACS and profiled by RNA-Seq. Samples from metastatic ($T_{met}$, n=9), non-metastatic ($T_{non-met}$, n=10) and early stage (KP-Early, n=3) tumors, as well as Kras-mutant, p53-intact (K, n=3) tumors were pooled and gene expression fold change was calculated relative to normal mouse lung (n=2) (FIG. 2B, upper panel). Proteases overexpressed in mouse lung tumors were identified, including several that had previously been identified in human disease (FIG. 2B, lower panel).

Figure 2C:
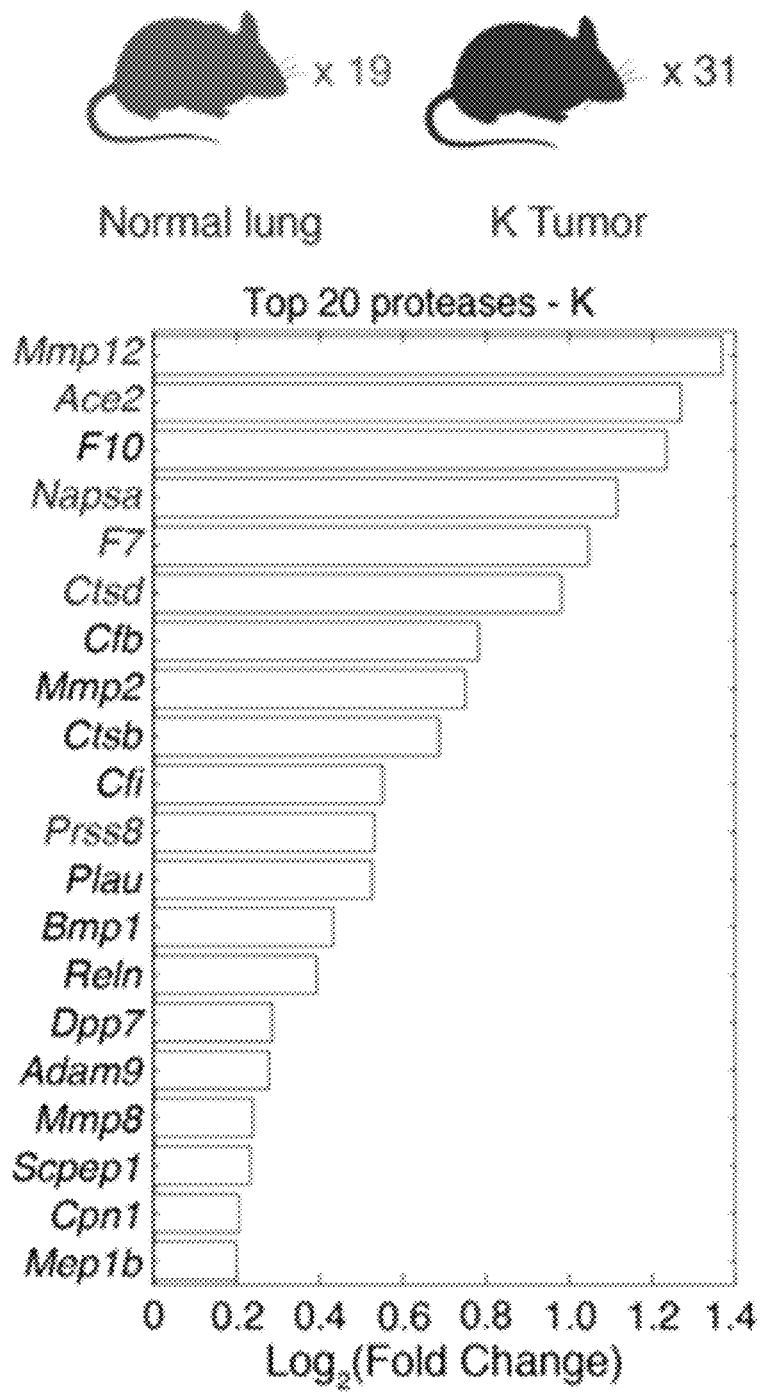

Because this dataset failed to take into account contributions from the tumor microenvironment and was also limited in its representation of early-stage disease, gene expression data from the K model (Sweet-Cordero et al., Nat Genet 37, 48-55, 2005), which is transcriptionally similar to early-stage KP tumors and human lung adenomas (Chuang et al., Nat Med 23, 291-300, 2017), was also analyzed. Significance analysis of microarrays (SAM) was used to identify proteases with increased expression in K mice (FIG. 2C).

Figure 2D:
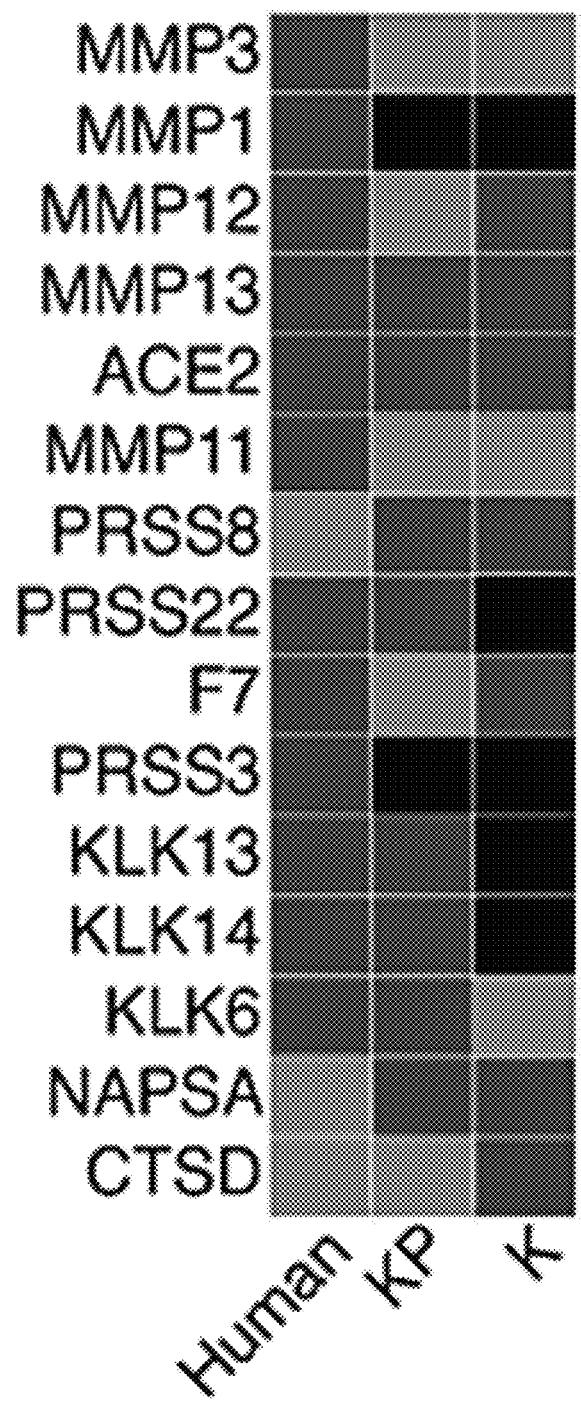
Figure 2E:
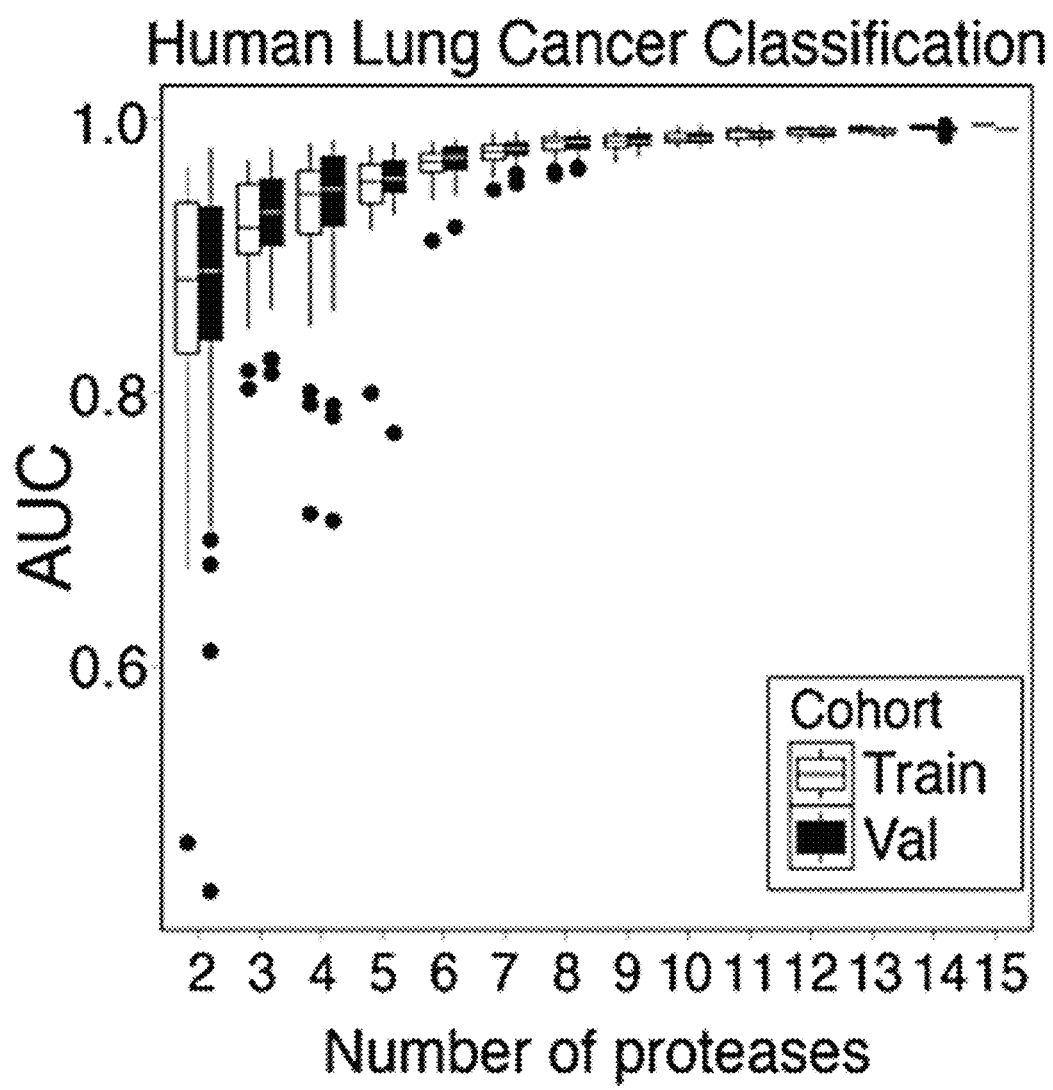

A set of 15 proteases overexpressed across all or a subset of the mouse and human datasets was then selected as a "LUAD protease panel", having six metallo-, seven serine and two aspartic proteases (FIG. 2D). The performance of the TCGA dataset was then evaluated in classifying human lung cancer from healthy lungs on the transcriptional level. Generalized linear model classification was performed using the Caret package, using the 15 LUAD proteases as features. Receiver operating characteristic (ROC) analysis revealed that the area under the curve (AUC) increases with increasing information (i.e. number of proteases), achieving nearly perfect classification with all 15 proteases in both training and validation cohorts (FIG. 2E).

Figure 2F:
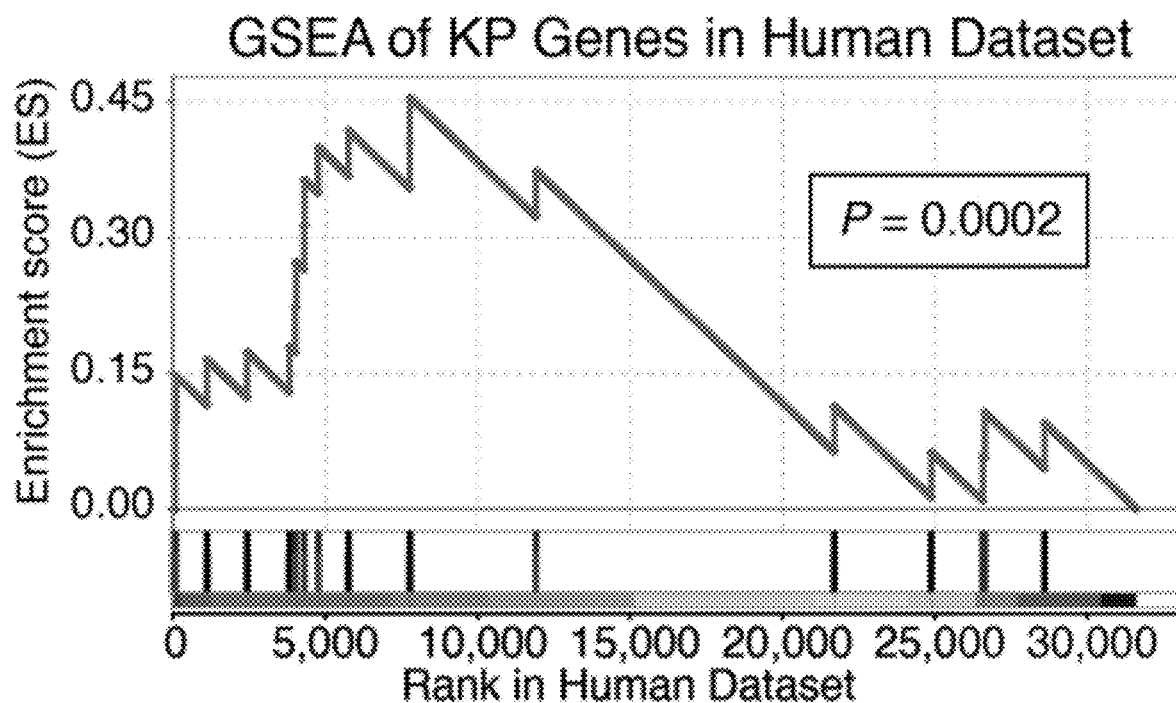

To validate homology of mouse lung cancer with human disease, gene set enrichment analysis (GSEA) (Subramanian et al., Proc Natl Acad Sci USA 102, 15545-15550, 2005) was performed in the TCGA dataset using the top 20 overexpressed proteases in the KP model (FIG. 2F). GSEA assesses the extent to which a particular gene set (S) is enriched in a gene expression dataset by rank-ordering all genes in the dataset and walking down the list, increasing the enrichment score each time a gene in S is encountered, and decreasing it otherwise. This approach revealed significant enrichment of 14 of the top 20 KP-expressed protease genes in human lung adenocarcinoma, yielding a maximum enrichment score of 0.455 (P=0.0002).

Figure 18C:
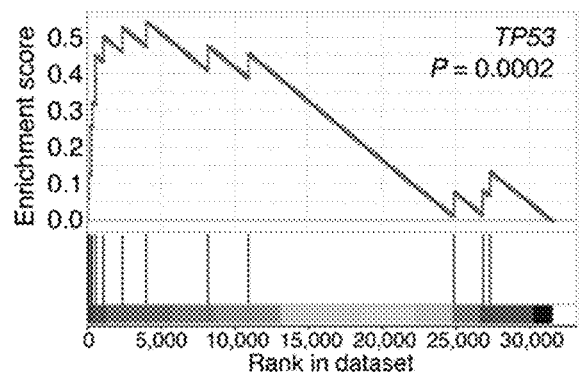
Figure 18D:
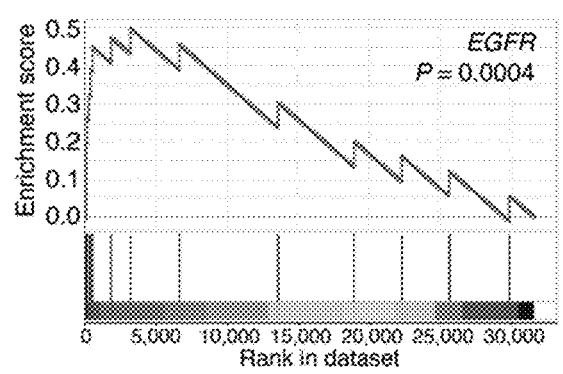
Figure 18E:
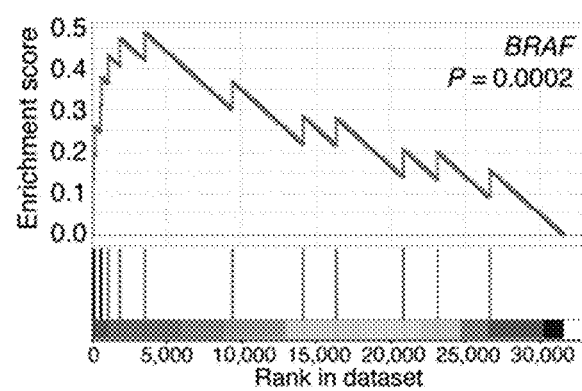
Figure 18F:
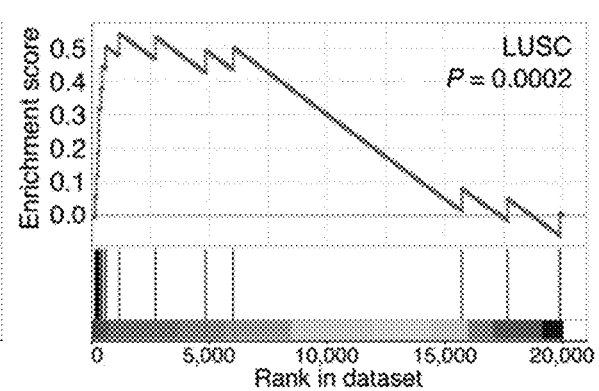

Additionally, this 15-gene panel was significantly enriched in stage I LUAD, as assessed by GSEA (FIG. 18A, P<0.0001), as well as all tested molecular subtypes of adenocarcinoma, including KRAS-mutant (FIG. 18B, P<0.0001), TP53-mutant (FIG. 18C, P=0.0002), EGFR-mutant (FIG. 18D, P=0.0004), and BRAF-mutant (FIG. 18E, P=0.0002) genetic subtypes. Finally, differential expression analysis of lung squamous cell carcinoma (LUSC) from the TCGA dataset was performed and GSEA using the same 15-gene panel was performed. It was found that the majority of LUAD protease genes were also upregulated in LUSC, yielding significant enrichment (FIG. 18F, P=0.0002).

Cleavage of Multiplexed Substrate Panel Follows Class-Specific Patterns

Figure 3A:
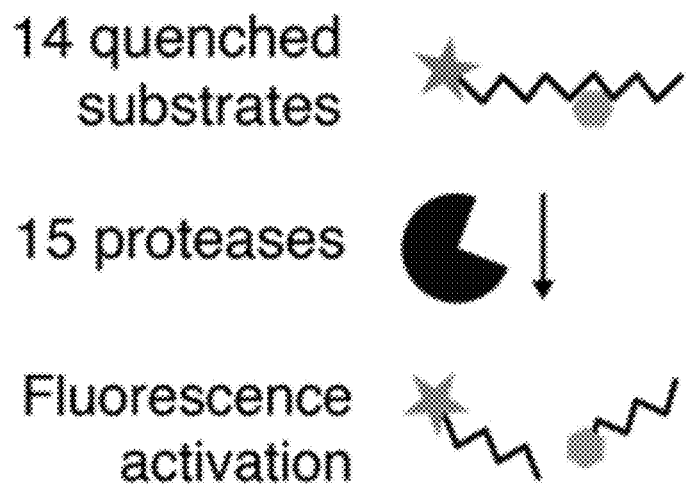
FIGS. 3A-3C show that LUAD substrate panel cleavage patterns are driven by protease class.
Figure 3B:
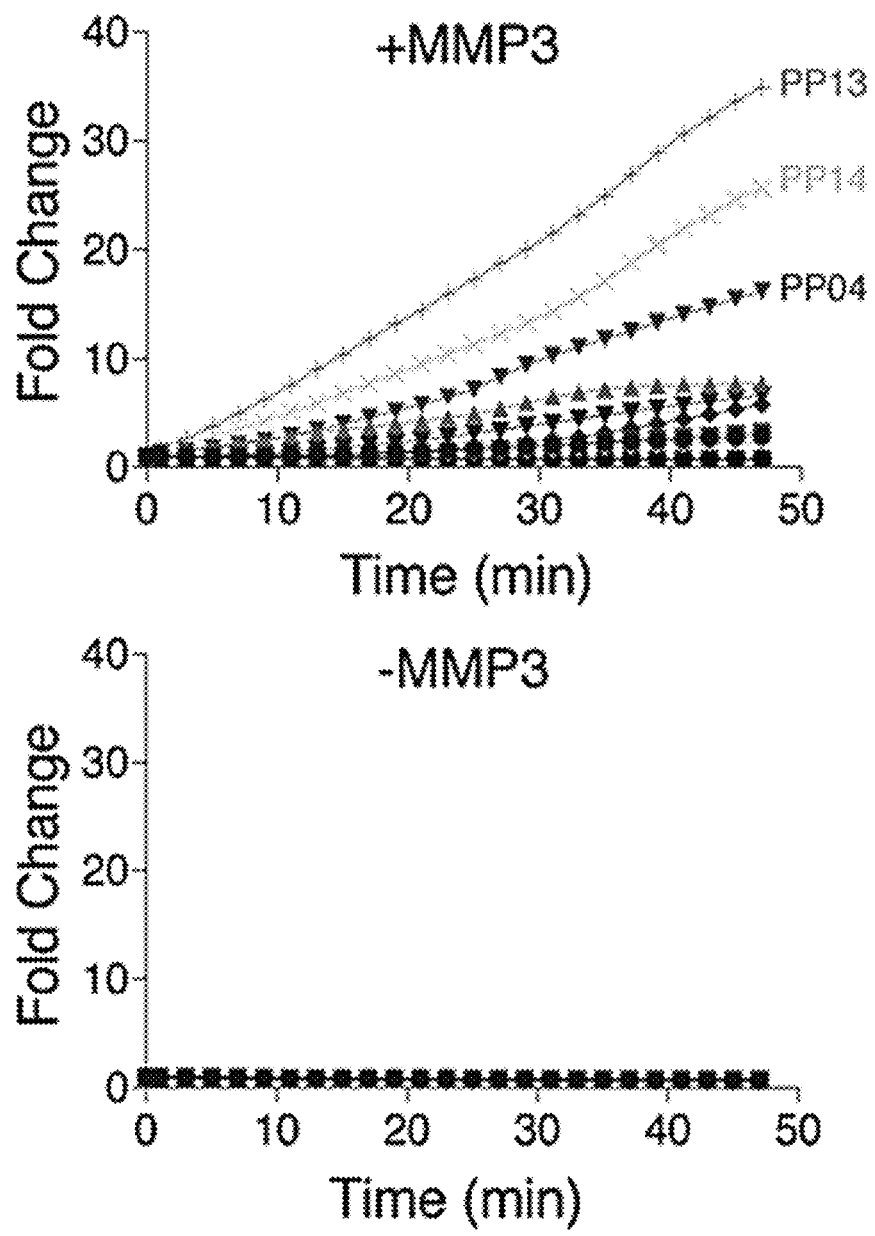
Figure 3C:
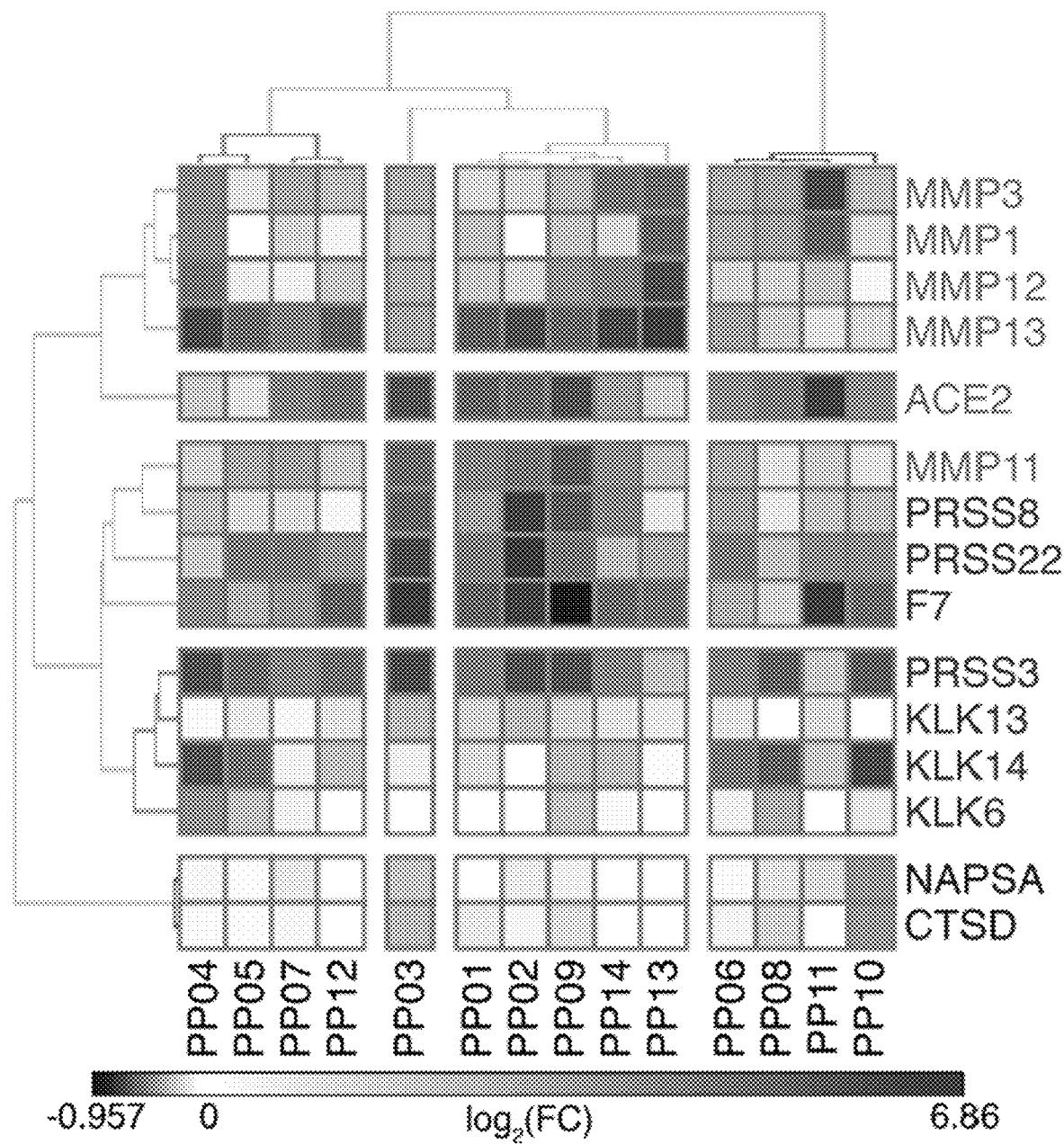

Hundreds of peptide sequences have been previously designed and validated as protease substrates, leveraging known catalytic specificities of different protease families, published datasets and substrate sequences in databases like cutDB and MEROPS (Igarashi et al., Nucleic Acids Res 35, D546-549, 2007; Rawlings et al., Nucleic Acids Res 46, D624-D632, 2018). Fourteen of these substrates were nominated in an effort to cover the specificity profiles of metallo-, serine and aspartic endoproteases, all of which were included in the LUAD protease panel, and the catalytic activity of each protease-substrate pair was characterized. Quenched probes that incorporated the 14 peptide substrates were synthesized such that they fluoresce upon proteolytic cleavage to enable real-time monitoring of protease activity in vitro (FIG. 3A and Table 2). Each probe was incubated with each protease in the panel and fluorescence was monitored over 45 minutes. Shown are sample kinetic plots monitoring dequenching of the 14 FRET-paired probes when incubated with (above) and without (below) recombinant matrix metalloproteinase 3 (MMP3) (FIG. 3B). Hierarchical clustering of fluorescence fold changes of each substrate was found to lead to the separation of proteases of different classes (FIG. 3C). It was also found that while certain probes are highly selective for individual classes of protease (e.g. PP13 and PP08 for MP and SP, respectively), others were cleaved well by proteases of multiple classes (e.g. PP04, PP10 for SP/MP and MP/SP/AP, respectively). See also FIG. 19.

TABLE 2

Peptide Sequences for In Vitro Recombinant Protease Screen

| Name | Fluorophore | Substrate | Quencher |
|---|---|---|---|
| PPQ1 | 5FAM | GGPQGIWGQK(CPQ2)-PEG2-C (SEQ ID NO: 29) | CPQ2 |
| PPQ2 | 5FAM | GGPVGLIGK(CPQ2)-PEG2-C (SEQ ID NO: 30) | CPQ2 |
| PPQ3 | 5FAM | GGPVPLSLVMK(CPQ2)-PEG2-C (SEQ ID NO: 31) | CPQ2 |
| PPQ4 | 5FAM | GGPLGLRSWK(CPQ2)-PEG2-C (SEQ ID NO: 32) | CPQ2 |
| PPQ5 | 5FAM | GGPLGVRGKK(CPQ2)-PEG2-C (SEQ ID NO: 33) | CPQ2 |
| PPQ6 | 5FAM | GGfPRSGGGK(CPQ2)-PEG2-C (SEQ ID NO: 34) | CPQ2 |
| PPQ7 | 5FAM | GGLGPKGQTGK(CPQ2)-kk-PEG2-C (SEQ ID NO: 35) | CPQ2 |
| PPQ8 | 5FAM | GGGSGRSANAKG-K(CPQ2)-PEG2-GC (SEQ ID NO: 36) | CPQ2 |
| PPQ9 | 5FAM | GKPISLISSG-K(CPQ2)-PEG2-GC (SEQ ID NO: 37) | CPQ2 |
| PPQ10 | 5FAM | GILSRIVGGG-K(CPQ2)-PEG2-GC (SEQ ID NO: 38) | CPQ2 |
| PPQ11 | 5FAM | GSGSKIIGGG-K(CPQ2)-PEG2-GC (SEQ ID NO: 39) | CPQ2 |
| PPQ12 | 5FAM | GGPLGMRGG-K(CPQ2)-GC (SEQ ID NO: 40) | CPQ2 |
| PPQ13 | 5FAM | GP-(Cha)-G-Cys(Me)-HAG-K(CPQ2)-GC (SEQ ID NO: 41) | CPQ2 |
| PPQ14 | 5FAM | GAPFEMSAG-K(CPQ2)-GC (SEQ ID NO: 42) | CPQ2 |

5FAM, 5-Carboxyfluorescein;
CPQ2, quencher;
PEG, polyethylene glycol;
Cha, 3-Cyclohexylalanine;
Cys(Me), methyl-cysteine;
lowercase letters, D-amino acids Pulmonary-Delivered Nanoparticles Distribute Throughout the Lung and Reach the Tumor Periphery The lung efficiently and rapidly exchanges compounds with the bloodstream owing to high surface area and very thin barriers: adult lungs have an area of ~100 m² and, in alveoli, type I cells can be <0.1 µm thick (Patton et al., Nat Rev Drug Discov 6, 67-74, 2007). Inhaled molecules and particles cross into the bloodstream by passive diffusion, trancytosis, or paracytosis, with rate and route of transit largely dependent on size and hydrophobicity (Patton et al., Nat Rev Drug Discov 6, 67-74, 2007).

Figure 4A:
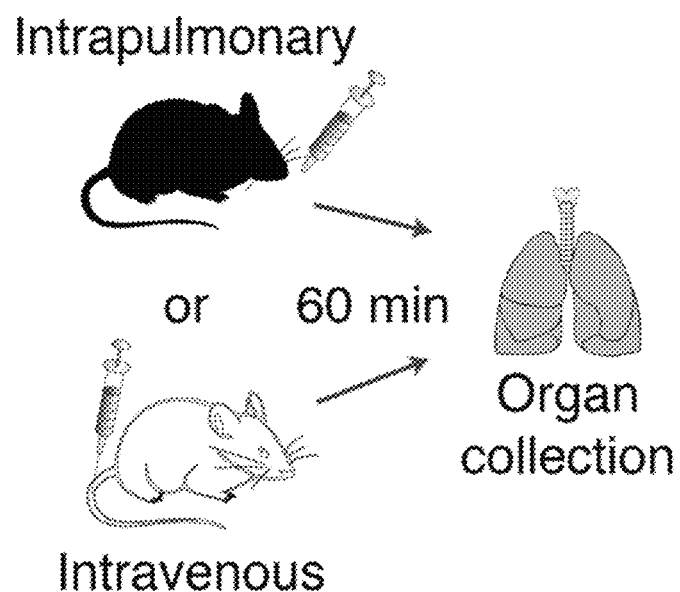
FIGS. 4A-4E show that intratracheally administered nanoparticle scaffolds penetrate deep within the lung and reach the periphery of KP tumors.
Figure 4B:
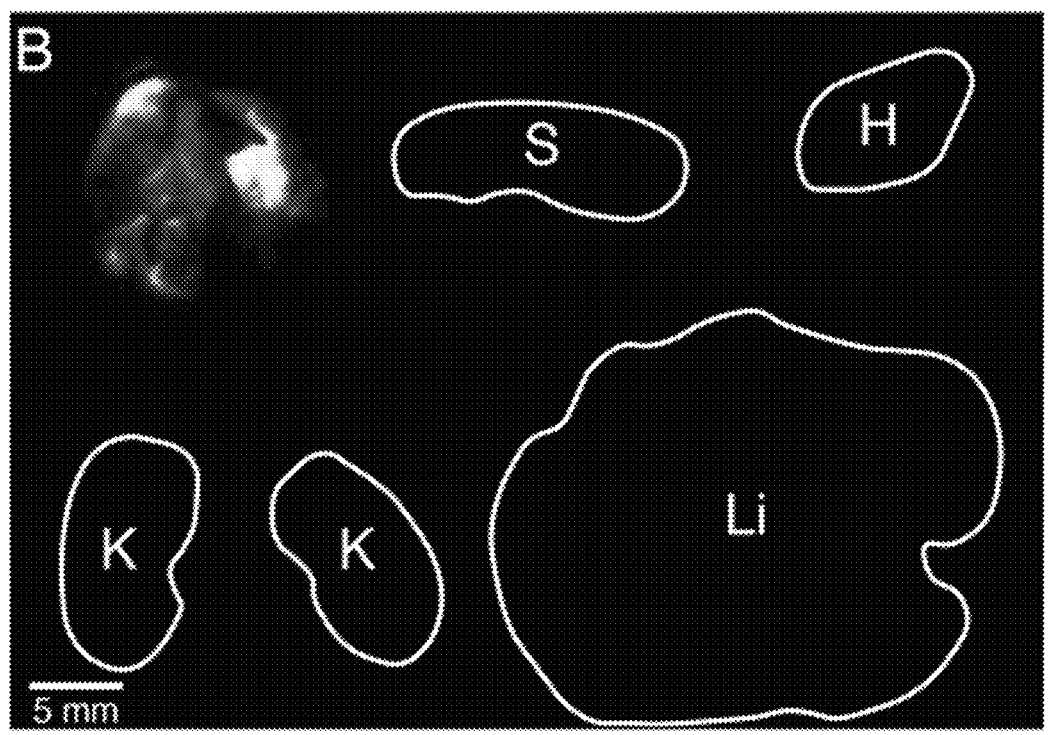
Figure 4C:
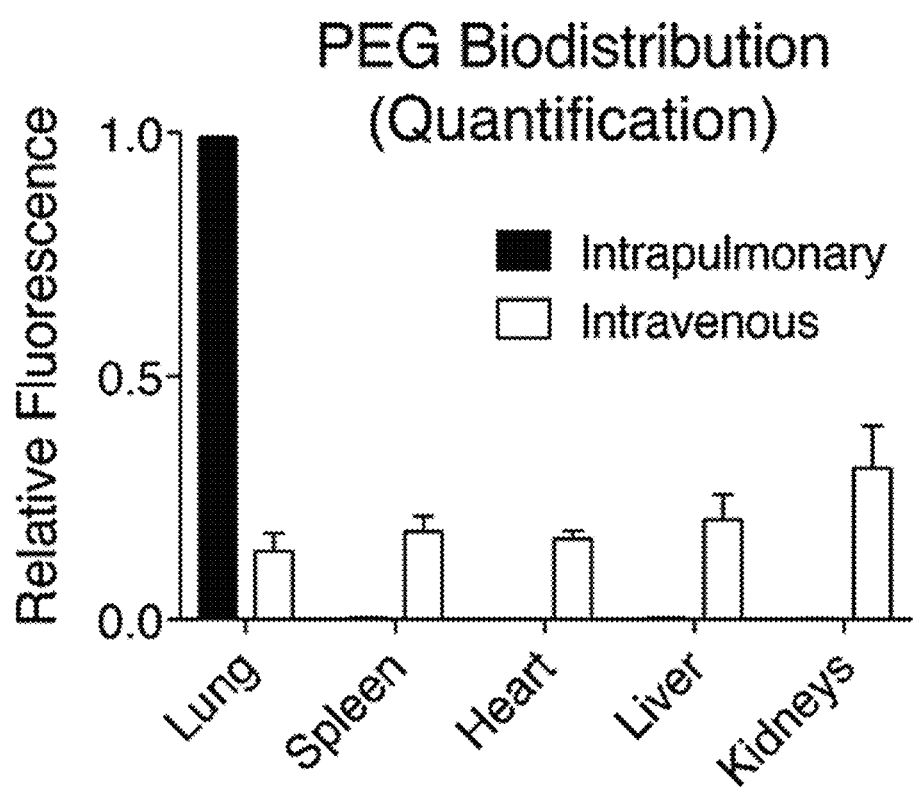
Figure 20:
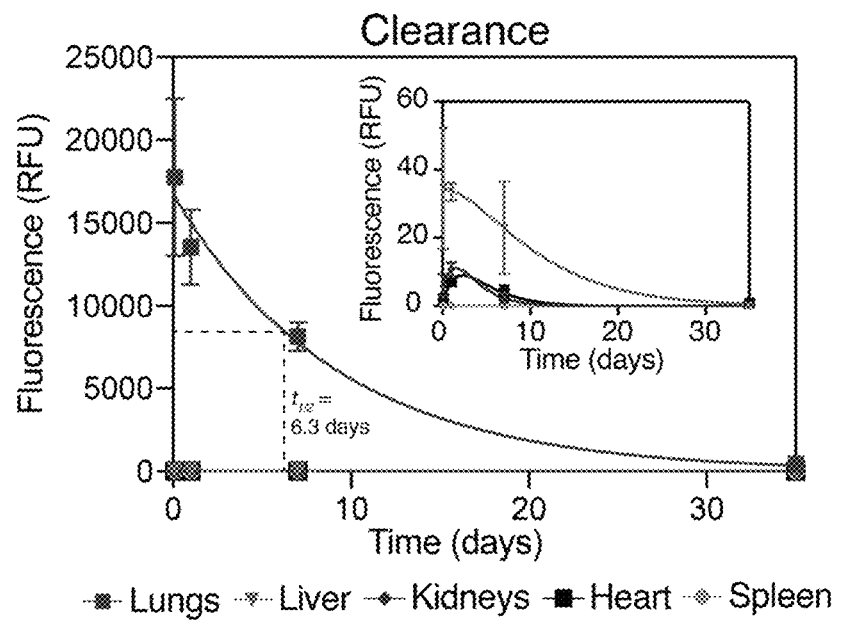
FIG. 20 includes data showing clearance of $PEG-8_{40\ kDa}$ nanoparticles from lungs followed single phase exponential decay kinetics. Fluorescence of lungs, liver, kidneys, heart, and spleen of mice after intrapulmonary delivery of VT750-labeled $PEG-8_{40\ kDa}$ (n=5 per time point). Error bars represent SD. Lung clearance data was fit with nonlinear regression using single phase exponential decay ($t_{1/2}$=6.3 days, $R^2$=0.86). In the inset, liver, kidneys, heart, and spleen fluorescence are presented on a smaller scale y-axis and were fit with nonlinear regression using two phase exponential growth and decay.
Figure 21A:
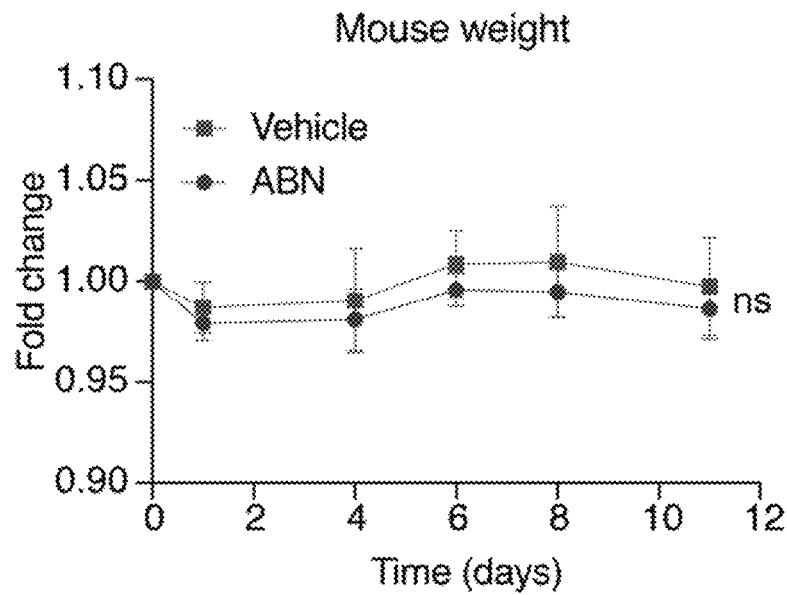
FIGS. 21A-21B include data showing that no toxicity was observed in mice treated with intrapulmonary ABNs.
Figure 21B:
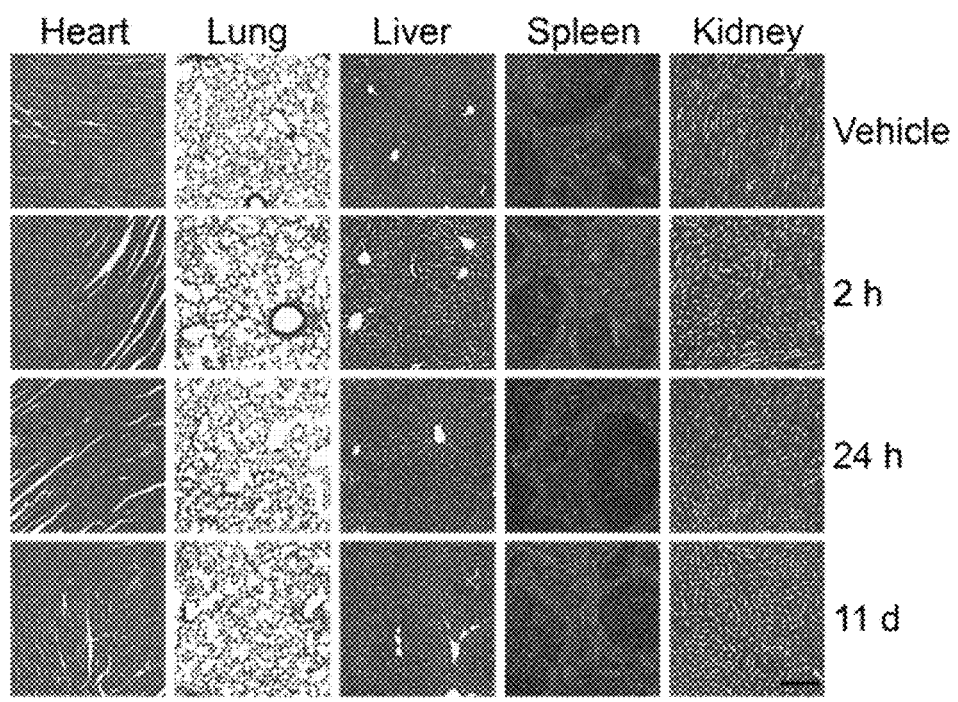

In an effort to adapt the ABN platform for highly sensitive and specific detection of early-stage lung cancer, the feasibility of localized intrapulmonary, rather than systemic intravenous, delivery was sought to be assessed. ABNs were built using a 40 kDa eight-arm poly(ethylene glycol) (PEG-$8_{40\ kDa}$) nanoparticle, coated with protease substrates bearing terminal mass-encoded reporters (FIG. 1B). The ABNs are largely free to sample lung extracellular protease activity over the time period during which urinary reporter accumulation is monitored. To assess biodistribution of ABNs following intrapulmonary delivery, the PEG-$8_{40\ kDa}$ scaffold was labeled with a near-infrared dye, VivoTag750 (VT750), the nanoparticles were delivered to mice by intratracheal (IT) intubation or intravenous (IV) injection and organs were collected after 60 minutes (FIG. 4A). Fluorescence imaging revealed deep delivery of nanoparticles to all lung lobes in mice receiving IT particles, but negligible delivery to other organs (FIGS. 4B-4C). In contrast, only 14% of organ fluorescence was confined to the lung in the IV group. In terms of absolute delivery of ABNs, lung fluorescence in the IT group was 263 times greater than liver fluorescence (p<0.0001). As blood is a rich, non-specific proteolytic matrix and achieving organ-specific biodistribution of systemically delivered nanoparticles remains difficult, IT ABNs offer distinct advantages over IV-delivered variants. In the IT-treated mice, the lung half-life of PEG-$8_{40\ kDa}$ was 6.3 days (FIG. 20). Finally, no toxicity was observed at both short (2 hours) and longer (24 hours and over 10 days) intervals after ABN administration in healthy control mice, as assessed by weight tracking (FIG. 21A) and histological assessment by a veterinary pathologist (FIG. 21B).

Figure 4D:
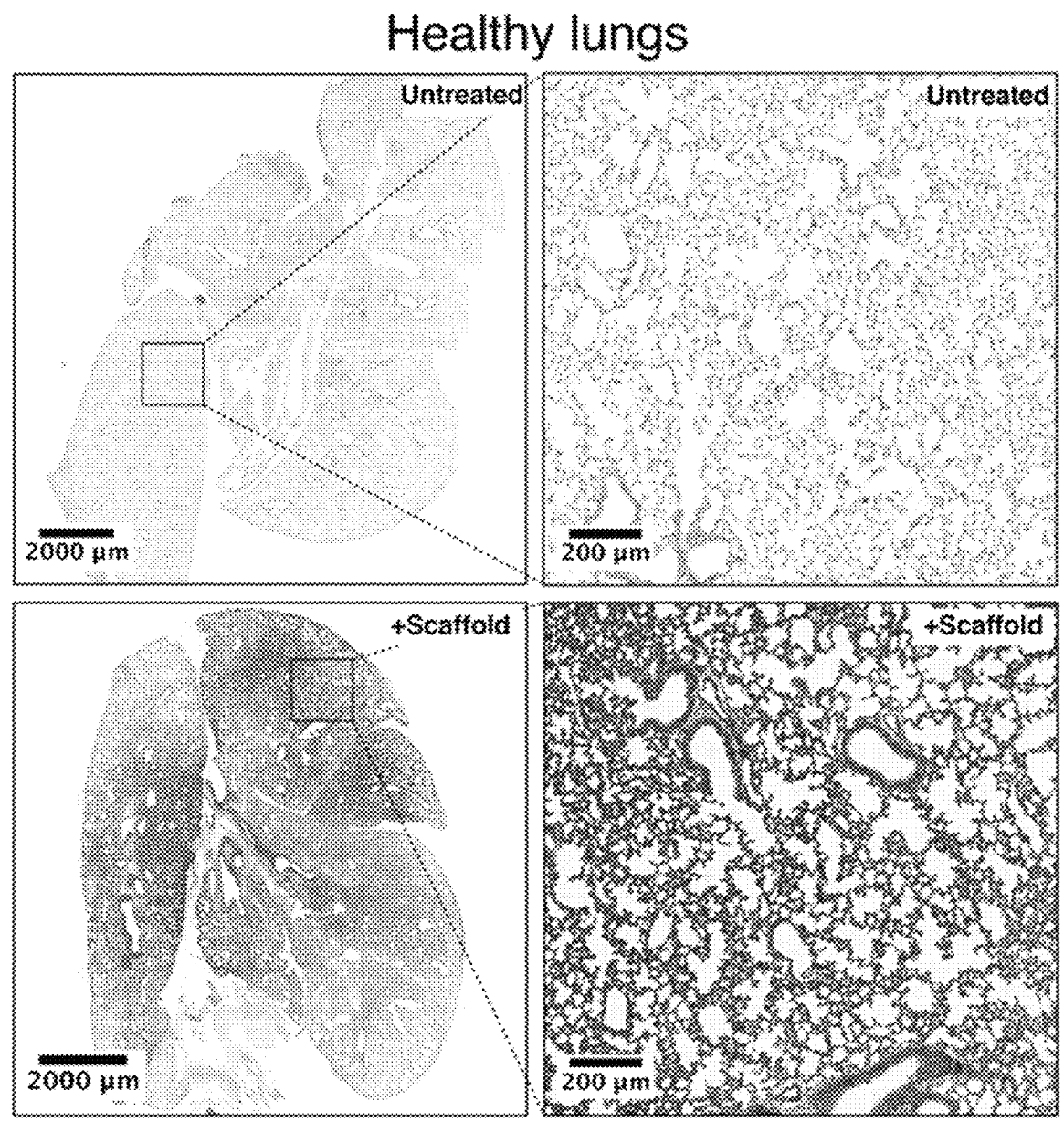

To assess microscopic distribution of the ABN scaffold within the lung following IT delivery, the PEG-$8_{40\ kDa}$ scaffold was labeled with biotin and the nanoparticles were administered to healthy mice by intratracheal intubation. Lungs were collected from mice 20-30 minutes post-IT delivery, fixed and stained for biotin. While lungs from untreated mice were negative for biotin (FIG. 4D, above), lungs from mice that received the scaffold demonstrated broad distribution of nanoparticles throughout the lung (FIG. 4D, below left) and specifically within terminal alveoli (FIG. 4D, below right).

Figure 4E:
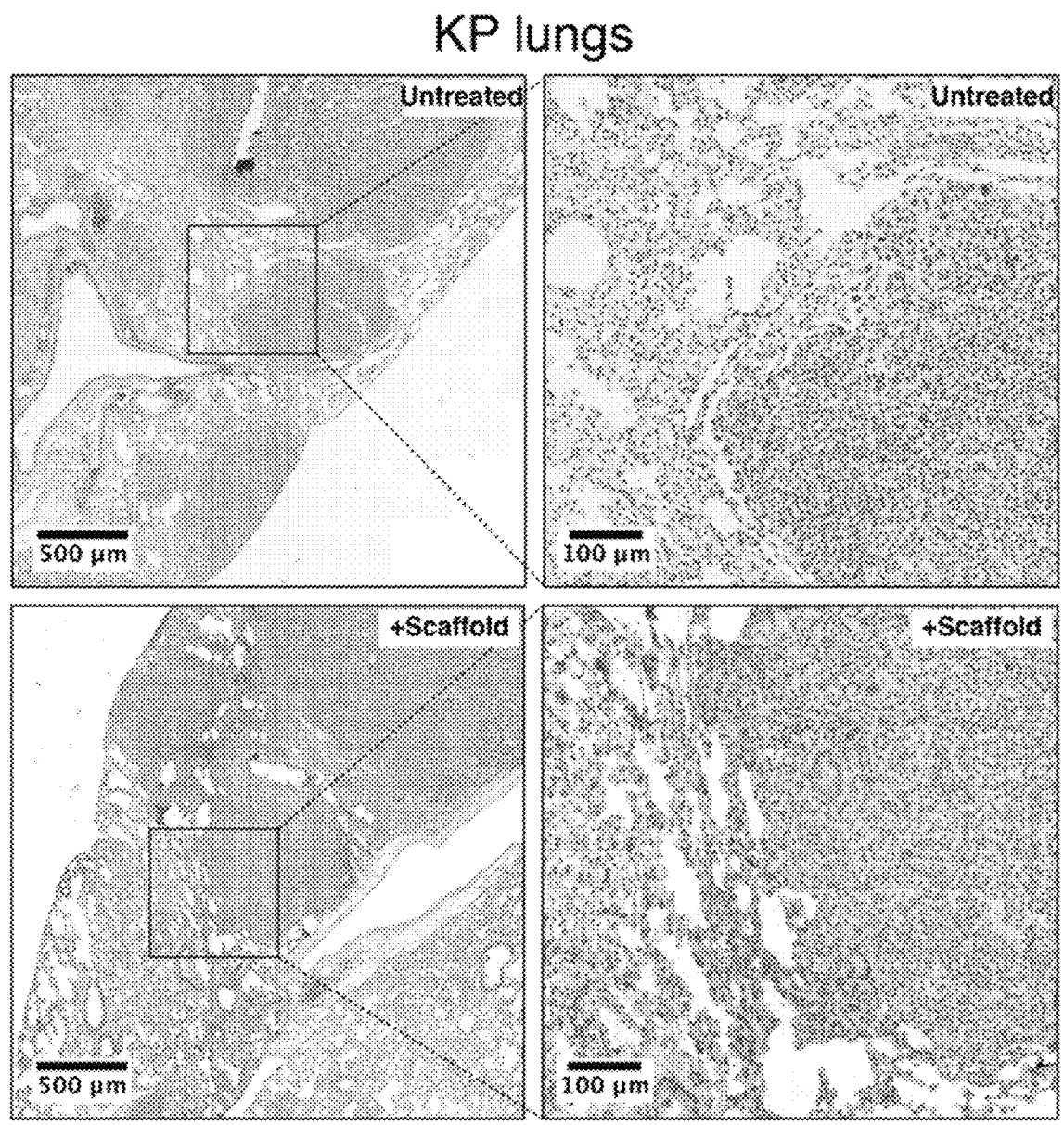

Biotin-labeled PEG-$8_{40\ kDa}$ scaffold was then administered in KP tumor-bearing mice, by intratracheal intubation, to assess whether these particles are able to reach the site of disease. Again, while lungs from untreated KP mice were negative for biotin (FIG. 4E, above), lungs from KP mice that received intrapulmonary delivery of the scaffold demonstrated presence of nanoparticles at the margin of tumors where protease activity is relevant to disease growth and invasion (FIG. 4E, below).

Figure 22A:
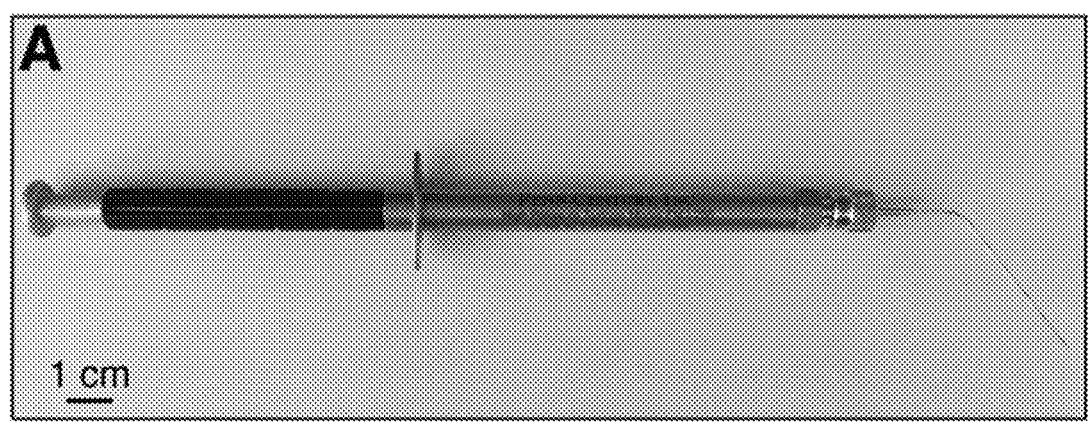
Figure 22B:
Figures 22C, 22D, 22E:
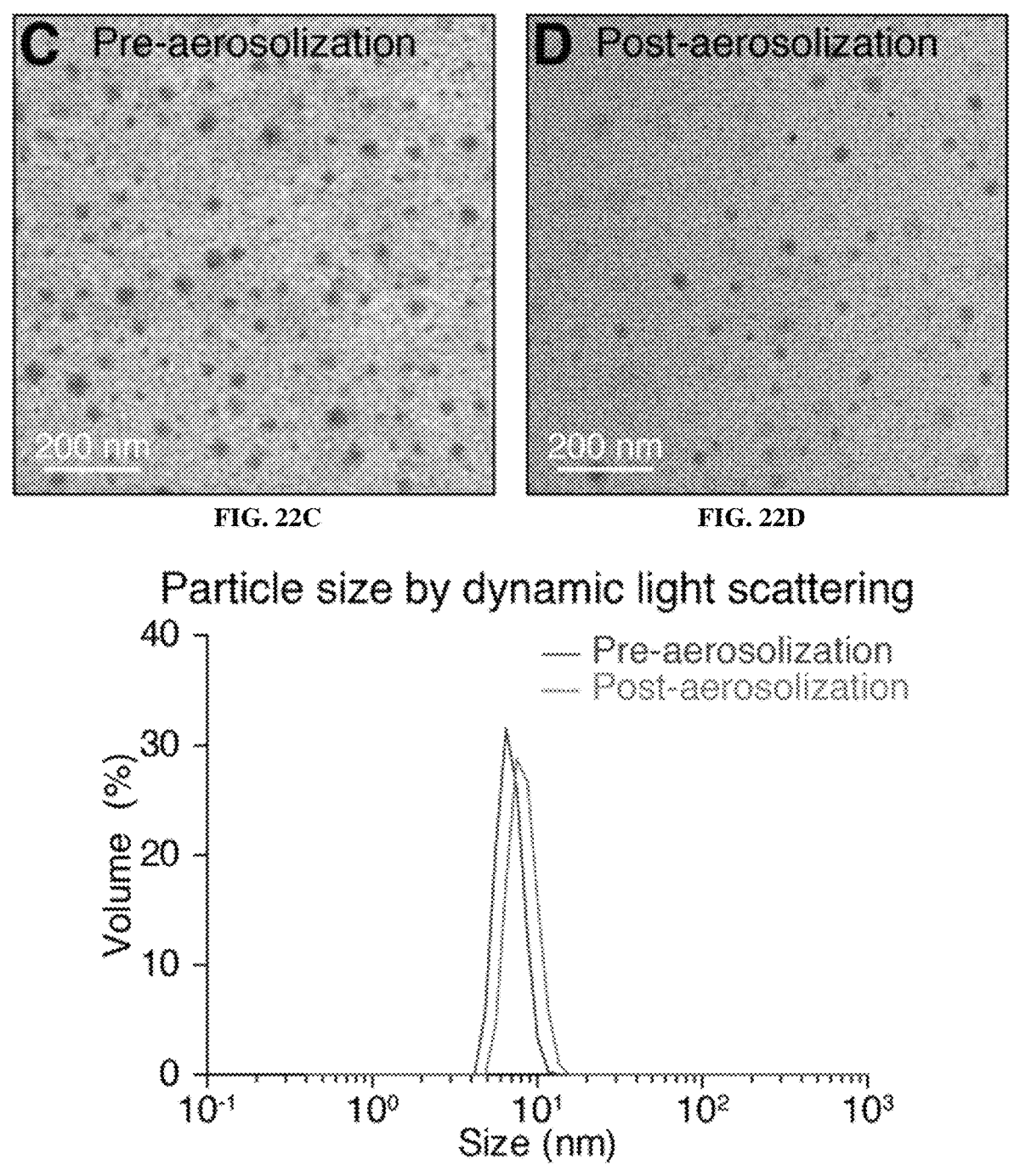
Figures 22F, 23A:
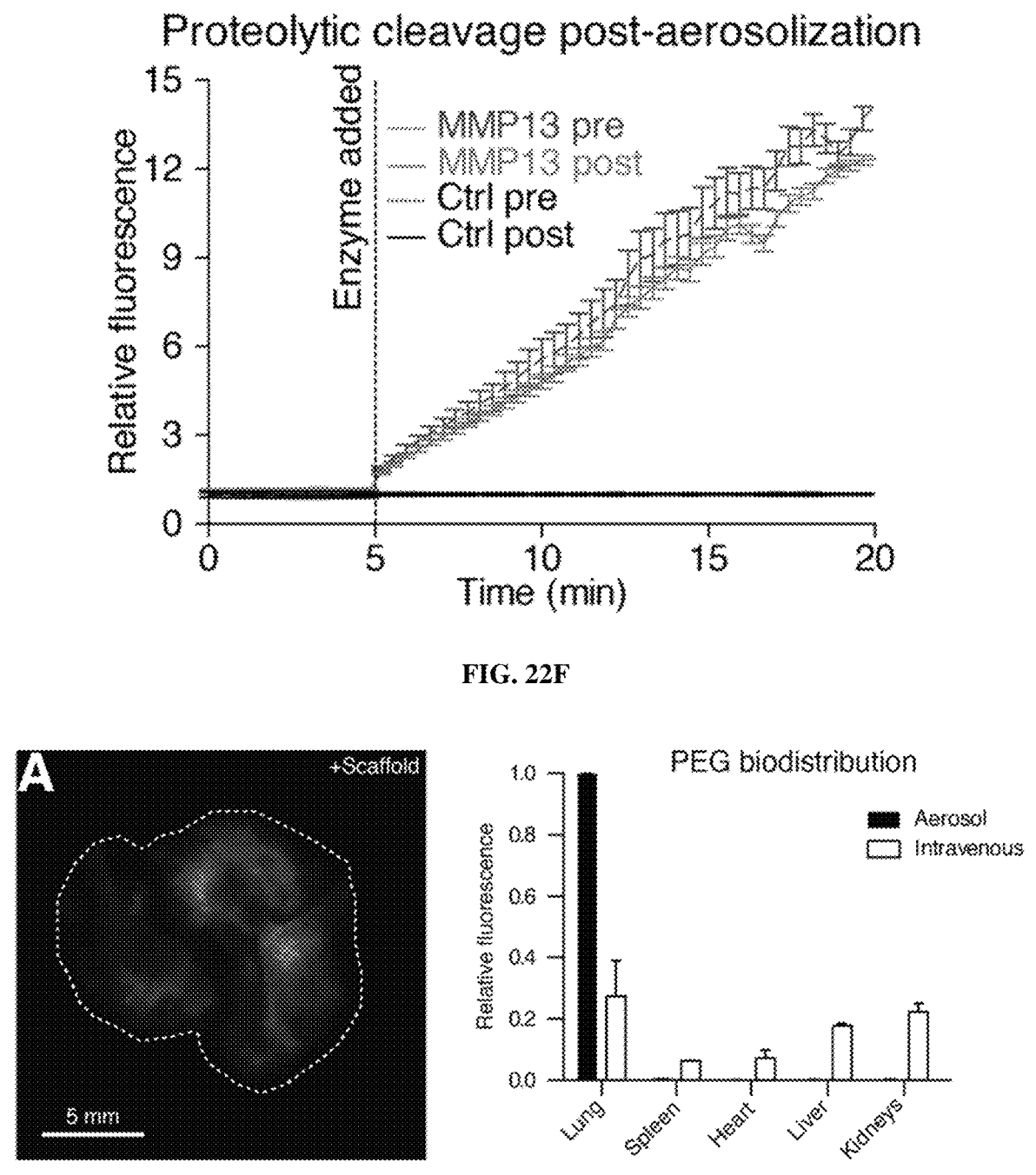

As a step toward developing a more clinically relevant delivery method, particle durability and biodistribution after aerosolization were also characterized. The PEG carrier particles were directly aerosolized (FIG. 22A-22B) and found no aggregation or changes in particle size distribution, as assessed by transmission electron microscopy (TEM) (FIG. 22C-22D) and dynamic light scattering (DLS) (FIG. 22E). Furthermore, PEG-PPQ5 pre- and post-aerosolization was equally sensitive to in vitro cleavage by recombinant MMP13 (FIG. 22F).

Figure 23C:
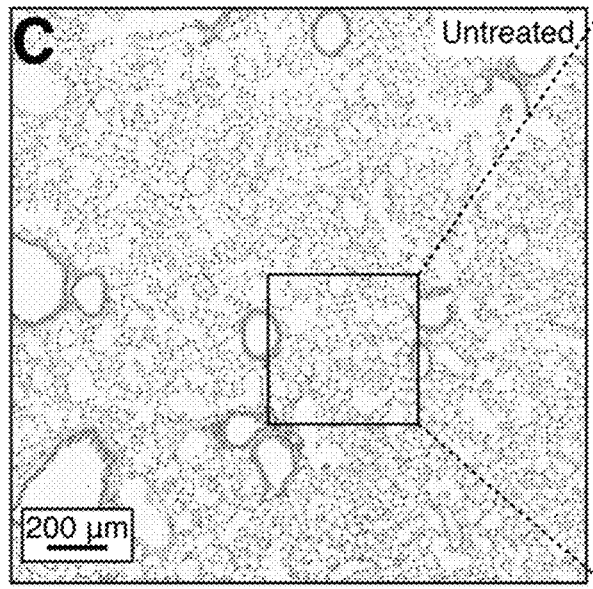
Figure 23D:
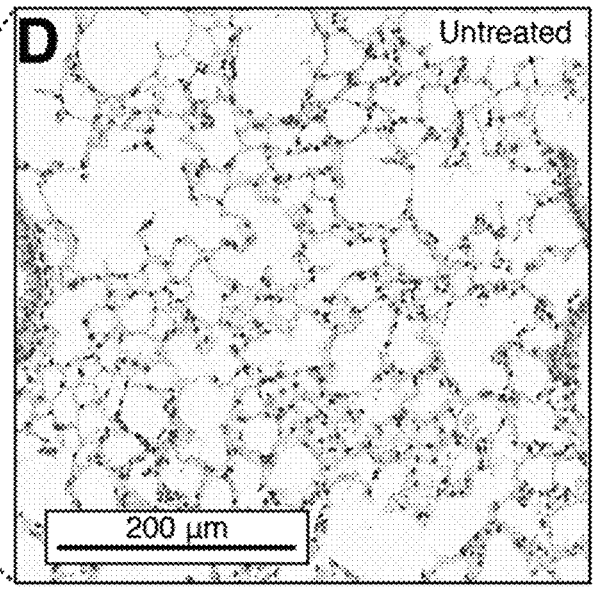
Figure 23E:
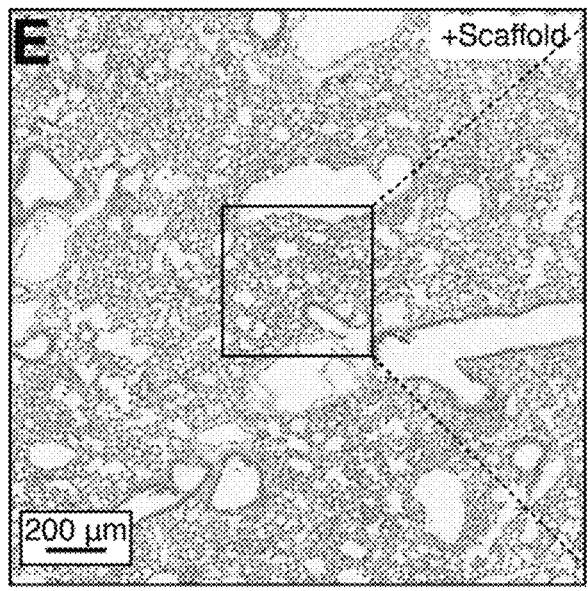
Figure 23F:
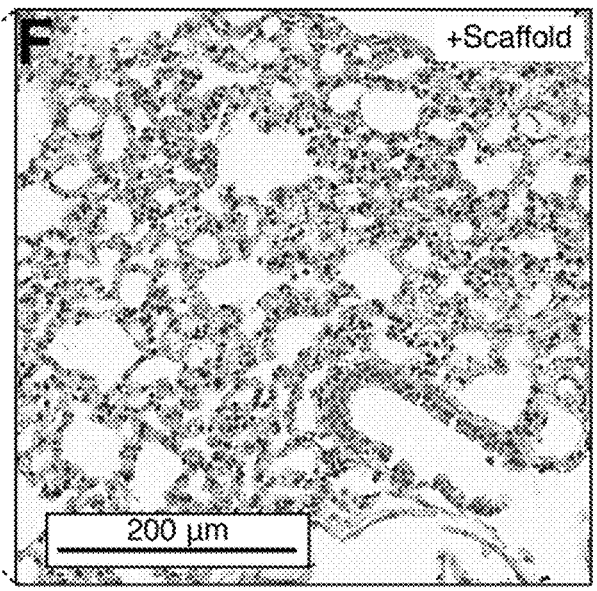

Finally, the PEG nanoparticles were functionalized with either a near-infrared dye for biodistribution studies or biotin for histological assessment and used pressure-driven aerosolization to perform intrapulmonary administration. Gross fluorescent visualization of VivoTag-750 revealed deep penetration throughout the lung and in all lobes (FIG. 23A), without distribution to other organs (FIG. 23B). Histological staining of fixed lungs collected from mice 10 minutes post-inhalation demonstrated no biotin staining in control lungs (FIG. 23C-D) and broad staining throughout the lung overall (FIG. 23E) and in terminal alveoli (FIG. 23F) in mice treated with aerosolized nanoparticles.

Figure 8A:
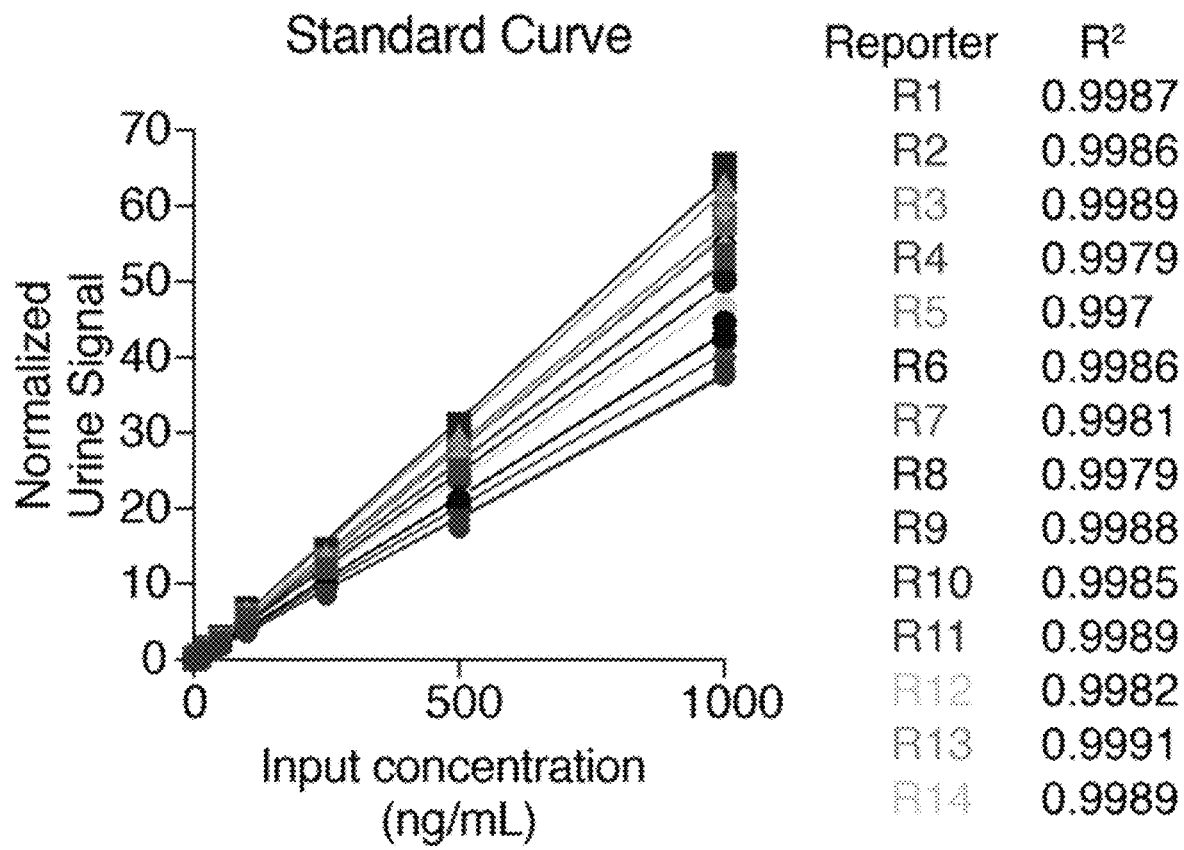
FIGS. 8A-8C show that free reporters enter the bloodstream after pulmonary delivery and are detectable in the urine by mass spectrometry.
Figure 8B:
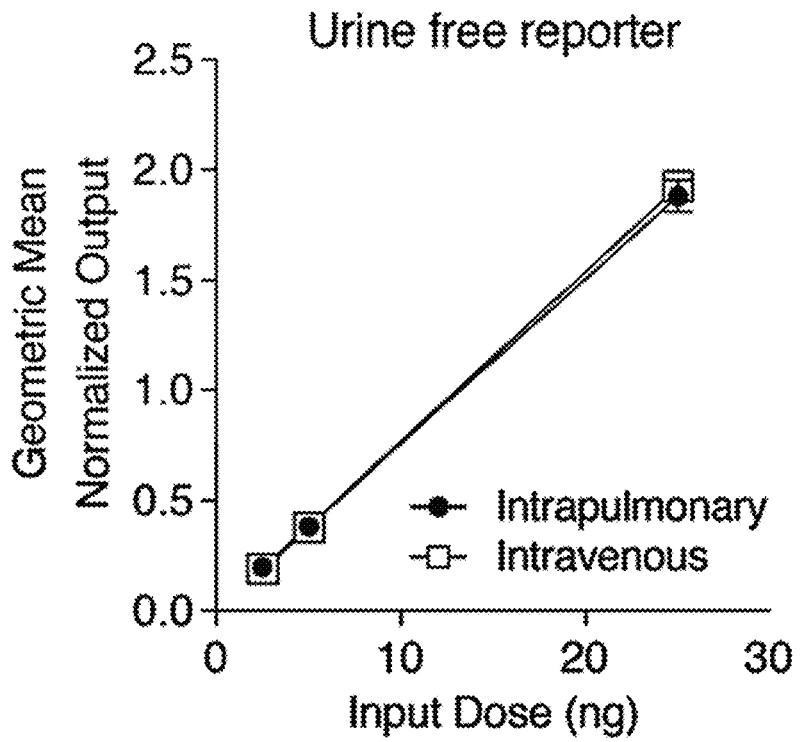

Mass-Encoded Reporters Filter from the Lung to the Urine Via the Blood and are Detectable by Mass Spectrometry To enable detection of a broad spectrum of disease-associated proteases in vivo, the 14 peptides of the LUAD substrate panel were appended with mass-encoded reporters (PP1-14; Table 3). Following substrate proteolysis, the reporters diffuse away from the nanoparticle scaffold and are sized so as to be able to efficiently cross into the bloodstream, where they can be concentrated into the urine by glomerular filtration (FIG. 1B). As previously described (Kwong et al., Nat Biotechnol 31, 63-70, 2013), variable labeling of the 14-mer Glu-Fibrinopeptide B (Glu-Fib) with stable isotope-labeled amino acids was used to uniquely barcode each of 14 peptide substrates. Multiple reaction monitoring via a liquid chromatography triple quadrupole mass spectrometer (LC-MS/MS) enables quantitative assessment of peptide-liberated urinary reporter concentration within a broad linear range (1-1000 ng/mL, FIG. 8A). Using mass-encoded free reporters, the filtration of Glu-Fib reporters into the urine after IT or IV administration was assessed and strong linearity of the MS assay for both routes of delivery for input doses between 2.5 ng and 25 ng ($R^2$=1.00, FIG. 8B) was found for both routes of delivery (slope$_{IT}$=0.075 ng$^{-1}$, slope$_{IV}$=0.077 ng$^{-1}$; FIG. 8B).

Figure 8C:
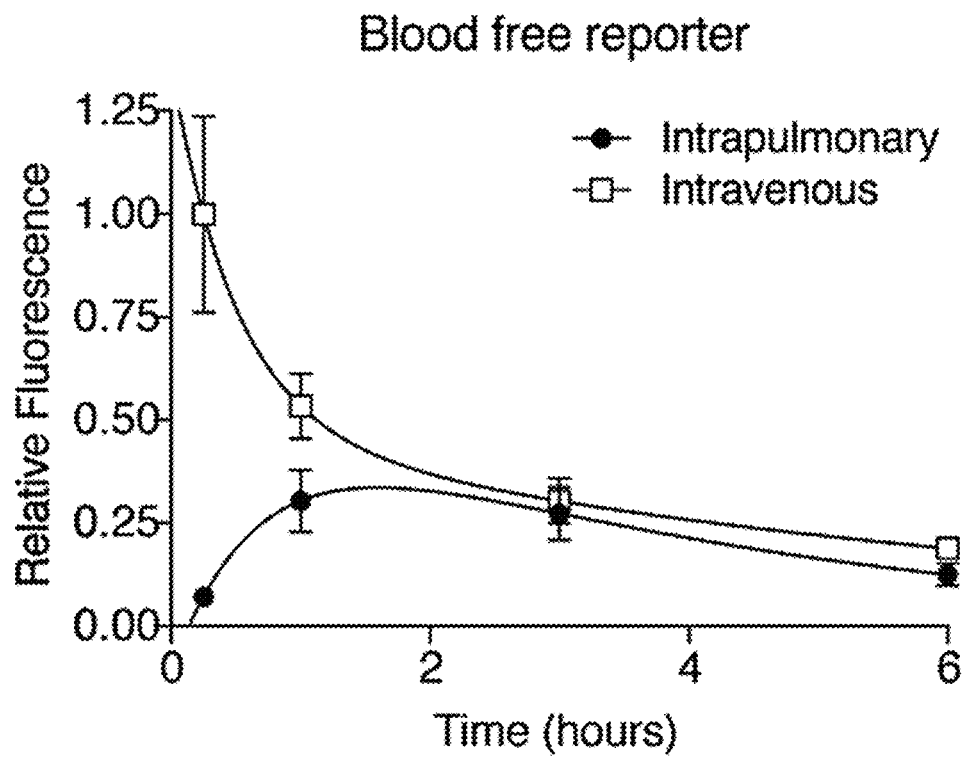

Blood pharmacokinetics of the free reporter was also investigated by administering a Cy7-labeled version of Glu-Fib both IT and IV. Pharmacokinetic data revealed characteristic single-exponential concentration decay following intravenous injection (FIG. 8C). In contrast, the pharmacokinetic behavior of the reporter following IT administration is suggestive of an initial phase of alveolar filtration into the blood (peaking at 1 to 2 hours after delivery), followed by renal filtration from the blood.

TABLE 3

ABN Sequences for In Vivo Urinary Diagnostics

| Name | Reporter | Photolabile Group | Substrate | Nanocarrier |
|------|----------|-------------------|-----------|-------------|
| PP1 | e(+2G)(+6V)ndneeGFFsAr (SEQ ID NO: 15) | ANP | PQGIWGQ (SEQ ID NO: 1) | PEG8-40 kDa |
| PP2 | eG(+6V)ndneeGF(+1F)s(+1A)r (SEQ ID NO: 16) | ANP | PVGLIG (SEQ ID NO: 2) | PEG8-40 kDa |
| PP3 | e(+3G)(+1V)ndneeGFFs(+4A)r (SEQ ID NO: 17) | ANP | PVPLSLVM (SEQ ID NO: 3) | PEG8-40 kDa |
| PP4 | e(+2G)Vndnee(+2G)FFs(+4A)r (SEQ ID NO: 18) | ANP | PLGLRSW (SEQ ID NO: 4) | PEG8-40 kDa |
| PP5 | eGVndnee(+3G)(+1F)Fs(+4A)r (SEQ ID NO: 19) | ANP | PLGVRGK (SEQ ID NO: 5) | PEG8-40 kDa |
| PP6 | e(+2G)(+6V)ndnee(+3G)(+1F)(+1F)s(+1A)r (SEQ ID NO: 20) | ANP | fPRSGGG (SEQ ID NO: 6) | PEG8-40 kDa |
| PP7 | eG(+6V)ndnee(+3G)(+1F)Fs(+4A)r (SEQ ID NO: 21) | ANP | LGPKGQTG (SEQ ID NO: 7) | PEG8-40 kDa |
| PP8 | e(+3G)(+1V)ndneeG(+10F)FsAr (SEQ ID NO: 22) | ANP | GSGRSANAKG (SEQ ID NO: 8) | PEG8-40 kDa |
| PP9 | eGVndneeGF(+10F)s(+4A)r (SEQ ID NO: 23) | ANP | KPISLISSG (SEQ ID NO: 9) | PEG8-40 kDa |
| PP10 | e(+2G)(+6V)ndneeG(+10F)(+1F)s(+1A)r (SEQ ID NO: 24) | ANP | ILSRIVGGG (SEQ ID NO: 10) | PEG8-40 kDa |
| PP11 | e(+3G)(+1V)ndnee(+2G)(+10F)Fs(+4A)r (SEQ ID NO: 25) | ANP | SGSKIIGGG (SEQ ID NO: 11) | PEG8-40 kDa |
| PP12 | eGVndneeG(+10F)(+10F)sAr (SEQ ID NO: 26) | ANP | PLGMRGG (SEQ ID NO: 12) | PEG8-40 kDa |
| PP13 | e(+2G)(+6V)ndnee(+3G)(+10F)(+1F)s(+4A)r (SEQ ID NO: 27) | ANP | P-(Cha)-G-Cys(Me)-HAG (SEQ ID NO: 13) | PEG8-40 kDa |
| PP14 | e(+3G)(+1V)ndnee(+2G)(+10F)(+10F)sAr (SEQ ID NO: 28) | ANP | APFEMSAG (SEQ ID NO: 14) | PEG8-40 kDa |

Figure 5C:
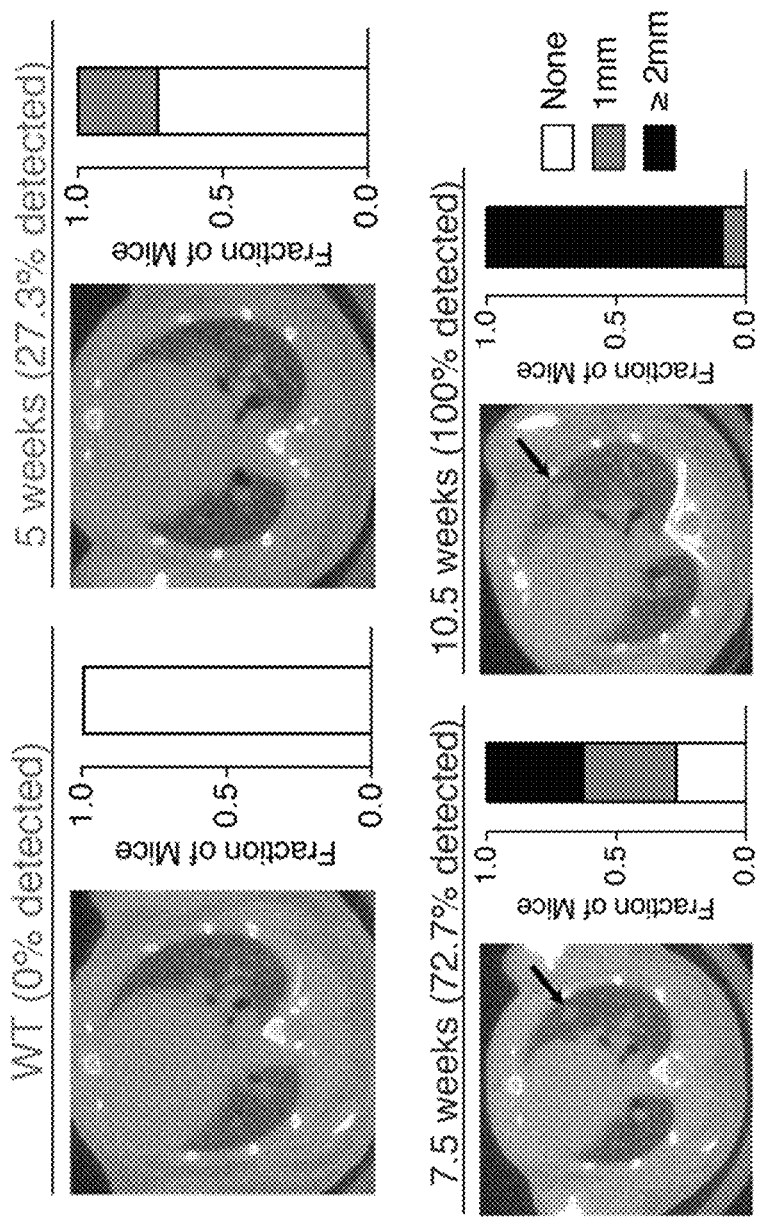

ANP, 3-Amino-3-(2-nitro-phenyl)propionic Acid;
Cha, 3-Cyclohexylalanine;
Cys(Me), methyl-cysteine;
lowercase letters, D-amino acids;
PEG8, 8-arm polyethylene glycol Early-Stage Lung Tumors in the KP Model are Detectable by ABNs With the observation that IT delivery of mass-encoded reporters leads to their partitioning from lung to circulation and subsequent concentration in the urine, disease progression in KP mice was sought to be longitudinally monitored with ABNs and the IT-delivered diagnostic was sought to be benchmarked against microCT. Development of tumor burden was monitored by performing microCT at 5 weeks, 7.5 weeks and 10.5 weeks (FIG. 5C, representative microCT slice at each time point, with arrow indicating development of a single nodule over time). Tumor burden was quantified on microCT by a blinded radiation oncologist at each time point (maximum nodule size shown as bar graph at right of each image). Median multiplicity by microCT was 0 (range 0-3) at 5 weeks, 2 (range 0-6) at 7.5 weeks and 4 (range 1-8) at 10.5 weeks. The sensitivity of microCT at 100% specificity was 27.3% at 5 weeks, 72.7% at 7.5 weeks and 100% at 10.5 weeks.

Figure 5D:
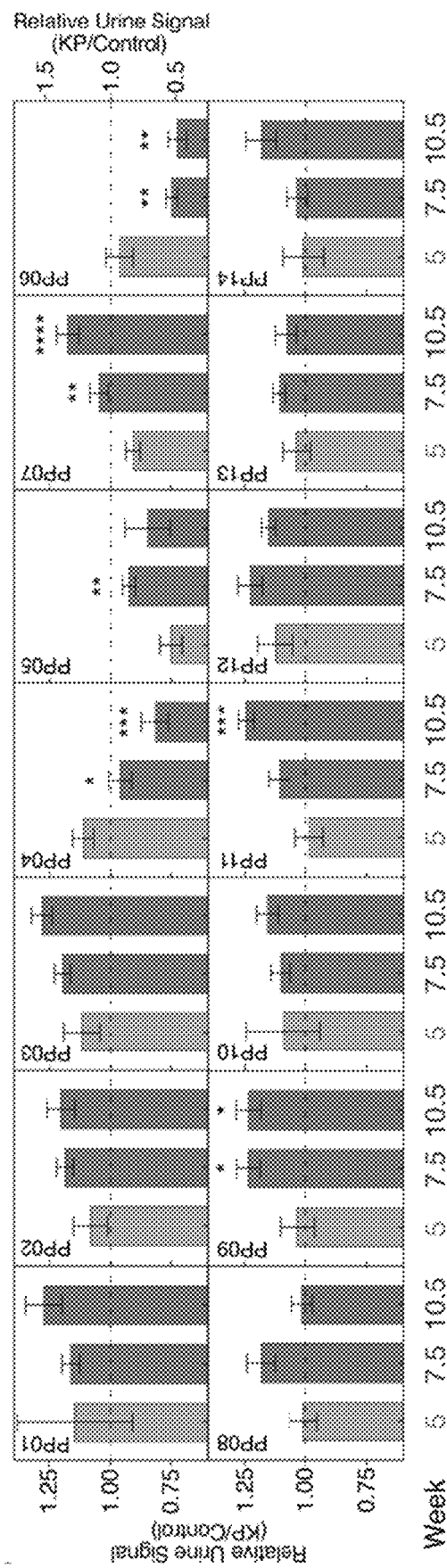
Figure 9:
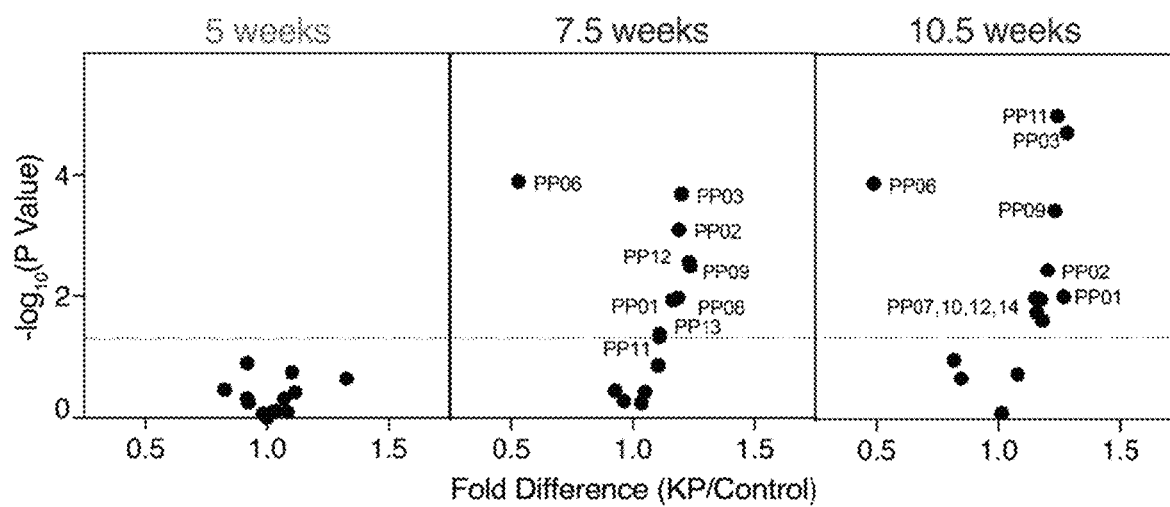
FIG. 9 includes a series of graphs showing multiple reporters are differentially enriched in the urine of healthy mice and KP mice at 7.5 and 10.5 weeks. Mean normalized urinary reporter concentrations in diseased mice and healthy mice were compared at 5 weeks, 7.5 weeks and 10.5 weeks and $-\log_{10}$(p value) was plotted against fold difference between disease and control. Dotted line is at p=0.05.

To characterize ABN performance in vivo, 14 protease-sensitive ABNs were administered to KP mice and healthy, age and sex-matched controls at 5, 7.5 and 10.5 weeks after tumor initiation. Mouse bladders were voided one hour after intrapulmonary delivery and all fresh urine produced during the subsequent hour (from 60-120 minutes after administration) was pooled and collected. LC-MS/MS was performed and peak area ratios (defined as peak area of urinary reporter divided by peak area of spiked-in internal standard) of protease-sensitive reporters were mean-normalized within each sample to reduce mouse-to-mouse variation. Several reporters differentiated KP mice from the healthy control group, with some reporter differences becoming amplified over time (e.g. PP11) and others exhibiting stage-specific differences (e.g. PP05) (FIG. 5D). At 7.5 weeks and 10.5 weeks, 9/14 and 10/14 reporters were significantly different between KP and healthy mice, respectively, ($p<0.05$) while none of the reporters differed at 5 weeks (FIG. 9).

Figure 5E:
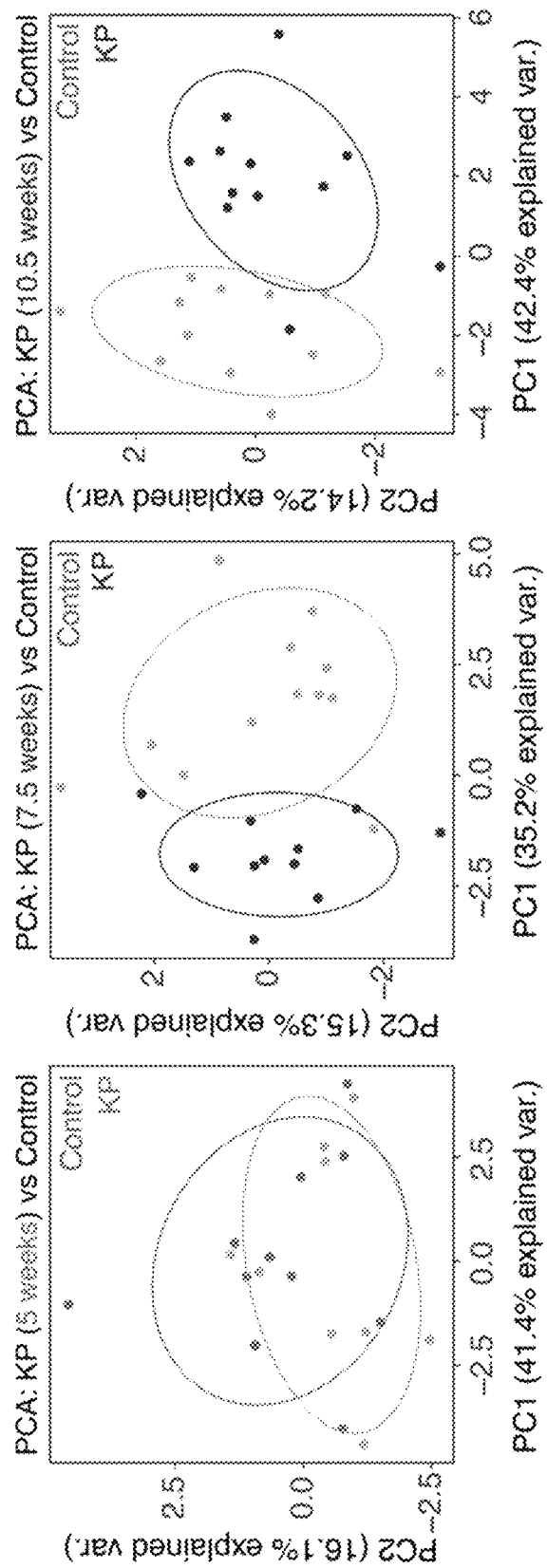

Accordingly, unsupervised clustering by principal component analysis (PCA) succeeded in separating most KP and control mice at the 7.5 week and 10.5 week time points, but not at 5 weeks (FIG. 5E).

ABNs Enable Disease Detection in Alk-Driven Adenocarcinoma

Figure 25B:
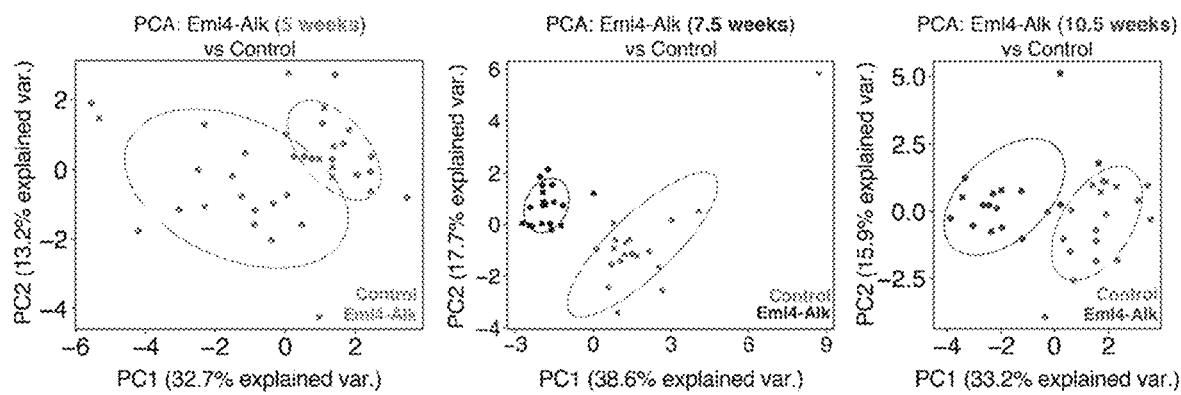

To assess the generalizability of ABNs to other genetic subtypes by leveraging the Eml4-Alk (EA) model Maddalo et al., Nature 516, 423-428 (2014), an autochthonous model in which intrapulmonary administration of adenovirus encoding two short guide RNAs (sgRNAs) and Cas9 results in translocation and fusion of the Eml4 and Alk genes, yielding lung adenocarcinoma that histologically resembles human disease. The same panel of 14 ABNs was administered in EA mice 5 weeks, 7.5 weeks, and 10.5 weeks after adenoviral induction and found differential urinary reporter signatures at all three time points (FIG. 25A), which separated diseased mice from healthy controls at all three time points, as revealed by PCA (FIG. 25B). Notably, while several reporters were differentially enriched in the urine of both KP and EA mice, others were unique to one model; the consistent enrichment of PP01, a robust metalloprotease-specific ABN (FIG. 19), in EA mice but not in KP mice suggests differential regulation of a subset of metalloproteases in these two models.

ABN Cleavage Signatures are Distinct in Malignant and Benign Disease Models

Figure 26C:
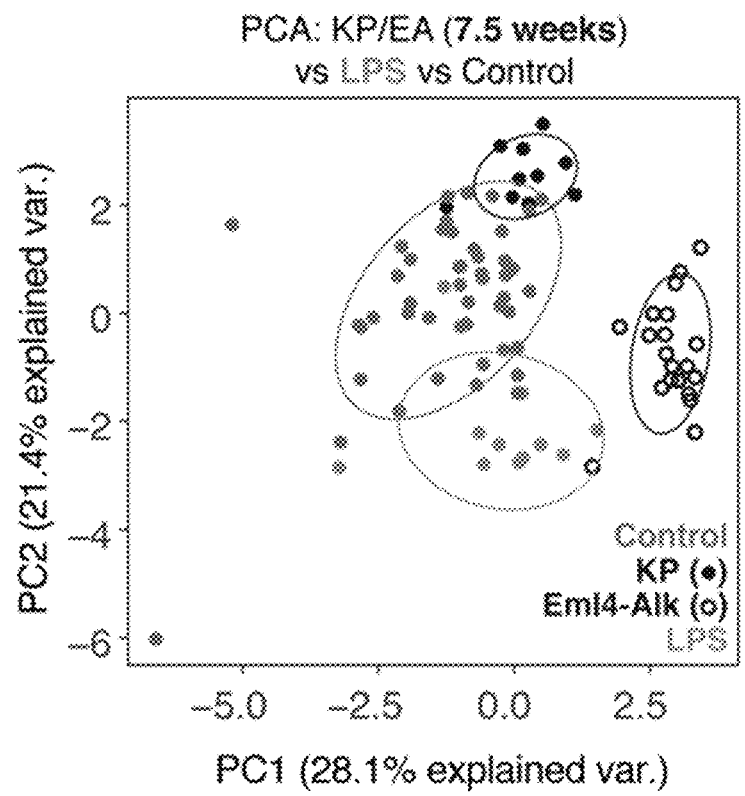

Existing lung cancer diagnostic modalities like LDCT suffer from high false positive rates, resulting in cost, anxiety, and morbidity to patients due to unnecessary invasive follow-up procedures Bach et al., JAMA—J. Am. Med. Assoc. 307, 2418-2429 (2012). It was determined whether multiplexed measurements of pulmonary protease activity could be used to discriminate malignant disease from benign disease. To assess the specificity of ABNs for lung cancer versus benign inflammatory disease, a well-established model of lung inflammation, induced by intratracheal administration of lipopolysaccharide (LPS), was used (Poroyko et al., Am. J. Physiol. Cell. Mol. Physiol. 309, L76-L83 (2015)). It was found that several reporters were differentially enriched in the urine of $KP_{7.5\ wk}$ mice (FIG. 26A) and $EA_{7.5\ wk}$ mice (FIG. 26B) relative to LPS-treated mice, enabling near-perfect separation of KP, EA, LPS, and healthy mice by unsupervised dimensionality reduction (FIG. 26C).

Machine Learning Classification Enables Prospective Disease Diagnosis

Figure 6A:
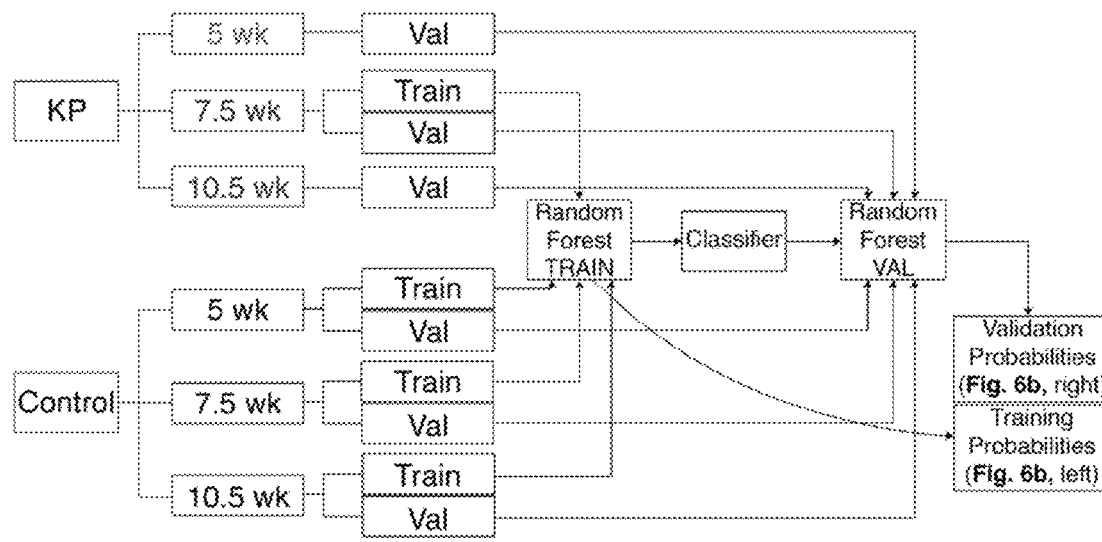
FIGS. 6A-6C show that ABNs enable highly sensitive and specific detection of early-stage lung cancer.
Figure 6B:
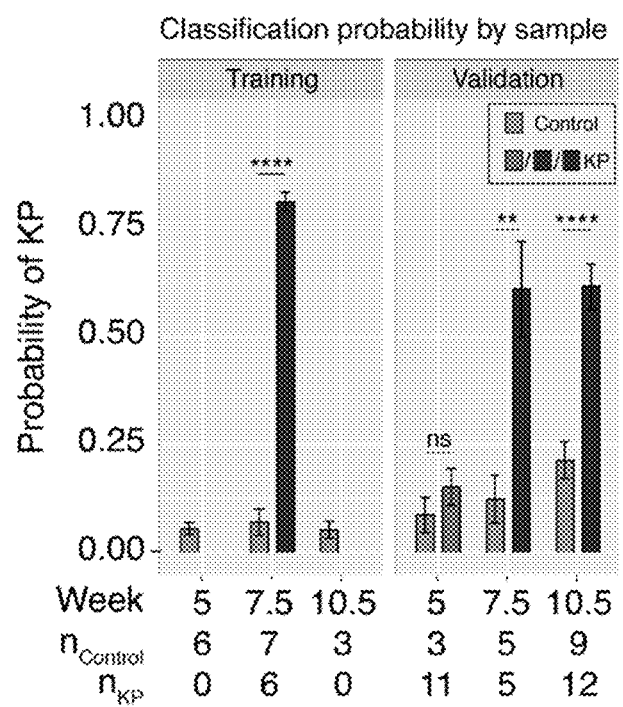
Figure 6C:
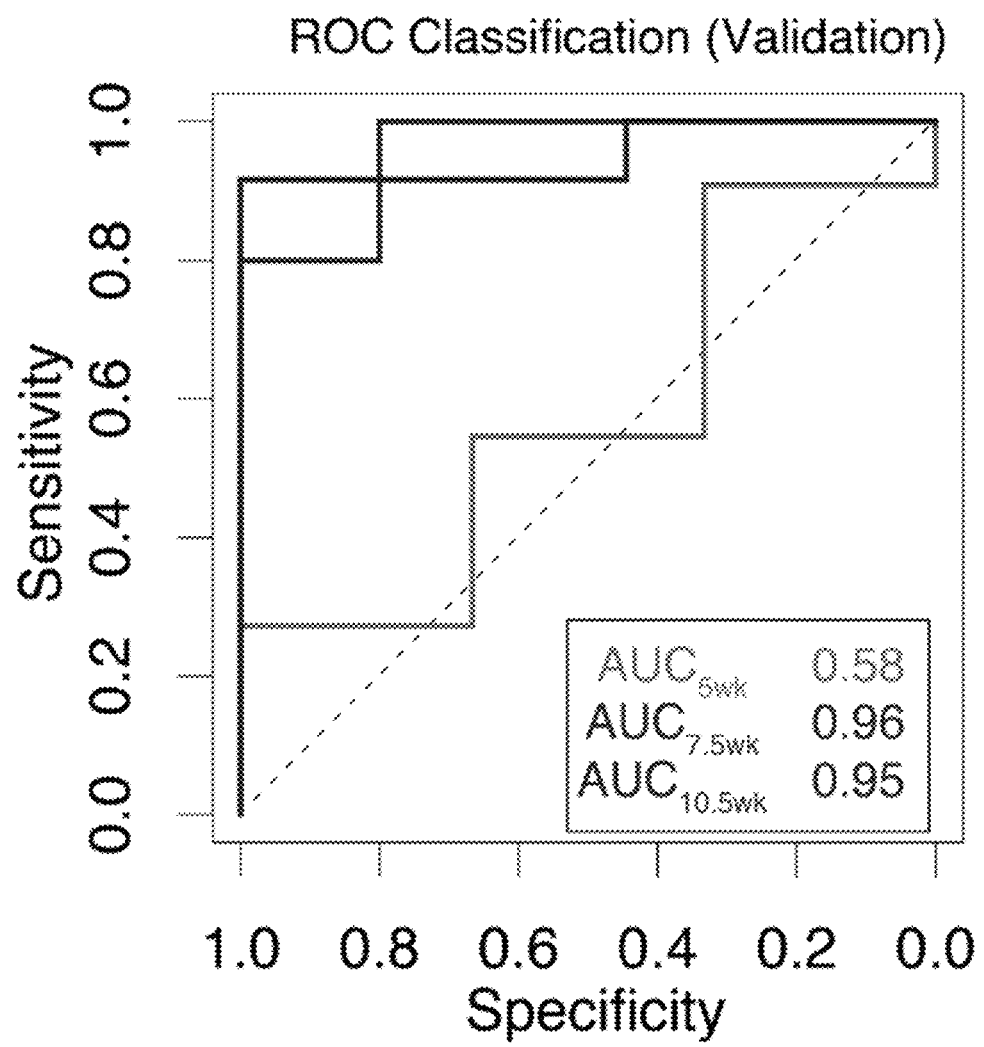

A random forest classifier was then sought to be built to enable prospective diagnosis of lung cancer in KP mice. Random forest is a high-performance classifier, applicable to a wide variety of classification tasks, that generates a collection of decision trees (a "forest") that are sampled to produce classification results (Breiman, Machine Learning 45, 5-32, 2001). A random forest classifier was trained using 50% of control mice at 5 weeks, 7.5 weeks and 10.5 weeks, as well as 50% of KP mice at 7.5 weeks (FIG. 6A). The classifier assigned a probability that each mouse belonged to either the KP cohort or the healthy control cohort (FIG. 6B, "Training" panel), achieving perfect separation of control and KP mice. The classifier was then sought to be tested on an independent validation cohort consisting of classifier-naive KP mice at 5 weeks, 7.5 weeks and 10.5 weeks post-induction, as well as the remaining control mice from each time point. KP mice were significantly more likely to be classified as "KP" than were control mice at 7.5 weeks and 10.5 weeks but not at 5 weeks (FIG. 6B, "Validation" panel). Accordingly, ROC analysis on the validation subset of this probability data revealed no classification power at 5 weeks ($AUC_{5\ wks}$, 0.58) but excellent classification at 7.5 weeks and 10.5 weeks ($AUC_{7.5\ wks}$, 0.96; $AUC_{10.5\ wks}$, 0.95), suggesting that the tumor microenvironment is insufficiently proteolytically active at 5 weeks, but that tumor size and protease activity are sufficiently advanced at subsequent time-points to yield a disease-specific urinary reporter pattern (FIG. 6C). At 100% specificity, ABNs exhibited sensitivity of 80% at 7.5 weeks and 92% at 10.5 weeks, outperforming microCT in the detection of millimeter-scale tumors at 7.5 weeks (FIG. 5C). Together, these data illustrate the power of multiplexed, lung-specific ABNs to intercept lung tumors early in disease development.

In this work, the first use of a novel class of biomarkers, ABNs, is described in lung cancer. It was found that that ABNs, when delivered by intratracheal instillation, performed with diagnostic specificity of 100% and sensitivity of 80-92% for local, early-stage disease in a model of Kras and p53 mutant lung adenocarcinoma (FIG. 6C). In some aspects, the approach overcomes the intrinsic sensitivity limitation of blood-based diagnostic assays for early-stage disease by profiling disease activity directly within the tumor microenvironment and providing multiple steps of signal amplification. In some embodiments, it was further ensured by delivery via intratracheal instillation, that 100% of ABNs reach the lung and bypass nonspecific activation in off-target organs (FIGS. 4B-4C).

Improved screening tools are needed for lung cancer, as most patients present to the clinic when their disease has reached too advanced a stage for potentially curative therapy (e.g. surgical resection and/or chemoradiation) to be administered (Howlader et al., SEER Cancer Statistics Review, 1975-2011. (ed. Institute, N.C.) (2014)). Existing diagnostic technologies like low-dose CT have poor specificity, high cost, and are not scalable owing to significant personnel and equipment requirements (Black et al., N Engl J Med 371, 1793-1802 (2014)). While there exist no widely accepted endogenous biomarkers for lung cancer (Etzioni et al., Nat Rev Cancer 3, 243-252 (2003)), several recently reported molecular diagnostic strategies hold promise. Gene expression-mediated classification of bronchial brushings affords improved sensitivity over bronchoscopy alone (75% for bronchoscopy, 97% for classifier plus bronchoscopy), but this approach is invasive and does not provide a significant specificity advantage (Silvestri et al., N Engl J Med 373, 243-251 (2015)). In patients with advanced-stage disease, ctDNA can be detected and profiled for mutational burden, but the sensitivity of this approach is poor for early-stage, local disease (~47% across tumor types) (Newman et al., Nat Med 20, 548-554 (2014); Wan et al., Nat Rev Cancer 17, 223-238 (2017)). Multiplexed ctDNA profiling may be combined with protein biomarkers (as in CancerSEEK) to improve diagnostic accuracy for early-stage disease (Cohen et al., Science 359, 926-930 (2018)). However, while the sensitivity of this approach is high for certain cancer types, it is modest at 60% for lung cancer. Finally, analysis of volatiles in exhaled breath (by mass spectrometry or nanosensor arrays) has been shown to distinguish lung cancer patients from healthy controls, but further validation is needed to verify the specificity of these volatiles for malignant, rather than benign, pulmonary diseases (Peng et al., Nat Nanotechnol 4, 669-673 (2009); van der Schee et al., Chest 147, 224-231 (2015)). Combining ABNs with orthogonal diagnostic approaches that leverage ctDNA, protein biomarkers, CTCs and/or volatiles will likely enhance accuracy of early detection over any one modality alone.

It is anticipated that multiplexing of ABNs with orthogonal protease specificities would capture the significant diversity expected in human disease, a hypothesis supported by the finding that, on the transcriptional level, incorporation of all 15 genes in the LUAD protease panel yielded near-perfect sensitivity and specificity in classifying human LUAD from NAT (FIG. 1E).

Future work could emphasize validating and enhancing the specificity of ABNs for malignant, rather than benign, disease. Without being bound by a particular theory, it is hypothesized that intrapulmonary ABNs would perform well in distinguishing patients with cancer from those with common benign diseases, as proteases associated with lung cancer are not overexpressed in COPD or ILD (FIGS. 7A-7D). For example, the specificity of ABNs for malignancy can be improved by starting with a large, diverse panel of FRET-paired peptide substrates and screening these against ex vivo tissue specimens from patients with LUAD, COPD, ILD, granulomas and hamartomas, the latter two being frequent causes of false positives in imaging studies (Ost et al., N Engl J Med 348, 2535-2542 (2003)). Substrates can then be downselected on the basis of preferential cleavage by LUAD tissue to yield a highly specific panel.

In summary, intrapulmonary ABNs perform with high sensitivity and specificity for detection of local, early-stage lung cancer in mice. This performance, in some aspects, is enabled by integrating across gene expression datasets of human and mouse lung adenocarcinoma to identify candidate proteases, screening these candidates against FRET-paired peptide substrates in vitro, and directly delivering ABNs incorporating these substrates into the lungs of mice. Clinically, ABNs may be an effective alternative to screening by low-dose CT, reducing cost, exposure to harmful radiation and, in theory, false positive rates. In the future, ABNs may also have utility in serially monitoring patients for progression, remission and recurrence, or even molecularly profiling tumors in vivo.

Materials and Methods

Study Design

For differential expression analysis of protease genes in KP mice, genes for which neither normal lung sample was nonzero were excluded, as calculation of fold changes (Tumor/Normal) would otherwise yield undefined values. For AUROC analysis in the LGRC dataset, genes for which greater than half of the samples had FPKM values of zero were excluded. During selection of KP and healthy control mice from the breeding colony, experimenters were blinded to all characteristics but age, sex, and genotype. For random forest classification, mice were randomly assigned to training and test cohorts using a randomly generated seed.

Gene Expression Analysis

Human RNA-Seq data was generated by the TCGA Research Network (http://cancergenome.nih.gov; all 527 primary lung adenocarcinoma cases (Network, C.G.A.R., Nature 511, 543-550 (2014)) and the Lung Genomics Research Consortium (LGRC; all 89 patients (Kusko et al., Am J Respir Crit Care Med 194, 948-960 (2016)). The list of human extracellular protease genes was obtained from UniProt using the following query: (keyword: "Protease [KW-0645]") locations:(location:secreted) AND reviewed: yes AND organism: "Homo sapiens (Human) [9606]". Differential expression analysis on the TCGA data was performed using the DESeq2 differential expression library in the R statistical environment (Team, R.C. R, R Foundation for Statistical Computing, Vienna, Austria, 2017; Love et al., Genome Biol 15, 550 (2014)). Area under the receiver operating characteristic curve (AUROC) analysis was performed for the TCGA and LGRC datasets using FPKM values from disease samples (LUAD, ILD and COPD) and their respective controls (NAT for LUAD, normal lung for ILD and COPD), using GraphPad Prism version 7.0a for Mac OS X, GraphPad Software, La Jolla California USA, www.graphpad.com. Genes in the LGRC dataset for which at least half of the samples had FPKM values greater than zero were included in the AUROC analysis, but all zero values were excluded. FPKM values for the KP model (Chuang et al., Nat Med 23, 291-300 (2017)) were downloaded from GEO. Top 20 extracellular endoproteases were identified by averaging FPKM values across all tumor bearing mice (K, KP-Early, $T_{non-met}$ and $T_{met}$) and dividing by the average FPKM values for normal mice. Genes for which neither of the two normal lung samples had nonzero FPKM values were excluded. Microarray counts for the K dataset (Sweet-Cordero e al., Nat Genet 37, 48-55 (2005)) were downloaded from GEO. Gene expression fold changes were determined by performing quantitative significance analysis of microarrays (SAM) using the "Standard" regression method, 100 permutations, and 10 neighbors for KNN (Tusher et al., Proc Natl Acad Sci USA 98, 5116-5121 (2001)).

Pre-ranked gene analysis (GSEA) was performed on the LUAD and LUSC gene expression dataset from TCGA, using a gene set containing the top 20 overexpressed proteases in the KP model (FIG. 2D) or the 15 genes of the LUAD protease panel (FIG. 18) (Chuang et al., Nat Med 23, 291-300 (2017)). The pre-ranked list of $\log_2$(Fold Change) was generated previously by DESeq2. 10000 permutations by gene set were performed to calculate the P value. GSEA was performed via the GenePattern online software (Reich et al., Nat Genet 38, 500-501 (2006)) and the GSEA desktop application using the "classic" scoring scheme.

Fluorogenic Substrate Characterization

Fluorogenic protease substrates were synthesized by CPC Scientific. Recombinant proteases were purchased from Enzo Life Sciences, R&D Systems and Haematologic Technologies. For recombinant protease assays, fluorogenic substrates PPQ1-14 (1 µM final concentration) were incubated in 30 µL final volume in appropriate enzyme buffer, according to manufacturer specifications, with 12.5 nM recombinant enzyme at 37° C. (FIG. 3). Proteolytic cleavage of substrates was quantified by increases in fluorescence over time by fluorimeter (Tecan Infinite M200 Pro). Enzyme cleavage rates were quantified as relative fluorescence increase over time normalized to fluorescence before addition of protease. Hierarchical clustering was performed in GENE-E, using fluorescence fold changes at 45 minutes.

Intratracheal Instillation and In Vivo Aerosolization Studies

For all mouse experiments, anesthesia was induced by isofluorane inhalation (Zoetis), and mice were monitored during recovery. For intratracheal instillation studies, a volume of 50 µl was administered by passive inhalation following intratracheal intubation with a 22 G flexible plastic catheter (Exel), as described elsewhere (DuPage et al., Nat. Protoc. 4, 1064-1072 (2009)). All aerosolization experiments used a MICROSPRAYER® Aerosolizer—Model MSA-250-M (Penn-Century. Inc. Wyndmoor, PA) with a volume of 50 µl/mouse by placing the aerosolizer tip in the trachea immediately proximal to the carina and rapidly depressing the plunger.

Biodistribution Studies

Biodistribution studies were performed in C57BL/6 mice. VT750-NHS Ester (PerkinElmer) was coupled to 8-arm 40 kDa PEG-amine (PEG-$8_{40\ kDa}$-amine, JenKem) at a 4:1 molar ratio, reacted overnight and purified by spin filtration. For biodistribution studies, PEG-$8_{40\ kDa}$-VT750 (50 µL volume, 5 µM concentration by VT750 absorbance) was administered by passive inhalation following intratracheal intubation with a 22 G flexible plastic catheter (Exel), as described elsewhere (DuPage et al., Nat Protoc 4, 1064-1072 (2009)) (FIGS. 4B-4C) or aerosolization (FIG. 23A-23B). Mice in the IV cohort were intravenously administered an equal dose of PEG-$8_{40\ kDa}$-VT750. Mice were monitored during recovery from isoflurane anesthesia. Animals were sacrificed by $CO_2$ asphyxiation 60 min post-inhalation/injection and organs were removed for imaging (LICOR Odyssey). Organ fluorescence was quantified in Fiji (Schindelin et al., Nat Methods 9, 676-682 (2012)) by manually outlining organs, using the "Measure" feature and taking the mean intensity.

Blood for pharmacokinetics measurements was collected using retro-orbital bleeds and 15 μL glass capillary collection tubes. Blood was diluted in 40 μL PBS with 5 mM EDTA to prevent clotting, centrifuged for 5 min at 5,000×g and fluorescent reporter concentration was quantified in 384-well plates relative to standards (LICOR Odyssey).

For immunohistochemical visualization of nanoparticles following IT administration, EZ-Link NHS-Biotin (Thermo Scientific) was coupled to PEG-$8_{40\ kDa}$-amine at 2:1 molar ratio and reacted overnight, followed by spin filtration. Pulmonary delivery of PEG-$8_{40\ kDa}$-biotin (50 μL volume, 10 μM concentration) was performed by intratracheal instillation (FIG. 4D-E) or aerosolization (FIGS. 23C-23F). Fixation was performed 10-30 minutes later by inflating lungs with 10% formalin. Lungs were excised, fixed in 10% formalin at 4° C. overnight and embedded in paraffin blocks. 5 m tissue slices were stained for biotin using the streptavidin-HRP ABC kit (Vector Labs) with DAB. Slides were scanned using the 20× objective of the Pannoramic 250 Flash III whole slide scanner (3DHistech).

Mouse Model and In Vivo Characterization

Male B6/SV129 $Kras^{LSL-G12D/+}$; $Trp53^{fl/fl}$ (KP) mice between 18 and 30 weeks old were used for lung adenocarcinoma experiments. Tumors were initiated, as described previously (DuPage et al., Nat Protoc 4, 1064-1072 (2009)), by the intratracheal administration of 50 μL of adenovirus-SPC-Cre ($2.5\times10^8$ PFU in Opti-MEM with 10 mM $CaCl_2$)) under isoflurane anesthesia. Control cohorts consisted of age and sex-matched KP mice that did not undergo intratracheal administration of adenovirus. Tumor growth was monitored by micro computed tomography (microCT) imaging (General Electric) and was scored by a blinded radiation oncologist using MicroView (Parallax Innovations) (Table 4). Tumor volumes were calculated by using the ROI sphere/elliptical tool.

ABN constructs (GluFib-Substrate-PEG-$8_{40\ kDa}$) for urinary experiments were synthesized by CPC Scientific (Sunnyvale, CA). ABNs were dosed (50 μL total volume, 20 μM concentration per ABN) by intratracheal intubation, as described above. Bladders were voided 60 minutes after ABN administration and all urine produced 60-120 min after ABN administration was collected using custom tubes in which the animals rest upon 96-well plates that capture urine. Urine was pooled and frozen at −80° C. until analysis by LC-MS/MS.

LC-MS/MS Reporter Quantification

Liquid chromatography/tandem mass spectrometry was performed by Syneos Health (Princeton, NJ) using a Sciex 6500 triple quadrupole instrument. Briefly, urine samples were treated with UV irradiation to photocleave the ANP linker and liberate the Glu-Fib reporter from residual peptide fragments. Samples were extracted by solid-phase extraction and analyzed by multiple reaction monitoring by LC-MS/MS to quantify concentration of each Glu-Fib mass variant. Analyte quantities were normalized to a spiked-in internal standard and concentrations were calculated from a standard curve using peak area ratio (PAR) to the internal standard. Mean normalization was performed on PAR values to account for mouse-to-mouse differences in ABN inhalation efficiency and urine concentration.

Classification

Principal component analysis (PCA) was performed on mean normalized PAR values in the R statistical environment (Team, R.C. R, R Foundation for Statistical Computing, Vienna, Austria, 2017) using the prcomp function. Binary classification was performed using the Caret package (Kuhn, M. caret: Classification and Regression Training. (2017)) in the R statistical environment). Generalized linear model was used for RNA-seq data and random forest (Breiman, Machine Learning 45, 5-32 (2001)) was used for ABN classification of urine samples. Pre-specified training and validation cohorts were randomly assigned (75% training/25% validation for RNA-seq data, 50% training/50% validation for urine data). Classifiers used cross-validation on the training cohort and were trained with optimization for AUC.

Toxicity Studies

ABN constructs (GluFib-Substrate-PEG-$8_{40\ kDa}$) were synthesized by CPC Scientific (Sunnyvale, CA). ABNs were dosed (50 μL total volume, 20 μM concentration per ABN in mannitol buffer (0.28 M mannitol, 5 mM sodium phosphate monobasic, 15 mM sodium phosphate dibasic, pH 7.0-7.5)) by intratracheal instillation into healthy male C57BL/6 mice. The mass of each mouse was monitored for 11 days post-administration and compared with masses of control mice administered mannitol buffer. Heart, lung, liver, spleen, and kidney tissues were collected from the mice at 2 h, 24 h, or 11 days post-administration, fixed in 10% formalin, paraffin embedded, stained with haematoxylin and eosin, and then examined by a veterinary pathologist (Dr. Roderick Bronson).

Clearance Studies

VT750-NHS Ester (PerkinElmer) was coupled to 8-arm 40 kDa PEG-amine (PEG-$8_{40\ kDa}$-amine, JenKem) at a 4:1 molar ratio, reacted overnight, and purified by spin filtration (Amicon Ultra centrifugal filter units, Sigma). Mice were lightly anesthetized via isoflurane inhalation, and PEG-$8_{40\ kDa}$-VT750 (50 μl volume, 20 μM concentration by VT750 absorbance) was administered by intratracheal instillation (FIG. 20). Animals were sacrificed by $CO_2$ asphyxiation at the indicated timepoints and organs were removed for imaging (LICOR Odyssey). Organ fluorescence was quantified in Fiji (63) by manually outlining organs, using the "Measure" feature, and taking the mean intensity. Kinetic data was fit using nonlinear regression in GraphPad 8.0 (Prism). Lung data was fit to an exponential decay model ($Y=Y_0e^{(-Kt)}$; Y, fluorescence; $Y_0$, initial fluorescence; K, rate constant; t, time), and all other organ data was fit to a two-phase growth and decay model ($Y=A1e^{(-t/B1)}+A2e^{(-t/B2)}$; Y, fluorescence; t, time; A1/A2/B1/B2, constants)

In Vitro Aerosolization Studies

Analysis of nanoparticle stability and protease cleavage susceptibility following aerosolization used 0.1 m-filtered 250 μM PEG-$8_{40\ kDa}$ scaffold (FIGS. 22B-22E) or 5 μM PPQ5 PEG-$8_{40\ kDa}$ nanosensors (FIG. 22F). Protease cleavage assays of aerosolized nanoparticles used 50 nM of recombinant human MMP13 (Enzo).

Colorectal Cancer Xenograft Model

For xenograft studies, LS174T (ATCC CL-188) cells were cultured in Eagle's Minimal Essential Medium (EMEM, ATCC) supplemented with 10% (v/v) FBS (Gibco)

and 1% (v/v) penicillin-streptomycin (CellGro). Cells were passaged and harvested for inoculation when confluence reached 80%. Female NCR nude mice (4-5 weeks, Taconic) were injected bilaterally with $3\times10^6$ LS174T cells, resuspended in Opti-MEM (ThermoFisher), per flank. Ten days after inoculation, tumor-bearing mice and age-matched controls were administered ABN constructs via intratracheal intubation. Bladders were voided 60 minutes after ABN administration, and all urine produced 60-120 min after ABN administration was collected. Urine was pooled and frozen at $-80°$ C. until analysis by LC-MS/MS.

EA Lung Adenocarcinoma Model

Tumors were initiated in male C57BL/6 mice between 6 and 10 weeks old as described previously (50), by intratracheal administration of 50 µL adenovirus expressing the Ad-EA vector (Viraquest) ($1.5\times10^8$ PFU in Opti-MEM with 10 mM $CaCl_2$)). Control cohorts consisted of age and sex-matched mice that did not undergo intratracheal administration of adenovirus.

Lipopolysaccharide (LPS) Model

Lung inflammation was induced in 18 to 20 week-old male C57BL/6 mice via intratracheal administration of 0.3 mg of LPS (Sigma Aldrich) in 50 µl water, under isoflurane anesthesia. LPS-treated mice and age and sex-matched healthy controls were administered ABNs 3 days after LPS induction.

Figure 27A:
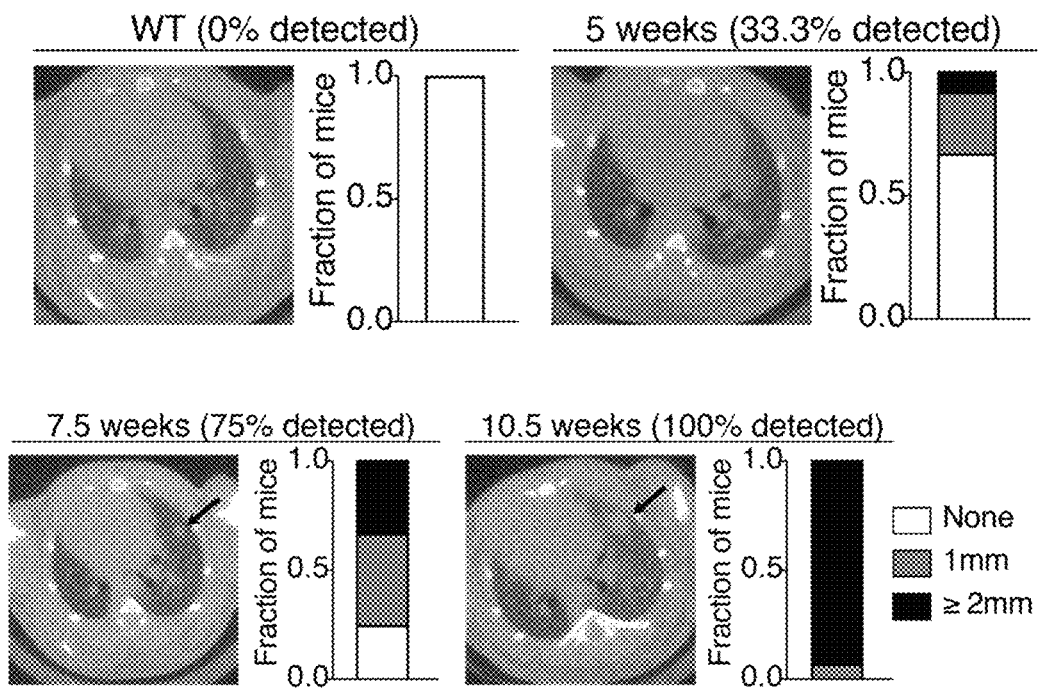
FIGS. 27A-27B include data showing that lung protease nanosensors distinguished between diseased and healthy mice.

Example 2. Lung Protease Nanosensors Sensitively and Specifically Detect Lungs Disease and can be Used with Random Forest Classification Analysis to Diagnose Disease It was determined whether the lung protease nanosensors could be used to longitudinally monitor disease progression in KP mice and their diagnostic performance against microcomputed tomography (microCT) was also benchmarked. After initiating disease via administration of adenovirus, tumor development was monitored by performing microCT at 5 weeks ($KP_{5\ wk}$), 7.5 weeks ($KP_{7.5\ wk}$), and 10.5 weeks ($KP_{10.5\ wk}$) after adenoviral induction (FIG. 27A, Table 4). The sensitivity of microCT at 100% specificity was 33.3% at 5 weeks, 75% at 7.5 weeks, and 100% at 10.5 weeks. In Table 4, $V_{avg}$, average tumor volume. MicroCT sensitivity is defined as the number of mice with detectable tumors divided by the total number of mice at each time point.

TABLE 4

Quantification of tumor burden in KP mice by microCT.

| Mouse | 5 weeks | | 7.5 weeks | | 10.5 weeks | |
|---|---|---|---|---|---|---|
| | Multi-plicity | Volume (mm³) | Multi-plicity | Volume (mm³) | Multi-plicity | Volume (mm³) |
| KP1 | 0 | 0 | 1 | 0.5 | 1 | 0.5 |
| KP2 | 0 | 0 | 0 | 0 | 3 | 5.2 |
| KP3 | 1 | 1.8 | 3 | 2.8 | 6 | 13 |
| KP4 | 3 | 2.8 | 3 | 6.5 | 6 | 27 |
| KP5 | 0 | 0 | 0 | 0 | 5 | 17.8 |
| KP6 | 0 | 0 | 6 | 4.4 | 6 | 22.7 |
| KP7 | 2 | 4.7 | 4 | 7 | 4 | 16.8 |
| KP8 | 0 | 0 | 2 | 1 | Motion Artifact | Motion Artifact |
| KP9 | 0 | 0 | 2 | 4.7 | 3 | 42.6 |
| KP10 | 0 | 0 | 0 | 0 | 3 | 16.8 |
| KP11 | 0 | 0 | 2 | 4.7 | 2 | 4.7 |

TABLE 4-continued

Quantification of tumor burden in KP mice by microCT.

| Mouse | 5 weeks | | 7.5 weeks | | 10.5 weeks | |
|---|---|---|---|---|---|---|
| | Multi-plicity | Volume (mm³) | Multi-plicity | Volume (mm³) | Multi-plicity | Volume (mm³) |
| KP12 | 1 | 0 | 1 | 1.8 | 8 | 43.9 |
| MicroCT Sensitivity | 33.3% | | 75% | | 100% | |
| $V_{avg}$ (mm³) | 0.775 | | 2.78 | | 19.2 | |

Figure 24A:
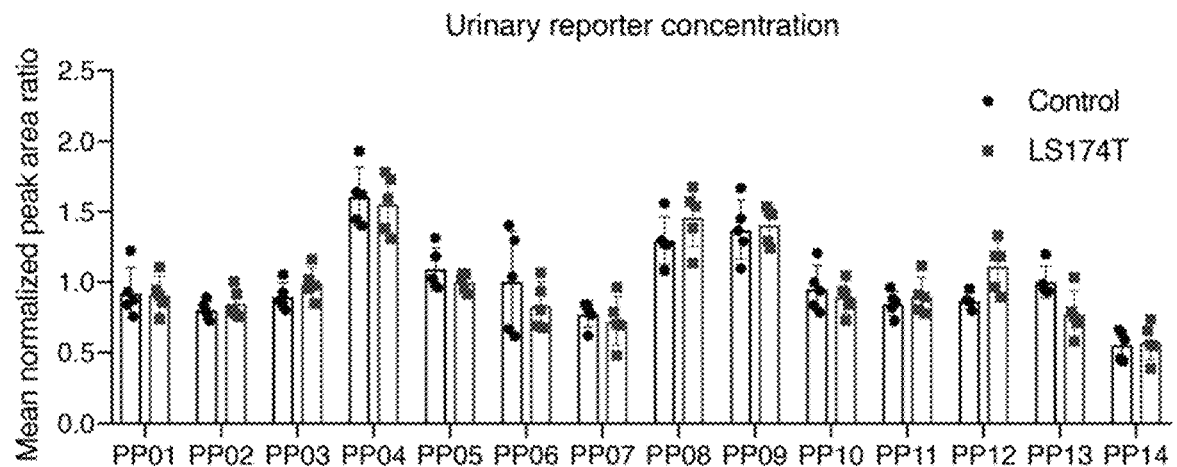
FIGS. 24A-24B include data showing that extrapulmonary disease was undetectable by intrapulmonary ABNs.
Figure 24B:
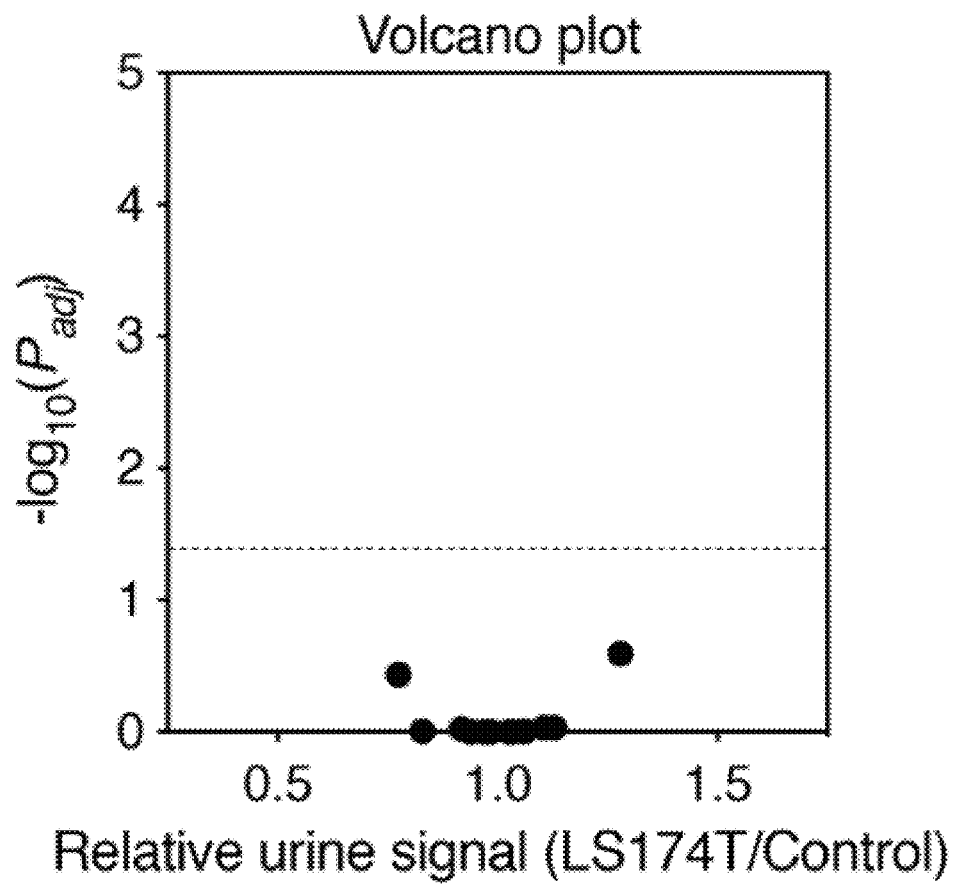
Figure 27B:
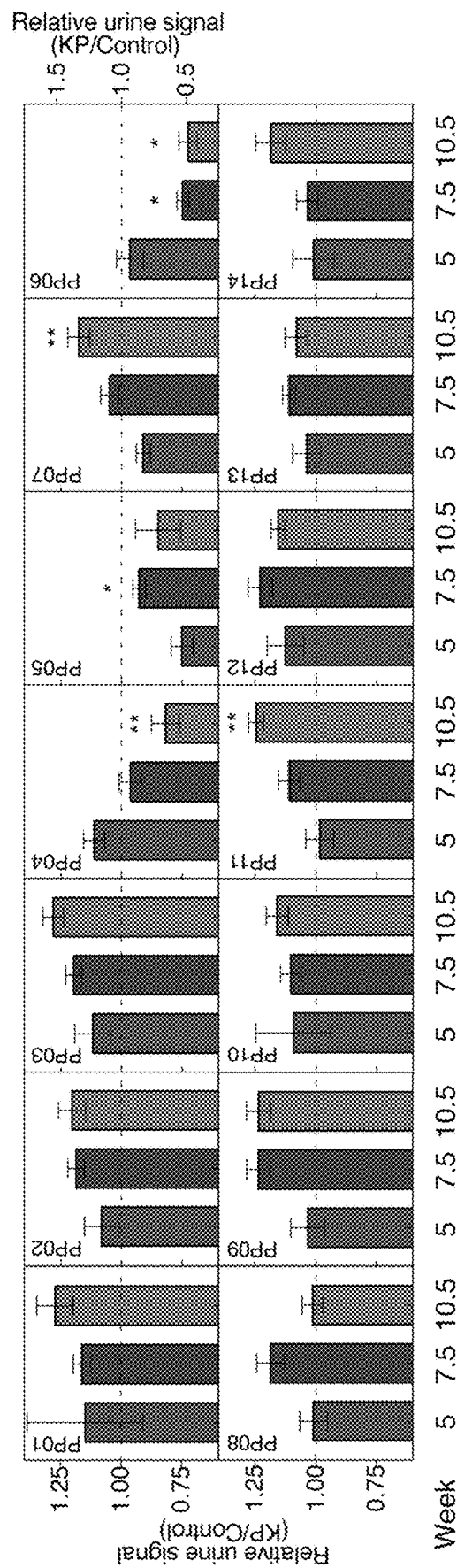

All 14 protease-sensitive ABNs were administered to the lungs of KP mice and age and sex-matched healthy controls at 5, 7.5, and 10.5 weeks after tumor initiation. Several reporters differentiated KP mice from healthy controls, with some reporter differences becoming amplified over time (e.g. PP07, PP11) (FIG. 27B). At 7.5 weeks and 10.5 weeks, 5/14 reporters were significantly different between KP and healthy mice ($P_{adj}<0.05$), while none of the reporters differed at 5 weeks (FIG. 28). In contrast, intratracheal administration of the same 14-plex panel to mice bearing flank xenograft tumors (average tumor volume of 448 mm³) derived from a human colorectal cancer cell line yielded no differential urinary reporters (FIGS. 24A-24B). Of the 5 reporters enriched in $KP_{7.5\ wk}$ urine, three (PP02, PP03, and PP09) were also enriched in $KP_{10.5\ wk}$ urine, and these sequences corresponded to peptides cleaved by metalloproteases or both metalloproteases and aspartic proteases in vitro. However, the most significantly enriched reporter in the urine of KP mice at 10.5 weeks (PP11) corresponded to a peptide cleaved only by serine proteases in vitro.

It was determined whether the lung nanosensors could be prospectively applied to diagnose disease. The random forest classifier (Breiman et al., Mach. Learn. 45, 5-32 (2001).) was trained using the urinary ABN reporter output from a subset of $KP_{7.5\ wk}$ and $EA_{7.5\ wk}$ mice (as "disease") and healthy mice (as "control") (Table 5) and tested its ability to classify each LUAD model from healthy control mice in an independent test cohort. In Table 5, cohort numbers used to train and test random forest classifiers applied in FIGS. 17A-17C (KP v. Healthy, Eml4-Alk v. Healthy, LUAD v. Healthy) and FIG. 17D (LUAD v. Benign). ROC analysis revealed strong classification of $KP_{7.5\ wk}$ and $KP_{10.5\ wk}$ ($AUC_{7.5\ wk}$ s=0.95; $AUC_{10.5\ wk}$ s=0.93) (FIG. 17A), as well as EA mice at all three time points ($AUC_{5\ wk}$ s=0.96, $AUC_{7.5\ wk}$ s=0.98; $AUC_{10.5\ wk}$ s=0.93) (FIG. 17B). The classifier was also evaluated on a test cohort that combined both LUAD models and again found strong classification at 7.5 weeks and 10.5 weeks ($AUC_{7.5\ wk}$ s=0.97; $AUC_{10.5\ wk}$ s=0.93) (FIG. 17C). A second classifier was then trained, this time incorporating LPS-treated mice (Table 5), and found that it performed with high accuracy in discriminating $KP_{7.5\ wk}$, $EA_{7.5\ wk}$, and a combination of the two (termed "$LUAD_{7.5\ wk}$") from healthy and LPS-treated mice ($AUC_{EA}=0.98$; $AUC_{KP}=0.97$; $AUC_{LUAD}=0.97$) (FIG. 17D).

TABLE 5

Composition of train and test cohorts for random forest classification.

| | 5 weeks | | 7.5 weeks | | 10.5 weeks | |
|---|---|---|---|---|---|---|
| | Train | Test | Train | Test | Train | Test |
| KP v. Healthy (FIG. 6A) | | | | | | |
| Healthy | 0 | 9 | 12 | 6 | 0 | 12 |
| KP | 0 | 11 | 6 | 5 | 0 | 12 |

TABLE 5-continued

Composition of train and test cohorts for random forest classification.

| | 5 weeks | | 7.5 weeks | | 10.5 weeks | |
|---|---|---|---|---|---|---|
| | Train | Test | Train | Test | Train | Test |
| Eml4-Alk Eml4-Alk v. Healthy (FIG. 6B) | 0 | 0 | 6 | 0 | 0 | 0 |
| Healthy | 0 | 17 | 12 | 13 | 0 | 19 |
| KP | 0 | 0 | 6 | 0 | 0 | 0 |
| Eml4-Alk LUAD v. Healthy (FIG. 6C) | 0 | 19 | 6 | 14 | 0 | 16 |
| Healthy | 0 | 26 | 12 | 19 | 0 | 31 |
| KP | 0 | 11 | 6 | 5 | 0 | 12 |
| Eml4-Alk LUAD v. Benign (FIG. 6D) | 0 | 19 | 6 | 14 | 0 | 16 |
| Healthy | 0 | 0 | 12 | 19 | 0 | 0 |
| KP | 0 | 0 | 6 | 5 | 0 | 0 |
| Eml4-Alk | 0 | 0 | 6 | 14 | 0 | 0 |
| LPS | 0 | 0 | 6 | 5 | 0 | 0 |

Materials and Methods

Materials and methods are the same as indicated in Example 1 except as indicated below.

Study Design

It was determined whether intrapulmonary administration of a multiplexed library of ABNs could be used to detect localized, early-stage, lung cancer. All animal studies were conducted in compliance with institutional and national policies. Experiments involving intrapulmonary delivery of ABNs in KP mice consisted of 12 KP mice and 12 healthy control mice; experiments involving intrapulmonary delivery of ABNs in EA mice consisted of 20 EA mice and 20 healthy control mice. These mice were monitored, by intratracheal ABN administration and microCT, at 5 weeks, 7.5 weeks, and 10.5 weeks after tumor induction. Sample size was selected to ensure a sample size greater than or equal to five for both training and test groups at each time point and for each treatment group. Urine samples with peak area ratio (PAR) values of zero for two or more analytes were excluded, as these samples represented failed ABN deliveries and would confound analysis.

Statistical Analysis and Machine Learning Classification

For random forest classification, mice were randomly assigned to training and test cohorts using a randomly generated seed.

For all urine experiments, PAR values were normalized to ABN stock concentrations and then mean normalized across all reporters in a given urine sample prior to further statistical analysis. Significantly different reporters were identified by unpaired two tailed t-test followed by correction for multiple hypotheses using the Holm-Sidak method in GraphPad Prism 7.0. Principal component analysis (PCA) was performed on mean normalized PAR values and implemented in MATLAB R2019b (Mathworks, Natick, MA). For disease classification based on urinary ABN signatures, randomly assigned sets of paired data samples consisting of features (i.e., the mean-normalized PAR values for 14 urinary reporters) and labels (i.e., KP, EA, etc.) were used to train random forest (Brieman, Mach. Learn. 45, 5-32 (2001)) classifiers implemented with the TreeBagger class in MATLAB R2019b. Estimates of out-of-bag error were used for cross-validation, and trained classifiers were tested on randomly assigned, held-out, independent test cohorts. The specific composition of train-test cohorts is provided in Table 5. Ten independent train-test trials were run for each classification problem, and classification performance was evaluated with receiver operating characteristic (ROC) statistics calculated in MATLAB. Classifier performance was reported as the mean accuracy and area under the curve (AUC) across the ten independent trials.

Example 3. Protease Activity Sensors Noninvasively Classify Bacterial Infections and Antibiotic Responses Protease Substrates Respond to Host and Bacterial Proteases In Vitro.

To develop ABNs for the diagnosis and monitoring of *Pseudomonas aeruginosa* infection, candidate proteases upregulated at sites of infection were identified, as well as those produced by the pathogen itself. Based on the robust neutrophil and macrophage recruitment response to bacterial infection (Mayadas et al., Annu Rev Pathol Mech Dis, 9, 181-218, 2014), a candidate substrate was first designed for elastases, including neutrophil elastase (Castillo et al., Anal Biochem, 99, 53, 1979; Elston et al., Anal Biochem, 368, 87, 2007). In addition, a substrate was designed for *P. aeruginosa* protease LasA, a virulence factor known to be secreted by strain PA01 (Elston et al., Anal Biochem, 368, 87, 2007; Kaman et al., PLoS One, 8, e81428, 2013; Spencer et al., J Mol Biol, 396, 908, 2010). After testing the candidate substrates for their cleavage specificity in vitro, they were conjugated to nanoparticle cores to form ABNs. By administering these LasA- or elastase-sensitive ABNs to the lung, it is predicted that this tool will enable interrogation of proteolytic activity within this organ, and result in the cleavage-dependent liberation of small reporter fragments that clear via the kidneys and concentrate in the urine (FIG. 10A). The reporters are designed to permit subsequent signal detection via ELISA and/or fluorescence for diagnosis of infection. To this end, each substrate was formulated for ELISA readout via ligand-encoded reporters by including a biotin distal to the protease-cleavable sequence (LAS-E and ELA-E) or were alternatively formulated for fluorescence measurement (LAS-Q and ELA-Q) by flanking the protease-cleavable sequence with a fluorophore-quencher FRET pair (FIG. 10B).

Figure 14A:
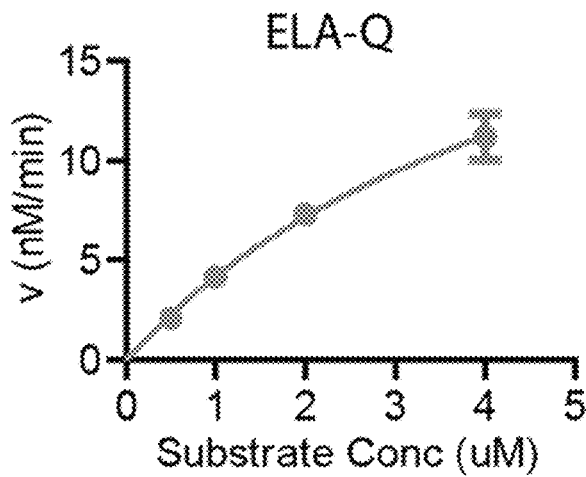
FIGS. 14A-14B shows cleavage of substrates by PA01 supernatant. Supernatant from PA01 culture was collected and incubated with various concentrations of FRET-paired substrates ELA-Q (FIG. 14A) and LAS-Q (FIG. 14B) and cleavage was monitored by fluorescence signal.
Figure 14B:
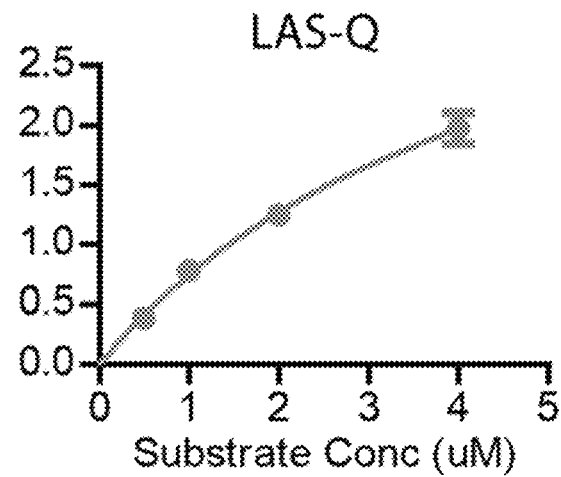

The specificity of LAS and ELA for *P. aeruginosa* cleavage was tested by collecting supernatants from PA01 or *Staphylococcus aureus* cultures and incubating them with FRET-paired substrates LAS-Q and ELA-Q in 384 well plates. Significant increases were observed in fluorescence signal after cleavage of ELA-Q by proteases from both bacterial supernatants, but greater selectivity for cleavage of LAS-Q by PA01 (FIG. 10C). This pattern likely stems from *S. aureus* also secreting an analogous elastase that could cleave ELA-Q, yet this bacterial strain does not express a protease with function similar to LasA (Shaw, Microbiology, 150, 217, 2004; Potempa et al., J Biol Chem, 263, 2664, 1988). Addition of $ZnCl_2$ to PA01 supernatant suppressed the cleavage signal of both LAS-Q and ELA-Q, supporting the interpretation that the observed signal generation arises due to proteolytic cleavage (Kessler et al., J Biol Chem, 272, 9884, 1997) (FIG. 1C). By Michaelis-Menten type analysis, it was confirmed that the ELA substrate was more potently cleaved by proteases over a range of concentrations (FIG. 14). To investigate whether the LAS and ELA substrates are also susceptible to cleavage by host proteases, each was incubated with recombinant mouse proteases. Both substrates resist cleavage by MMP7, MMP13, and thrombin, but ELA-Q and—to a lesser extent, LAS-Q—are each cleaved by neutrophil elastase (FIG. 10D). Together, these results suggest that the substrates should be cleaved by to *P. aeruginosa*-derived proteases (LAS and ELA), and also yield a signal mediated by a host's immune response to the infection (ELA), and thus it is anticipated that the LAS substrate signal should exhibit greater specificity for bacterial protease cleavage.

Figure 10E:
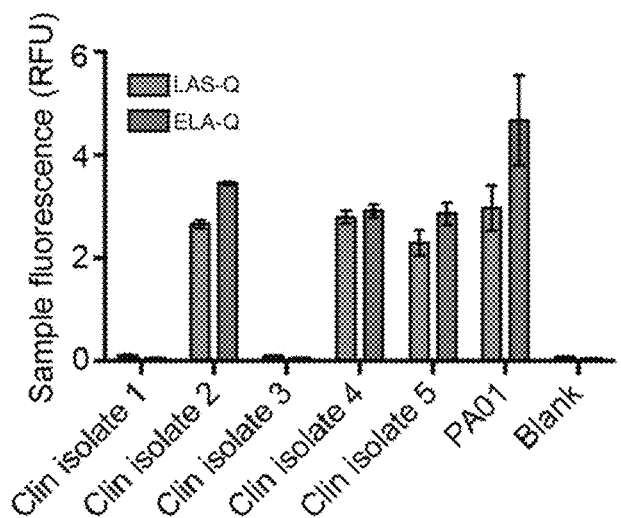

Once it was observed that the two peptide substrates were cleaved when exposed to the supernatant of PA01 lab strain bacteria, it was sought to test whether the candidate sensors also exhibit sensitivity to proteases produced by samples of *P. aeruginosa* obtained from infected patients. Supernatant was collected from cultures of five clinical isolate strains and incubated with LAS-Q and ELA-Q. Significant cleavage of both substrates was observed by 3 of the 5 strains (FIG. 10E). Consistent with the results from PA01 and the Michaelis-Menten analyses, the ELA-Q substrate was more extensively cleaved by these bacterial-derived proteases.

Figure 10F:
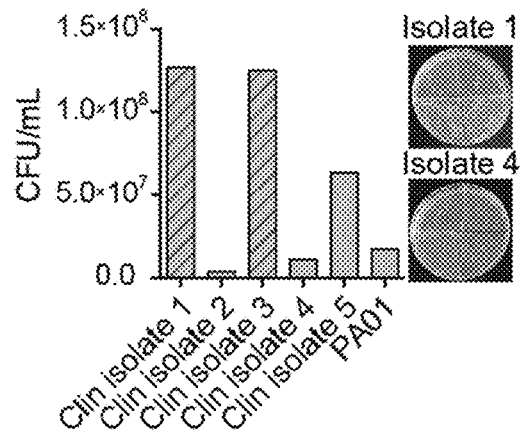
Figure 15:
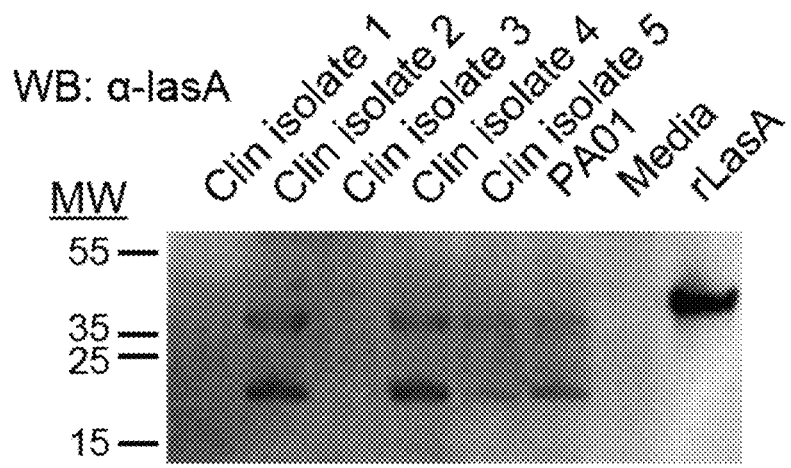
FIG. 15 shows characterization of LasA secretion by *P. aeruginosa* strains. Anti-LasA immunoblot of supernatant protein from *P. aeruginosa* clinical isolates and the laboratory strain PA01, with fresh bacterial growth media, and recombinant LasA protein controls, all run on an SDS-PAGE gel. The slight difference in gel migration between supernatant and recombinant protein samples is likely due to the presence of a 6×His-SUMO tag on the recombinant protein.

After observing that the sensors were not responsive to 2 of the 5 clinical isolate strains, a possible outcome was that there might be a range of LasA protein secretion or activation between the bacterial samples. Given that LasA activity is known to mediate lysis of staphylococci (Kessler et al., J Biol CHem, 268, 7503, 1993), it was first tested whether a correlation was observed between the capacity to mediate nanosensor substrate cleavage and anti-*Staphylococcus aureus* activity amongst these clinical isolates. Supernatants were collected from PA01 and the five clinical isolates and cultures of *S. aureus* strain USA300 were grown. USA300 was then sub-cultured in the *P. aeruginosa* supernatants and colony forming units were quantified in the cultures over time by plating dilutions of culture aliquots on LB agar. Suppression of *S. aureus* growth was observed by PA01 supernatant (86% decrease) and supernatants from clinical isolates 2, 4, and 5 (97%, 91%, and 50%, respectively) relative to clinical isolates 1 and 3 (FIG. 10F). Next, to test whether LasA protein was being secreted by the clinical isolate strains a Western blot was performed on supernatant protein. This analysis found that the non-cleaving strains lacked LasA in their supernatant, whereas supernatant from the substrate-cleaving strains contained substantial levels of LasA protein (FIG. 15), supporting the possible outcome that the LAS-Q sensor is detectable only in the presence of LasA protease activity.

ABNs Detect *P. aeruginosa* Infection In Vivo.

Figure 11A:
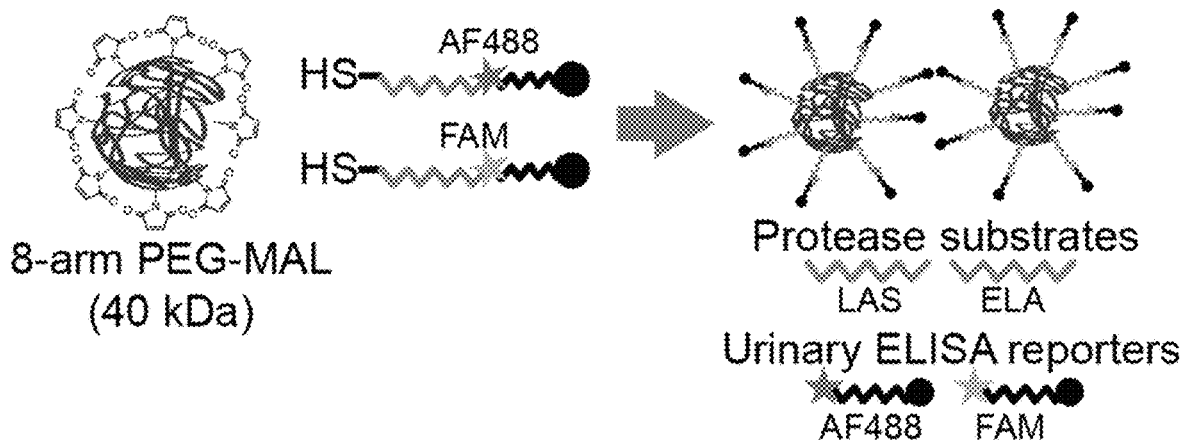
Figure 11B:
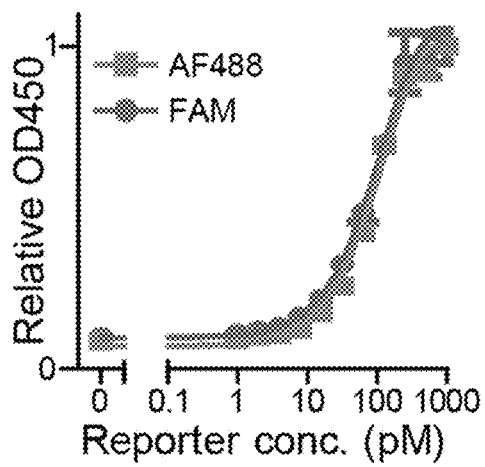
Figure 16:
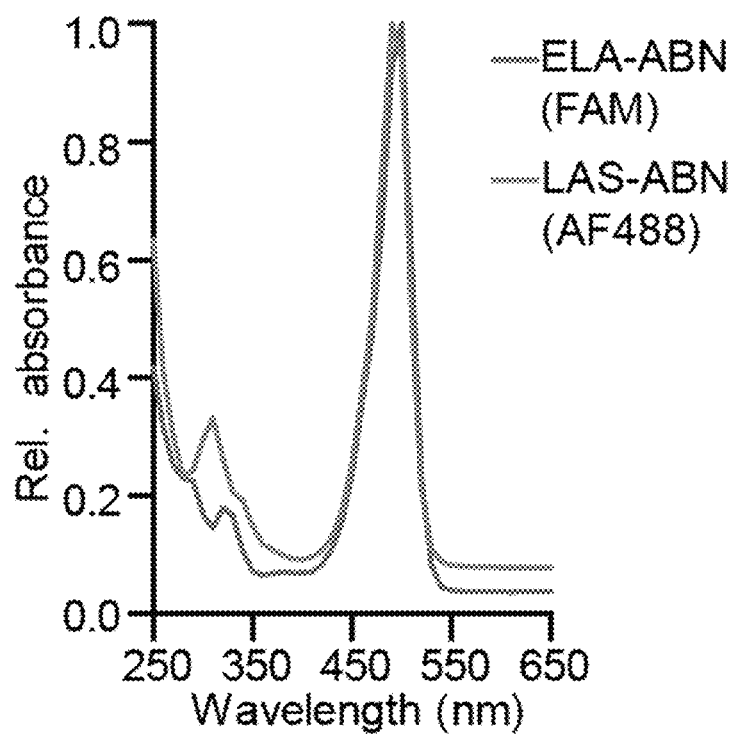
FIG. 16 shows absorbance spectra of activity-based nanosensors. Absorbance spectra were collected for activity-based nanosensors responsive to elastases (ELA-ABN, bottom curve) or LasA (LAS-ABN, top curve), showing FAM and Alexa Fluor 488 absorbance peaks, respectively.

Next, an intratracheal instillation model of bacterial pneumonia was used with lab strain PA01, as it shows the highest cleavage of the sensors in vitro, demonstrates consistent infection dynamics in mice, and allows for robust comparison between experiments, to evaluate the ability of these ABNs to detect and monitor *P. aeruginosa* lung infection in vivo (Dudani et al., Adv Funct Mater, 26, 2919, 2016; Kwon et al., Adv Mater, 29, 1701527, 2017). Peptide substrates were coupled to 40 kDa 8-arm PEG-MAL via terminal cysteines on each peptide to generate ABNs for use in vivo (Dudani et al., Adv Funct Mater, 26, 2919, 2016; Kwong et al., Proc Natl Acad Sci, 112, 12627, 2015). Each substrate is barcoded with an independent ligand and a biotin on a stable urinary peptide reporter that can be measured by a sandwich ELISA after proteolysis of the substrate, release of the reporter, and clearance into the urine (Warren et al., Proc Natl Acad Sci USA, 111, 3671, 2014; Lin et al., ACS Nano, 0) (FIGS. 11A and 16). The selection of a pair of distinct, ligand-encoded reporters enables simultaneous, multiplexed administration of the two nanosensors. Following initiation of the infection, ABNs were injected intravenously after 24 hours and collected urine an hour after the administration of the nanosensors. Characterization of the ligand-encoded reporters present in the urine indicated that each can be detected at the picomolar level, far more sensitively than is required based on the typical reporter concentration observed in the urine, by ELISA (FIG. 11B). ELISAs for LAS-E and ELA-E reporters showed significant increases in each (1.8-fold and 2.6-fold, respectively) after initiation of infection relative to pre-infection measurements, and all but one individual mouse showed an increase in signal for both reporters after initiation of infection (FIG. 11C). To characterize the sensitivity and specificity of these ABNs for differentiating infected from healthy mice, receiver operating characteristic (ROC) curves were constructed, which demonstrate that LAS and ELA sensors are individually able to distinguish infected from healthy mice based on their urinary reporter signal (AUCs of 0.86 and 1.00 respectively; FIG. 11D).

ABNs Monitor Bacterial Infection and Resolution after Antibiotic Therapy.

To evaluate whether the presently disclosed ABNs could be used to monitor clearance of infection, PA01 was instilled intratracheally into mice, the pair of ABNs was administered the following day to confirm and set a baseline for infection in each individual, and then antibiotic treatment was initiated with ciprofloxacin, a commonly used broad spectrum antibiotic with activity against gram-negative bacteria, including PA01 (Zeiler et al., Ciprofloxacin, 14, 1986). The diagnostic ABN injection and urine collection was repeated 7 days post-infection (with an interceding 4 days of drug treatment) to determine whether the substrates could monitor recovery from infection following effective antibiotic treatment (FIG. 12A). After ciprofloxacin treatment, LAS urine signal returned to baseline, though ELA remained elevated (1.2-fold and 2.2-fold above baseline, respectively; FIGS. 3B and 3C). Constructing ROC curves to test whether the sensors could distinguish between healthy and infected mice again showed robust capability to diagnose infection with both LAS and ELA (AUC 0.92 and 1.00, respectively) when administered prior to drug treatment. However, ROC curve analysis of the urine signal after treatment (relative to infected mice prior to treatment) indicated that only the LAS ABN could identify successful treatment (AUC 0.88).

Figure 12B:
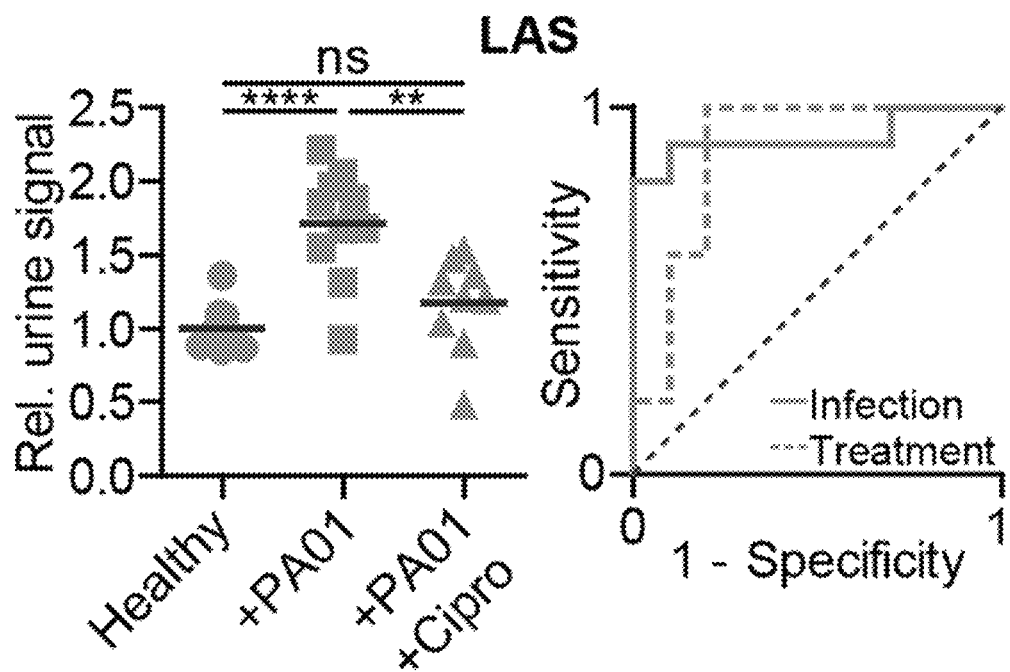
Figure 12C:
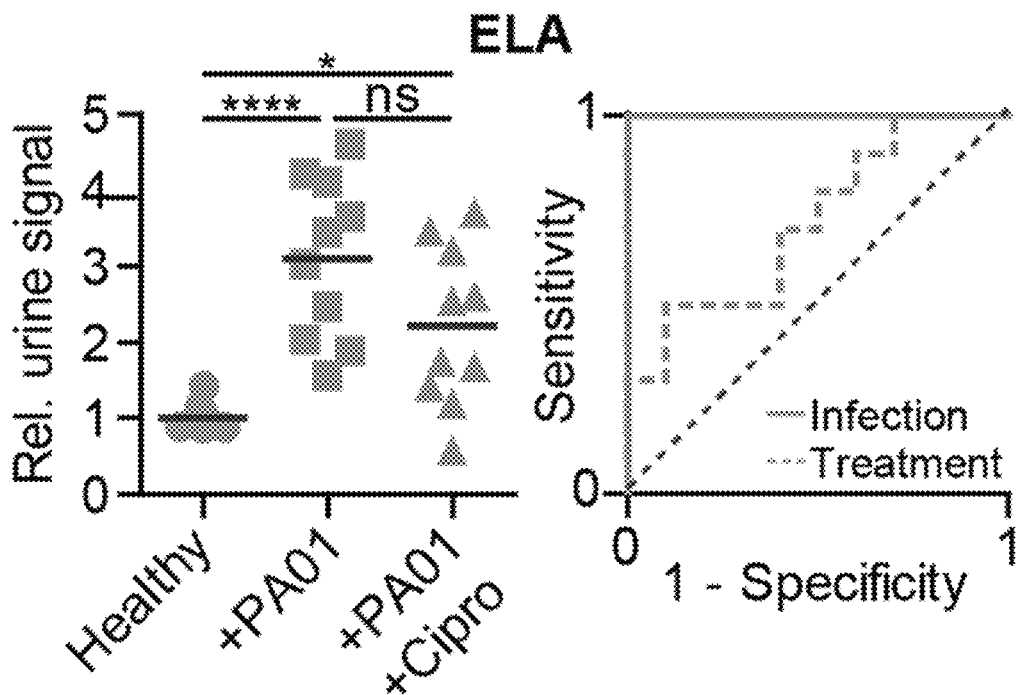
Figure 12D:
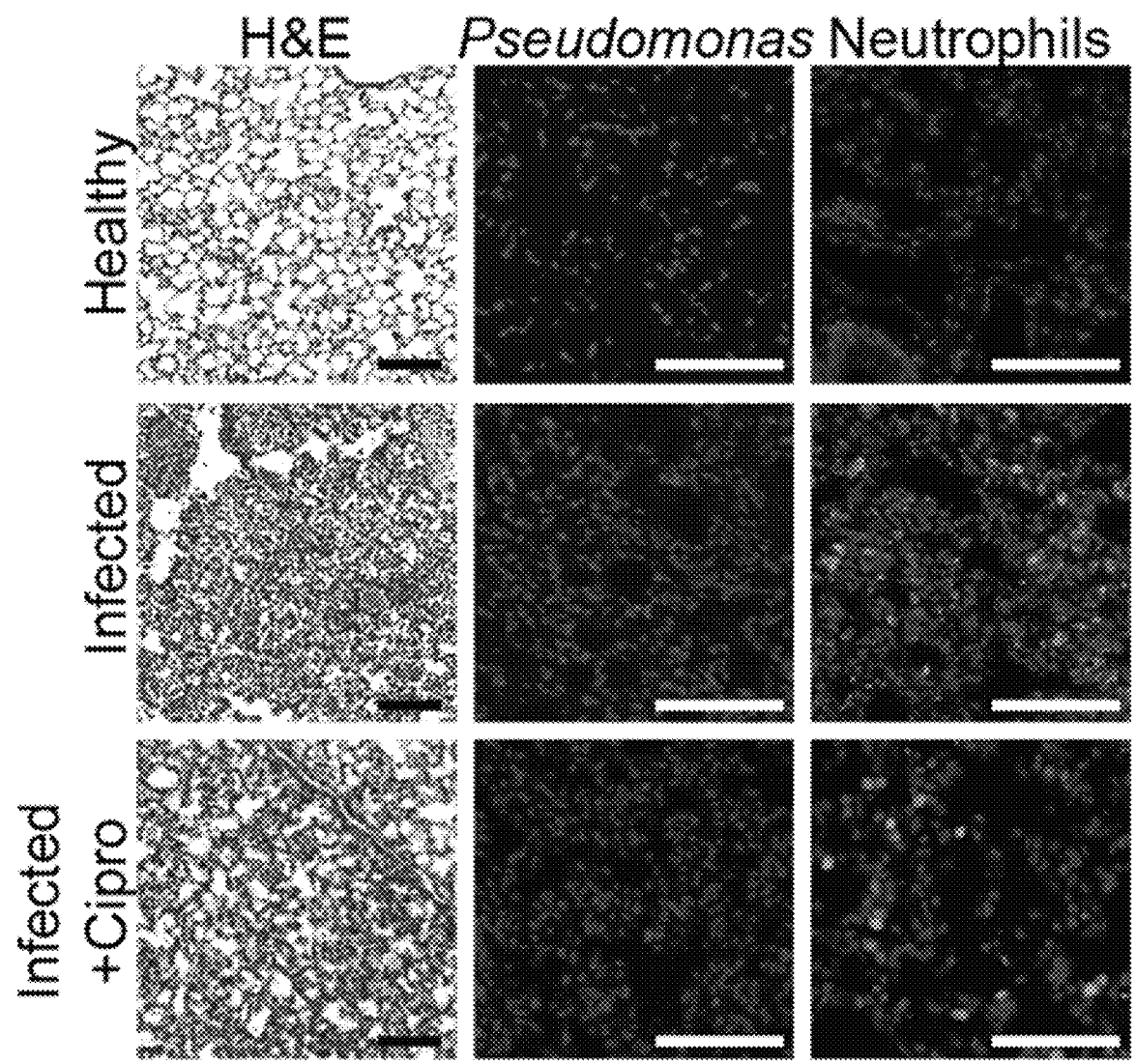
Figures 12E, 12F:
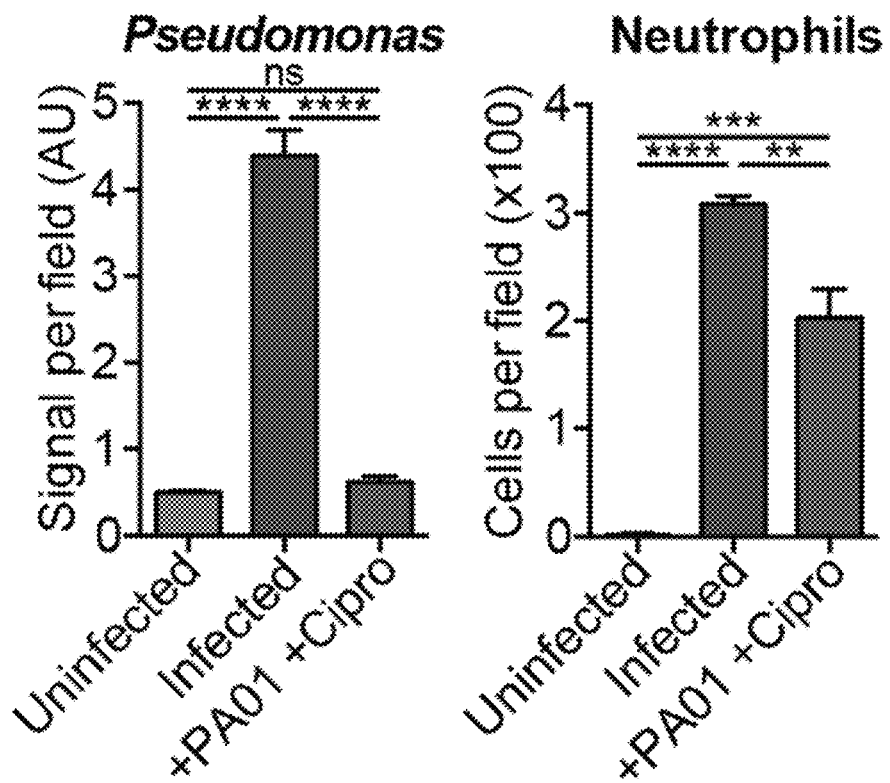

The persisting elevation in ELA urine signal at day 7 meant ELA ABNs were unable to measure treatment success, and suggested there may be remnant inflammation within the lungs of treated mice even after antibiotic therapy and resolution of infection (FIGS. 12B and 12C). To test whether inflammation remained after antibiotic therapy, histological and immunofluorescence analysis of lung sections were performed from infected and treated mice. As expected based on urinary readouts, histology and immunofluorescent staining of lung sections show residual inflammation and elevated presence of neutrophils after ciprofloxacin treatment, but no *Pseudomonas* (FIG. 12D). Quantification of immunofluorescence signal from *Pseudomonas* showed significantly higher signal in lungs of infected mice relative to uninfected or ciprofloxacin-treated mice (7-9-fold), but no significant difference in signal between uninfected and ciprofloxacin-treated mice with resolved infections (FIG. 12E). Additionally, quantification of neutrophils within the lungs of uninfected, infected, and ciprofloxacin-treated mice showed robust increase in neutrophil numbers within infected mice relative to uninfected mice, as well as an ~30% decrease in neutrophil count in lungs of mice after antibiotic treatment, still well above the uninfected baseline (FIG. 12F). These results suggest the persisting presence of immune cell-derived proteases drives cleavage of the ELA-E substrate, but the absence of PA01 LasA to cleave LAS-E, supporting the hypothesis that urinary measurements reflect features of the lung microenvironment post-infection. The robust diagnostic capability of ELA to identify infection but poor ability to monitor treatment, paired with the robust ability for LAS to specifically monitor treatment highlights the importance of multiplexing and measuring both host and pathogen factors.

Acute Administration of ABNs Differentiates Successful Versus Insufficient Antibiotic Therapies.

Figure 13A:
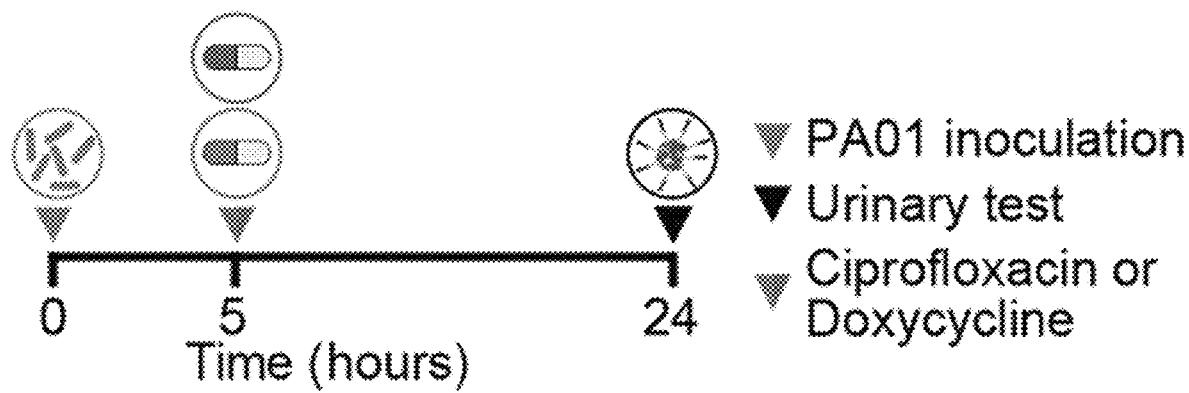
Figure 13F:
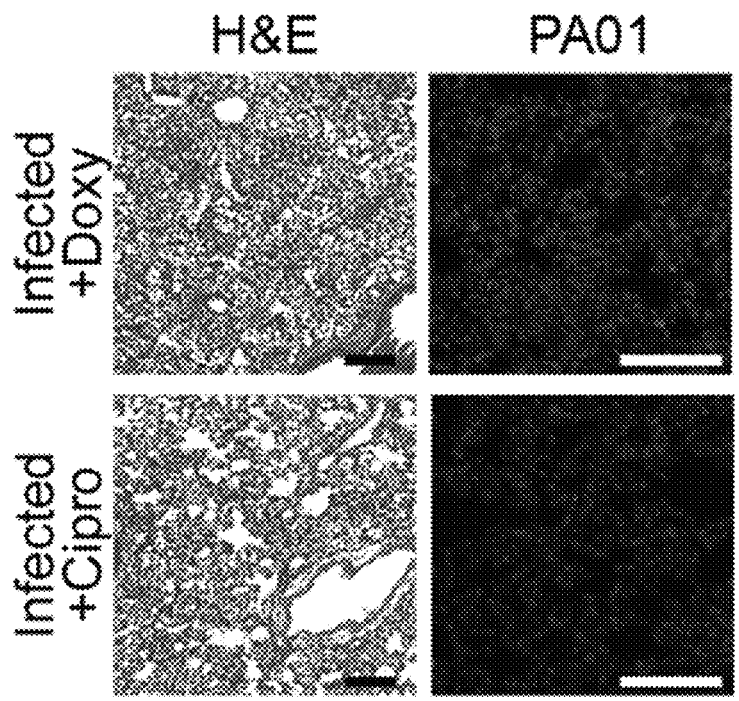
Figure 13G:
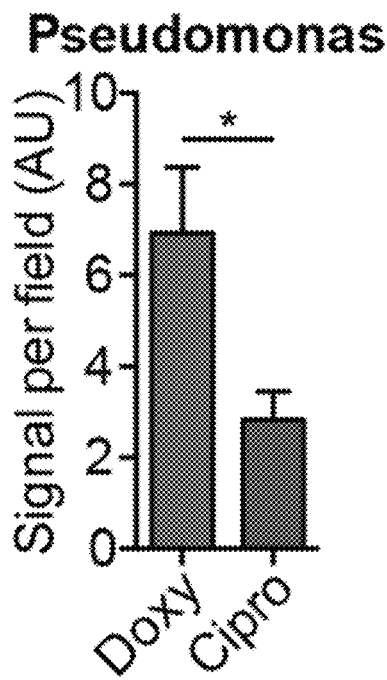

Individual responses to antimicrobial treatment can be highly variable, dependent upon the strain of pathogen and the presence of antibiotic resistance, and current clinical tests take 24-72 hours to identify antibiotic susceptibility (Caliendo et al., Clin Infect Dis, 57, S139, 2013). In addition, current clinical tests used to visualize lung infections (e.g., chest X-ray and computed tomography) are often unable to distinguish active infections from those that have been adequately treated until several weeks after antibiotic therapy is complete, because the airspace opacifications characteristic of pneumonia remain apparent on routine radiography screens (Bruns et al., J Gen Intern Med, 25, 203, 2010). Therefore, the ability of the infection-tracking ABNs to identify successful versus insufficient treatment on an acute time-scale shortly after therapeutic initiation was sought to be evaluated. Only 5 hours after establishing lung infections with PA01, antibiotic treatment was initiated with either ciprofloxacin (efficacious against *P. aeruginosa*) or doxycycline (ineffective against gram-negative bacteria including *P. aeruginosa*) (FIG. 13A). The following day, multiplexed LAS-E and ELA-E ABNs were administered and urine was collected. ELISAs for protease-liberated reporters in the urine detected elevated LAS signal in the urine of doxycycline-treated mice but not in those treated with ciprofloxacin, whereas the ELA signal was robustly elevated in both antibiotic treatment groups relative to healthy controls. Comparing the urine signal from the two treatment groups, it is observed that LAS signal is significantly lower in ciprofloxacin-treated mice than in doxycycline-treated mice, whereas ELA signal between the two groups is not significantly different (FIGS. 13B and 13D). Constructing ROC curves to query whether the sensors could detect effective treatment (comparing doxycycline to ciprofloxacin treatment) reveals that LAS does characterize acute drug sensitivity versus resistance (FIG. 13C, AUC=0.893), whereas ELA is unable to differentiate treatment groups (FIG. 13E, AUC=0.536). This data is in line with the timeline in which an infection is expected to activate an innate immune response, in that neutrophil infiltration occurs on the order of a few hours in mice (Zhang et al., Immunol Rev, 173, 39, 2000). To assay whether lingering inflammatory cells were observed in the infected, antibiotic treated animals, histology and immunofluorescence analyses were performed in lung sections and marked lung inflammation and elevated neutrophils were observed in both doxycycline- and ciprofloxacin-treated mice, consistent with elevated ELA signal in both (FIG. 13F). However, a significantly lower *Pseudomonas* immunofluorescent signal was present in the lungs of ciprofloxacin-treated mice compared to the doxycycline-treated group (~60% decrease, FIG. 13G). The persistent *Pseudomonas* immunostaining observed following ciprofloxacin treatment might be derived from residual *Pseudomonas* antigens remaining from lysed bacteria that had not yet been cleared by the immune system. Alternatively, the reduced LAS sensor reading in these treated mice could reflect a suppression of LasA secretion from bacteria as they are killed by the potent antibiotic. Thus, ABNs are able to noninvasively report on the status of the infection and lung microenvironment, and taken together, these data support the potential to use ABNs to test the performance of antibiotics in vivo, without requiring sputum cultures or the reliance on slowly evolving clinical metrics such as fever or malaise.

Discussion

Here, a multiplexed, activity-based nanosensor set was developed for the detection of *P. aeruginosa* pneumonia, a disease associated with high morbidity and mortality. Together, the data demonstrate that the engineered ABN platform is deployable to the context of infection, both for the specific identification of *P. aeruginosa* lung infections and for the monitoring of their treatment. The strategy to measure both host- and pathogen-derived protease activity provides a noninvasive window into the lung microenvironment over the course of disease and resolution. This approach facilitates the rapid identification of infection and the monitoring of bacterial clearance following antibiotic treatment. In this study, an intratracheal instillation method is utilized for the development of *P. aeruginosa* infections, which relies on an inoculation of a large bolus of bacteria for infection to take hold. As such, one potential limitation of this work is the limit of detection for bacterial burden within the lung. Detection of pneumonia with burdens of $>10^6$ CFU of bacteria has been shown to be disseminated throughout the lung, but established mouse models are limited in their ability to generate focal infections that are more directly analogous to human disease, or those with lower bacterial burdens. It is expected that the limit of bacterial detection could be lowered by direct pulmonary administration of ABNs, such as by nebulization of the particles (Patton et al., Nat Rev Drug Discov, 6, 67, 2007).

An exciting aspect of the urine-based nanosensor detection platform is that it can be readily interfaced with paper tests, or lateral flow assays, as the analytical readout, which can be imaged using a cell phone camera (Dudani et al., Adv Funct Mater, 26, 2919, 2016; Warren et al., Proc Natl Acad Sci USA, 111, 3671, 2014). This adaptation could enable at-home or out-patient monitoring, as well as use in low resource settings. Additionally, while the pair of nanosensors described here is able to detect PA01 infection, it may not cover all *P. aeruginosa* strains or other bacterial species. For example, the presently disclosed screen of 5 clinical isolates highlights that not all strains of *P. aeruginosa* secrete detectable levels of LasA. Greater multiplexing would overcome this limitation, such as by adding detectors for other pathogen-derived proteases, including virulence factors LepA, Protease IV, and AprA. This greater multiplexing could also facilitate the application of ABNs to robustly classify viral from bacterial infections, which represents a challenging stumbling block in the diagnosis of childhood pneumonia (Sweeney et al., Sci Transl Med, 8, 346ra91, 2016), among other at-risk demographics.

Collectively, the work described here demonstrates the capacity to use protease activity measurements to identify, monitor, and characterize bacterial lung infections. Notably, this method could also be adapted via the design of alternative peptide substrates for different host- and pathogen-derived proteases to be applicable to a wide range of clinical pathologies. Through the co-administration of a pair of peptide substrates, ABNs succeeded in differentiating between healthy and infected mice, and also monitored the course of disease after treatment, thereby distinguishing between appropriate and ineffective antibiotic regimens soon after therapeutic administration. These results offer a proof-of-principle demonstration that could be adapted for new applications, such as to identify distinct disease etiologies, to monitor severity of disease, and to illuminate and/or track an immune response during the course of an infection.

Materials and Methods

Bacterial Pneumonia Model and Antibiotic Treatment.

All animal studies were approved by Massachusetts Institute of Technology's Committee on Animal Care. For infection studies, 5-7 week old female CD-1 mice were inoculated intratracheally with $1.25 \times 10^6$ CFU of *P. aeruginosa* strain PA01 in 50 µL of PBS. Bacteria were cultured overnight in LB broth, then subcultured and grown to log phase (OD600≈0.5). Bacteria were pelleted, washed with sterile PBS, and then resuspended to the requisite concentration for intratracheal administration. Mice were administered buprenorphine and meloxicam several hours after infection. For antibiotic treatment studies, mice were injected intraperitoneally with 40 mg/kg ciprofloxacin or 30 mg/kg doxycycline twice per day for up to 6 days.

Histochemistry of Tissue Sections.

Animals were perfused with PBS followed by 10% formalin solution. The lungs were resected and fixed in formalin before paraffin embedding and sectioning. For gross histological evaluation of inflammation, lung sections were stained with hematoxylin and eosin. For immunofluorescent visualization of bacteria and neutrophils, lungs were stained with anti-*pseudomonas* (Abeam, 1:500) or anti-neutrophil (Abeam, 1:500) antibodies. Appropriately labeled secondary antibodies (Invitrogen) were used to detect primary antibodies. Fluorescence images were acquired on a Perkin Elmer Pannoramic250. Quantification of neutrophil signal was completed by capturing 3-5 representative fields from each stained lung section and counting positive cells. Quantification of *pseudomonas* signal was completed by capturing 3-5 representative fields from each stained lung section and measuring total positive area after uniform thresholding of each single-channel fluorescence image (ImageJ).

Synthesis of Peptides and NPs.

All peptides were synthesized by CPC Scientific, Inc. For in vitro studies, intramoleculary quenched peptides were used by flanking the cleavable sequence with a FAM fluorophore and Dabcyl quencher. In vivo protease sensitive substrates were synthesized to contain a urinary reporter comprised of a protease resistant D-stereoisomer of Glutamate-Fibrinopeptide B with one of three ligand handles that could be captured by an antibody. Sequences are listed in Table 1.

For in vivo studies, peptides were conjugated to multivalent 40 kDa PEG-MAL (Jenkem). Cysteine-terminated peptides were added to sterile-filtered PEG and reacted overnight. Unreacted peptide was filtered using spin filters (Millipore, MWCO=10 kDa). Nanoparticles were stored in PBS at 4° C. Peptide concentrations were quantified by absorbance (Tecan).

In Vitro Substrate Cleavage Assays.

Supernatant from PA01 and *S. aureus* were collected and added to substrates in 384 well plates and dequenching of FAM was monitored at 37° C. (Tecan). Fluorescence change at 30 minutes was reported. For recombinant protease assays, enzyme was added to the substrates in enzyme-specific buffer (MMP7 & 9 buffer: 50 mM Tris, 150 mM NaCl, 5 mM $CaCl_2$), 10 M $ZnCl2$, pH 7.5; Thrombin: PBS; NE: 100 mM HEPES, 500 mM NaCl, 0.05% Tween 20) in a 384 well plate for time-lapse fluorimetry to measure dequenching at 37° C. (Tecan).

Western Blot of Bacterial Supernatants.

Supernatants from PA01 and clinical isolate strains were collected from overnight cultures by centrifugation. 1 mL of supernatant or fresh media control was added to 250 µL of 50% trichloroacetic acid, then incubated for 15 minutes on ice to precipitate protein. Protein precipitates were collected by centrifugation, washed, and dried, then resuspended in LDS sample buffer (Invitrogen) with DTT. Samples were run on a 4-12% bis-tris gel (Invitrogen) along with 50 ng of recombinant LasA protein (MyBioSource), transferred to PVDF transfer membrane (Thermo Scientific). The membrane was blocked with 5% milk and blotted with HRP-conjugated anti-LasA (MyBioSource, 1:10000), and visualized with SuperSignal West Pico PLUS chemiluminescent substrate (Thermo Scientific).

Stapholysis Assay of Bacterial Supernatants.

Supernatants from PA01 and clinical isolate strains were collected from overnight cultures by centrifugation. *S. aureus* was cultured overnight then subcultured in fresh LB and grown up to mid-log phase. *S. aureus* was then diluted 1:4 into each of the *P. aeruginosa* culture supernatants and grown for 6 hours, with aliquots taken and plated onto LB agar at various timepoints for CFU quantification.

In Vivo Assay for Protease Activity.

At each timepoint, 200 µL of nanosensor cocktail were injected at a concentration of 1 µM per peptide in sterile PBS via the tail vein. After nanoparticle injection, mice were placed in custom housing with a 96-well plate base for urine collection. After 1 h, their bladders were voided to collect between 100-200 µl of urine.

ELISA to Quantify Urinary Reporters.

Sandwich ELISAs were performed as previously described (Warren et al., Proc Natl Acad Sci USA, 111, 3671, 2014). Briefly, capture antibodies (anti-fluorescein, GeneTex; anti-DNP and anti-AF488, Invitrogen) were coated onto Bacti plates (Thermo). Plates were washed and blocked and diluted urine (1000 to 10000-fold in PBS) was added. Detection was performed using NeutrAvidin-HRP (Pierce) and addition of Ultra-TMB as the substrate for HRP. After quenching with HCl, absorbance at 450 nm was measured. Concentration was calculated based on a standard curve ladder of peptide reporters liberated from the injected dose of ABNs, diluted from 1 µM starting concentration to 1 nM and below.

Clinical Isolates.

*P. aeruginosa* strains isolated from de-identified clinical samples were generously provided by Dr. Deborah Hung, MD, PhD (Massachusetts General Hospital). Cultures of each were grown in LB broth overnight, then were subcultured in fresh LB and each strain grown to OD-matched mid log phase (OD600~0.5). Supernatants were collected by centrifugation and substrate cleavage was monitored as described above.

Statistical Analyses.

All statistical analyses were performed in GraphPad (Prism 5.0). Details of statistical tests are provided in the legend of each figure.

What is claimed is:

1. A method comprising
    detecting a detectable marker in a blood sample or urine sample obtained from a subject that has been administered to the lung of the subject by inhalation or intratracheal administration a lung protease nanosensor comprising:
    (a) (i) a multi-arm polyethylene glycol molecule (multi-arm PEG) scaffold and/or (ii) a polyethylene glycol (PEG) scaffold with a molecular weight equal to or greater than 40 kDa; linked to
    (b) a substrate,
    wherein the substrate is conjugated to a detectable marker, wherein the detectable marker is released from the nanosensor when exposed to a protease present in a lung, and
    wherein the subject has or is suspected of having lung cancer.

2. The method of 1, wherein the lung protease nanosensor is delivered to the lung using an aerosol delivery device which is not reliant on propellant or compressed air.

3. The method of claim 1, wherein the substrate comprises a sequence selected from the group consisting of SEQ ID NOs: 1-14.

4. The method of claim 1, wherein the lung protease nanosensor comprises the scaffold linked to a plurality of substrates, wherein each substrate is conjugated to a detectable marker, whereby the detectable marker is capable of being released from the nanosensor when exposed to a protease present in a lung.

5. The method of claim 1, wherein the scaffold is greater than 5 nm in size.

6. The method of claim 1, wherein the detectable marker is less than 3 nm in size.

7. The method of claim 1, wherein the lung protease nanosensor comprises the multi-arm PEG scaffold.

8. The method of claim 1, wherein the subject is administered a composition comprising at least two lung protease nanosensors.

9. The method of claim 8, wherein the substrate of each lung protease nanosensor is independently selected from the group consisting of a substrate that is capable of being cleaved by ACE2, CTSD, F7, KLK13, KLK14, KLK6, MMP1, MMP11, MMP12, MMP13, MMP3, NAPSA, PRSS22, PRSS3, PRSS8, and combinations thereof.

10. The method of claim 1, wherein inhalation comprises dry powder inhalation and/or nebulization of the lung protease nanosensor.

11. The method of claim 1, wherein the detectable marker comprises a peptide.

12. A method for classifying lung disease in a subject, the method comprising:
   (i) detecting in a biological sample obtained from a subject that has been administered one or more lung protease nanosensors, wherein the one or more lung protease nanosensors have been administered to the lung of the subject by inhalation or intratracheal administration: one or more detectable markers that have been released from the one or more lung protease nanosensors when exposed to an enzyme present in the lung of the subject, wherein each of the one or more lung protease nanosensors comprises:
   (a) (1) a multi-arm polyethylene glycol molecule (multi-arm PEG) scaffold and/or (2) a polyethylene glycol (PEG) scaffold with a molecular weight equal to or greater than 40 kDa; linked to
   (b) a substrate,
   wherein the substrate is conjugated to a detectable marker,
   wherein the detectable marker is released from the nanosensor when exposed to a protease present in a lung, and
   wherein the biological sample is a blood sample or urine sample; and
   (ii) classifying the subject as having a type of lung disease based on the identity of the detectable markers present in the biological sample, wherein the presence of the detectable markers in the biological sample is indicative of one or more cancer-associated enzymes being present in an active form within the lung of the subject.

13. A method of treating lung cancer in a subject, the method comprising administering a therapeutic agent for treatment of lung cancer to or performing a therapeutic intervention on a subject who has been classified as having lung cancer according to the method of claim 12.

14. A method comprising:
   (a) administering to the lung of a subject, by inhalation or intratracheal administration, a lung protease nanosensor comprising:
   (i) (1) a multi-arm polyethylene glycol molecule (multi-arm PEG) scaffold and/or (2) a polyethylene glycol (PEG) scaffold with a molecular weight equal to or greater than 40 kDa; linked to
   (ii) a lung infection substrate,
   wherein the substrate is conjugated to a detectable marker,
   wherein the substrate includes a detectable marker,
   whereby the detectable marker is released from the lung protease nanosensor when exposed to a protease present in the lung, and
   wherein the subject has or is suspected of having a lung infection; and
   (b) detecting and quantifying the detectable marker from a blood sample or a urine sample from the subject.

15. The method of claim 14, wherein the subject has been administered an antibiotic.

16. The method of claim 15, wherein the antibiotic has been administered prior to (a) or (b).

17. The method of claim 14, wherein the lung infection is a *Pseudomonas aeruginosa* infection.

18. The method of claim 14, wherein the protease is a pathogen protease.

19. The method of claim 14, wherein the biological sample is urine.

20. The method of claim 14, wherein the lung protease nanosensor comprises the multi-arm PEG scaffold.

* * * * *

SEQUENCE LISTING

<160> NUMBER OF SEQ ID NOS: 48

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1

Pro Gln Gly Ile Trp Gly Gln
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 2

Pro Val Gly Leu Ile Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Pro Val Pro Leu Ser Leu Val Met
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 4

Pro Leu Gly Leu Arg Ser Trp
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Pro Leu Gly Val Arg Gly Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Phe

```
<400> SEQUENCE: 6

Phe Pro Arg Ser Gly Gly Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Leu Gly Pro Lys Gly Gln Thr Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 8

Gly Ser Gly Arg Ser Ala Asn Ala Lys Gly
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 9

Lys Pro Ile Ser Leu Ile Ser Ser Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 10

Ile Leu Ser Arg Ile Val Gly Gly Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 11

Ser Gly Ser Lys Ile Ile Gly Gly Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 12
```

```
Pro Leu Gly Met Arg Gly Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is 3-cyclohexylalanine
<220> FEATURE:
<221> NAME/KEY: MISC_FEATURE
<222> LOCATION: (4)..(4)
<223> OTHER INFORMATION: Methyl-cysteine

<400> SEQUENCE: 13

Pro Xaa Gly Cys His Ala Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 14

Ala Pro Phe Glu Met Ser Ala Gly
1               5

<210> SEQ ID NO 15
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+2
<220> FEATURE:
<221> NAME/KEY: MISC_FEATURE
<222> LOCATION: (3)..(3)
<223> OTHER INFORMATION: Isotope V+6
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
```

```
<222> LOCATION: (14)..(14)
<223> OTHER INFORMATION: d-Arg

<400> SEQUENCE: 15

Glu Gly Val Asn Asp Asn Glu Glu Gly Phe Phe Ser Ala Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (3)..(3)
<223> OTHER INFORMATION: Isotope V+6
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (11)..(11)
<223> OTHER INFORMATION: Isotope P+1
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+1
<220> FEATURE:
<221> NAME/KEY: MISC_FEATURE
<222> LOCATION: (14)..(14)
<223> OTHER INFORMATION: d-Arg

<400> SEQUENCE: 16

Glu Gly Val Asn Asp Asn Glu Glu Gly Phe Phe Ser Ala Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+3
<220> FEATURE:
<221> NAME/KEY: MISC_FEATURE
<222> LOCATION: (3)..(3)
```

```
<223> OTHER INFORMATION: Isotope V+1
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
<221> NAME/KEY: MISC_FEATURE
<222> LOCATION: (14)..(14)
<223> OTHER INFORMATION: d-Arg

<400> SEQUENCE: 17

Glu Gly Val Asn Asp Asn Glu Glu Gly Phe Phe Ser Ala Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+2
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+2
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
```

```
<221> NAME/KEY: MISC_FEATURE
<222> LOCATION: (14)..(14)
<223> OTHER INFORMATION: d-Arg

<400> SEQUENCE: 18

Glu Gly Val Asn Asp Asn Glu Glu Gly Phe Phe Ser Ala Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+3
<220> FEATURE:
<221> NAME/KEY: MISC_FEATURE
<222> LOCATION: (10)..(10)
<223> OTHER INFORMATION: Isotope F+1
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
<221> NAME/KEY: MISC_FEATURE
<222> LOCATION: (14)..(14)
<223> OTHER INFORMATION: d-Arg

<400> SEQUENCE: 19

Glu Gly Val Asn Asp Asn Glu Glu Gly Phe Phe Ser Ala Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+2
<220> FEATURE:
<221> NAME/KEY: MISC_FEATURE
```

```
<222> LOCATION: (3)..(3)
<223> OTHER INFORMATION: Isotope V+6
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+3
<220> FEATURE:
<221> NAME/KEY: MISC_FEATURE
<222> LOCATION: (10)..(11)
<223> OTHER INFORMATION: Isotope F+1
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+1
<220> FEATURE:
<221> NAME/KEY: MISC_FEATURE
<222> LOCATION: (14)..(14)
<223> OTHER INFORMATION: d-Arg

<400> SEQUENCE: 20

Glu Gly Val Asn Asp Asn Glu Glu Gly Phe Phe Ser Ala Arg
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (3)..(3)
<223> OTHER INFORMATION: Isotope V+6
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+3
```

```
<220> FEATURE:
<221> NAME/KEY: MISC_FEATURE
<222> LOCATION: (10)..(10)
<223> OTHER INFORMATION: Isotope F+1
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
<221> NAME/KEY: MISC_FEATURE
<222> LOCATION: (14)..(14)
<223> OTHER INFORMATION: d-Arg

<400> SEQUENCE: 21

Glu Gly Val Asn Asp Asn Glu Glu Gly Phe Phe Ser Ala Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+3
<220> FEATURE:
<221> NAME/KEY: MISC_FEATURE
<222> LOCATION: (3)..(3)
<223> OTHER INFORMATION: Isotope V+1
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (10)..(10)
<223> OTHER INFORMATION: Isotope F+10
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (14)..(14)
<223> OTHER INFORMATION: d-Arg

<400> SEQUENCE: 22

Glu Gly Val Asn Asp Asn Glu Glu Gly Phe Phe Ser Ala Arg
1               5                   10

<210> SEQ ID NO 23
<211> LENGTH: 14
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (11)..(11)
<223> OTHER INFORMATION: Isotope F+10
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
<221> NAME/KEY: MISC_FEATURE
<222> LOCATION: (14)..(14)
<223> OTHER INFORMATION: d-Arg

<400> SEQUENCE: 23

Glu Gly Val Asn Asp Asn Glu Glu Gly Phe Phe Ser Ala Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+2
<220> FEATURE:
<221> NAME/KEY: MISC_FEATURE
<222> LOCATION: (3)..(3)
<223> OTHER INFORMATION: Isotope V+6
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
```

```
<223> OTHER INFORMATION: d-Glu
<220> FEATURE:
<221> NAME/KEY: MISC_FEATURE
<222> LOCATION: (10)..(10)
<223> OTHER INFORMATION: Isotope F+10
<220> FEATURE:
<221> NAME/KEY: MISC_FEATURE
<222> LOCATION: (11)..(11)
<223> OTHER INFORMATION: Isotope F+1
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+1
<220> FEATURE:
<221> NAME/KEY: MISC_FEATURE
<222> LOCATION: (14)..(14)
<223> OTHER INFORMATION: d-Arg

<400> SEQUENCE: 24

Glu Gly Val Asn Asp Asn Glu Glu Gly Phe Phe Ser Ala Arg
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+3
<220> FEATURE:
<221> NAME/KEY: MISC_FEATURE
<222> LOCATION: (3)..(3)
<223> OTHER INFORMATION: Isotope V+1
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+2
<220> FEATURE:
<221> NAME/KEY: MISC_FEATURE
<222> LOCATION: (10)..(10)
<223> OTHER INFORMATION: Isotope F+10
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
```

```
<221> NAME/KEY: MISC_FEATURE
<222> LOCATION: (14)..(14)
<223> OTHER INFORMATION: d-Arg

<400> SEQUENCE: 25

Glu Gly Val Asn Asp Asn Glu Glu Gly Phe Phe Ser Ala Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (10)..(11)
<223> OTHER INFORMATION: Isotope F+10
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (14)..(14)
<223> OTHER INFORMATION: d-Arg

<400> SEQUENCE: 26

Glu Gly Val Asn Asp Asn Glu Glu Gly Phe Phe Ser Ala Arg
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+2
<220> FEATURE:
<221> NAME/KEY: MISC_FEATURE
<222> LOCATION: (3)..(3)
<223> OTHER INFORMATION: Isotope V+6
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
```

```
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+3
<220> FEATURE:
<221> NAME/KEY: MISC_FEATURE
<222> LOCATION: (10)..(10)
<223> OTHER INFORMATION: Isotope F+10
<220> FEATURE:
<221> NAME/KEY: MISC_FEATURE
<222> LOCATION: (11)..(11)
<223> OTHER INFORMATION: Isotope F+1
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: Isotope A+4
<220> FEATURE:
<221> NAME/KEY: MISC_FEATURE
<222> LOCATION: (14)..(14)
<223> OTHER INFORMATION: d-Arg

<400> SEQUENCE: 27

Glu Gly Val Asn Asp Asn Glu Glu Gly Phe Phe Ser Ala Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (2)..(2)
<223> OTHER INFORMATION: Isotope G+3
<220> FEATURE:
<221> NAME/KEY: MISC_FEATURE
<222> LOCATION: (3)..(3)
<223> OTHER INFORMATION: Isotope V+1
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (9)..(9)
<223> OTHER INFORMATION: Isotope G+2
```

```
<220> FEATURE:
<221> NAME/KEY: MISC_FEATURE
<222> LOCATION: (10)..(11)
<223> OTHER INFORMATION: Isotope F+10
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (14)..(14)
<223> OTHER INFORMATION: d-Arg

<400> SEQUENCE: 28

Glu Gly Val Asn Asp Asn Glu Glu Gly Phe Phe Ser Ala Arg
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: modified by CPQ2-PEG2

<400> SEQUENCE: 29

Gly Gly Pro Gln Gly Ile Trp Gly Gln Lys Cys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: modified by CPQ2-PEG2

<400> SEQUENCE: 30

Gly Gly Pro Val Gly Leu Ile Gly Lys Cys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: modified by CPQ2-PEG2

<400> SEQUENCE: 31

Gly Gly Pro Val Pro Leu Ser Leu Val Met Lys Cys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
```

```
<223> OTHER INFORMATION: modified by CPQ2-PEG2

<400> SEQUENCE: 32

Gly Gly Pro Leu Gly Leu Arg Ser Trp Lys Cys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: modified by CPQ2-PEG2

<400> SEQUENCE: 33

Gly Gly Pro Leu Gly Val Arg Gly Lys Lys Cys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: d-Phe
<220> FEATURE:
<221> NAME/KEY: MISC_FEATURE
<222> LOCATION: (10)..(10)
<223> OTHER INFORMATION: modified by CPQ2-PEG2

<400> SEQUENCE: 34

Gly Gly Phe Pro Arg Ser Gly Gly Gly Lys Cys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: modified by CPQ2
<220> FEATURE:
<221> NAME/KEY: MISC_FEATURE
<222> LOCATION: (12)..(13)
<223> OTHER INFORMATION: d-Lys
<220> FEATURE:
<221> NAME/KEY: MISC_FEATURE
<222> LOCATION: (13)..(13)
<223> OTHER INFORMATION: modified by PEG2

<400> SEQUENCE: 35

Gly Gly Leu Gly Pro Lys Gly Gln Thr Gly Lys Lys Lys Cys
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (13)..(13)
<223> OTHER INFORMATION: modified by CPQ2-PEG2

<400> SEQUENCE: 36

Gly Gly Gly Ser Gly Arg Ser Ala Asn Ala Lys Gly Lys Gly Cys
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: modified by CPQ2-PEG2

<400> SEQUENCE: 37

Gly Lys Pro Ile Ser Leu Ile Ser Ser Gly Lys Gly Cys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: modified by CPQ2-PEG2

<400> SEQUENCE: 38

Gly Ile Leu Ser Arg Ile Val Gly Gly Gly Lys Gly Cys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: modified by CPQ2-PEG2

<400> SEQUENCE: 39

Gly Ser Gly Ser Lys Ile Ile Gly Gly Gly Lys Gly Cys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: modified by CPQ2

<400> SEQUENCE: 40

Gly Gly Pro Leu Gly Met Arg Gly Gly Lys Gly Cys
1               5                   10

<210> SEQ ID NO 41
<211> LENGTH: 11
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is 3-cyclohexylalanine
<220> FEATURE:
<221> NAME/KEY: MISC_FEATURE
<222> LOCATION: (5)..(5)
<223> OTHER INFORMATION: methyl-cysteine
<220> FEATURE:
<221> NAME/KEY: MISC_FEATURE
<222> LOCATION: (9)..(9)
<223> OTHER INFORMATION: modified by CPQ2

<400> SEQUENCE: 41

Gly Pro Xaa Gly Cys His Ala Gly Lys Gly Cys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: modified by CPQ2

<400> SEQUENCE: 42

Gly Ala Pro Phe Glu Met Ser Ala Gly Lys Gly Cys
1               5                   10

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Leu Gly Gly Gly Ala
1               5

<210> SEQ ID NO 44
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 44

Ala Ala Phe Ala
1

<210> SEQ ID NO 45
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: modified by FAM

<400> SEQUENCE: 45
```

Gly Leu Gly Gly Gly Ala Gly Lys
1               5

<210> SEQ ID NO 46
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (3)..(3)
<223> OTHER INFORMATION: d-Val
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (10)..(11)
<223> OTHER INFORMATION: d-Phe
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: d-Ala
<220> FEATURE:
<221> NAME/KEY: MISC_FEATURE
<222> LOCATION: (14)..(14)
<223> OTHER INFORMATION: d-Arg
<220> FEATURE:
<221> NAME/KEY: MISC_FEATURE
<222> LOCATION: (15)..(15)
<223> OTHER INFORMATION: modified by AF488

<400> SEQUENCE: 46

Glu Gly Val Asn Asp Asn Glu Glu Gly Phe Phe Ser Ala Arg Lys Gly
1               5                   10                  15

Gly Leu Gly Gly Gly Ala Gly Cys
            20

<210> SEQ ID NO 47
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: modified by FAM

<400> SEQUENCE: 47

Gly Ala Ala Phe Ala Gly Lys
1               5

```
<210> SEQ ID NO 48
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: d-Glu
<220> FEATURE:
<221> NAME/KEY: MISC_FEATURE
<222> LOCATION: (3)..(3)
<223> OTHER INFORMATION: d-Val
<220> FEATURE:
<221> NAME/KEY: MISC_FEATURE
<222> LOCATION: (4)..(4)
<223> OTHER INFORMATION: d-Asn
<220> FEATURE:
<221> NAME/KEY: MISC_FEATURE
<222> LOCATION: (5)..(5)
<223> OTHER INFORMATION: d-Asp
<220> FEATURE:
<221> NAME/KEY: MISC_FEATURE
<222> LOCATION: (6)..(6)
<223> OTHER INFORMATION: d-Asn
<220> FEATURE:
<221> NAME/KEY: MISC_FEATURE
<222> LOCATION: (7)..(8)
<223> OTHER INFORMATION: d-Glu
<220> FEATURE:
<221> NAME/KEY: MISC_FEATURE
<222> LOCATION: (10)..(11)
<223> OTHER INFORMATION: d-Phe
<220> FEATURE:
<221> NAME/KEY: MISC_FEATURE
<222> LOCATION: (12)..(12)
<223> OTHER INFORMATION: d-Ser
<220> FEATURE:
<221> NAME/KEY: MISC_FEATURE
<222> LOCATION: (13)..(13)
<223> OTHER INFORMATION: d-Ala
<220> FEATURE:
<221> NAME/KEY: MISC_FEATURE
<222> LOCATION: (14)..(14)
<223> OTHER INFORMATION: d-Arg
<220> FEATURE:
<221> NAME/KEY: MISC_FEATURE
<222> LOCATION: (15)..(15)
<223> OTHER INFORMATION: modified by FAM

<400> SEQUENCE: 48

Glu Gly Val Asn Asp Asn Glu Glu Gly Phe Phe Ser Ala Arg Lys Gly
1               5                   10                  15

Gly Ala Ala Phe Ala Gly Cys
            20
```